(12) United States Patent
Nagahara et al.

(10) Patent No.: US 8,980,322 B2
(45) Date of Patent: Mar. 17, 2015

(54) CONTROLLED RELEASE COMPOSITION

(75) Inventors: Naoki Nagahara, Osaka (JP); Keiko Miyamoto, Osaka (JP); Yohko Akiyama, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1405 days.

(21) Appl. No.: 10/549,150

(22) PCT Filed: Mar. 16, 2004

(86) PCT No.: PCT/JP2004/003483
§ 371 (c)(1),
(2), (4) Date: Sep. 15, 2005

(87) PCT Pub. No.: WO2004/082665
PCT Pub. Date: Sep. 30, 2004

(65) Prior Publication Data
US 2006/0177509 A1 Aug. 10, 2006

(30) Foreign Application Priority Data
Mar. 17, 2003 (JP) .................................. 2003-072858

(51) Int. Cl.
A61K 9/14 (2006.01)
A61K 9/20 (2006.01)
A61K 9/48 (2006.01)
A61K 9/24 (2006.01)

(52) U.S. Cl.
CPC ...................................... *A61K 9/209* (2013.01)
USPC ............ 424/484; 424/451; 424/464; 424/489

(58) Field of Classification Search
None
See application file for complete search history.

(56) References Cited

U.S. PATENT DOCUMENTS

| | | | |
|---|---|---|---|
| 4,892,741 A | 1/1990 | Ohm et al. | |
| 5,374,730 A * | 12/1994 | Slemon et al. ............. | 546/273.7 |
| 5,972,389 A * | 10/1999 | Shell et al. .................... | 424/501 |
| 6,610,323 B1 | 8/2003 | Lundberg et al. | |
| 6,730,321 B2 * | 5/2004 | Ting et al. ...................... | 424/473 |
| 2001/0046964 A1 * | 11/2001 | Percel et al. .................... | 514/29 |
| 2002/0051814 A1 | 5/2002 | Chen | |
| 2003/0073714 A1 | 4/2003 | Breder et al. | |
| 2003/0077297 A1 * | 4/2003 | Chen et al. .................... | 424/400 |

FOREIGN PATENT DOCUMENTS

| | | |
|---|---|---|
| EP | 0 776 660 | 6/1997 |
| JP | 6-11699 | 2/1994 |
| JP | 9-143073 | 6/1997 |
| JP | 2000-178193 | 6/2000 |
| JP | 2001-526211 | 12/2001 |
| JP | 2001-526213 | 12/2001 |
| WO | 99/32091 | 7/1999 |
| WO | WO 9932091 A1 * | 7/1999 |
| WO | WO 9932093 A1 * | 7/1999 |
| WO | 99/51209 | 10/1999 |
| WO | 00/35448 | 6/2000 |
| WO | 01/51050 | 7/2001 |
| WO | 03/013525 | 2/2003 |
| WO | 2004/035020 | 4/2004 |
| WO | 2004/080439 | 9/2004 |

OTHER PUBLICATIONS

T. Sirkia et al., "Development and biopharmaceutical evaluations of a new press-coated prolonged-release salbutamol supphate tablet in man", European Journal of Pharmaceutical Sciences, vol. 1, pp. 195-201, 1994.
Notice of Reasons for Refusal mailed Mar. 22, 2011 in corresponding Japanese Application No. 2004-075037, with English translation.
Supplementary European Search Report issued Nov. 11, 2009 in the corresponding European Patent Application No. 04 72 0975 in the English language.

* cited by examiner

*Primary Examiner* — Susan Tran
(74) *Attorney, Agent, or Firm* — Wenderoth, Lind & Ponack, L.L.P.

(57) ABSTRACT

The present invention provides a controlled release composition showing release of an active ingredient (proton pump inhibitor) controlled in two or more steps at different release rates, which contains 1) a release-controlled part A capable of controlling release of the active ingredient to occur at a predetermined rate, 2) a release-controlled part B capable of controlling release of the active ingredient to occur at a predetermined rate lower than the release rate of the release-controlled part A, and where necessary, 3) a release-controlled part C capable of controlling release of the active ingredient to occur at a predetermined rate faster than the release rate of the release-controlled part B, wherein the release of the active ingredient from the release-controlled part B precedes the release of the active ingredient from the release-controlled part A (when release-controlled part C is contained, the release of the active ingredient from the release-controlled part C precedes the release of the active ingredient from the release-controlled part B).

6 Claims, 2 Drawing Sheets

CONTROLLED RELEASE COMPOSITION

This application is a U.S. national stage of International Application No. PCT/JP2004/003483 filed Mar. 16, 2004.

TECHNICAL FIELD

The present invention relates to a controlled release composition showing a multistep release profile with different release rates, which is afforded by combining release-controlled parts in multi-layers, where the release of an active ingredient is controlled.

BACKGROUND ART

An oral preparation is a dosage form most frequently used among pharmaceutical products. Many oral preparations capable of maintaining drug efficacy with the administration of once or twice a day have been developed in recent years to improve QOL. While synthesis of compounds showing kinetics of sustained drug efficacy with the administration of once or twice a day has been tried in the synthetic stage of the compound itself, the kinetics are quite often modified by designing a long acting preparation with ingenuity in formulation.

As the dissolution property of a long acting preparation, which is suitable for prolonged blood concentration of a drug, zero-order release has been reported. This is based on an idea that, when absorbability of a drug from the gastrointestinal tract does not show changes depending on the absorption sites, prolonged drug concentration in plasma can be achieved by releasing the drug at a constant rate over the whole area in the gastrointestinal tract (small intestine, large intestine) after taking a preparation. However, the inside of the gastrointestinal tract is not the same, and pH, amount of digestive juice, mechanical force on the preparation, effective surface area and the like vary depending on the sites. Thus, a preparation that shows zero-order dissolution in an in vitro dissolution test does not necessarily show similar dissolution property and absorbability in the gastrointestinal tract. Depending on the kind of the drug to be an active ingredient, the blood concentration cannot be maintained within an effective therapeutic range for a long period of time. Therefore, a development design of a long acting preparation, which is based on a different release-control strategy suitable for drug property and environment in the gastrointestinal tract, has been desired (e.g., WO 99/51209, JP-B-6-11699, JP-A-9-143073, Eur. J. Pharm. Sci., 1: 195-201 (1994)).

Controlled release preparations containing, as an active ingredient, a compound having a proton pump inhibitory activity such as omeprazole and the like are generally described in some literatures (US 2002-0051814, JP-A-2002-532425). However, there is no report yet on the release-control strategy that should be employed to achieve desired sustained drug efficacy.

It is an object of the present invention to provide a long acting preparation, wherein the release of the active ingredient (e.g., proton pump inhibitor) is controlled in multisteps, and the active ingredient is released in the gastrointestinal tract over a long period of time.

DISCLOSURE OF THE INVENTION

The present inventors considered that a desired blood concentration could not be maintained in the large intestine where the amount of digestive juice decreases, because dissolution of a drug (proton pump inhibitor) from a preparation is markedly lower than predicted in vitro. To prevent decrease in the drug dissolution property and absorbability in the large intestine, they tried to develop a preparation showing a dissolution pattern where the drug dissolution property in the last half, which corresponds to the dissolution from the lower small intestine to near the large intestine, is promoted (higher release rate). As a result, by coating a core showing immediate release or sustained release with relatively fast drug dissolution with a composition containing a drug and a sustained-release base material at a ratio different than that of the core, they have succeeded in realizing a sustained release in the first half due to the drug dissolution from the coated layer and immediate release or sustained release with an increased release rate in the last half due to the drug dissolution from the core. Furthermore, by coating the controlled release composition with a drug containing-composition showing immediate release, they have succeeded in improving the initial rise of the drug blood concentration after oral administration, and conducted further studies, which resulted in the completion of the present invention.

Accordingly, the present invention relates to

[1] a controlled release composition showing release of an active ingredient controlled in two or more steps at different release rates, which comprises 1) a release-controlled part A comprising a proton pump inhibitor as an active ingredient, which is capable of controlling release of the active ingredient to occur at a predetermined rate; and 2) a release-controlled part B comprising a proton pump inhibitor as an active ingredient, which is capable of controlling release of the active ingredient to occur at a predetermined rate lower than the release rate of the release-controlled part A;

wherein the release of the active ingredient from the release-controlled part B precedes the release of the active ingredient from the release-controlled part A,

[2] the controlled release composition of the above-mentioned [1], further comprising a release-controlled part C comprising an active ingredient the same as or different from the active ingredient contained in the release-controlled part A and/or the release-controlled part B, which part C is capable of controlling release of the active ingredient to occur at a predetermined rate faster than the release rate of the release-controlled part B;

wherein the release of the active ingredient from the release-controlled part C precedes the release of the active ingredient from the release-controlled part B,

[3] the controlled release composition of the above-mentioned [1] or [2], wherein the release-controlled part A is coated with the release-controlled part B,

[4] the controlled release composition of the above-mentioned [3], wherein the release-controlled part B is coated with the release-controlled part C,

[5] the controlled release composition of the above-mentioned [2], wherein the active ingredient contained in the release-controlled part C is a proton pump inhibitor,

[6] the controlled release composition of any of the above-mentioned [1] to [3], wherein the proton pump inhibitor contained in each release-controlled part is the same or different and each is a compound represented by the following formula (I'):

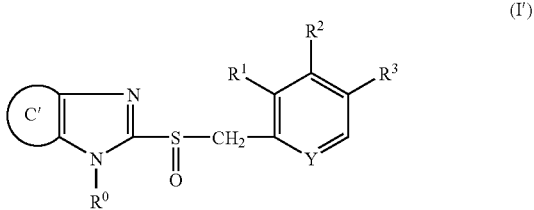

(I')

wherein ring C' is a benzene ring optionally having substituent(s) or an aromatic monocyclic heterocycle optionally having substituent(s), $R^0$ is a hydrogen atom, an aralkyl group optionally having substituent(s), an acyl group or an acyloxy group, $R^1$, $R^2$ and $R^3$ are the same or different and each is a hydrogen atom, an alkyl group optionally having substituent(s), an alkoxy group optionally having substituent(s) or an amino group optionally having substituent(s), and Y is a nitrogen atom or CH, or a salt thereof or an optically active form thereof,

[7] the controlled release composition of any of the above-mentioned [3] to [5], wherein the proton pump inhibitor contained in each release-controlled part is lansoprazole or a prodrug thereof or a salt thereof or an optically active form thereof,

[8] the controlled release composition of the above-mentioned [2], wherein the active ingredient is contained in each release-controlled part in a weight ratio of A:5-95%, B:5-95% and C:0-40% (provided that when C:0%, the release-controlled part C does not exist),

[9] the controlled release composition of the above-mentioned [2], wherein the active ingredient is contained in each release-controlled part in a weight ratio of A:20-75%, B:20-75% and C:5-30%,

[10] the controlled release composition of the above-mentioned [2], which is a solid composition for oral administration, wherein the release of the active ingredient contained in the release-controlled part C completes within 2 hr after administration,

[11] the controlled release composition of the above-mentioned [1] or [2], wherein the release-controlled part B is a sustained-release matrix comprising an active ingredient and a hydrophilic polymer,

[12] the controlled release composition of the above-mentioned [1] or [2], wherein the release-controlled part A is a sustained-release matrix comprising an active ingredient and a hydrophilic polymer,

[13] the controlled release composition of the above-mentioned [1] or [2], wherein the release of the active ingredient from the release-controlled part B is maintained for 1-18 hr.

[14] the controlled release composition of the above-mentioned [1] or [2], wherein the release of the active ingredient from the release-controlled part A is maintained for 30 min-6 hr,

[15] the controlled release composition of the above-mentioned [2], wherein the release from the release-controlled part C is immediate release,

[16] the controlled release composition of the above-mentioned [1] or [2], wherein the dosage form is selected from the group consisting of tablet, granule, pellet and capsule, and the like.

The controlled release composition of the present invention shows a drug release profile characterized by a sustained drug release in the first and middle stages or middle stage, and a more rapid drug release in the last stage, and when used as a proton pump inhibitor preparation for oral administration, it provides an effect in that it improves drug dissolution property in the lower small intestine—near the large intestine and maintains an effective drug blood concentration for an extended period of time.

BEST MODE FOR EMBODYING THE INVENTION

Figure 1:
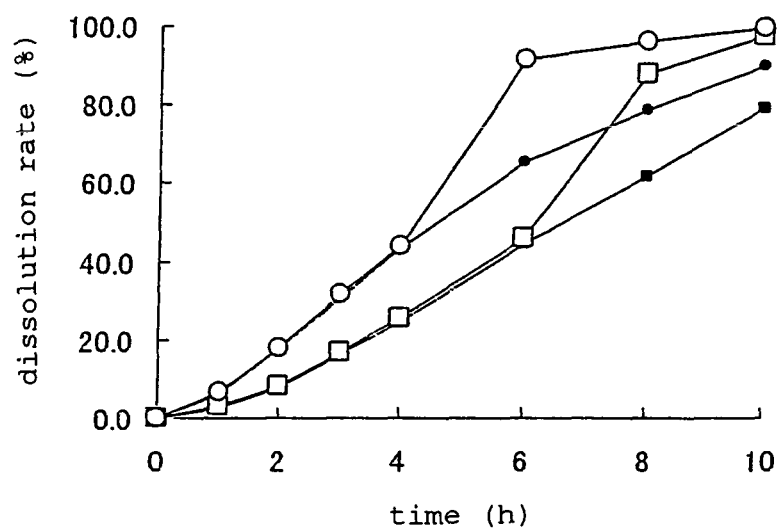
FIG. 1 shows drug dissolution profiles of the controlled release compositions of the present invention containing the release-controlled parts A and B [preparation 1 (○) and preparation 2 (□)] and a sustained-release preparation having the same composition as that of the release-controlled part B [comparative preparation 1 (●) and comparative preparation 2 (■)], wherein the vertical axis shows dissolution rate (%) and the transverse axis shows time (h) after the start of the test.

The controlled release composition of the present invention shows release of an active ingredient, which is controlled in two or more steps with different release rates, and has at least two release-controlled parts (release-controlled part A and release-controlled part B) containing the active ingredient (the active ingredients contained in the release-controlled part A and the release-controlled part B may be the same or different).

As used herein, the "release-controlled part" means a functional unit containing an active ingredient, which is capable of controlling release of the active ingredient to occur at a predetermined rate. When one release-controlled part is coated with other release-controlled part, said other part defines the start of the control of release from the release-controlled part inside the coating, by way of disintegration and dissolution thereof, but other than that, it is not involved in the control of release of the active ingredient from said one release-controlled part. For example, when the above-mentioned release-controlled part A is coated with the release-controlled part B, release of the active ingredient contained in the release-controlled part A starts upon disintegration, dissolution and the like of the release-controlled part B to expose the release-controlled part A, after the completion or during the release (release of the majority of the active ingredient has been completed) of the active ingredient from the release-controlled part B. The release thereafter is controlled by the release-controlled part A.

The release-controlled part A is a functional unit responsible for the final release controlling step (corresponding to dissolution of oral preparation in the lower small intestine to near the large intestine) of the controlled release composition of the present invention, wherein the release of the active ingredient is controlled in two or more steps, and acts as an immediate release part or a sustained release part (second sustained release part) where the release rate of the active ingredient is faster than in the release-controlled part B mentioned below. In the present specification, the "immediate release part" is a release-controlled part showing an active ingredient release profile characterized by immediate release, and the immediate release means that the dissolution rate of an active ingredient at 30 min after the start of the test is not less than 85% when the Japanese Pharmacopoeia Dissolution Test Method 2 (Paddle Method) is performed using a suitable test solution (500 mL or 900 mL) at a paddle rotation of 100 rpm. As used herein, as the test solution, for example, a test solution is used, which shows the concentration of an active ingredient of not more than ⅓ of the saturated solubility of the active ingredient, when the active ingredient in a preparation is dissolved by 100% in a test solution. As the test solution, one conventionally employed in the preparation technical field, such as water, buffer and the like, is used. For a dissolution test of the active ingredient of the release-controlled part A, the solution 2 of the Japanese Pharmacopoeia dissolution test or water is preferably used.

On the other hand, in the present specification, the "sustained release part" is a release-controlled part showing an active ingredient release profile characterized by sustained release, and the sustained release means that the dissolution rate of an active ingredient at 30 min after the start of the test is less than 85% when the Japanese Pharmacopoeia Dissolution Test Method 2 (Paddle Method) is performed using a suitable test solution (500 mL or 900 mL) at a paddle rotation of 100 rpm. As used herein, as the test solution, those similar to the above-mentioned are used. When the release-controlled part A is a sustained release part, the release rate $V_A$ of the active ingredient from the release-controlled part is not particularly limited as long as it satisfies the above-mentioned definition of the sustained release and is greater than the release rate $V_B$ of the active ingredient from the release-controlled part B, but preferably, the dissolution rate of the active ingredient at 30 min after the start of the test in the above-mentioned dissolution test is 15-85%, more preferably 25-85%, further preferably 50-85%.

Alternatively, the release profile of the active ingredient from the release-controlled part A is also characterized in that the sustained release of the active ingredient from the release-controlled part A preferably occurs for about 30 min—about 6 hr, more preferably about 30 min—about 3 hr, when the controlled release composition of the present invention is applied to the intended use (e.g., upon oral administration in the case of an oral preparation).

When the release-controlled part A is an immediate release part, the release-controlled part may be an active ingredient itself. It is preferable that it should contain, in addition to the active ingredient, a carrier acceptable in the field relating to the use of the composition (e.g., pharmacologically acceptable carrier in the case of a pharmaceutical composition).

The active ingredient to be contained in the release-controlled part A is not particularly limited, and various substances effective for the prophylaxis or treatment of diseases [for example, anti-inflammatory drugs such as indomethacin, acetoaminophen and the like, analgesics such as morphine and the like, cardiovascular system acting drugs such as diazepam, diltiazem and the like, antihistamine drugs such as chlorpheniramine maleate and the like, antitumor drugs such as fluorouracil, aclarubicin and the like, hypnotics such as midazolam and the like, anti-congestion drugs such as ephedrine and the like, diuretics such as hydrochlorothiazide, furosemide and the like, bronchodilators such as theophylline and the like, antitussives such as codeine and the like, antiarrhythmic drugs such as quinidine, digoxin and the like, antidiabetic drugs such as tolbutamide, pioglitazone, troglidazone and the like, vitamins such as ascorbic acid and the like, anticonvulsant agents such as phenytoin and the like, topical anesthetics such as lidocain and the like, adrenal cortex hormones such as hydrocortisone and the like, drugs acting on the central nervous system such as donepezil (trade name: aricept, Eisai Co., Ltd.) and the like, anti-hyperlipidemic agents such as pravastatin and the like, antibiotics such as amoxicillin, cefalexin and the like, dipeptidylpeptidase (DPP)-IV inhibitors useful for the prophylaxis or treatment and the like of diabetes, steroid $C_{17,20}$ lyase inhibitors useful for the prophylaxis or treatment and the like of prostate cancer and breast cancer, gastric motility enhancers such as mosapride, cisapride and the like, therapeutic drugs for gastritis, stomach esophagus reflux symptoms and stomach and duodenal ulcer, such as $H_2$-blockers (e.g., famotidine, ranitidine, cimetidine etc.), benzimidazole proton pump inhibitors (PPI) (e.g., lansoprazole, prodrugs thereof and optically active forms thereof (R form and S form, preferably R form), omeprazole and optically active forms thereof (S form: esomeprazole), rabeprazole and optically active forms thereof, pantoprazole and optically active forms thereof etc.), imidazopyridine PPIs (e.g., tenatoprazole etc.) and the like], detergent components, flavors, fertilizers, deodrants, animal and disinfectants, insecticides, herbicides, plant growth control substances and the like can be mentioned.

Preferably, the active ingredient is PPI, steroid $C_{17,20}$ lyase inhibitor or DPP-IV inhibitor, more preferably PPI. Specific examples of these active ingredients are shown in the following.

A. Proton Pump Inhibitor (PPI)

As PPI, acid-labile imidazole compounds represented by the following formula (I'), particularly acid-labile benzimidazole compounds represented by (I), such as lansoprazole, an optically active form thereof and the like, imidazole compound derivatives (prodrug type PPI) represented by the following formulas (II) and (III), which are relatively stable to acid, salts thereof and optically active forms thereof and the like can be particularly mentioned.

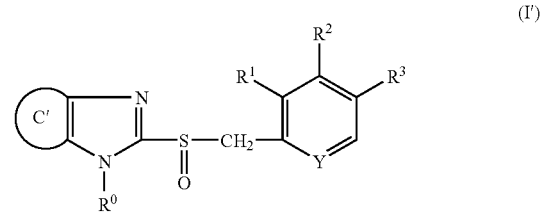

(I')

wherein ring C' is a benzene ring optionally having substituent(s) or an aromatic monocyclic heterocycle optionally having substituent(s), $R^0$ is a hydrogen atom, an aralkyl group optionally having substituent(s), an acyl group or an acyloxy group, $R^1$, $R^2$ and $R^3$ are the same or different and each is a hydrogen atom, an alkyl group optionally having substituent(s), an alkoxy group optionally having substituent(s) or an amino group optionally having substituent(s), and Y is a nitrogen atom or CH.

Of the compounds represented by the above-mentioned formula (I'), a compound wherein ring C' is a benzene ring optionally having substituent(s) is particularly represented by the following formula (I).

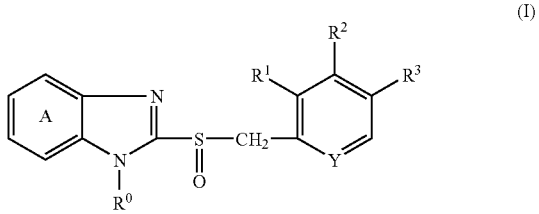

That is, in the formula (I), ring A is a benzene ring optionally having substituent(s), and $R^0$, $R^1$, $R^2$, $R^3$ and Y are as defined in the above-mentioned formula (I').

In the aforementioned formula (I), a preferable compound is a compound wherein ring A is a benzene ring optionally having substituent(s) selected from a halogen atom, an optionally halogenated $C_{1-4}$ alkyl group, an optionally halogenated $C_{1-4}$ alkoxy group and a 5- or 6-membered heterocyclic group, $R^0$ is a hydrogen atom, an optionally substituted aralkyl group, an acyl group or an acyloxy group, $R^1$ is a $C_{1-6}$ alkyl group, a $C_{1-6}$ alkoxy group, a $C_{1-6}$ alkoxy-$C_{1-6}$ alkoxy group or a di-$C_{1-6}$ alkylamino group, $R^2$ is a hydrogen atom, a $C_{1-6}$ alkoxy-$C_{1-6}$ alkoxy group or an optionally halogenated $C_{1-6}$ alkoxy group, $R^3$ is a hydrogen atom or a $C_{1-6}$ alkyl group, and Y is a nitrogen atom.

Particularly preferred is a compound represented by the formula (Ia):

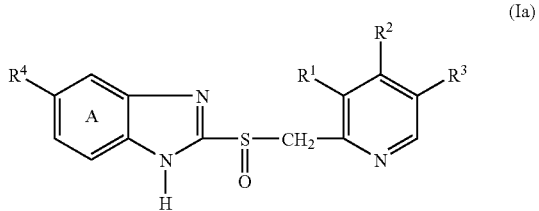

wherein $R^1$ is a $C_{1-3}$ alkyl group or a $C_{1-3}$ alkoxy group, $R^2$ is a $C_{1-3}$ alkoxy group optionally halogenated or substituted by a $C_{1-3}$ alkoxy group, $R^3$ is a hydrogen atom or a $C_{1-3}$ alkyl group, and $R^4$ is a hydrogen atom, an optionally halogenated $C_{1-3}$ alkoxy group or a pyrrolyl group (e.g., 1-, 2- or 3-pyrrolyl group).

In the formula (Ia), a compound wherein $R^1$ is a $C_{1-3}$ alkyl group, $R^2$ is an optionally halogenated $C_{1-3}$ alkoxy group, $R^3$ is a hydrogen atom, and $R^4$ is a hydrogen atom or an optionally halogenated $C_{1-3}$ alkoxy group is particularly preferable.

In the compound represented by the above-mentioned formula (I) [hereinafter to be referred to as compound (I)], as the "substituent" of the "benzene ring optionally having substituent(s)" for ring A, for example, a halogen atom, a cyano group, a nitro group, an alkyl group optionally having substituent(s), a hydroxy group, an alkoxy group optionally having substituent(s), an aryl group, an aryloxy group, a carboxy group, an acyl group, an acyloxy group, a 5- to 10-membered heterocyclic group and the like can be mentioned. About 1 to 3 of these substituents may be substituted on the benzene ring. When the number of the substituents is not less than 2, the respective substituents may be the same or different. Of these substituents, a halogen atom, an alkyl group optionally having substituent(s), an alkoxy group optionally having substituent(s) and the like are preferable.

As the halogen atom, fluorine, chlorine, bromine atom and the like can be mentioned. Fluorine is particularly preferable.

As the "alkyl group" of the "alkyl group optionally having substituent(s)", for example, a $C_{1-7}$ alkyl group (e.g., methyl, ethyl, propyl, isopropyl, butyl, isobutyl, sec-butyl, tert-butyl, pentyl, hexyl, heptyl group and the like) can be mentioned. As the "substituent" of the "alkyl group optionally having substituent(s)", for example, a halogen atom, a hydroxy group, a $C_{1-6}$ alkoxy group (e.g., methoxy, ethoxy, propoxy, butoxy etc.), a $C_{1-6}$ alkoxy-carbonyl group (e.g., methoxycarbonyl, ethoxycarbonyl, propoxycarbonyl group etc.), a carbamoyl group and the like can be mentioned, wherein the number of these substituents may be about 1 to 3. When the number of the substituents is not less than 2, the respective substituents may be the same or different.

As the "alkoxy group" of the "alkoxy group optionally having substituent(s)", for example, a $C_{1-6}$ alkoxy group (e.g., methoxy, ethoxy, propoxy, isopropoxy, butoxy, isobutoxy, pentoxy etc.) and the like can be mentioned. As the "substituent" of the "alkoxy group optionally having substituent(s)", those similar to the "substituent" of the above-mentioned "alkyl group optionally having substituent(s)" can be mentioned, and the number of the substituents is also similar.

As the "aryl group", for example, a $C_{6-14}$ aryl group (e.g., phenyl, 1-naphthyl, 2-naphthyl, biphenyl, 2-anthryl group etc.) and the like can be mentioned.

As the "aryloxy group", for example, a $C_{6-14}$ aryloxy group (e.g., phenyloxy, 1-naphthyloxy, 2-naphthyloxy group etc.) and the like can be mentioned.

As the "acyl group", for example, formyl, alkylcarbonyl, alkoxycarbonyl, carbamoyl, alkylcarbamoyl, alkylsulfinyl, alkylsulfonyl groups and the like can be mentioned.

As the "alkylcarbonyl group", a $C_{1-6}$ alkyl-carbonyl group (e.g., acetyl, propionyl group etc.) and the like can be mentioned.

As the "alkoxycarbonyl group", for example, a $C_{1-6}$ alkoxy-carbonyl group (e.g., methoxycarbonyl, ethoxycarbonyl, propoxycarbonyl, butoxycarbonyl group etc.) and the like can be mentioned.

As the "alkylcarbamoyl group", a N—$C_{1-6}$ alkyl-carbamoyl group (e.g., methylcarbamoyl, ethylcarbamoyl group etc.), a N,N-di$C_{1-6}$ alkyl-carbamoyl group (e.g., N,N-dimethylcarbamoyl, N,N-diethylcarbamoyl group etc.) and the like can be mentioned.

As the "alkylsulfinyl group", for example, a $C_{1-7}$ alkylsulfinyl group (e.g., methylsulfinyl, ethylsulfinyl, propylsulfinyl, isopropylsulfinyl group etc.) can be mentioned.

As the "alkylsulfonyl group", for example, a $C_{1-7}$ alkylsulfonyl group (e.g., methylsulfonyl, ethylsulfonyl, propylsulfonyl, isopropylsulfonyl group etc.) can be mentioned.

As the "acyloxy group", for example, an alkylcarbonyloxy group, an alkoxycarbonyloxy group, a carbamoyloxy group, an alkylcarbamoyloxy group, an alkylsulfinyloxy group, an alkylsulfonyloxy group and the like can be mentioned.

As the "alkylcarbonyloxy group", a $C_{1-6}$ alkyl-carbonyloxy group (e.g., acetyloxy, propionyloxy group etc.) and the like can be mentioned.

As the "alkoxycarbonyloxy group", for example, a $C_{1-6}$ alkoxy-carbonyloxy group (e.g., methoxycarbonyloxy, ethoxycarbonyloxy, propoxycarbonyloxy, butoxycarbonyloxy group etc.) and the like can be mentioned.

As the "alkylcarbamoyloxy group", a $C_{1-6}$ alkyl-carbamoyloxy group (e.g., methylcarbamoyloxy, ethylcarbamoyloxy group etc.) and the like can be mentioned.

As the "alkylsulfinyloxy group", for example, a $C_{1-7}$ alkylsulfinyloxy group (e.g., methylsulfinyloxy, ethylsulfinyloxy, propylsulfinyloxy, isopropylsulfinyloxy group etc.) can be mentioned.

As the "alkylsulfonyloxy group", for example, a $C_{1-7}$ alkylsulfonyloxy group (e.g., methylsulfonyloxy, ethylsulfonyloxy, propylsulfonyloxy, isopropylsulfonyloxy group etc.) can be mentioned.

As the "5- to 10-membered heterocyclic group", for example, a 5- to 10-membered (preferably 5- or 6-membered) heterocyclic group containing, besides carbon atoms, one or more (e.g., 1-3) hetero atom(s) selected from a nitrogen atom, a sulfur atom and an oxygen atom, can be mentioned, and as specific examples, 2- or 3-thienyl group, 2-, 3- or 4-pyridyl group, 2- or 3-furyl group, 1-, 2- or 3-pyrrolyl group, 2-, 3-, 4-, 5- or 8-quinolyl group, 1-, 3-, 4- or 5-isoquinolyl group, 1-, 2- or 3-indolyl group and the like can be mentioned. Of these, preferred is a 5- or 6-membered heterocyclic group such as 1-, 2- or 3-pyrrolyl group and the like.

Ring A is preferably a benzene ring optionally having 1 or 2 substituents selected from a halogen atom, an optionally halogenated $C_{1-4}$ alkyl group, an optionally halogenated $C_{1-4}$ alkoxy group and a 5- or 6-membered heterocyclic group.

In the above-mentioned formula (I'), as the "aromatic monocyclic heterocycle" of the "aromatic monocyclic heterocycle optionally having substituent(s)" for ring C', for example, a 5- or 6-membered aromatic monocyclic heterocycle such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetraxole, pyridine, pyridazine, pyrimidine, pyrazine, triazine etc., and the like can be mentioned. As the "aromatic monocyclic heterocycle" for ring C', the "benzene ring optionally having substituent(s)" for the above-mentioned ring A and the "pyridine ring optionally having substituent(s)" are particularly preferable. The "pyridine ring optionally having substituent(s)" for ring-C' may have, at substitutable position(s), 1 to 4 substituents similar to the "benzene ring optionally having substituent(s)" for the above-mentioned ring A.

The position where the "aromatic monocyclic heterocycle" of the "aromatic monocyclic heterocycle optionally having substituent(s)" is condensed with the imidazole moiety is not particularly limited.

In the above-mentioned formula (I') or (I), as the "aralkyl group" of the "aralkyl group optionally having substituent(s)" for $R^0$, for example, a $C_{7-16}$ aralkyl group (e.g., $C_{6-10}$ aryl$C_{1-6}$ alkyl group such as benzyl, phenethyl etc. and the like) and the like can be mentioned. As the "substituent" of the "aralkyl group optionally having "substituent(s)", those similar to the "substituent" of the above-mentioned "alkyl group optionally having substituent(s)" can be mentioned, wherein the number of the substituents is about 1 to 4. When the number of the substituents is not less than 2, the respective substituents may be the same or different.

As the "acyl group" for $R^0$, for example, the "acyl group" described as a substituent for the above-mentioned ring A can be mentioned.

As the "acyloxy group" for $R^0$, for example, the "acyloxy group" described as a substituent for the above-mentioned ring A can be mentioned.

Preferable $R^0$ is a hydrogen atom.

In the above-mentioned formula (I') or (I), as the "alkyl group optionally having substituent(s)" for $R^1$, $R^2$ or $R^3$, the "alkyl group optionally having substituent(s)" described as a substituent for the above-mentioned ring A can be mentioned.

As the "alkoxy group optionally having substituent(s)" for $R^1$, $R^2$ or $R^3$, the "alkoxy group optionally having substituent(s)" described as a substituent for the above-mentioned ring A can be mentioned.

As the "amino group optionally having substituent(s)" for $R^1$, $R^2$ or $R^3$, for example, an amino group, a mono-$C_{1-6}$ alkylamino group (e.g., methylamino, ethylamino etc.), a mono-$C_{6-14}$ arylamino group (e.g., phenylamino, 1-naphthylamino, 2-naphthylamino etc.), a di-$C_{1-6}$ alkylamino group (e.g., dimethylamino, diethylamino etc.), a di-$C_{6-14}$ arylamino group (e.g., diphenylamino etc.) and the like can be mentioned.

Preferable $R^1$ is a $C_{1-6}$ alkyl group, a $C_{1-6}$ alkoxy group, a $C_{1-6}$ alkoxy-$C_{1-6}$ alkoxy group or a di-$C_{1-6}$ alkylamino group. More preferable $R^1$ is a $C_{1-3}$ alkyl group or a $C_{1-3}$ alkoxy group.

Preferable $R^2$ is a hydrogen atom, a $C_{1-6}$ alkoxy-$C_{1-6}$ alkoxy group or an optionally halogenated $C_{1-6}$ alkoxy group. More preferable $R^2$ is a $C_{1-3}$ alkoxy group optionally halogenated or substituted by a $C_{1-3}$ alkoxy group.

Preferable $R^3$ is a hydrogen atom or a $C_{1-6}$ alkyl group. More preferable $R^3$ is a hydrogen atom or a $C_{1-3}$ alkyl group (particularly a hydrogen atom).

Preferable Y is a nitrogen atom.

As specific examples of compound (I), the following compounds can be mentioned.

2-[[[3-Methyl-4-(2,2,2-trifluoroethoxy)-2-pyridinyl]methyl]sulfinyl]-1H-imidazole (lansoprazole), 2-[[(3,5-dimethyl-4-methoxy-2-pyridinyl)methyl]sulfinyl]-5-methoxy-1H-benzimidazole, 2-[[[4-(3-methoxypropoxy)-3-methyl-2-pyridinyl]methyl]sulfinyl]-1H-benzimidazole sodium salt, 5-difluoromethoxy-2-[[(3,4-dimethoxy-2-pyridinyl)methyl]sulfinyl]-1H-benzimidazole and the like.

Of these compounds, lansoprazole, i.e., 2-[[[3-methyl-4-(2,2,2-trifluoroethoxy)-2-pyridinyl]methyl]sulfinyl]-1H-benzimidazole is particularly preferable.

Besides the above-mentioned PPI of benzimidazole compound, PPI of an imidazopyridine compound can be preferably applied to the present invention. As the PPI of such imidazopyridine compound, for example, tenatoprazole can be mentioned.

The compound (I') including the above-mentioned compound (I) and imidazopyridine compounds may be racemates and may be optically active forms such as R-form, S-form and the like. For example, an optically active form of lansoprazole, namely, optically active forms such as (R)-2-[[[3-methyl-4-(2,2,2-trifluoroethoxy)-2-pyridinyl]methyl]sulfinyl]-1H-benzimidazole and (S)-2-[[[3-methyl-4-(2,2,2-trifluoroethoxy)-2-pyridinyl]methyl]sulfinyl]-1H-benzimidazole and the like are particularly preferable for the present invention. While lansoprazole, lansoprazole R-form and lansoprazole S-form and the like are generally preferable in crystal forms, since they are stabilized by processing into preparations as mentioned blow and more stabilized by adding a basic inorganic salt and further forming an intermediate coating layer, not only crystals but also amorphous forms can be used.

As the salts of compound (I') and compound (I), pharmaceutically acceptable salts are preferable. For example, salts with inorganic bases, salts with organic bases, salts with basic amino acids and the like can be mentioned.

As preferable examples of the salts with inorganic bases, for example, alkali metal salts such as sodium salt, potassium salt and the like; alkaline earth metal salts such as calcium salt, magnesium salt and the like; ammonium salt and the like can be mentioned.

As preferable examples of the salts with organic bases, for example, salts with alkylamines (trimethylamine, triethylamine and the like), heterocyclic amines (pyridine, picoline and the like), alkanolamines (ethanolamine, diethanolamine, triethanolamine and the like), dicyclohexylamine, N,N'-dibenzylethylenediamine and the like can be mentioned.

As preferable examples of the salts with basic amino acids, for example, salts with arginine, lysine, ornithine and the like can be mentioned.

Of these salts, preferred are alkali metal salts and alkaline earth metal salts. Sodium salt is particularly preferable.

Compounds (I') and (I) can be manufactured by a method known per se, and they can be manufactured by methods described in, for example, JP-A-61-50978, U.S. Pat. No. 4,628,098, JP-A-10-195068, WO 98/21201, JP-A-52-62275, JP-A-54-141783 and the like or methods analogous thereto. The optically active compound (I) can be obtained by a method using optical resolution (fractional recrystallization, chiral column method, diastereomer method, a method using microorganism or enzyme and the like), asymmetric oxidation and the like. A lansoprazole R form can be also produced by a production methods described in, for example, WO 00-78745, WO 01/83473 and the like, and the like.

As the benzimidazole compound having an antiulcer activity to be used in the present invention, lansoprazole, omeprazole, rabeprazole, pantoprazole, leminoprazole, tenatoprazole (TU-199) and the like, optically active forms thereof and pharmaceutically acceptable salts thereof are preferable, and lansoprazole, an optically active form thereof, particularly R form are more preferable. While lansoprazole, an optically active form thereof, particularly R form are preferably crystals, they may be amorphous forms. They are conveniently applied to prodrugs of these PPIs.

As preferable prodrugs of these, prodrugs encompassed in compound (I) or (I'), and additionally, compounds represented by the following formulas (II) and (III) can be mentioned.

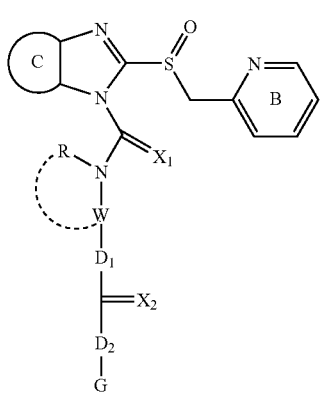

(II)

As the compound represented by the above-mentioned formula (II) [hereinafter to be referred to as compound (II)], for example, compounds described in WO 03/105845 can be mentioned. Namely, in compound (II), it is a compound wherein ring B is a "pyridine ring optionally having substituent(s)".

The pyridine ring of the "pyridine ring optionally having substituent(s)" for ring B optionally has 1 to 4 substituents at substitutable positions thereof. As the substituents, for example, a halogen atom (e.g., fluorine, chlorine, bromine, iodine etc.), a hydrocarbon group optionally having substituent(s) (e.g., alkyl group having 1 to 6 carbon atoms such as methyl group, ethyl group, n-propyl group etc., and the like), an amino group optionally having substituent(s) (e.g., amino; amino group mono- or di-substituted by alkyl group having 1 to 6 carbon atoms such as methylamino, dimethylamino, ethylamino, diethylamino group etc., and the like), an amido group (e.g., formamido, $C_{1-3}$ acylamino group such as acetamido etc., and the like), a lower alkoxy group optionally having substituent(s) (e.g., alkoxy group having 1 to 6 carbon atoms such as methoxy, ethoxy, 2,2,2-trifluoroethoxy, 3-methoxypropoxy group etc., and the like), a lower alkylenedioxy group (e.g., $C_{1-3}$ alkylenedioxy group such as methylenedioxy, ethylenedioxy etc., and the like) and the like can be mentioned.

As the substituent which the substituent of the "pyridine ring optionally having substituent(s)" for ring B may have, for example, a halogen atom (e.g., fluorine, chlorine, bromine, iodine etc.), a lower alkyl group (e.g., alkyl group having 1 to 6 carbon atoms such as methyl, ethyl, propyl group etc., and the like), a lower alkenyl group (e.g., alkenyl group having 2 to 6 carbon atoms such as vinyl, allyl group etc., and the like), a lower alkynyl group (e.g., alkynyl group having 2 to 6 carbon atoms such as ethynyl, propargyl group etc. and the like), a cycloalkyl group (e.g., cycloalkyl group having 3 to 8 carbon atoms such as cyclopropyl, cyclobutyl, cyclopentyl, cyclohexyl group etc. and the like), a lower alkoxy group (e.g., alkoxy group having 1 to 6 carbon atoms such as methoxy, ethoxy group etc., and the like), a nitro group, a cyano group, a hydroxy group, a thiol group, a carboxyl group, a lower alkanoyl group (e.g., formyl; $C_{1-6}$ alkyl-carbonyl group such as acetyl, propionyl, butyryl group etc., and the like), a lower alkanoyloxy group (e.g., formyloxy; $C_{1-6}$ alkyl-carbonyloxy group such as an acetyloxy, propionyloxy group etc., and the like), a lower alkoxycarbonyl group (e.g., $C_{1-6}$ alkoxy-carbonyl group such as methoxycarbonyl, ethoxycarbonyl, propoxycarbonyl group etc., and the like), an aralkyloxycarbonyl group (e.g., $C_{7-11}$ aralkyloxy-carbonyl group such as benzyloxycarbonyl group etc., and the like), an aryl group (e.g., aryl group having 6 to 14 carbon atoms such as phenyl, naphthyl group etc., and the like), an aryloxy group (e.g., aryloxy group having 6 to 14 carbon atoms such as phenyloxy, naphthyloxy group etc., and the like), an arylcarbonyl group (e.g., $C_{6-14}$ aryl-carbonyl group such as benzoyl, naphthoyl group etc., and the like), an arylcarbonyloxy group (e.g., $C_{6-14}$ aryl-carbonyloxy group such as benzoyloxy, naphthoyloxy group etc., and the like), a carbamoyl group optionally having substituent(s) (e.g., carbamoyl; carbamoyl group mono- or di-substituted by alkyl group having 1 to 6 carbon atoms, such as methylcarbamoyl, dimethylcarbamoyl group etc., and the like), an amino group optionally having substituent(s) (e.g., amino; amino group mono- or di-substituted by alkyl group having 1 to 6 carbon atoms, such as methylamino, dimethylamino, ethylamino, diethylamino group etc., and the like) and the like can be mentioned, with no particular limitation on the number of substituents and substitution positions.

While the number of substituents and substitution positions of "pyridine ring optionally having substituent(s)" for ring B are not particularly limited, it is preferable that 1 to 3 of the above-mentioned substituents be substituted at any of the 3-, 4- and/or 5-position(s) on the pyridine ring.

As the "pyridine ring optionally having substituent(s)" for ring B, 3-methyl-4-(2,2,2-trifluoroethoxy)-2-pyridyl is preferable.

In the present invention, ring C is a "benzene ring optionally having substituent(s)" or an "aromatic monocyclic heterocycle optionally having substituent(s)", which is condensed with the imidazole moiety, with preference given to the former.

The benzene ring of the "benzene ring optionally having substituent(s)" for ring C optionally has 1 to 4 substituents at substitutable positions thereof. As the substituents, for example, a halogen atom (e.g., fluorine, chlorine, bromine, iodine etc.), a hydrocarbon group optionally having substituent(s) (e.g., alkyl group having 1 to 6 carbon atoms such as methyl group, ethyl group, n-propyl group etc., and the like), an amino group optionally having substituent(s) (e.g., amino; amino group mono- or di-substituted by alkyl group having 1 to 6 carbon atoms, such as methylamino, di-methylamino, ethylamino, diethylamino group etc., and the like), an amido group (e.g., formamido, $C_{1-3}$ acylamino group such as acetamido etc., and the like), a lower alkoxy group optionally having substituent(s) (e.g., alkoxy group having 1 to 6 carbon atoms such as methoxy, ethoxy, difluoromethoxy group etc., and the like), a lower alkylenedioxy group (e.g., $C_{1-3}$ alkylenedioxy group such as methylenedioxy, ethylenedioxy etc., and the like) and the like can be mentioned.

As the substituent which the substituent of the "benzene ring optionally having substituent(s)" for ring C may have, for example, a halogen atom (e.g., fluorine, chlorine, bromine, iodine etc.), a lower alkyl group (e.g., alkyl group having 1 to 6 carbon atoms, such as methyl, ethyl, propyl group etc., and the like), a lower alkenyl group (e.g., alkenyl group having 2 to 6 carbon atoms such as vinyl, allyl group etc., and the like), a lower alkynyl group (e.g., alkynyl group having 2 to 6 carbon atoms such as ethynyl, propargyl group etc., and the like), a cycloalkyl group (e.g., cycloalkyl group having 3 to 8 carbon atoms such as cyclopropyl, cyclobutyl, cyclopentyl, cyclohexyl group etc., and the like), a lower alkoxy group (e.g., alkoxy group having 1 to 6 carbon atoms such as methoxy, ethoxy group etc., and the like), a nitro group, a cyano group, a hydroxy group, a thiol group, a carboxyl group, a lower alkanoyl group (e.g., formyl; $C_{1-6}$ alkyl-carbonyl group such as acetyl, propionyl, butyryl group etc., and the like), a lower alkanoyloxy group (e.g., formyloxy; $C_{1-6}$ alkyl-carbonyloxy group such as acetyloxy, propionyloxy group etc., and the like), a lower alkoxycarbonyl group (e.g., $C_{1-6}$ alkoxycarbonyl group such as methoxycarbonyl, ethoxycarbonyl, propoxycarbonyl group etc., and the like), an aralkyloxycarbonyl group (e.g., $C_{7-17}$ aralkyloxy-carbonyl group such as benzyloxycarbonyl group etc., and the like), an aryl group (e.g., aryl group having 6 to 14 carbon atoms such as phenyl, naphthyl group etc., and the like), an aryloxy group (e.g., aryloxy group having 6 to 14 carbon atoms such as phenyloxy, naphthyloxy group etc., and the like), an arylcarbonyl group (e.g., $C_{6-14}$-aryl-carbonyl group such as benzoyl, naphthoyl group etc., and the like), an arylcarbonyloxy group (e.g., $C_{6-14}$ aryl-carbonyloxy group such as benzoyloxy, naphthoyloxy group etc., and the like), a carbamoyl group optionally having substituent(s) (e.g., carbamoyl; carbamoyl group mono- or di-substituted by alkyl group having 1 to 6 carbon atoms, such as methylcarbamoyl, dimethylcarbamoyl group etc., and the like), an amino group optionally having substituent(s) (e.g., amino; amino group mono- or di-substituted by alkyl group having 1 to 6 carbon atoms, such methylamino, dimethylamino, ethylamino, diethylamino group etc., and the like) and the like can be mentioned, with no particular limitation on the number of substituents and substitution portions.

As the "benzene ring optionally having substituent(s)" for C ring, benzene ring is preferable.

As the "aromatic monocyclic heterocycle" of the "aromatic monocyclic heterocycle optionally having substituent(s)" for ring C, for example, a 5- or 6-membered aromatic monocyclic heterocycle such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine and the like, and the like can be mentioned. Of these "aromatic monocyclic heterocycles" for ring C, pyridine ring is particularly preferable. It may have 1 to 4 substituents similar to those of the "benzene ring optionally having substituent(s)" for ring C at the substitutable positions thereof.

The position where the "aromatic monocyclic heterocycle" of the "aromatic monocyclic heterocycle optionally having substituent(s)" is fused with an imidazole moiety is not particularly limited.

In the present invention, $X_1$ and $X_2$ are each an oxygen atom or a sulfur atom. Both $X_1$ and $X_2$ are preferably oxygen atoms.

In the present invention, W is a "divalent chain hydrocarbon group optionally having substituent(s)", or a divalent group represented by the formula:

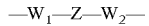

wherein $W_1$ and $W_2$ are each a "divalent chain hydrocarbon group" or a bond, and Z is a divalent hydrocarbon ring group optionally having substituent(s)", a "divalent heterocyclic group optionally having substituent(s)", an oxygen atom, $SO_n$, wherein n is 0, 1 or 2, or >N-E wherein E is a hydrogen atom, a hydrocarbon group optionally having substituent(s), a heterocyclic group optionally having substituent(s), a lower alkanoyl group, a lower alkoxycarbonyl group, an aralkyloxycarbonyl group, a thiocarbamoyl group, a lower alkylsulfinyl group, a lower alkylsulfonyl group, a sulfamoyl group, a mono-lower alkylsulfamoyl group, a di-lower alkylsulfamoyl group, an arylsulfamoyl group, an arylsulfinyl group, an arylsulfonyl group, an arylcarbonyl group, or a carbamoyl group optionally having substituent(s), when Z is an oxygen atom, $SO_n$ or >N-E, $W_1$ and $W_2$ are each a "divalent chain hydrocarbon group". Particularly, W is preferably a "divalent chain hydrocarbon group optionally having substituent(s)".

As the "divalent chain hydrocarbon group" of the "divalent chain hydrocarbon group optionally having substituent(s)" for W and the "divalent chain hydrocarbon group" for $W_1$ or $W_2$, for example, a $C_{1-6}$ alkylene group (e.g., methylene, ethylene, trimethylene etc.), a $C_{2-6}$ alkenylene group (e.g., ethenylene etc.), a $C_{2-6}$ alkynylene group (e.g., ethynylene etc.) and the like can be mentioned. The divalent chain hydrocarbon group for W may have 1 to 6 substituents similar to those for the "benzene ring optionally having substituent(s)" for ring C at substitutable positions thereof.

As the "divalent chain hydrocarbon group" of the "divalent chain hydrocarbon group optionally having substituent(s)" for W and the "divalent chain hydrocarbon group" for $W_1$ or $W_2$, a methylene group and an ethylene group are preferable. As W, an ethylene group is particularly preferable. When Z is an oxygen atom, $SO_n$ or >N-E (n and E are as defined above), the "divalent chain hydrocarbon group" for $W_1$ is preferably a hydrocarbon group having 2 or more carbon atoms.

As the "hydrocarbon ring" of the "divalent hydrocarbon ring group optionally having substituent(s)" for Z, for example, an alicyclic hydrocarbon ring, an aromatic hydrocarbon ring and the like can be mentioned, with preference given to one having 3 to 16 carbon atoms, which may have 1 to 4 substituents similar to those for the "benzene ring optionally having substituent(s)" for ring C at substitutable positions thereof. As the hydrocarbon ring, for example, a cycloalkane, a cycloalkene, an arene and the like are used.

As the cycloalkane for the "divalent hydrocarbon ring group optionally having substituent(s)" for Z, for example, a lower cycloalkane and the like are preferable, and, for example, a $C_{3-10}$ cycloalkane such as cyclopropane, cyclobutane, cyclopentane, cyclohexane, cycloheptane, cyclooctane, bicyclo[2.2.1]heptane, adamantane etc., and the like are generally used.

As the cycloalkene for the "divalent hydrocarbon ring group optionally having substituent(s)" for Z, for example, a lower cycloalkene is preferable, and, for example, $C_{4-9}$ cycloalkene such as cyclopropene, cyclobutene, cyclopentene, cyclohexene, cycloheptene, cyclooctene etc., and the like are generally used.

As the arene for the "divalent hydrocarbon ring group optionally having substituent(s)" for Z, for example, a $C_{6-14}$ arene such as benzene, naphthalene, phenanthrene etc., and the like are preferable, and, for example, benzene and the like are generally used.

As the heterocycle for the "divalent heterocyclic group optionally having substituent(s)" for Z, a 5- to 12-membered "aromatic heterocycle" or "saturated or unsaturated non-aromatic heterocycle" containing, as ring-constituting atoms (ring atoms), 1 to 3 (preferably 1 or 2) kinds of at least 1 (preferably 1 to 4, more preferably 1 or 2) hetero atoms selected from an oxygen atom, a sulfur atom and a nitrogen atom etc., and the like can be mentioned, which may have 1 to 4 substituents similar to those for the "benzene ring optionally having substituent(s)" for ring C at substitutable positions thereof.

As the aromatic heterocycle for the "divalent heterocyclic group optionally having substituent(s)" for Z, an aromatic monocyclic heterocycle, an aromatic fused heterocycle and the like can be mentioned.

As the "aromatic monocyclic heterocycle", for example, a 5- or 6-membered aromatic monocyclic heterocycle such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine etc., and the like can be mentioned.

As the "aromatic fused heterocycle", for example, a 8- to 12-membered aromatic fused heterocycle such as benzofuran, isobenzofuran, benzothiophene, isobenzothiophene, indole, isoindole, 1H-indazole, benzimidazole, benzoxazole, 1,2-benzisoxazole, benzothiazole, 1,2-benzisothiazole, 1H-benzotriazole, quinoline, isoquinoline, cinnoline, quinazoline, quinoxaline, phthalazine, naphthyridine, purine, pteridine, carbazole, carboline, acridine, phenoxazine, phenothiazine, phenazine, phenoxathiin, thianthrene, phenanthridine, phenanthroline, indolizine, pyrrolo[1,2-b]pyridazine, pyrazolo[1,5-a]pyridine, imidazo[1,2-a]pyridine, imidazo[1,5-a]pyridine, imidazo[1,2-b]pyridazine, imidazo[1,2-a]pyrimidine, 1,2,4-triazolo[4,3-a]pyridine, 1,2,4-triazolo[4,3-b]pyridazine etc., and the like can be mentioned.

As the saturated or unsaturated non-aromatic heterocycle for the "divalent heterocyclic group optionally having substituent(s)" for Z, for example, a 3- to 8-membered (preferably 5- or 6-membered) saturated or unsaturated (preferably saturated) non-aromatic heterocycle (aliphatic heterocycle) such as oxirane, azetidine, oxetane, thietane, pyrrolidine, tetrahydrofuran, tetrahydrothiophene, piperidine, tetrahydropyran, tetrahydrothiopyran, morpholine, thiomorpholine, piperazine, azepane, oxepane, thiepane, oxazepane, thiazepane, azocane, oxocane, thiocane, oxazocane, thiazocane etc., and the like can be mentioned. These may be oxo-substituted and may be, for example, 2-oxoazetidine, 2-oxopyrrolidine, 2-oxopiperidine, 2-oxazepane, 2-oxazocane, 2-oxotetrahydrofuran, 2-oxotetrahydropyran, 2-oxotetrahydrothiophene, 2-oxothiane, 2-oxopiperazine, 2-oxooxepane, 2-oxooxazepane, 2-oxothiepane, 2-oxothiazepane, 2-oxooxocane, 2-oxothiocane, 2-oxooxazocane, 2-oxothiazocane and the like.

The two bonds from the "hydrocarbon ring group" of the "divalent hydrocarbon ring group optionally having substituent(s)" or the "heterocyclic group" of the "divalent heterocyclic group optionally having substituent(s)" for Z may be present at any possible position.

The "hydrocarbon group optionally having substituent(s)" and "heterocyclic group optionally having substituent(s)" for E are as defined in the following.

As the "lower alkanoyl group" for E, for example, formyl, a $C_{1-6}$ alkyl-carbonyl group such as acetyl, propionyl, butyryl, isobutyryl etc., and the like can be used.

As the "lower alkoxycarbonyl group" for E, for example, a $C_{1-6}$ alkoxy-carbonyl group such as methoxycarbonyl, ethoxycarbonyl, propoxycarbonyl, butoxycarbonyl etc., and the like are used.

As the "aralkyloxycarbonyl" for E, for example, a $C_{7-11}$ aralkyloxy-carbonyl group such as benzyloxycarbonyl etc., and the like are used.

As the "lower alkylsulfinyl group" for E, for example, a $C_{1-6}$ alkylsulfinyl group such as methylsulfinyl, ethylsulfinyl etc., and the like are used.

As the "lower alkylsulfonyl group" for E, for example, a $C_{1-6}$ alkylsulfonyl group such as methylsulfonyl, ethylsulfonyl etc., and the like are used.

As the "mono-lower alkylsulfamoyl group" for E, for example, a mono-$C_{1-6}$ alkylsulfamoyl group such as methylsulfamoyl, ethylsulfamoyl etc., and the like are used.

As the "di-lower alkylsulfamoyl group" for E, for example, a di-$C_{1-6}$ alkylsulfamoyl group such as dimethylsulfamoyl, diethylsulfamoyl etc., and the like are used.

As the "arylsulfamoyl group" for E, for example, a $C_{6-10}$ arylsulfamoyl group such as phenylsulfamoyl, naphthylsulfamoyl etc., and the like are used.

As the "arylsulfinyl group" for E, for example, a $C_{6-10}$ arylsulfinyl group such as phenylsulfinyl, naphthylsulfinyl etc., and the like are used.

As the "arylsulfonyl group" for E, for example, a $C_{6-10}$ arylsulfonyl group such as phenylsulfonyl, naphthylsulfonyl etc., and the like are used.

As the "arylcarbonyl group" for E, for example, a $C_{6-10}$ aryl-carbonyl group such as benzoyl, naphthoyl etc., and the like are used.

The "carbamoyl group optionally having substituent(s)" for E is, for example, a group of the formula —$CONR_2R_3$ wherein $R_2$ and $R_3$ are each a hydrogen atom, a hydrocarbon group optionally having substituent(s) or a heterocyclic group optionally having substituent(s), and in the formula —$CONR_2R_3$, $R_2$ and $R_3$ may form a ring together with the adjacent nitrogen atom, and the like.

In the present invention, R is a "hydrocarbon group optionally having substituent(s)" or a "heterocyclic group optionally having substituent(s)", and R can be bonded to W. Of these, a $C_{1-6}$ hydrocarbon group optionally having substituent(s) is preferable and a lower ($C_{1-6}$) alkyl group is particularly preferable. The "hydrocarbon group optionally having substituent(s)" and "heterocyclic group optionally having substituent(s)" for R are as defined in the following. A detailed explanation of the case where R is bonded to W is given in the following.

In the present invention, $D_1$ and $D_2$ are each a bond, an oxygen atom, a sulfur atom or >$NR_1$, and in the formula, $R_1$ is a hydrogen atom or a hydrocarbon group optionally having substituent(s). However, the present invention excludes a case where both of $D_1$ and $D_2$ are bonds. Among others, each of $D_1$ and $D_2$ is preferably a bond or an oxygen atom, and particularly preferably, $D_1$ is an oxygen atom and $D_2$ is an oxygen atom or a bond. The "hydrocarbon group optionally having substituent(s)" for $R_1$ is as defined in the following.

In the present invention, G is a "hydrocarbon group optionally having substituent(s)" or a "heterocyclic group optionally having substituent(s)". Of these, a $C_{1-6}$ hydrocarbon group optionally having substituent(s) or a saturated heterocyclic group optionally having substituent(s), which contains, as ring-constituting atoms, 1 to 4 hetero atoms selected from an oxygen atom, a sulfur atom and a nitrogen atom is preferable. As G, among others, a $C_{1-6}$ hydrocarbon group optionally having substituent(s) or a saturated oxygen-containing heterocyclic group optionally having substituent(s), which further contains, as ring-constituting atoms, 1 to 3 hetero atoms selected from an oxygen atom, a sulfur atom and a nitrogen atom is preferable. The "hydrocarbon group optionally having substituent(s)" and "heterocyclic group optionally having substituent(s)" for G are as defined in the following.

As the "hydrocarbon group" of the "hydrocarbon group optionally having substituent(s)" for the above-mentioned E, R, $R_1$ or G, for example, a saturated or unsaturated aliphatic hydrocarbon group, a saturated or unsaturated alicyclic hydrocarbon group, a saturated or unsaturated alicyclic-aliphatic hydrocarbon group, an aromatic hydrocarbon group, an aromatic-saturated or unsaturated alicyclic hydrocarbon group and the like can be mentioned, with preference given to those having 1 to 16, more preferably 1 to 6, carbon atoms. As specific examples thereof, an alkyl group, an alkenyl group, an alkynyl group, a cycloalkyl group, a cycloalkenyl group, a cycloalkylalkyl group, a cycloalkenylalkyl group, an aryl group and an arylalkyl group and the like are generally used.

For example, the "alkyl group" is preferably a lower alkyl group ($C_{1-6}$ alkyl group) and the like, and, for example, a $C_{1-6}$ alkyl group such as methyl, ethyl, propyl, isopropyl, butyl, isobutyl, sec-butyl, tert-butyl, pentyl, 1-ethylpropyl, hexyl etc., and the like are generally used. For R, a lower alkyl group ($C_{1-6}$ alkyl group) is preferable, a methyl group is particularly preferable.

For example, the "alkenyl group" is preferably a lower alkenyl group and the like, and, for example, a $C_{2-7}$ alkenyl group such as vinyl, 1-propenyl, allyl, isopropenyl, butenyl, isobutenyl, 2,2-dimethyl-pent-4-enyl etc., and the like are generally used.

For example, the "alkynyl group" is preferably a lower alkynyl group and the like, and, for example, a $C_{2-6}$ alkynyl group such as ethynyl, propargyl, 1-propynyl etc., and the like are generally used.

For example, the "cycloalkyl group" is preferably a lower cycloalkyl group and the like, and, for example, a $C_{3-10}$ cycloalkyl group such as cyclopropyl, cyclobutyl, cyclopentyl, cyclohexyl, cycloheptyl, cyclooctyl, bicyclo[2.2.1]heptanyl, adamantyl etc., and the like are generally used.

For example, the "cycloalkenyl group" is preferably a lower cycloalkenyl group, and, for example, a $C_{3-10}$ cycloalkenyl group such as cyclopropenyl, cyclobutenyl, cyclopentenyl, cyclohexenyl, cycloheptenyl, cyclooctenyl, bicyclo [2.2.1]hept-5-en-2-yl etc., and the like are generally used.

For example, the "cycloalkylalkyl group" is preferably a lower cycloalkylalkyl group, and, for example, a $C_{4-9}$ cycloalkylalkyl group such as cyclopropylmethyl, cyclopropylethyl, cyclobutylmethyl, cyclopentylmethyl, cyclohexylmethyl, cyclohexylethyl etc., and the like are generally used.

For example, the "cycloalkenylalkyl group" is preferably a lower cycloalkenylalkyl group, and, for example, a $C_{4-9}$ cycloalkenylalkyl such as cyclopentenylmethyl, cyclohexenylmethyl, cyclohexenylethyl, cyclohexenylpropyl, cycloheptenylmethyl, cycloheptenylethyl, bicyclo[2.2.1]hept-5-en-2-ylmethyl etc., and the like are generally used.

For example, the "aryl group" is preferably a $C_{6-14}$ aryl group such as phenyl, 1-naphthyl, 2-naphthyl, biphenylyl, 2-anthryl etc., and the like, and, for example, phenyl group and the like are generally used.

The "arylalkyl group" has, as the aryl moiety, the "aryl group" defined above, and as the alkyl moiety, the "alkyl group" defined above. Of these, for example, a $C_{6-14}$ aryl-$C_{1-6}$ alkyl group is preferable, and, for example, benzyl, phenethyl and the like are generally used.

As the substituent that the "hydrocarbon group" of the "hydrocarbon group optionally having substituent(s)" for the above-mentioned E, R, $R_1$ or G may have, for example, a halogen atom (e.g., fluorine, chlorine, bromine, iodine etc.), a nitro group, a cyano group, a hydroxy group, a thiol group, a sulfo group, a sulphino group, a phosphono group, an optionally halogenated lower alkyl group (e.g., $C_{1-6}$ alkyl such as methyl, ethyl, propyl, isopropyl, butyl, isobutyl, sec-butyl, tert-butyl, pentyl, 1-ethylpropyl, hexyl and the like; mono-, di- or tri-halogeno-$C_{1-6}$ alkyl group such as chloromethyl, dichloromethyl, trichloromethyl, fluoromethyl, difluoromethyl, trifluoromethyl, 2-bromoethyl, 2,2,2-trifluoroethyl, pentafluoroethyl, 3,3,3-trifluoropropyl, 4,4,4-trifluorobutyl, 5,5,5-trifluoropentyl, 6,6,6-trifluorohexyl etc., and the like), an oxo group, an amidino group, an imino group, an alkylenedioxy group (e.g., $C_{1-3}$ alkylenedioxy group such as methylenedioxy, ethylenedioxy etc., and the like), a lower alkoxy group (e.g., $C_{1-6}$ alkoxy group such as methoxy, ethoxy, propoxy, isopropoxy, butoxy, isobutoxy, pentyloxy, hexyloxy etc., and the like), an optionally halogenated lower alkoxy group (e.g., mono-, di- or tri-halogeno-$C_{1-6}$ alkoxy group such as chloromethyloxy, dichloromethyloxy, trichloromethyloxy, fluoromethyloxy, difluoromethyloxy, trifluoromethyloxy, 2-bromoethyloxy, 2,2,2-trifluoroethyloxy, pentafluoroethyloxy, 3,3,3-trifluoropropyloxy, 4,4,4-trifluorobutyloxy, 5,5,5-trifluoropentyloxy, 6,6,6-trifluorohexyloxy etc., and the like), a lower alkylthio group (e.g., $C_{1-6}$ alkylthio group such as methylthio, ethylthio, propylthio, isopropylthio, butylthio, isobutylthio, pentylthio, hexylthio etc., and the like), a carboxyl group, a lower alkanoyl group (e.g., formyl; $C_{1-6}$ alkyl-carbonyl group such as acetyl, propionyl, butyryl, isobutyryl etc., and the like), a lower alkanoyloxy group (e.g., formyloxy; $C_{1-6}$ alkyl-carbonyloxy group such as acetyloxy, propionyloxy, butyryloxy, isobutyryloxy etc., and the like), a lower alkoxycarbonyl group (e.g., $C_{1-6}$ alkoxy-carbonyl group such as methoxycarbonyl, ethoxycarbonyl, propoxycarbonyl, butoxycarbonyl etc., and the like), an aralkyloxycarbonyl group (e.g., $C_{7-11}$ aralkyloxy-carbonyl group such as benzyloxycarbonyl etc., and the like), a thiocarbamoyl group, a lower alkylsulfinyl group (e.g., $C_{1-6}$ alkylsulfinyl group such as methylsulfinyl, ethylsulfinyl etc., and the like), a lower alkylsulfonyl group (e.g., $C_{1-6}$ alkylsulfonyl group such as methylsulfonyl, ethylsulfonyl etc., and the like), a sulfamoyl group, a mono-lower alkylsulfamoyl group (e.g., mono-$C_{1-6}$ alkylsulfamoyl group such as methylsulfamoyl, ethylsulfamoyl etc., and the like), a di-lower alkylsulfamoyl group (e.g., di-$C_{1-6}$ alkylsulfamoyl group such as dimethylsulfamoyl, diethylsulfamoyl etc., and the like), an arylsulfamoyl group (e.g., $C_{6-10}$ arylsulfamoyl group such as phenylsulfamoyl, naphthylsulfamoyl etc., and the like), an aryl group (e.g., $C_{6-10}$ aryl group such as phenyl, naphthyl etc., and the like), an aryloxy group (e.g., $C_{6-10}$ aryloxy group such as phenyloxy, naphthyloxy etc., and the like), an arylthio group (e.g., $C_{6-10}$ arylthio group such as phenylthio, naphthylthio etc., and the like), an arylsulfinyl group (e.g., $C_{6-10}$ arylsulfinyl group such as phenylsulfinyl, naphthylsulfinyl etc., and the like), an arylsulfonyl group (e.g., $C_{6-10}$ arylsulfonyl group such as phenylsulfonyl, naphthylsulfonyl etc., and the like), an arylcarbonyl group (e.g., $C_{6-10}$ aryl-carbonyl group such as benzoyl, naphthoyl etc., and the like), an arylcarbonyloxy group (e.g., $C_{6-10}$ arylcarbonyloxy group such as benzoyloxy, naphthoyloxy etc., and the like), an optionally halogenated lower alkylcarbonylamino group (e.g., optionally halogenated $C_{1-6}$ alkyl-carbonylamino group such as acetylamino, trifluoroacetylamino etc., and the like), a carbamoyl group optionally having substituent(s) (e.g., a group of the formula —$CONR_2R_3$ wherein $R_2$ and $R_3$ are each a hydrogen atom, a hydrocarbon group optionally having substituent(s) or a heterocyclic group optionally having substituent(s) and in the formula —$CONR_2R_3$, $R_2$ and $R_3$ may form a ring together with the adjacent nitrogen atom), an amino group optionally having substituent(s) (e.g., a group of the formula —$NR_2R_3$ wherein $R_2$ and $R_3$ are as defined above and in the formula —$NR_2R_3$, $R_2$ and $R_3$ may form a ring together with the adjacent nitrogen atom), a ureido group optionally having substituent(s) (e.g., a group of the formula —$NHCONR_2R_3$ wherein $R_2$ and $R_3$ are as defined above and in the formula —$NHCONR_2R_3$, $R_2$ and $R_3$ may form a ring together with the adjacent nitrogen atom), a carboxamide group optionally having substituent(s) (e.g., a group of the formula —$NR_2COR_3$ wherein $R_2$ and $R_3$ are as defined above), a sulfonamide group optionally having substituent(s) (e.g., a group of the formula —$NR_2SO_2R_3$ wherein $R_2$ and $R_3$ are as defined above), a heterocyclic group optionally having substituent(s) (as defined for $R_2$ or $R_3$) and the like are used.

As the "hydrocarbon group" of the "hydrocarbon group optionally having substituent(s)" for $R_2$ or $R_3$, for example, a lower alkyl group (e.g., alkyl group having 1 to 6 carbon atoms such as methyl, ethyl, propyl group etc., and the like), a lower alkenyl group (e.g., alkenyl group having 2 to 6 carbon atoms such as vinyl, allyl group etc., and the like), a lower alkynyl group (e.g., alkynyl group having 2 to 6 carbon atoms such as ethynyl, propargyl group etc., and the like), a cycloalkyl group (e.g., cycloalkyl group having 3 to 8 carbon atoms such as cyclopropyl, cyclobutyl, cyclopentyl, cyclohexyl group etc., and the like), a cycloalkenyl group (e.g., cycloalkenyl group having 3 to 8 carbon atoms such as cyclobutenyl, cyclopentenyl, cyclohexenyl group etc., and the like), a cycloalkylalkyl group (e.g., $C_3$-$C_8$ cycloalkyl-$C_1$-$C_6$ alkyl group such as cyclopropylmethyl, cyclobutylmethyl, cyclopentylmethyl, cyclohexylmethyl group etc., and the like), a cycloalkenylalkyl group (e.g., $C_3$-$C_8$ cycloalkenyl-$C_1$-$C_6$ alkyl group such as cyclobutenylmethyl, cyclopentenylmethyl, cyclohexenylmethyl group etc., and the like), an aryl group (e.g., aryl group having 6 to 14 carbon atoms-such as phenyl, naphthyl group etc., and the like), an arylalkyl group (e.g., $C_6$-$C_{14}$ aryl-$C_1$-$C_6$ alkyl group, such as benzyl, naphthylmethyl group etc., and the like) and the like can be mentioned.

As the "heterocyclic group" of the "heterocyclic group optionally having substituent(s)" for $R_2$ or $R_3$, a 5- to 12-membered monocyclic or fused heterocyclic group containing 1 or 2 kinds of 1 to 4 hetero atoms selected from a nitrogen atom, a sulfur atom and an oxygen atom, such as pyridyl, pyrrolidinyl, piperazinyl, piperidinyl, 2-oxazepinyl, furyl, decahydroisoquinolyl, quinolyl, indolyl, isoquinolyl, thienyl, imidazolyl, morpholinyl etc., and the like can be mentioned. As the substituent of the "hydrocarbon group optionally having substituent(s)" and "heterocyclic group optionally having substituent(s)" for $R_2$ or $R_3$, for example, a halogen atom (e.g., fluorine, chlorine, bromine, iodine etc.), a lower alkyl group (e.g., alkyl group having 1 to 6 carbon atoms such as methyl, ethyl, propyl group etc., and the like), a lower alkenyl group (e.g., alkenyl group having 2 to 6 carbon atoms such as vinyl, allyl group etc., and the like), a lower alkynyl group (e.g., alkynyl group having 2 to 6 carbon atoms such as ethynyl, propargyl group etc., and the like), a cycloalkyl group (e.g., cycloalkyl group having 3 to 8 carbon atoms such as cyclopropyl, cyclobutyl, cyclopentyl, cyclohexyl group etc., and the like), a lower alkoxy group (e.g., alkoxy group having 1 to 6 carbon atoms such as methoxy, ethoxy group etc., and the like), a nitro group, a cyano group, a hydroxy group, a thiol group, a carboxyl group, a lower alkanoyl group (e.g., formyl; $C_{1-6}$ alkyl-carbonyl group such as acetyl, propionyl, butyryl group etc., and the like), a lower alkanoyloxy group (e.g., formyloxy; $C_{1-6}$ alkyl-carbonyloxy group such as acetyloxy, propionyloxy group etc., and the like), a lower alkoxycarbonyl group (e.g., $C_{1-6}$ alkoxy-carbonyl group such as methoxycarbonyl, ethoxycarbonyl, propoxycarbonyl group etc., and the like), an aralkyloxycarbonyl group (e.g., $C_{7-17}$ aralkyloxy-carbonyl group such as benzyloxycarbonyl group etc., and the like), an aryl group (e.g., aryl group having 6 to 14 carbon atoms such as phenyl, naphthyl group etc., and the like), an aryloxy group (e.g., aryloxy group having 6 to 14 carbon atoms such as phenyloxy, naphthyloxy group etc., and the like), an arylcarbonyl group (e.g., $C_{6-14}$ aryl-carbonyl group such as benzoyl, naphthoyl group etc., and the like), an arylcarbonyloxy group (e.g., $C_{6-14}$ arylcarbonyloxy group such as benzoyloxy, naphthoyloxy group and the like), a carbamoyl group optionally having substituent(s) (e.g., carbamoyl; carbamoyl group mono- or di-substituted by alkyl group having 1 to 6 carbon atoms, such as methylcarbamoyl, dimethylcarbamoyl group etc., and the like), an amino group optionally having substituent(s) (e.g., amino; amino group mono- or di-substituted by alkyl group having 1 to 6 carbon atoms, such as methylamino, dimethylamino, ethylamino, diethylamino group etc., and the like) and the like can be mentioned. The number and the position of the substitutions are not particularly limited.

As the ring formed by $R_2$ and $R_3$ together with the adjacent nitrogen atom, for example, pyrrolidine, piperidine, homopiperidine, morpholine, piperazine, tetrahydroquinoline, tetrahydroisoquinoline and the like can be mentioned.

The "hydrocarbon group" of the "hydrocarbon group optionally having substituent(s)" for the above-mentioned E, R, $R_1$ or G may have 1 to 5, preferably 1 to 3, the aforementioned substituents at substitutable positions of the hydrocarbon group, wherein, when the number of substituent(s) is not less than 2, respective substituents may be the same or different.

As the "heterocyclic group" of the "heterocyclic group optionally having substituent(s)" for the above-mentioned E, R or G, a 5- to 12-membered aromatic heterocyclic group and saturated or unsaturated non-aromatic heterocyclic group containing, as ring-constituting atoms (ring atoms), 1 to 3 (preferably 1 or 2) kinds of at least 1 (preferably 1 to 4, more-preferably 1 to 3) hetero atoms selected from an oxygen atom, a sulfur atom and a nitrogen atom and the like can be mentioned. As the mentioned above, as the "heterocyclic group" of the "heterocyclic group optionally having substituent(s)" for G, a saturated oxygen-containing heterocyclic group containing, as ring atoms, 1 to 4, more preferably 1 to 3, hetero atoms selected from an oxygen atom, a sulfur atom and a nitrogen atom etc., and the like are preferable, particularly a 5- to 12-membered saturated oxygen-containing heterocyclic group and the like are preferable.

As the "aromatic heterocyclic group", an aromatic monocyclic heterocyclic group, an aromatic fused heterocyclic group and the like can be mentioned.

As the "aromatic monocyclic heterocyclic group", for example, a 5- or 6-membered aromatic monocyclic heterocyclic group such as furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc., and the like can be mentioned.

As the "aromatic fused heterocyclic group", for example, a 8- to 12-membered aromatic fused heterocyclic group (preferably a heterocycle wherein the aforementioned 5- or 6-membered aromatic monocyclic heterocycle is condensed with a benzene ring, or a heterocycle wherein the same or different two heterocycle of the aforementioned 5- or 6-membered aromatic monocyclic heterocyclic group are condensed), such as benzofuranyl, isobenzofuranyl, benzothienyl, isobenzothienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl etc., and the like can be mentioned.

As the "saturated or unsaturated non-aromatic heterocyclic group", for example, a 3- to 8-membered (preferably 5- or 6-membered) saturated or unsaturated (preferably saturated) non-aromatic heterocyclic group (aliphatic heterocyclic group) such as oxiranyl, azetidinyl, oxetanyl, thietanyl, pyrrolidinyl, tetrahydrofuryl, thiolanyl, piperidinyl, tetrahydropyranyl, thianyl, morpholinyl, thiomorpholinyl, piperazinyl, azepanyl, oxepanyl, thiepanyl, oxazepanyl, thiazepanyl, azocanyl, oxocanyl, thiocanyl, oxazocanyl, thiazocanyl and the like can be mentioned. These may be oxo-substituted and, for example, 2-oxoazetidinyl, 2-oxopyrrolidinyl, 2-oxopiperidinyl, 2-oxazepanyl, 2-oxazocanyl, 2-oxotetrahydrofuryl, 2-oxotetrahydropyranyl, 2-oxothiolanyl, 2-oxothianyl, 2-oxopiperazinyl, 2-oxooxepanyl, 2-oxooxazepanyl, 2-oxothiepanyl, 2-oxothiazepanyl, 2-oxooxocanyl, 2-oxothiocanyl, 2-oxooxazocanyl, 2-oxothiazocanyl and the like can be mentioned. A 5-membered non-aromatic heterocyclic group such as 2-oxopyrrolidinyl and the like is preferable.

As the substituent that the "heterocyclic group" of the "heterocyclic group optionally having substituent(s)" for the above-mentioned E, R or G may have, for example, those similar to the "substituent" of the "hydrocarbon group optionally having substituent(s)" for the aforementioned E, R, $R_1$ and G or the like are used.

The "heterocyclic group" of the "heterocyclic group optionally having substituent(s)" for E, R or G may each have 1 to 5, preferably 1 to 3, substituents mentioned above at substitutable positions of the heterocyclic group, and when the number of substituents is two or more, respective substituents may be the same or different.

The bond between R and W in the compound of the present invention is explained below. When R and W are bonded, the position of the bond between R and W is not particularly limited as long as R and W can be bonded.

The bondable position of R is the position where the "hydrocarbon group" and "substituent" of the "hydrocarbon group optionally having substituent(s)" defined above for R can be bonded, and the position where the "heterocyclic group" and "substituent" of the "heterocyclic group optionally having substituent(s)" defined above for R can be bonded.

As the bondable position of W, a bondable position of the "divalent chain hydrocarbon group" of the "divalent chain hydrocarbon group optionally having substituent(s)" defined above for W, a bondable position of the "divalent chain hydrocarbon group" defined above for $W_1$ or $W_2$, a bondable position of the "hydrocarbon ring" of the "hydrocarbon ring optionally having substituents" defined above for ring Z, and a bondable position of the "heterocycle" of the "heterocyclic group optionally having substituents" defined above for ring Z can be mentioned.

R and W can be bonded at the bondable position thereof and can form a ring together with the adjacent nitrogen atom. As such ring, for example, a saturated nitrogen-containing ring (e.g., azetidine, pyrrolidine, piperidine, homopiperidine etc.), an unsaturated nitrogen-containing ring (e.g., tetrahydropyridine etc.), an aromatic nitrogen-containing ring (e.g., pyrrole etc.), a hetero ring (e.g., piperazine, morpholine etc.) containing, besides the nitrogen atom to which R and W are adjacent, at least one hetero atom selected from the group consisting of a nitrogen, an oxygen and a sulfur, a fused ring (e.g., indole, indoline, isoindole, isoindoline, tetrahydroquinoline, tetrahydroisoquinoline etc.) and the like can be mentioned. Of these, a 4- to 7-membered ring is preferable.

The ring formed by R and W, which are bonded at each bondable position thereof, together with the adjacent nitrogen atom, may have 1 to 4 substituents at substitutable positions thereof. When the number of substituents is 2 or more, respective substituents may be the same or different. As the substituent, the substituents of the "hydrocarbon group optionally having substituent(s)" and "heterocyclic group optionally having substituent(s)" defined for R, and the substituent of the "divalent chain hydrocarbon group optionally having substituent(s)" defined for W can be mentioned. Specifically, a halogen atom (e.g., fluorine, chlorine, bromine, iodine etc.), a $C_{1-6}$ alkyl group such as methyl, ethyl, propyl, isopropyl, butyl, isobutyl, sec-butyl, tert-butyl, pentyl, 1-ethylpropyl, hexyl etc., and the like can be mentioned.

By the bond between R and W, for example,

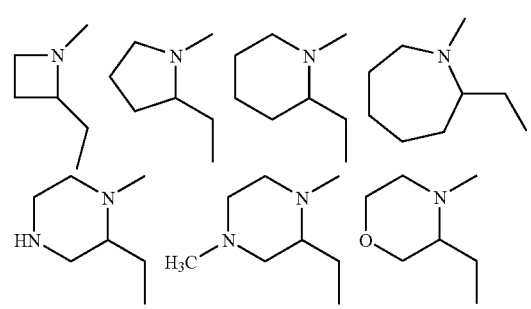

-continued

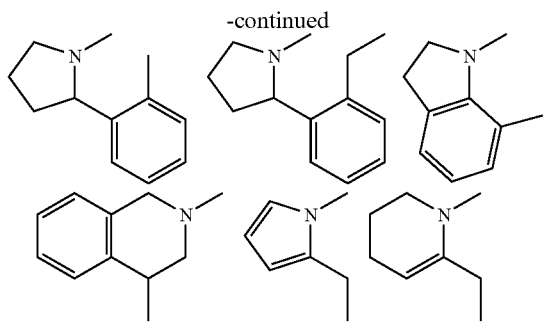

and the like are formed, but the ring is not limited to these. These may have substituent(s) as defined above, and it would be understood for those of ordinary skill in the art that they may also have an isomer.

In the present invention, X is a leaving group such as a halogen atom, a benzotriazolyl group, a (2,5-dioxypyrrolidin-1-yl)oxy group and the like. Of these, a halogen atom such as fluorine, chlorine, bromine, iodine and the like is preferable, and chlorine is particularly preferable.

In the present invention, M is a hydrogen atom, a metal cation or a quaternary ammonium ion.

In the present invention, as the "metal cation", an alkali metal ion (e.g., $Na^+$, $K^+$, $Li^+$, $Cs^+$ and the like) can be mentioned, with preference given to $Na^+$.

In the present invention, as the "quaternary ammonium ion", tetramethylammonium ion, tetraethylammonium ion, tetrapropylammonium ion, tetrabutylammonium ion and the like can be mentioned, with preference given to tetrabutylammonium ion.

In the compound (II), a pharmacologically acceptable basic salt can be formed between an acidic group in a molecule and an inorganic base or an organic base etc, and a pharmacologically acceptable acid addition salt can be formed between a basic group in a molecule and an inorganic acid or an organic acid etc.

As the inorganic basic salt of compound (II), salts with alkali metals (e.g., sodium, potassium and the like), alkaline earth metals (e.g., calcium and the like), ammonia etc., and the like can be mentioned, and as the organic basic salt of compound (II), salts with dimethylamine, triethylamine, piperazine, pyrrolidine, piperidine, 2-phenylethylamine, benzylamine, ethanolamine, diethanolamine, pyridine, collidine etc., and the like can be mentioned.

As the acid addition salt of compound (II), inorganic acid salts (e.g., hydrochloride, sulfate, hydrobromide, phosphate and the like), organic acid salts (e.g., acetate, trifluoroacetate, succinate, maleate, fumarate, propionate, citrate, tartrate, lactate, oxalate, methanesulfonate, p-toluenesulfonate and the like) and the like can be mentioned.

The compound (II) of the present invention encompasses hydrates. As the "hydrate", 0.5 hydrate-5.0 hydrate can be mentioned. Of these, 0.5 hydrate, 1.0 hydrate, 1.5 hydrate and 2.0 hydrate are preferable.

The compound (II) of the present invention encompasses racemates and optically active compounds. As the optically active compound, such compound wherein one enantiomer is in enantiomer excess (e.e.) of not less than 90% is preferable, more preferably in enantiomer excess of not less than 99%. As the optically active form, an (R)-form represented by the formula

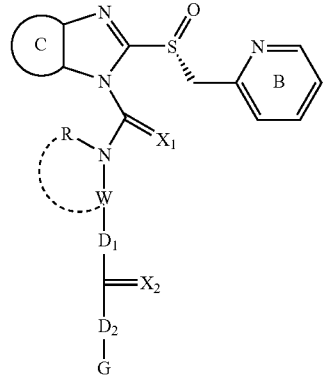

wherein each symbol is as defined above, is preferable. As the preferable compounds encompassed in compound (II), for example, the following specific compounds can be mentioned.

That is,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl trimethylacetate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl cyclohexanecarboxylate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl benzoate,
2-[methyl[[2-[[[3-methyl-4-(2,2,2-trifluoroethoxy)-2-pyridyl]methyl]sulfinyl]-1H-benzimidazol-1-yl]carbonyl]amino]ethyl benzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-methoxybenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3-chlorobenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4-difluorobenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-trifluoromethoxybenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-fluorobenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4,5-trimethoxybenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 2-pyridinecarboxylate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl methoxyacetate,
ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
isopropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, isopropyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate, benzyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate, 2-methoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, 2-[ethyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate, 2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate, ethyl 2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, 2-[cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate, 2-[cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl ethyl carbonate, 2-[[[(R)-2-[[[3-methyl-4-(2,2,2-trifluoroethoxy)-2-pyridyl]methyl]sulfinyl]-1H-benzimidazol-1-yl]carbonyl](phenyl)amino]ethyl acetate, 2-[[[2-[[[3-methyl-4-(2,2,2-trifluoroethoxy)-2-pyridyl]methyl]sulfinyl]-1H-benzimidazol-1-yl]carbonyl](phenyl)amino]ethyl acetate, tert-butyl [2-[methyl[[(R)-2-[[[3-methyl-4-(2,2,2-trifluoroethoxy)-2-pyridyl]methyl]sulfinyl]-1H-benzimidazol-1-yl]carbonyl]amino]-3-pyridyl]methyl carbonate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]benzyl acetate, 2-[[2-(acetyloxy)ethyl][[(R)-2-[[[3-methyl-4-(2,2,2-trifluoroethoxy)-2-pyridyl]methyl]sulfinyl)-1H-benzimidazol-1-yl]carbonyl]amino]ethyl acetate,

[(2S)-1-[[(R)-2-[[[3-methyl-4-(2,2,2-trifluoroethoxy)-2-pyridyl]methyl]sulfinyl]1H-benzimidazol-1-yl]carbonyl]-2-pyrrolidinyl]methyl acetate, ethyl [methyl[[(R)-2-[[[3-methyl-4-(2,2,2-trifluoroethoxy)-2-pyridyl]methyl]sulfinyl]-1H-benzimidazol-1-yl]carbonyl]amino]acetate, 2-[[[5-methoxy-2-[[(4-methoxy-3,5-dimethyl-2-pyridyl)methyl]sulfinyl]-1H-benzimidazol-1-yl]carbonyl](methyl)amino]ethyl benzoate, 3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl benzoate, 2-[methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate, ethyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate, ethyl 2-[methyl[[(S)-2-[[[3-methyl-4-(2,2,2-trifluoroethoxy)-2-pyridyl]methyl]sulfinyl]-1H-benzimidazol-1-yl]carbonyl]amino]ethyl carbonate, ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate, 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl acetate, 2-[[[5-methoxy-2-[[(4-methoxy-3,5-dimethyl-2-pyridyl)methyl]sulfinyl]-3H-imidazo[4,5-b]pyridin-3-yl]carbonyl](phenyl)amino]ethyl acetate, 4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl acetate, ethyl 4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl carbonate, ethyl 3-[methyl[[(R)-2-[[[3-methyl-4-(2,2,2-trifluoroethoxy)-2-pyridyl]methyl)sulfinyl]-1H-benzimidazol-1-yl]carbonyl]amino]propyl carbonate, 3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl acetate, 3-[methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl diacetate, diethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl biscarbonate, 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl 3-chlorobenzoate, 2-[methyl[[2-[[[3-methyl-4-(2,2,2-trifluoroethoxy)-2-pyridyl]methyl]sulfinyl]-1H-benzimidazol-1-yl]carbonyl]amino]ethyl acetate, 2-ethoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, 3-methoxypropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl N,N-dimethylglycinate, S-[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl]thioacetate, ethyl 2-[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]ethyl carbonate, ethyl 2-[methyl[[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]carbonyl]amino]ethyl carbonate, ethyl 2-[[[5-methoxy-2-[[(4-methoxy-3,5-dimethyl-2-pyridyl)methyl]sulfinyl]-1H-benzimidazol-1-yl]carbonyl](methyl)amino]ethyl carbonate, 2-[[[5-methoxy-2-[[(4-methoxy-3,5-dimethyl-2-pyridyl)methyl]sulfinyl]-1H-benzimidazol-1-yl]carbonyl](phenyl)amino]ethyl acetate, ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate, ethyl 2-[[[2-[[[4-(3-methoxypropoxy)-3-methyl-2-pyridyl]methyl]sulfinyl]-1H-benzimidazol-1-yl]carbonyl](methyl)amino]ethyl carbonate, 2-[[[2-[[[4-(3-methoxypropoxy)-3-methyl-2-pyridyl]methyl]sulfinyl]-1H-benzimidazol-1-yl]carbonyl](phenyl)amino]ethyl acetate, 2-[[[5-(difluoromethoxy)-2-[[(3,4-dimethoxy-2-pyridyl)methyl]sulfinyl]-1H-benzimidazol-1-yl]carbonyl](methyl)amino]ethyl ethyl carbonate, 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methylpiperidine-4-carboxylate,
2-[[4-(aminocarbonyl)phenyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methyl-4-piperidinyl carbonate,
2-[[4-(aminocarbonyl)phenyl][[2-[[[3-methyl-4-(2,2,2-trifluoroethoxy)-2-pyridyl]methyl]sulfinyl]-1H-benzimidazol-1-yl]carbonyl]amino]ethyl acetate,
(−)-ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate and
(+)-ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate, a salt thereof and the like can be mentioned.

Of these, the following compounds and salts thereof are preferable.
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate,
ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate,
2-[methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate,
ethyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate,
ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate,
2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl acetate,
2-[methyl[[2-[[[3-methyl-4-(2,2,2-trifluoroethoxy)-2-pyridyl]methyl]sulfinyl]-1H-benzimidazol-1-yl]carbonyl]amino]ethyl acetate,
ethyl 2-[[[5-methoxy-2-[[(4-methoxy-3,5-dimethyl-2-pyridyl)methyl]sulfinyl]-1H-benzimidazol-1-yl]carbonyl](methyl)amino]ethyl carbonate,
ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate,
ethyl 2-[[[2-[[[4-(3-methoxypropoxy)-3-methyl-2-pyridyl]methyl]sulfinyl]-1H-benzimidazol-1-yl]carbonyl)(methyl]amino]ethyl carbonate, and
2-[[[5-(difluoromethoxy)-2-[[(3,4-dimethoxy-2-pyridyl)methyl]sulfinyl]-1H-benzimidazol-1-yl]carbonyl](methyl)amino]ethyl ethyl carbonate.

Compound (II) can be produced by, for example, the method described in WO 03/105845. To be precise, Compound (II) can be produced by the following Method A, B and the like.

(Method A)

The compound (II) or a salt thereof can be obtained by condensation of compound (IV) or a salt thereof with compound (V) or a salt thereof in the presence or absence of a base. As the salt of compound (IV) and the salt of compound (V), the above-mentioned salts of compound (II) can be mentioned. For example, acid addition salts such as inorganic acid salts (e.g., hydrochloride, sulfate, hydrobromide, phosphate and the like), organic acid salts (e.g., acetate, trifluoroacetate, succinate, maleate, fumarate, propionate, citrate, tartrate, lactate, oxalate, methanesulfonate, p-toluenesulfonate and the like), and the like can be mentioned.

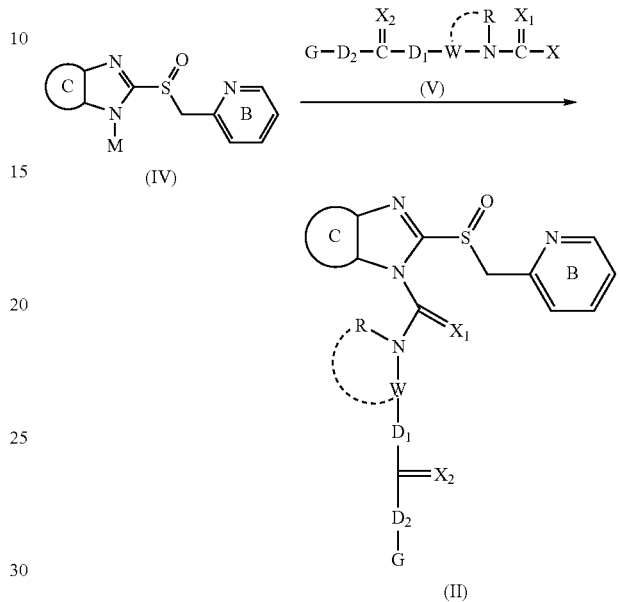

wherein each symbol is as defined above.

The reaction of Method A is generally carried out in a solvent, and a solvent that does not inhibit the reaction of Method A is selected as appropriate. As such solvent, ethers (e.g., dioxane, tetrahydrofuran, diethyl ether, tert-butyl methyl ether, diisopropyl ether, ethylene glycol dimethyl ether and the like), esters (e.g., ethyl formate, ethyl acetate, butyl acetate and the like), halogenated hydrocarbons (e.g., dichloromethane, chloroform, carbon tetrachloride, trichlene, 1,2-dichloroethane and the like), hydrocarbons (e.g., n-hexane, benzene, toluene and the like), amides (e.g., formamide, N,N-dimethylformamide, N,N-dimethylacetamide and the like), ketones (e.g., acetone, methyl ethyl ketone, methyl isobutyl ketone and the like), nitriles (e.g., acetonitrile, propionitrile and the like) and the like, as well as dimethyl sulfoxide, sulfolane, hexamethylphosphoramide, water and the like can be mentioned, which may be used alone or as a mixed solvent. The amount of the solvent to be used is not particularly limited as long as the reaction mixture can be stirred, which is generally 2- to 100-fold amount by weight, preferably 5- to 50-fold amount by weight, relative to 1 mol of compound (IV) or a salt thereof.

The amount of compound (V) or a salt thereof to be used is generally 1-10 mol, preferably 1-3 mol, relative to 1 mol of compound (IV) or a salt thereof.

The reaction of Method A is carried out within a temperature range of from about 0° C. to 100° C., preferably 20° C. to 80° C.

The reaction time of Method A varies depending on the kind of compounds (IV), (V) or a salt thereof and solvent, reaction temperature and the like, but it is generally 1 min.-96 hrs., preferably 1 min.-72 hrs., more preferably 15 min.-24 hrs.

As the base in Method A, for example, inorganic bases (e.g., sodium carbonate, potassium carbonate, calcium carbonate, sodium hydrogencarbonate etc.), tertiary amines (e.g., triethylamine, tripropylamine, tributylamine, cyclohexyldimethylamine, pyridine, lutidine, γ-collidine, N,N-dimethylaniline, N-methylpiperidine, N-methylpyrrolidine, N-methylmorpholine, 4-dimethylaminopyridine and the like); alkylene oxides (e.g., propylene oxide, epichlorohydrin etc.) and the like can be mentioned. The amount of the base to be used is generally 1 mol-10 mol, preferably 1 mol-3 mol, relative to 1 mol of compound (IV) or a salt thereof.

The compound (IV) or a salt thereof can be produced according to the method described in JP-A-61-50978, U.S. Pat. No. 4,628,098 and the like or a method similar thereto.

The compound (V) or a salt thereof can be produced according to a method known per se or a method analogous thereto. For example, when X is a chlorine atom, the compound (V) can be obtained by reacting a compound represented by the formula (VII):

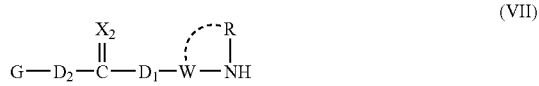

(VII)

wherein each symbol is as defined above, or a salt thereof with phosgene, trichloromethyl chloroformate, bis(trichloromethyl) carbonate, thiophosgene and the like in the presence of an acid scavenger in a solvent (e.g., tetrahydrofuran, acetonitrile, dichloromethane etc.). Alternatively, compound (V) can be also obtained by treating an ethylcarbamate compound, which is obtained by reacting compound (VII) or a salt thereof with ethyl chloroformate, with phosphorus oxychloride according to the method described in SGnthetic Communications, vol. 17, p. 1887 (1987) or a method analogous thereto. As the salt of compound (VII), for example, acid addition salts such as inorganic acid salts (e.g., hydrochloride, sulfate, hydrobromide, phosphate etc.), organic acid salts (e.g., acetate, trifluoroacetate, succinate, maleate, fumarate, propionate, citrate, tartrate, lactate, oxalate, methanesulfonate, p-toluenesulfonate etc.), and the like can be mentioned.

As the acid scavenger used here, for example, inorganic bases (e.g., sodium carbonate, potassium carbonate, calcium carbonate, sodium hydrogencarbonate etc.), tertiary amine (e.g., triethylamine, tripropylamine, tributylamine, cyclohexyldimethylamine, pyridine, lutidine, γ-collidine, N,N-dimethylaniline, N-methylpiperidine, N-methylpyrrolidine, N-methylmorpholine, 4-dimethylaminopyridine etc.) and the like can be mentioned.

The compound (VII) and a salt thereof can be produced according to a method known per se or a method analogous thereto. For example, when $D_1$ is other than a bond, compound (VII) can be obtained by condensing a compound represented by the formula (VIII):

(VIII)

wherein $R_4$ is a hydrogen atom or a nitrogen-protecting group, and other symbols are as defined above, or a salt thereof with a carboxylic acid or thionic acid represented by the formula (IX):

(IX)

wherein each symbol is as defined above, or a reactive derivative thereof (e.g., anhydride, halide etc.), or a salt thereof in a suitable solvent (e.g., ethyl acetate, tetrahydrofuran, dichloromethane, N,N-dimethylformamide etc.), followed by deprotection as necessary. As the salt of compound (VIII), for example, acid addition salts such as inorganic acid salts (e.g., hydrochloride, sulfate, hydrobromide, phosphate etc.), organic acid salts (e.g., acetate, trifluoroacetate, succinate, maleate, fumarate, propionate, citrate, tartrate, lactate, oxalate, methanesulfonate, p-toluenesulfonate etc.) etc., and the like can be mentioned.

Alternatively, when $D_1$ is a bond, compound (VII) can be obtained by condensing a carboxylic acid or thionic acid represented by the formula (X):

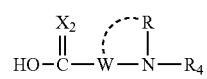

(X)

wherein each symbol is as defined above, or a reactive derivative thereof (e.g., anhydride, halide etc.), or a salt thereof with a compound represented by G-$D_2$-H in a suitable solvent (e.g., ethyl acetate, tetrahydrofuran, dichloromethane, N,N-dimethylformamide etc.), followed by deprotection as necessary. As the salt of compound (X), for example, acid addition salts such as inorganic acid salts (e.g., hydrochloride, sulfate, hydrobromide, phosphate etc.), organic acid salts (e.g., acetate, trifluoroacetate, succinate, maleate, fumarate, propionate, citrate, tartrate, lactate, oxalate, methanesulfonate, p-toluenesulfonate etc.) and the like, salts with alkali metals (e.g., sodium, potassium etc.), alkaline earth metals (e.g., calcium etc.), ammonia etc., salts with organic bases such as dimethylamine, triethylamine, piperazine, pyrrolidine, piperidine, 2-phenylethylamine, benzylamine, ethanolamine, diethanolamine, pyridine, collidine etc., and the like can be mentioned.

As the protecting group for $R_4$ in the formula (VIII) and the formula (X), for example, a formyl group, a $C_{1-6}$ alkyl-carbonyl group (e.g., acetyl, ethylcarbonyl etc.), a benzyl group, a tert-butyloxycarbonyl group, a benzyloxycarbonyl group, an allyloxycarbonyl group, a $C_{7-10}$ aralkyl-carbonyl group (e.g., benzylcarbonyl etc.), a trityl group and the like are used. These groups may be substituted by 1 to 3 halogen atoms (e.g., fluorine, chlorine, bromine etc.), a nitro group and the like.

As a method for removing such protecting groups, a method known per se or a method analogous thereto is used, which is, for example, a method using an acid, a base, reduction, UV light, palladium acetate etc., and the like are used.
(Method B)

The compound (II) and a salt thereof can be obtained by subjecting compound (VI) or a salt thereof to oxidative reaction.

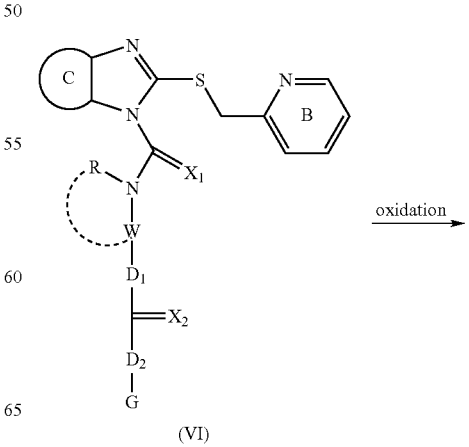

(VI)

-continued

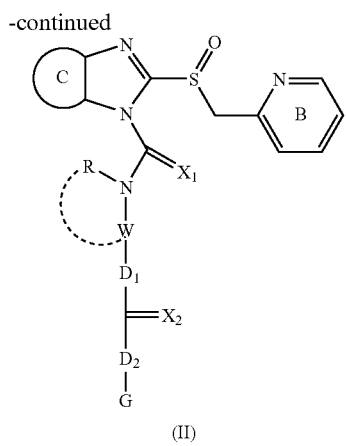

(II)

wherein each symbol is as defined above.

The reaction in Method B can be carried out using an oxidant such as nitric acid, hydrogen peroxide, peroxyacid, peroxyacid ester, ozone, dinitrogen tetraoxide, iodosobenzene, N-halosuccinimide, 1-chlorobenzotriazole, tert-butyl hypochlorite, diazabicyclo[2.2.2]octane-bromine complex, sodium metaperiodate, selenium dioxide, manganese dioxide, chromic acid, ammonium cerium nitrate, bromine, chlorine, sulfuryl chloride, magnesium monoperoxyphthalate and the like. The amount of the oxidant to be used is generally 0.5 mol-2 mol, preferably 0.8 mol-1.2 mol, relative to 1 mol of compound (VI) or a salt thereof. The oxidation may be carried out using the above-mentioned oxidant such as hydrogen peroxide and peroxyacids in the presence of a catalyst such as vanadium acetate, vanadium oxide acetylacetonate, titanium tetraisopropoxide and the like.

The reaction of Method B is generally carried out in a solvent inert to the above-mentioned oxidation reaction. As the "inert solvent", water, alcohols (e.g., methanol, ethanol, 1-propanol, 2-propanol etc.), ketones (e.g., acetone, methyl ethyl ketone etc.), nitriles (e.g., acetonitrile, propionitrile etc.), amides (e.g., formamide, N,N-dimethylformamide etc.), ethers (e.g., diethyl ether, tert-butyl methyl ether, diisopropyl ether, dioxane, tetrahydrofuran etc.), sulfoxides (e.g., dimethyl sulfoxide etc.) and polar solvents (e.g., sulfolane, hexamethylphosphoramide etc.) can be mentioned, which may be used alone or as a mixed solvent thereof. The "inert solvent" is used in generally 1- to 100-fold amount by weight relative to compound (VI) or a salt thereof.

The reaction temperature is generally from −80° C. to 80° C., preferably from 0° C. to 30° C.

The reaction time is generally 1 min.-6 hrs., preferably 15 min.-1 hr.

The compound (VI), which is a starting material in Method B, can be obtained by, for example a reaction similar to that in Method A, by the use of a compound represented by the following formula (XI):

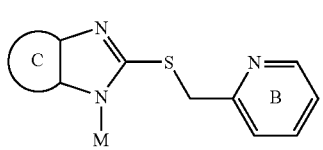

(XI)

wherein each symbol is as defined above, instead of compound (IV).

The compound (XI) can be synthesized according to the methods described in the following references or a method analogous thereto: JP-A-61-50978, JP-A-54-141783, JP-A-61-22079, JP-A-1-6270, JP-A-63-146882.

As the salt of compound (VI), those similar to the above-mentioned salts of the compound (II), which are acid addition salts such as inorganic acid salts (e.g., hydrochloride, sulfate, hydrobromide, phosphate and the like), organic acid salts (e.g., acetate, trifluoroacetate, succinate, maleate, fumarate, propionate, citrate, tartrate, lactate, oxalate, methanesulfonate, p-toluenesulfonate and the like) and the like can be mentioned.

The compound (II) or a salt thereof obtained by the above-mentioned Method A or B can be isolated and purified from the reaction mixture by a separation means known per se (e.g., concentration, concentration under reduced pressure, solvent extraction, crystallization, recrystallization, phase transfer, chromatography and the like). Since compound (II) and a salt thereof obtained by the above-mentioned Method A or B encompass any isomers thereof, optically pure compound (II) and a salt thereof can be obtained by, for example, subjecting compound (II) or a salt thereof to optical resolution, or asymmetric oxidation of compound (VI) or a salt thereof.

The method of optical resolution includes methods known per se, such as a fractional recrystallization method, a chiral column method, a diastereomer method, and so forth. Asymmetric oxidation includes methods known per se, such as the method described in WO96/02535 and the like.

The "fractional recrystallization method" includes a method in which a salt is formed between a racemate and an optically active compound [e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.], which salt is separated by fractional recrystallization etc., and, if desired, subjected to a neutralization process to give a free optical isomer.

The "chiral column method" includes a method in which a racemate or a salt thereof is applied to a column for optical isomer separation (chiral column). In the case of liquid chromatography, for example, optical isomers are separated by adding a racemate to a chiral column such as ENANTIO-OVM (produced by Tosoh Corporation), the DAICEL CHIRAL series (produced by Daicel Corporation) and the like, and developing the racemate in water, a buffer (e.g., phosphate buffer), an organic solvent (e.g., hexane, ethanol, methanol, isopropanol, acetonitrile, trifluoroacetic acid, diethylamine, triethylamine, etc.), or a solvent mixture thereof. In the case of gas chromatography, for example, a chiral column such as CP-Chirasil-DeX CB (produced by GL Science) and the like is used to separate optical isomers.

The "diastereomer method" includes a method in which a racemate and an optically active reagent are reacted to give a diastereomeric mixture, which is then subjected to ordinary separation means (e.g., fractional recrystallization, chromatography, etc.) to obtain either diastereomer, which is subjected to a chemical reaction (e.g., acid hydrolysis, base hydrolysis, hydrogenolysis, etc.) to cut off the optically active reagent moiety, whereby the desired optical isomer is obtained. Said "optically active reagent" includes, for example, optically active organic acids such as MTPA [α-methoxy-α-(trifluoromethyl)phenylacetic acid], (−)-methoxyacetic acid and the like, optically active alkoxymethyl halides such as (1R-endo)-2-(chloromethoxy)-1,3,3-trimethylbicyclo[2.2.1]heptane etc., and the like.

In addition, a benzimidazole compound represented by the following formula (III):

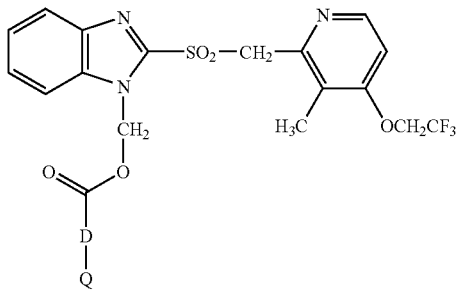

and a salt thereof can be mentioned as specific examples of the above-mentioned prodrug.

In the above-mentioned formula (III), D is an oxygen atom or a bond, and Q is a hydrocarbon group optionally having substituent(s).

The "hydrocarbon group" of the "hydrocarbon group optionally having substituent(s)" for Q encompasses an aliphatic or aromatic hydrocarbon group, wherein the aliphatic hydrocarbon group means a saturated or unsaturated, linear, branched chain or cyclic hydrocarbon group. As the hydrocarbon group, a hydrocarbon group having 1 to 14 carbon atoms is preferable. For example, a $C_{1-6}$ alkyl group, a $C_{2-6}$ alkenyl group, a $C_{2-6}$ alkynyl group, a $C_{3-8}$ cycloalkyl group and a $C_{6-14}$ aryl group can be mentioned, a $C_{1-6}$ alkyl group, a $C_{3-8}$ cycloalkyl group and a $C_{6-14}$ aryl group are preferable, and a $C_{1-6}$ alkyl group and a $C_{3-8}$ cycloalkyl group are more preferable.

The above-mentioned "alkyl group" is a linear or branched chain alkyl group, with preference given to an alkyl group having 1 to 6 carbon atoms ("$C_{1-6}$ alkyl group"). For example, methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl and the like can be mentioned, with preference given to an alkyl group having 1 to 4 carbon atoms. For Q, methyl, ethyl, isopropyl and tert-butyl are especially preferable, and tert-butyl is particularly preferable.

The above-mentioned "$C_{2-6}$ alkenyl group" is a linear or branched chain alkenyl group having 2 to 6 carbon atoms. For example, vinyl, n-propenyl, isopropenyl, n-butenyl, isobutenyl, sec-butenyl, tert-butenyl, n-pentenyl, isopentenyl, neopentenyl, 1-methylpropenyl, n-hexenyl, isohexenyl, 1,1-dimethylbutenyl, 2,2-dimethylbutenyl, 3,3-dimethylbutenyl, 3,3-dimethylpropenyl, 2-ethylbutenyl and the like can be mentioned, with preference given to an alkenyl group having 2 to 4 carbon atoms, and vinyl, n-propenyl and isopropenyl are particularly preferable.

The above-mentioned "$C_{2-6}$ alkynyl group" is a linear or branched chain alkynyl group having 2 to 6 carbon atoms. For example, ethynyl, n-propynyl (1-propynyl), isopropynyl (2-propynyl), n-butynyl, isobutynyl, sec-butynyl, tert-butynyl, n-pentynyl, isopentynyl, neopentynyl, 1-methylpropynyl, n-hexynyl, isohexynyl, 1,1-dimethylbutynyl, 2,2-dimethylbutynyl, 3,3-dimethylbutynyl, 3,3-dimethylpropynyl, 2-ethylbutynyl and the like can be mentioned, with preference given to an alkynyl group having 2 to 3 carbon atoms, and ethynyl, 1-propynyl and 2-propynyl are particularly preferable.

The above-mentioned "$C_{3-8}$ cycloalkyl group" is a cyclic cycloalkyl group having 3 to 8 carbon atoms. For example, cyclopropyl, cyclobutyl, cyclopentyl, cyclohexyl, cycloheptyl, cyclooctyl and the like can be mentioned, with preference given to a cycloalkyl group having 5 to 7 carbon atoms, and cyclopentyl, cyclohexyl, cycloheptyl are especially preferable, and cyclohexyl is particularly preferable.

The above-mentioned "aryl group" is a monocyclic or fused polycyclic aromatic hydrocarbon group, with preference given to an aromatic hydrocarbon group having 6 to 14 carbon atoms ($C_{6-14}$ aryl group). For example, phenyl, naphthyl, anthryl, phenanthryl, acenaphthylenyl and acenaphthylenyl can be mentioned, with preference given to an aromatic hydrocarbon group having 6 to 10 carbon atoms. For Q, phenyl is particularly preferable.

The above-mentioned "hydrocarbon group" may be substituted and as the substituent, for example, a $C_{6-14}$ aryl group, a hydroxyl group, a halogen, a $C_{1-6}$ alkoxy group optionally substituted by halogen, a $C_{7-12}$ aralkyloxy group, a $C_{1-5}$ alkoxy-carbonyl group, a $C_{1-6}$ alkyl group optionally substituted by halogen, an amino group optionally substituted by $C_{1-6}$ alkyl group and the like can be mentioned.

As the substituent of the "alkyl group optionally having substituent(s)", for example, an aryl group, a hydroxyl group, a halogen, an alkoxy group optionally substituted by 1 to 5 halogens, a $C_{7-12}$ aralkyloxy group, a $C_{1-5}$ alkoxy-carbonyl group and the like can be mentioned. The number of the substituents is 1-5, preferably 1-3.

As the substituent of the "aryl group optionally having substituent(s)", for example, a halogen, an alkyl group optionally substituted by 1 to 5 halogens, an aryl group, a hydroxyl group, an alkoxy group optionally substituted by 1 to 5 halogens, a $C_{7-12}$ aralkyloxy group, a $C_{1-5}$ alkoxy-carbonyl group and the like can be mentioned. The number of the substituents is 1-5, preferably 1-3.

The above-mentioned "$C_{1-6}$ alkyl group", "$C_{2-6}$ alkenyl group" and "$C_{2-6}$ alkynyl group" may be substituted, and as the substituent, (i) a $C_{6-14}$ aryl group, (ii) a hydroxyl group, (iii) a halogen, (iv) a $C_{1-6}$ alkoxy group optionally substituted by halogen, (v) a $C_{7-12}$ aralkyloxy group, (vi) a $C_{1-5}$ alkoxy-carbonyl group, (vii) an acylamino group, (viii) an amino group optionally substituted by $C_{1-6}$ alkyl group, and the like can be mentioned, with preference given to (i)-(vii). The number of the substituents is 1-5, preferably 1-3.

The above-mentioned "$C_{3-8}$ cycloalkyl group" and "$C_{6-14}$ aryl group" may be substituted, and as the substituent, (i) a $C_{6-14}$ aryl group, (ii) a hydroxyl group, (iii) a halogen, (iv) a $C_{1-6}$ alkoxy group optionally substituted by halogen, (v) a $C_{7-12}$ aralkyloxy group, (vi) a $C_{1-5}$ alkoxy-carbonyl group, (vii) a $C_{1-6}$ alkyl group optionally substituted by halogen, (viii) an amino group optionally substituted by $C_{1-6}$ alkyl group, and the like can be mentioned, with preference given to (i)-(vii). The number of the substituents is 1-5, preferably 1-3.

In the formula (III), Q is preferably a $C_{1-6}$ alkyl group, a $C_{2-6}$ alkenyl group or a $C_{2-6}$ alkynyl group, each optionally having substituent(s) selected from the group consisting of (i) a $C_{6-14}$ aryl group, (ii) a hydroxyl group, (iii) a halogen, (iv) a $C_{1-6}$ alkoxy group optionally substituted by halogen, (v) a $C_{7-12}$ aralkyloxy group, (vi) a $C_{1-5}$ alkoxy-carbonyl group and (vii) an acylamino group, or a $C_{3-8}$ cycloalkyl group or a $C_{6-14}$ aryl group, each optionally having substituent(s) selected from the group consisting of (i) a $C_{6-14}$ aryl group, (ii) a hydroxyl group, (iii) a halogen, (iv) a $C_{1-6}$ alkoxy group optionally substituted by halogen, (v) a $C_{7-12}$ aralkyloxy group, (vi) $C_{1-5}$ alkoxy-carbonyl group and (vii) a $C_{1-6}$ alkyl group optionally substituted by halogen, more preferably, (1) a $C_{1-6}$ alkyl group optionally having 1 to 5 substituents selected from the group consisting of (i) a $C_{6-14}$ aryl group, (ii) a hydroxyl group, (iii) a halogen, (iv) a $C_{1-6}$ alkoxy group optionally substituted by 1 to 5 halogens, (v) a $C_{7-12}$ aralkyloxy group and (vi) a $C_{1-5}$ alkoxy-carbonyl group, or (2) a $C_{6-14}$ aryl group optionally having 1 to 5 substituents selected from the group consisting of (i) a halogen, (ii) a $C_{1-6}$ alkyl group optionally substituted by 1 to 5 halogens, (iii) a $C_{6-14}$ aryl group, (iv) a hydroxyl group, (v) a $C_{1-6}$ alkoxy group optionally substituted by 1 to 5 halogens, (vi) a $C_{7-12}$ aralkyloxy group and (vii) a $C_{1-5}$ alkoxy-carbonyl group, still more preferably, a $C_{1-6}$ alkyl group optionally having substituent(s) selected from the group consisting of (i) a $C_{6-14}$ aryl group, (ii) a hydroxyl group, (iii) a halogen, (iv) a $C_{1-6}$ alkoxy group optionally substituted by halogen, (v) a $C_{7-12}$ aralkyloxy group, (vi) a $C_{1-5}$ alkoxy-carbonyl group and (vii) an acylamino group, or a $C_{3-8}$ cycloalkyl group or a $C_{6-14}$ aryl group, each optionally having substituent(s) selected from the group consisting of (i) a $C_{6-14}$ aryl group, (ii) a hydroxyl group, (iii) a halogen, (iv) a $C_{1-6}$ alkoxy group optionally substituted by halogen, (v) a $C_{7-12}$ aralkyloxy group, (vi) a $C_{1-5}$ alkoxy-carbonyl group and (vii) a $C_{1-6}$ alkyl group optionally substituted by halogen.

Of these, Q is preferably a $C_{1-6}$ alkyl group optionally substituted $C_{6-14}$ aryl group, or a $C_{6-14}$ aryl group, and particularly preferably a phenyl group, or a methyl or tert-butyl group.

In the compound (III), pharmacologically acceptable basic salt can be formed between an acidic group in a molecule and an inorganic base or an organic base and the like, and a pharmacologically acceptable acid addition salt can be formed between a basic group in a molecule and an inorganic acid or an organic acid and the like.

As one of the preferable embodiments of compound (III) of the present invention, a compound wherein D is a bond, and Q is an alkyl group optionally having substituent(s) or an aryl group optionally having substituent(s) can be mentioned.

As the inorganic basic salts of compound (III), for example, salts with alkali metals (e.g., sodium, potassium etc.), alkaline earth metals (e.g., calcium etc.), ammonia and the like, and the like, and as the organic basic salts of compound (III), for example, salts with dimethylamine, triethylamine, piperazine, pyrrolidine, piperidine, 2-phenylethylamine, benzylamine, ethanolamine, diethanolamine, pyridine, collidine and the like, and the like can be mentioned.

As the acid addition salts of compound (III), for example, inorganic acid salts (e.g., hydrochloride, sulfate, hydrobromide, phosphate etc.), organic acid salts (e.g., acetate, trifluoroacetate, succinate, maleate, fumarate, propionate, citrate, tartrate, lactate, oxalate, methanesulfonate, p-toluenesulfonate etc.) and the like can be mentioned.

The compound (III) of the present invention encompasses hydrates. As the "hydrate", 0.5 hydrate-5.0 hydrate can be mentioned. Of these, 0.5 hydrate, 1.0 hydrate, 1.5 hydrate and 2.0 hydrate are preferable.

The compound (III) of the present invention encompasses racemate and optically active compounds. As the optically active compound, one wherein one enantiomer shows not less than 90% enantiomer excess (e.e.), more preferably not less than 99% enantiomer excess, is preferable. As an optically active form, an (R) form represented by the formula

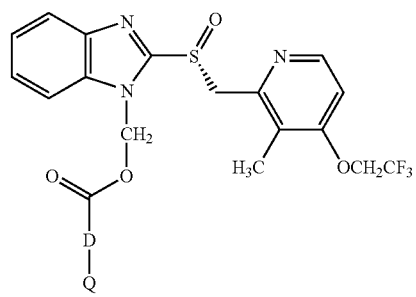

wherein the symbols in the formula are as defined above, is preferable.

The compound (III) can be manufactured by a method known per se, and by methods described in, for example, JP-A-2002-187890, WO 02/30920 and the like or methods analogous thereto. The optically active compound (III) can be obtained by a method using optical resolution (fractional recrystallization, chiral column method, diastereomer method, a method using microorganism or enzyme and the like), asymmetric oxidation and the like. As PPI of other benzimidazole compound derivatives, the compound described in WO 03/27098 can be also applied to the present invention.

B. Steroid $C_{17,20}$ Lyase Inhibitor

As specific examples of steroid $C_{17,20}$ lyase inhibitor, in the following compounds can be mentioned.

[1] A compound described in WO02/40484, which is represented by the formula:

wherein n is an integer of 1 to 3 and Ar is an aromatic ring optionally having substituent(s), or a salt thereof.

As preferable examples of the compound represented by the formula (I)-A, in the following compounds can be mentioned.

[2] The compound of the above-mentioned [1], wherein Ar is a monocyclic or bicyclic aromatic fused ring optionally having substituent(s).

[3] The compound of the above-mentioned [1], wherein Ar is an optionally substituted aromatic ring comprising 5 to 10 atoms containing 0 to 4 hetero atoms as ring-constituting atoms, which ring is bonded via a carbon atom.

[4] The compound of the above-mentioned [1], wherein Ar is a group represented by the formula:

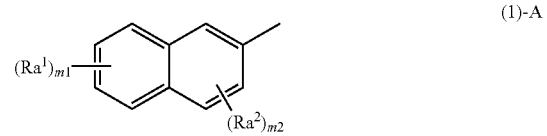

wherein m1 is an integer of 1 to 4, m2 is an integer of 0 to 3, and $Ra^1$ and $Ra^2$ are the same or different and each is independently a hydrogen atom, a hydroxy group optionally having a substituent, a thiol group optionally having a substituent, an amino group optionally having substituent(s), an acyl group, a halogen atom or a hydrocarbon group optionally having substituent(s), a group represented by the formula:

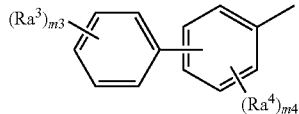

(2)-A wherein m3 is an integer of 1 to 5, m4 is an integer of 0 to 4, and $Ra^3$ and $Ra^4$ are the same or different and each is are each independently a hydrogen atom, a hydroxy group optionally having a substituent, a thiol group optionally having a substituent, an amino group optionally having substituent(s), an acyl group, a halogen atom or a hydrocarbon group optionally having substituent(s), or a group represented by the formula:

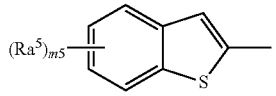

(3)-A wherein m5 is an integer of 1 to 4, and $Ra^5$ is a hydrogen atom, a hydroxy group optionally having a substituent, a thiol group optionally having a substituent, an amino group optionally having substituent(s), an acyl group, a halogen atom or a hydrocarbon group optionally having substituent(s).

[5] The compound of the above-mentioned [1], wherein Ar is a group represented by the formula:

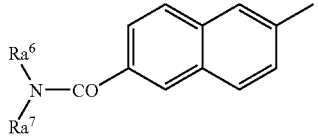

(1-1)-A wherein $Ra^6$ and $Ra^7$ are the same or different and each is are each independently a hydrogen atom or a lower alkyl group, or a group represented by the formula:

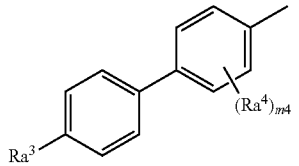

(2-1)-A wherein m4 is an integer of 0 to 4, and $Ra^3$ and $Ra^4$ are the same or different and each is independently a hydrogen atom, a hydroxy group optionally having a substituent, a thiol group optionally having a substituent, an amino group optionally having substituent(s), an acyl group, a halogen atom or a hydrocarbon group optionally having substituent(s).

[6] The compound of the above-mentioned [1], wherein Ar is a group represented by the formula:

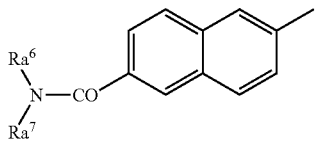

(1-1)-A wherein $Ra^6$ and $Ra^7$ are the same or different and each is independently a hydrogen atom or a lower alkyl group.

[7] The compound of the above-mentioned [1], which is an enantiomer wherein the steric configuration is an S configuration.

[8] The compound of the above-mentioned [1], which is an enantiomer wherein the steric configuration is an R configuration.

Each symbol in each formula is defined as follows.

N is an integer of 1 to 3, with preference given to 1.

m1 is an integer of 1 to 4, with preference given to 1 or 2, particularly 1.

m2 is an integer of 0 to 3, with preference given to 0 or 1, particularly 0.

m3 is an integer of 1 to 5, with preference given to 1 to 3, particularly 1.

m4 is an integer of 0 to 4, with preference given to 0 or 1, particularly 0.

m5 is an integer of 1 to 4, with preference given to 1 or 2, particularly 1.

m6 is an integer of 0 to 3, with preference given to 0 or 1, particularly 0.

As the hydroxy group optionally having a substituent for $Ra^1$, $Ra^2$, $Ra^3$, $Ra^4$ or $Ra^5$, an unsubstituted hydroxyl group, and in addition, for example, a lower alkoxy (e.g., $C_{1-4}$ alkoxy group such as methoxy, ethoxy, propoxy and the like), a lower alkanoyloxy (e.g., $C_{1-4}$ alkanoyloxy such as acetyloxy, propionyloxy and the like), a carbamoyloxy optionally having substituent(s) (e.g., unsubstituted carbamoyloxy, and further, for example, carbamoyloxy substituted by 1 or 2 $C_{1-4}$ alkyl groups, such as methylcarbamoyloxy, ethylcarbamoyloxy, dimethylcarbamoyloxy, diethylcarbamoyloxy, ethylmethylcarbamoyloxy and the like) and the like can be mentioned.

As the thiol group optionally having a substituent for $Ra^1$, $Ra^2$, $Ra^3$, $Ra^4$ or $Ra^5$, an unsubstituted thiol group, and in addition, for example, a lower alkylthio (e.g., $C_{1-4}$ alkylthio group such as methylthio, ethylthio, propylthio and the like), a lower alkanoylthio (e.g., $C_{1-4}$ alkanoylthio such as acetylthio, propionylthio and the like) and the like can be mentioned.

As the amino group optionally having substituent(s) for $Ra^1$, $Ra^2$, $Ra^3$, $Ra^4$ or $Ra^5$, an unsubstituted amino group, and in addition, for example, a lower alkylamino (e.g., $C_{1-4}$ alkylamino group such as methylamino, ethylamino, propylamino and the like), a di-lower alkylamino (e.g., di-$C_{1-4}$ alkylamino such as dimethylamino, diethylamino and the like), a $C_{1-4}$ alkanoylamino (e.g., acetylamino, propionylamino etc.) and the like can be mentioned.

As the acyl group for $Ra^1$, $Ra^2$, $Ra^3$, $Ra^4$ or $Ra^5$, for example, an alkanoyl group (e.g., $C_{1-6}$ alkanoyl such as formyl, acetyl, propionyl and the like), an alkylsulfonyl group (e.g., $C_{1-4}$ alkylsulfonyl such as methylsulfonyl, ethylsulfonyl and the like), an aroyl group (e.g., benzoyl, toluoyl, naphthoyl etc.), a carbamoyl group optionally having substituent(s) (e.g., mono- or di-$C_{1-10}$ alkylcarbamoyl group such as methylcarbamoyl, ethylcarbamoyl, dimethylcarbamoyl, diethylcarbamoyl and the like, mono- or di-$C_{6-14}$ arylcarbamoyl group such as phenylcarbamoyl, diphenylcarbamoyl and the like, mono- or di-$C_{7-16}$ aralkylcarbamoyl group such as benzylcarbamoyl, dibenzylcarbamoyl and the like, and the like), a sulfamoyl group optionally having substituent(s) (e.g., mono- or di-$C_{1-10}$ alkylsulfamoyl group such as methylsulfamoyl, ethylsulfamoyl, dimethylsulfamoyl, diethylsulfamoyl and the like, mono- or di-$C_{6-14}$ arylsulfamoyl group such as phenylsulfamoyl, diphenylsulfamoyl and the like, mono- or di-$C_{7-16}$ aralkylsulfamoyl group such as benzylsulfamoyl, dibenzylsulfamoyl and the like, and the like) and the like can be mentioned.

As the halogen for $Ra^1$, $Ra^2$, $Ra^3$, $Ra^4$ or $Ra^5$, fluorine, chlorine, bromine and iodine can be mentioned.

As the "hydrocarbon group" of the "hydrocarbon group optionally having substituent(s)" for $Ra^1$, $Ra^2$, $Ra^3$, $Ra^4$ or $Ra^5$, for example, a chain hydrocarbon group, a cyclic hydrocarbon group and the like can be mentioned.

As the chain hydrocarbon group, for example, a linear or branched chain hydrocarbon group having carbon 1 to 10 carbon atoms and the like can be mentioned. Specifically, for example, an alkyl group, an alkenyl group and the like can be mentioned. Of these, an alkyl group is particularly preferable. As the "alkyl group", for example, a $C_{1-10}$ alkyl group such as methyl, ethyl, n-propyl, isopropyl, butyl, isobutyl, sec-butyl, tert-butyl, n-pentyl, isopentyl, neopentyl, n-hexyl, isohexyl and the like, and the like can be mentioned, with preference given to a $C_{1-6}$ alkyl group (e.g., methyl, ethyl, n-propyl, isopropyl, n-butyl, sec-butyl, tert-butyl etc.). As the "alkenyl group", for example, a $C_{2-10}$ alkenyl group such as vinyl, 1-propenyl, allyl, isopropenyl, 1-butenyl, 2-butenyl, 3-butenyl, isobutenyl, sec-butenyl and the like, and the like can be mentioned, with preference given to a $C_{2-6}$ alkenyl group (e.g., vinyl, 1-propenyl, allyl etc.). As the "alkynyl group", for example, a $C_{2-10}$ alkynyl group such as ethynyl, 1-propynyl, propargyl and the like, and the like can be mentioned, with preference given to a $C_{2-6}$ alkynyl group (e.g., ethynyl etc.).

As the cyclic hydrocarbon group, for example, a cyclic hydrocarbon group having 3 to 18 carbon atoms can be mentioned. Specifically, for example, an alicyclic hydrocarbon group, an aromatic hydrocarbon group and the like can be mentioned.

As the "alicyclic hydrocarbon group", for example, a monocyclic or fused polycyclic group consisting of 3 to 10 carbon atoms can be mentioned. Specifically, a cycloalkyl group, a cycloalkenyl group and a bi- or tri-cyclic fused ring of these and a $C_{6-14}$ aryl group (e.g., benzene etc.) and the like, and the like can be mentioned. As the "cycloalkyl group", for example, a $C_{3-6}$ cycloalkyl group such as cyclopropyl, cyclobutyl, cyclopentyl, cyclohexyl and the like, and the like can be mentioned, and as the "cycloalkenyl group", for example, a $C_{3-6}$ cycloalkenyl group such as cyclopropenyl, cyclobutenyl, cyclopentenyl, cyclohexenyl and the like, and the like can be mentioned.

As the "aromatic hydrocarbon group", for example, a monocyclic aromatic hydrocarbon group, a fused polycyclic aromatic hydrocarbon group and the like, which consist of 6 to 18 carbon atoms, can be mentioned. Specifically, a $C_{6-14}$ aryl group such as phenyl, 1-naphthyl, 2-naphthyl, 2-indenyl, 2-anthryl and the like can be mentioned, with preference given to a $C_{6-10}$ aryl group (e.g., phenyl etc.) and the like.

The substituent that the "chain hydrocarbon group" for the "hydrocarbon group optionally having substituent(s)" may have is not particularly limited. For example, a halogen atom, a hydroxyl group, an alkoxy group, an acyloxy group, an alkylthio group, an acylamino group, a carboxyl group, an alkoxycarbonyl group, an oxo group, an alkylcarbonyl group, a cycloalkyl group, an aryl group, an aromatic heterocyclic group and the like can be mentioned. These substituents are substituted on the "chain hydrocarbon group" within the chemically acceptable range, and the number of the substituents is 1 to 5, preferably 1 to 3. When the number of the substituents is not less than 2, the respective substituents may be the same or different.

As the substituent that the "cyclic hydrocarbon group" for the "hydrocarbon group optionally having substituent(s)" may have is not particularly limited. For example, a halogen atom, a hydroxyl group, an alkoxy group, an acyloxy group, an alkylthio group, an alkylsulfonyl group, a mono- or di-alkylamino group, an acylamino group, a carboxyl group, an alkoxycarbonyl group, an alkynylcarbonyl group, an alkyl group, a cycloalkyl group, an aryl group, an aromatic heterocyclic group and the like can be mentioned. These substituents are substituted on the "cyclic hydrocarbon group" within the chemically acceptable range, and the number of the substituents is 1 to 5, preferably 1 to 3. When the number of the substituents is not less than 2, the respective substituents may be the same or different.

As the "halogen atom", for example, fluorine, chlorine, bromine, iodine and the like can be mentioned. As the "alkoxy group", for example, a $C_{1-10}$ alkoxy group such as methoxy, ethoxy, propoxy, isopropoxy, butoxy, isobutoxy, sec-butoxy, pentyloxy, hexyloxy and the like, and the like can be mentioned. As the "acyloxy group", for example, formyloxy, a $C_{1-10}$ alkyl-carbonyloxy (e.g., acetoxy; propionyloxy etc.) and the like can be mentioned. As the "alkylthio group", for example, a $C_{1-10}$ alkylthio group such as methylthio, ethylthio, propylthio, isopropylthio and the like, and the like can be mentioned. As the "alkylsulfonyl group", for example, a $C_{1-10}$ alkylsulfonyl group such as methylsulfonyl, ethylsulfonyl, propylsulfonyl and the like, and the like can be mentioned. As the "acylamino group", for example, formylamino, diformylamino, a mono- or di-$C_{1-10}$ alkyl-carbonylamino (e.g., acetylamino, propionylamino, butyrylamino, diacetylamino etc.) and the like can be mentioned. As the "mono- or di-alkylamino group", those similar to the aforementioned lower alkylamino and di-lower alkylamino can be exemplified. As the "alkoxycarbonyl group", for example, a $C_{1-10}$ alkoxycarbonyl group such as methoxycarbonyl, ethoxycarbonyl, propoxycarbonyl, isopropoxycarbonyl, butoxycarbonyl and the like, and the like can be mentioned. As the "alkylcarbonyl group", for example, a $C_{1-10}$ alkylcarbonyl group such as acetyl, propionyl, butyryl, valeryl and the like, and the like can be mentioned. As the "alkynylcarbonyl group", for example, a $C_{3-10}$ alkynylcarbonyl group such as ethynylcarbonyl, 1-propynylcarbonyl, 2-propynylcarbonyl and the like, and the like can be mentioned. As the "cycloalkyl group", for example, a $C_{3-10}$ cycloalkyl group such as cyclopropyl, cyclobutyl, cyclopentyl, cyclohexyl and the like, and the like can be mentioned. As the "aryl group", for example, a $C_{6-14}$ aryl group such as phenyl, 1-naphthyl, 2-naphthyl and the like, and the like can be mentioned. As the "aromatic heterocyclic group", for example, a mono- to tri-cyclic aromatic heterocyclic groups containing, besides carbon atoms, 1 or 2 kinds of preferably 1 to 4 hetero atoms selected from nitrogen, oxygen and sulfur, and the like can be mentioned. Specifically, for example, thienyl, pyridyl, furylpyrazinyl, pyrimidinyl, imidazolyl, pyrazolyl, thiazolyl, isothiazolyl, oxazolyl, isoxazolyl, pyridazinyl, tetrazolyl, quinolyl, indolyl, isoindolyl and the like can be mentioned. As the "alkyl group", for example, a $C_{1-10}$ alkyl group such as methyl, ethyl, propyl, isopropyl, butyl, sec-butyl, tert-butyl, pentyl and the like, and the like can be mentioned.

The substituent that the aforementioned "hydrocarbon group" may have may futher have 1 to 5, preferably 1 to 3, substituents shown below within the chemically acceptable range. As such substituent, for example, a halogen atom (e.g., fluorine, chlorine, bromine etc.), a hydroxyl group and a $C_{1-6}$ alkoxy group (e.g., methoxy, ethoxy, propoxy, isopropoxy etc.) can be mentioned.

As the lower alkyl group for $Ra^6$ or $Ra^7$, for example, a linear, branched or cyclic alkyl group having 1 to 4 carbon atoms can be mentioned. Specifically, methyl, ethyl, n-propyl, isopropyl, butyl, isobutyl, sec-butyl, tert-butyl, cyclopropyl, cyclobutyl and the like can be mentioned.

The aromatic ring optionally having substituent(s) for Ar is, for example, a monocyclic or bicyclic fused aromatic ring optionally having 1 or more substituents and the like. In addition, an optionally substituted aromatic ring consisting of 5 to 10 atoms containing 0 to 4 hetero atom(s) as ring-constituting atom(s) (where the aromatic ring is bonded to a condensed imidazole ring in the formula (I)-A via a carbon atom rather than a hetero atom) can be also preferably exemplified as Ar.

As the substituent of the aromatic ring optionally having substituent(s) for Ar, a hydroxyl group optionally having a substituent, a thiol group optionally having a substituent, an amino group optionally having substituent(s), an acyl group, a halogen atom or a hydrocarbon group optionally having substituent(s) can be mentioned. As the "hydroxy group optionally having a substituent", the "amino group optionally having substituent(s)", the "acyl group", the "halogen atom" and the "hydrocarbon group optionally having substituent(s)", those exemplified for the above-mentioned $Ra^1$, $Ra^2$, $Ra^3$, $Ra^4$ or $Ra^5$, respectively, can be mentioned.

The compound of the present invention represented by the formula (I)-A may form a salt, and as the salt, acid addition salts such as inorganic acid salts (e.g., hydrochloride, sulfate, hydrobromide, phosphate etc.), organic acid salts (e.g., acetate, trifluoroacetate, succinate, maleate, fumarate, propionate, citrate, tartrate, lactate, oxalate, methanesulfonate, p-toluenesulfonate etc.) and the like can be mentioned.

The compound of the formula (I)-A and a salt thereof may be hydrates, which are encompassed in the present invention. Hereinafter the compound (I)-A also includes salts and hydrates.

The prodrug of compound (I)-A means a compound that is converted to compound (I)-A having a steroid $C_{17,20}$-lyase-inhibitory action in the body by reaction with an enzyme, gastric acid and the like.

As the prodrug of the compound (I)-A, a compound wherein an imidazole nitrogen of the compound (I)-A is acylated or alkylated [e.g., dimethylaminosulfonylated, acetoxymethylated, (5-methyl-2-oxo-1,3-dioxolen-4-yl)methoxycarbonylmethylated, pivaloyloxymethylated or benzyloxymethylated compound etc.]; a compound wherein a hydroxyl group of the compound (I)-A is acylated, alkylated, phosphorylated, sulfated, borated [e.g., compound wherein a hydroxyl group of the compound (I)-A is acetylated, palmitoylated, propanoylated, pivaloylated, succinylated, fumaylated, alanylated or dimethylaminomethylcarbonylated etc.], and the like are preferred. These compounds can be produced by a method known per se.

The prodrug of the compound (I)-A may be as it is or a pharmacologically acceptable salt. As examples of such salt, when the prodrug of the compound (I)-A has an acidic group such as carboxyl group and the like, salts with inorganic bases (e.g., alkali metals such as sodium, potassium and the like, alkaline earth metals such as calcium, magnesium etc., transition metals such as zinc, iron, copper etc., and the like), salts with organic bases (e.g., organic amines such as trimethylamine, triethylamine, pyridine, picoline, ethanolamine, diethanolamine, triethanolamine, dicyclohexylamine, N,N'-dibenzylethylenediamine etc., basic amino acids such as arginine, lysine, ornithine etc., etc.), and the like can be mentioned.

When the prodrug of the compound (I)-A has a basic group such as amino group and the like, salts with inorganic acids and organic acids (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc.), salts with acidic amino acids (e.g., aspartic acid, glutamic acid etc.) and the like can be mentioned.

The prodrug of the compound (I)-A may be a hydrate or a non-hydrate.

While the compound (I)-A has one or more asymmetric carbons in a molecule, both an R configuration compound and an S configuration compound due to the asymmetric carbons are encompassed in the present invention.

As the compound (I)-A, a compound, wherein the absolute configuration of carbon atom bonded by hydroxy group is S configuration, is preferable.

Of the compounds represented by the formula (I)-A, (±)-7-(5-methoxybenzo[b]thiophen-2-yl)-6,7-dihydro-5H-pyrrolo[1,2-c]imidazol-7-ol, (±)-7-(5-fluorobenzo[b]thiophen-2-yl)-6,7-dihydro-5H-pyrrolo[1,2-c]imidazol-7-ol, (±)-7-(4'-fluoro[1,1'-biphenyl]-3-yl)-6,7-dihydro-5H-pyrrolo[1,2-c]imidazol-7-ol, (±)-7-(4'-fluoro[1,1'-biphenyl]-4-yl)-6,7-dihydro-5H-pyrrolo[1,2-c]imidazol-7-ol, (±)-6-(7-hydroxy-6,7-dihydro-5H-pyrrolo[1,2-c]imidazol-7-yl)-N-methyl-2-naphthamide, (±)-N-cyclopropyl-6-(7-hydroxy-6,7-dihydro-5H-pyrrolo[1,2-c]imidazol-7-yl)-2-naphthamide, (±)-N-ethyl-6-(7-hydroxy-6,7-dihydro-5H-pyrrolo[1,2-c]imidazol-7-yl)-2-naphthamide, (±)-N-cyclobutyl-6-(7-hydroxy-6,7-dihydro-5H-pyrrolo[1,2-c]imidazol-7-yl)-2-naphthamide, (±)-6-(7-hydroxy-6,7-dihydro-5H-pyrrolo[1,2-c]imidazol-7-yl)-N-isopropyl-2-naphthamide, (±)-6-(7-hydroxy-6,7-dihydro-5H-pyrrolo[1,2-c]imidazol-7-yl)-2-naphthamide, (+)-7-(5-methoxybenzo[b]thiophen-2-yl)-6,7-dihydro-5H-pyrrolo[1,2-c]imidazol-7-ol, (+)-7-(5-fluorobenzo[b]thiophen-2-yl)-6,7-dihydro-5H-pyrrolo[1,2-c]imidazol-7-ol, (+)-7-(4'-fluoro[1,1'-biphenyl]-3-yl)-6,7-dihydro-5H-pyrrolo[1,2-c]imidazol-7-ol, (+)-7-(4'-fluoro[1,1'-biphenyl]-4-yl)-6,7-dihydro-5H-pyrrolo[1,2-c]imidazol-7-ol, (+)-6-(7-hydroxy-6,7-dihydro-5H-pyrrolo[1,2-c]imidazol-7-yl)-N-methyl-2-naphthamide, (+)-N-cyclopropyl-6-(7-hydroxy-6,7-dihydro-5H-pyrrolo[1,2-c]imidazol-7-yl)-2-naphthamide, (+)-N-ethyl-6-(7-hydroxy-6,7-dihydro-5H-pyrrolo[1,2-c]imidazol-7-yl)-2-naphthamide, (+)-N-cyclobutyl-6-(7-hydroxy-6,7-dihydro-5H-pyrrolo[1,2-c]imidazol-7-yl)-2-naphthamide, (+)-6-(7-hydroxy-6,7-dihydro-5H-pyrrolo[1,2-c]imidazol-7-yl)-N-isopropyl-2-naphthamide, (+)-6-(7-hydroxy-6,7-dihydro-5H-pyrrolo[1,2-c]imidazol-7-yl)-2-naphthamide, (−)-7-(5-methoxybenzo[b]thiophen-2-yl)-6,7-dihydro-5H-pyrrolo[1,2-c]imidazol-7-ol, (−)-7-(5-fluorobenzo[b]thiophen-2-yl)-6,7-dihydro-5H-pyrrolo[1,2-c]imidazol-7-ol, (−)-7-(4′-fluoro[1,1′-biphenyl]-3-yl)-6,7-dihydro-5H-pyr-rolo[1,2-c]imidazol-7-ol,
(−)-7-(4′-fluoro[1,1′-biphenyl]-4-yl)-6,7-dihydro-5H-pyr-rolo[1,2-c]imidazol-7-ol,
(−)-6-(7-hydroxy-6,7-dihydro-5H-pyrrolo[1,2-c]imidazol-7-yl)-N-methyl-2-naphthamide,
(−)-N-cyclopropyl-6-(7-hydroxy-6,7-dihydro-5H-pyrrolo[1,2-c]imidazol-7-yl)-2-naphthamide,
(−)-N-ethyl-6-(7-hydroxy-6,7-dihydro-5H-pyrrolo[1,2-c]imidazol-7-yl)-2-naphthamide,
(−)-N-cyclobutyl-6-(7-hydroxy-6,7-dihydro-5H-pyrrolo[1,2-C]imidazol-7-yl)-2-naphthamide,
(−)-6-(7-hydroxy-6,7-dihydro-5H-pyrrolo[1,2-c]imidazol-7-yl)-N-isopropyl-2-naphthamide,
(−)-6-(7-hydroxy-6,7-dihydro-5H-pyrrolo[1,2-c]imidazol-7-yl)-2-naphthamide and the like are particularly preferable.

As examples of other steroid $C_{17,20}$ lyase inhibitors, the compounds described in WO92/15404, WO93/20097, EP-A288053, EP-A413270, (1H-imidazol-1-yl)methyl-substituted benzimidazole derivatives described in JP-A-64-85975, the carbazole derivatives described in WO94/27989, WO96/14090 and WO97/00257, the azole derivatives described in WO95/09157, the 1H-benzimidazole derivatives described in U.S. Pat. No. 5,491,161, the dihydronaphthalene derivatives described in WO99/18075 and the like can be mentioned.

The compounds having a steroid $C_{17,20}$ lyase inhibitory activity, which are described in each of the above-mentioned publications can be produced by the method disclosed in each publication.

C. DPP-IV Inhibitor

In the present specification, the DPP-IV inhibitor means a compound that inhibits an enzyme activity of DPP-IV [Classification by the International Union of Biochemical and, Molecular Biology (IUBMB): EC3.4.14.5]. The compound may be peptidic or non-peptidic.

In addition, the DPP-IV inhibitor may have different forms between before and after administration to living organisms, as long as the DPP-IV inhibitory activity is maintained. In other words, the DPP-IV inhibitor may be an "active metabolite" having a DPP-IV inhibitory activity of a structure that changed due to the metabolism in living organisms. Furthermore, the DPP-IV inhibitor may be a "prodrug" that changes to an active form by reaction with enzyme, gastric acid and the like under physiological conditions in living organisms.

As specific examples of the DPP-IV inhibitor, the following compounds [1]-[8] can be mentioned.

[1] A compound described in WO02/062764, which is represented by the formula:

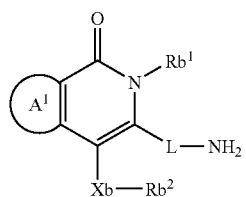

(I)-B wherein ring $A^1$ is an optionally substituted 5- to 10-membered aromatic ring,
$Rb^1$ and $Rb^2$ are the same or different and each is an optionally substituted hydrocarbon group or an optionally substituted heterocyclic group,
Xb is a bond, —O—, —S—, —SO—, —$SO_2$— or —$NRb^3$— ($Rb^3$ is a hydrogen atom or an optionally substituted hydrocarbon group);
L is a divalent hydrocarbon group, or a salt thereof.

As the salt of the compound represented by the formula (I)-B, a pharmacologically acceptable salt is preferable. As such salt, for example, salts with inorganic bases, salts with organic bases, salts with inorganic acids, salts with organic acids, salts with basic or acidic amino acids and the like can be mentioned.

As preferable examples of the salts with inorganic bases, alkali metal salts such as sodium salt, potassium salt and the like; alkaline earth metal salts such as calcium salt, magnesium salt and the like; aluminum salt; ammonium salt and the like can be mentioned.

As preferable examples of the salts with organic bases, salts with trimethylamine, triethylamine, pyridine, picoline, ethanolamine, diethanolamine, triethanolamine, dicyclohexylamine, N,N-dibenzylethylenediamine and the like can be mentioned.

As preferable examples of the salts with inorganic acids, salts with hydrochloric acid, hydrobromic acid, nitric acid, sulfuric acid, phosphoric acid and the like can be mentioned.

As preferable examples of the salts with organic acids, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like can be mentioned.

As preferable examples of the salts with basic amino acids, salts with arginine, lysine, ornithine and the like can be mentioned.

As preferable examples of the salts with acidic amino acids, salts with aspartic acid, glutamic acid and the like can be mentioned.

The compound represented by the formula (I)-B may be a non-hydrate or a hydrate, or a prodrug.

As preferable examples of the compound represented by the formula (I)-B, the following compounds can be mentioned.

(Compound I-a)
A compound wherein
ring $A^1$ is a benzene ring optionally having 1 or 2 substituents selected from
1) a cyano group;
2) a $C_{1-10}$ alkyl group (preferably ethyl) or a $C_{2-10}$ alkenyl group (preferably ethenyl), each optionally substituted by carbamoyl group or carboxyl group;
3) an optionally substituted hydroxy group [preferably an alkoxy group having 1 to 10 carbon atoms (preferably methoxy, isopropoxy) optionally having 1 to 3 substituents selected from a carbamoyl group, a carboxyl group and an alkoxycarbonyl group having 2 to 5 carbon atoms (preferably methoxycarbonyl); a hydroxy group; an aralkyloxy group having 7 to 13 carbon atoms (preferably benzyloxy)] [more preferably carbamoylmethoxy];
4) an acyl group [preferably a $C_{1-6}$ alkyl-carbonyl (preferably acetyl), a carbamoyl, a mono- or di-($C_{1-6}$ alkyl optionally having 1 to 3 substituents selected from a halogen atom and a $C_{1-6}$alkoxy-carbonyl)-carbamoyl (preferably methylcarbamoyl, ethylcarbamoyl, propylcarbamoyl, dimethylcarbamoyl, trifluoroethylcarbamoyl, ethoxycarbonylmethylcarbamoyl and the like), a $C_{3-10}$ cycloalkyl-carbamoyl (preferably cyclopropylcarbamoyl), a $C_{7-13}$ aralkyl-carbamoyl (preferably benzylcarbamoyl), a nitrogen-containing heterocycle-carbonyl (preferably pyrrolidinylcarbonyl, piperidinocarbonyl) optionally substituted by hydroxy, a $C_{1-6}$ alkylsulfonyl (preferably methylsulfonyl), a C$_{1-6}$ alkylsulfinyl (preferably methylsulfinyl), a carboxyl, a C$_{1-6}$ alkoxy-carbonyl (preferably methoxycarbonyl), thiocarbamoyl];
5) an optionally substituted amino group (preferably carbamoylamino);
6) an optionally substituted thiol group [preferably an alkylthio group having 1 to 10 carbon atoms (preferably methylthio) optionally substituted by carbamoyl group;
7) an optionally substituted heterocyclic group [preferably an aromatic heterocyclic group (preferably furyl, thienyl, oxazolyl, oxadiazolyl, thiazolyl, tetrazolyl, pyridyl, pyrrolyl, triazolyl) or a non-aromatic heterocyclic group (preferably dioxoisoindole, 5-oxoxadiazol-3-yl, 5-oxothiadiazol-3-yl), each optionally having 1 or 2 substituents selected from a C$_{1-6}$ alkyl group optionally substituted by 1 to 3 halogen atoms (preferably methyl, trifluoromethyl), a carboxyl group, an alkoxycarbonyl group having 2 to 8 carbon atoms (preferably ethoxycarbonyl), a cyano group, a carbamoyl group, an amino group, a mono- or di-C$_{2-10}$ alkanoylamino group (e.g., acetylamino, isopentanoylamino), a C$_{1-10}$ alkoxy-carbonylamino group (e.g., methoxycarbonylamino), a carbamoylamino group, a mono- or di-C$_{1-10}$ alkyl-carbamoylamino group (e.g., methylcarbamoylamino, dimethylcarbamoylamino), a C$_{6-14}$ arylcarbonylamino group (e.g., benzoylamino), a C$_{3-10}$ cycloalkyl-carbonylamino group, a C$_{7-13}$ aralkyloxy-carbonylamino group, a mono- or di-C$_{1-10}$ alkylsulfonylamino group (e.g., methylsulfonylamino, dimethylsulfonylamino), a C$_{6-14}$ arylsulfonylamino group and a C$_{1-6}$ alkoxy-carbamoylamino group (e.g., methoxycarbamoylamino)]; and
8) an amidino group;
Rb$^1$ is an alkyl group having 4 to 10 carbon atoms (preferably isobutyl, neopentyl) or a cycloalkylalkyl group having 4 to 10 carbon atoms (preferably cyclopropylmethyl);
Rb$^2$ is an aryl group having 6 to 14 carbon atoms (preferably phenyl) optionally having 1 or 2 substituents selected from a halogen atom (preferably fluorine, chlorine) and a C$_{1-6}$ alkyl (preferably methyl);
Xb is a bond; and
L is a C$_{1-10}$ alkylene (preferably —CH$_2$—)
(Compound I-b)
  A compound wherein
ring A$^1$ is a benzene ring optionally having 1 or 2 substituents selected from
1) a C$_{1-10}$ alkyl group (preferably ethyl) or a C$_{2-10}$ alkenyl group (preferably ethenyl), each optionally substituted by alkoxycarbonyl group having 2 to 8 carbon atoms (preferably ethoxycarbonyl) or carbamoyl group;
2) an optionally substituted hydroxy group [preferably an alkoxy group having 1 to 10 carbon atoms (preferably methoxy) optionally substituted by carbamoyl group; more preferably carbamoylmethoxy];
3) an acyl group (preferably carbamoyl, thiocarbamoyl, carboxyl);
4) an optionally substituted heterocyclic group [preferably an aromatic heterocyclic group (preferably furyl, thienyl, oxazolyl, oxadiazolyl, thiazolyl, tetrazolyl, pyridyl, pyrrolyl, triazolyl) or a non-aromatic heterocyclic group (preferably 5-oxoxadiazol-3-yl), each optionally having 1 or 2 substituents selected from a C$_{1-6}$ alkyl group (preferably methyl), a carboxyl group, an alkoxycarbonyl group having 2 to 8 carbon atoms (preferably ethoxycarbonyl), a cyano group, a carbamoyl group, an amino group, a mono- or di-C$_{2-10}$ alkanoylamino group (e.g., acetylamino, isopentanoylamino), a C$_{1-10}$ alkoxy-carbonylamino group (e.g., methoxycarbonylamino), a carbamoylamino group, a mono- or di-C$_{1-10}$ alkyl-carbamoylamino group (e.g., methylcarbamoylamino, dimethylcarbamoylamino), a C$_{6-14}$ aryl-carbonylamino group (e.g., benzoylamino), a C$_{3-10}$ cycloalkyl-carbonylamino group, a C$_{7-13}$ aralkyloxy-carbonylamino group, a mono- or di-C$_{1-10}$ alkylsulfonylamino group (e.g., methylsulfonylamino, dimethylsulfonylamino), a C$_{6-14}$ arylsulfonylamino group and a C$_{1-6}$ alkoxy-carbamoylamino group (e.g., methoxycarbamoylamino)];
Rb$^1$ is an alkyl group having 4 to 10 carbon atoms (preferably isobutyl, neopentyl) or a cycloalkylalkyl group having 4 to 10 carbon atoms (preferably cyclopropylmethyl);
Rb$^2$ is an alkyl group having 1 to 10 carbon atoms (preferably butyl) optionally substituted by 1 to 3 halogen atoms;
Xb is —O—;
L is a C$_{1-10}$ alkylene (preferably —CH$_2$—).
  Of the compounds represented by the formula (I)-B, 2-[3-(aminomethyl)-4-butoxy-2-isobutyl-1-oxo-1,2-dihydro-6-isoquinolyl]-1,3-thiazole-4-carbonitrile;
2-[3-(aminomethyl)-4-butoxy-2-isobutyl-1-oxo-1,2-dihydro-6-isoquinolyl]-1,3-thiazole-4-carboxylic acid;
2-[3-(aminomethyl)-4-butoxy-2-isobutyl-1-oxo-1,2-dihydro-6-isoquinolyl]-1,3-thiazole-4-carboxamide;
ethyl 2-[3-(aminomethyl)-4-butoxy-2-isobutyl-1-oxo-1,2-dihydro-6-isoquinolyl]-1,3-thiazole-4-carboxylate;
(E)-3-[3-(aminomethyl)-4-butoxy-2-isobutyl-1-oxo-1,2-dihydro-6-isoquinolyl]-2-propenamide;
(E)-3-[3-(aminomethyl)-2-isobutyl-4-phenyl-1-oxo-1,2-dihydro-6-isoquinolyl]-2-propenamide;
3-(aminomethyl)-2-isobutyl-1-oxo-4-phenyl-1,2-dihydro-6-isoquinolinecarboxamide;
2-{[3-(aminomethyl)-2-isobutyl-4-phenyl-1-oxo-1,2-dihydro-6-isoquinolyl[oxy}acetamide and the like are particularly preferable.
[2] N-(N'-substituted-glycyl)-2-cyano-pyrrolidine derivatives such as (2S)-1-{{{2-[(5-cyanopyridin-2-yl)amino]ethyl}amino}acetyl}-2-cyano-pyrrolidine (DPP-728) (described in WO98/19998) represented by the formula

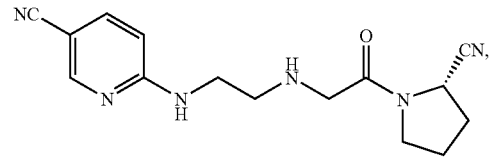

(2S)-1-{[(3-hydroxy-1-adamantyl)amino]acetyl}-2-cyano-pyrrolidine (LAF237) (described in WO00/34241) represented by the formula

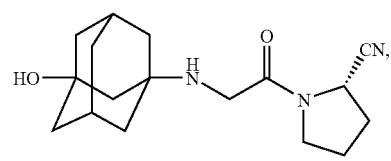

(2S)-1-{{{2-[(1-pyrimidin-2-ylpiperidin-4-yl}amino}acetyl}-2-cyano-pyrrolidine (described in WO02/30890),
(2S)-1-{{{2-[(pyrazin-2-yl)amino]ethyl}amino}acetyl}-2-cyano-pyrrolidine (described in WO02/51836), and the like.

[3] Thiazolidine or pyrrolidine derivatives (described in WO01/72290 and the like) such as L-threo-isoleucylthiazolidine (P32/98) represented by the formula

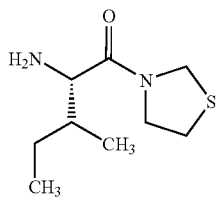

L-allo-isoleucylthiazolidine, L-threo-isoleucylpyrrolidine, L-allo-isoleucylpyrrolidine, L-valylpyrrolidine and the like.

[4] N-substituted-2-cyanopyrrole and 2-cyanopyrroline derivatives described in WO01/55105, with preference given to (S,S)-1-(2-amino-3,3-dimethylbutyryl)-2,5-dihydro-1H-pyrrole-2-carbonitrile.

[5] Heterocyclic compounds described in WO02/02560, with preference given to 7-benzyl-8-[6-(hydroxymethyl)-1,4-diazepan-1-yl]-1,3-dimethyl-3,7-dihydropurine-2,6-dione.

[6] Pyrrolidine derivatives condensed with cyclopropane described in WO01/68603, with preference given to (1S,3S,5S)-2-[(2S)-2-amino-3,3-dimethylbutyryl]-3-cyano-2-azabicyclo[3.1.0]hexane.

[7] Proline derivatives described in WO02/14271, with preference given to (2S)-1-[(2S,4S)-4-(3-chloro-4-cyanophenyl)amino-2-pyrrolidinylcarbonyl]-2-cyanopyrrolidine.

[8] Cyanopyrrolidine derivatives described in WO02/38541, with preference given to (2S,4S)-1-[(2S,3S)-2-amino-3-methyl-pentanoyl]-2-cyano-4-fluoropyrrolidine.

The compounds having a DPP-IV inhibitory activity, which are described in each of the above-mentioned publications can be produced by the method disclosed in each publication.

The content of the active ingredient relative to the whole release-controlled part A is, for example, about 1-100 wt %, preferably about 10—about 90 wt %, more preferably about 30—about 80 wt %.

As the pharmacologically acceptable carrier contained in the release-controlled part A, various organic or inorganic carrier substances conventionally used as preparation materials and, for example, excipient, lubricant, binder, disintegrant and the like can be mentioned. Where necessary, preparation additives such as preservative, antioxidant, stabilizer, coloring agent, sweetening agent and the like can be also used.

As preferable examples of the excipient, lactose, sucrose, D-mannitol, D-sorbitol, starch, pregelatinized starch, dextrin, crystalline cellulose, low-substituted hydroxypropylcellulose, carboxymethylcellulose sodium, gum arabic, dextrin, pullulan, light silicic anhydride, synthetic aluminum silicate, magnesium aluminometasilicate and the like can be mentioned.

As preferable examples of the lubricant, magnesium stearate, calcium stearate, talc, colloid silica and the like can be mentioned.

As preferable examples of the binder, pregelatinized starch, sucrose, gelatin, gum arabic, methylcellulose, carboxymethylcellulose, carboxymethylcellulose sodium, crystalline cellulose, sucrose, D-mannitol, trehalose, dextrin, pullulan, hydroxypropylcellulose, hydroxypropylmethylcellulose, polyvinylpyrrolidone and the like can be mentioned.

As preferable examples of the disintegrant, lactose, sucrose, starch, carboxymethylcellulose, carboxymethylcellulose calcium, croscarmellose sodium, sodium carboxymethyl starch, light silicic anhydride, low-substituted hydroxypropylcellulose (L-HPC (trade name: manufactured by Shin-Etsu Chemical Co., Ltd.)) and the like can be mentioned.

As preferable examples of the preservative, p-oxybenzoates, chlorobutanol, benzyl alcohol, phenethyl alcohol, dehydroacetic acid, sorbic acid and the like can be mentioned.

As preferable examples of the antioxidant, sulfite, ascorbate and the like can be mentioned.

Preparations and the like wherein the active ingredient is the above-mentioned PPI preferably contain a basic inorganic salt as a stabilizer.

As the basic inorganic salt to be used in the present invention, basic inorganic salts of sodium, potassium, magnesium or calcium can be mentioned, with preference given to basic inorganic salts of magnesium or calcium. More preferred is a basic inorganic salt of magnesium. These may be hydrates or solvates. In the following examples, hydrates and solvates are also included, though not particularly indicated.

As the basic inorganic salt of sodium, for example, sodium carbonate, sodium hydrogencarbonate, sodium hydroxide and the like can be mentioned.

As the basic inorganic salt of potassium, for example, potassium carbonate, potassium hydrogencarbonate, potassium hydroxide and the like can be mentioned.

As the basic inorganic salt of magnesium, for example, heavy magnesium carbonate, magnesium carbonate, magnesium oxide, magnesium hydroxide, magnesium aluminometasilicate, magnesium silicate, magnesium aluminate, synthetic hydrotalcite [$Mg_6Al_2(OH)_{16}.CO_3.4H_2O$] and aluminum magnesium hydroxide [$2.5MgO.Al_2O_3.xH_2O$], preferably heavy magnesium carbonate, magnesium carbonate, magnesium oxide, magnesium hydroxide and the like can be mentioned.

As the basic inorganic salt of calcium, precipitated calcium carbonate, calcium hydroxide and the like can be mentioned.

As the basic inorganic salt, heavy magnesium carbonate, magnesium carbonate, magnesium oxide, magnesium hydroxide and the like can be more preferably mentioned.

The basic inorganic salt to be used in the present invention may be any as long as its 1% aqueous solution or suspension shows basic pH (not less than pH 7).

The basic inorganic salts may contain one or more kinds thereof in combination, and the amount to be added is about 0.2—about 0.6 part by weight, preferably about 0.2—about 0.4 part by weight per 1 part by weight of PPI (benzimidazole compound and the like). Particularly, when PPI is lansoprazole or an optically active form thereof, a basic inorganic salt (preferably basic inorganic salt of magnesium or calcium, more preferably magnesium carbonate) is preferably contained in about 0.2—about 0.4 part by weight per 1 part by weight of PPI.

As preferable examples of the coloring agent, water-soluble edible tar pigments (e.g., foodcolors such as Food Red Nos. 2 and 3, Food yellow Nos. 4 and 5, Food Blue Nos. 1 and 2 and the like), water insoluble lake pigments (e.g., aluminum salt of the aforementioned water-soluble edible tar pigment), natural pigments (e.g., β-carotene, chlorophyll, red iron oxide) and the like can be mentioned.

As preferable examples of the sweetening agent, saccharin sodium, dipotassium glycyrrhizinate, aspartam, stevia and the like can be mentioned.

When the release-controlled part A is a sustained release part, the release mechanism of an active ingredient is not particularly limited, and any of release by passive diffusion from the inside of a base material, release caused by erosion of a base material, release in response to changes in the environmental pH, release utilizing the inner pressure caused by the swelling of a base material due to the absorption of the environmental moisture and the like may be employed.

When release by passive diffusion is to be utilized, the release-controlled part A further contains, in addition to the active ingredient (preferably further containing a pharmacologically acceptable carrier), a hydrophilic polymer, a liposoluble base material, or other sustained-release base materials.

In the present specification, a "hydrophilic polymer" means a polymer capable of controlling release of an active ingredient by becoming a hydrogel upon absorption of water and diffusing the active ingredient contained in the preparation, or by dissolution of itself in water.

In the controlled release composition of the present invention, the release rate of the active ingredient from each release-controlled part can be freely adjusted by controlling the viscosity and amount of addition of the hydrophilic polymer to be used as a base material.

The viscosity of the hydrophilic polymer contained in the release-controlled part A is, for example, preferably not less than 1 mPa·s, more preferably not less than 4 mPa·s, based on the viscosity of a 2 wt % aqueous solution (measurement temperature: 20° C.)

Specific examples of the hydrophilic polymer include hydroxypropylcellulose (HPC) such as HPC-SSL (trade name, manufactured by Nippon Soda Co., Ltd.) (viscosity of 2 wt % aqueous solution at 20° C.: 2.0-2.9 mPa·s), HPC-SL (trade name, manufactured by Nippon Soda Co., Ltd.) (viscosity of 2 wt % aqueous solution at 20° C.: 3.0-5.9 mPa·s), HPC-L (trade name, manufactured by Nippon Soda Co., Ltd.) (viscosity of 2 wt % aqueous solution at 20° C.: 6.0-10.0 mPa·s), HPC-M (trade name, manufactured by Nippon Soda Co., Ltd.) (viscosity of 2 wt % aqueous solution at 20° C.: 150-400 mPa·s), HPC-H (trade name, manufactured by Nippon Soda Co., Ltd.) (viscosity of 2 wt % aqueous solution at 20° C.: 1000-4000 mPa·s) and the like; hydroxypropylmethylcellulose such as TC-5S (trade name, manufactured by Shin-Etsu Chemical Co., Ltd.) (viscosity of 2 wt % aqueous solution at 20° C.: about 15 mPa·s), TC-5R (trade name, manufactured by Shin-Etsu Chemical Co., Ltd.) (viscosity of 2 wt % aqueous solution at 20° C.: about 6 mPa·s), TC-5E (trade name, manufactured by Shin-Etsu Chemical Co., Ltd.) (viscosity of 2 wt % aqueous solution at 20° C.: about 3 mPa·s), TC-5MW (trade name, manufactured by Shin-Etsu Chemical Co., Ltd.) (viscosity of 2 wt % aqueous solution at 20° C.: about 4 mPa·s), METOLOSE 60SH-50 (trade name, manufactured by Shin-Etsu Chemical Co., Ltd.) (viscosity of 2 wt % aqueous solution at 20° C.: about 50 mPa·s), METOLOSE 65SH-50 (trade name, manufactured by Shin-Etsu Chemical Co., Ltd.) (viscosity of 2 wt % aqueous solution at 20° C.: about 50 mPa·s), METOLOSE 90SH-100 (trade name, manufactured by Shin-Etsu Chemical Co., Ltd.) (viscosity of 2 wt % aqueous solution at 20° C.: about 100 mPa·s), METOLOSE 65SH-400 (trade name, manufactured by Shin-Etsu Chemical Co., Ltd.) (viscosity of 2 wt % aqueous solution at 20° C.: about 400 mPa·s), METOLOSE 90SH-400 (trade name, manufactured by Shin-Etsu Chemical Co., Ltd.) (viscosity of 2 wt % aqueous solution at 20° C.: about 400 mPa·s), METOLOSE 65SH-1500 (trade name, manufactured by Shin-Etsu Chemical Co., Ltd.) (viscosity of 2 wt % aqueous solution at 20° C.: about 1500 mPa·s), METOLOSE 60SH-4000 (trade name, manufactured by Shin-Etsu Chemical Co., Ltd.) (viscosity of 2 wt % aqueous solution at 20° C.: about 4000 mPa·s), METOLOSE 65SH-4000 (trade name, manufactured by Shin-Etsu Chemical Co., Ltd.) (viscosity of 2 wt % aqueous solution at 20° C.: about 4000 mPa·s), METOLOSE 90SH-4000 (trade name, manufactured by Shin-Etsu Chemical Co., Ltd.) (viscosity of 2 wt % aqueous solution at 20° C.: about 4000 mPa·s), METOLOSE 90SH-30000 (trade name, manufactured by Shin-Etsu Chemical Co., Ltd.) (viscosity of 2 wt % aqueous solution at 20° C.: about 30000 mPa·s) and the like; methylcellulose such as METOLOSE SM15 (trade name, manufactured by Shin-Etsu Chemical Co., Ltd.) (viscosity: about 15 mPa·s, 2 wt % aqueous solution, 20° C.), METOLOSE SM25 (trade name, manufactured by Shin-Etsu Chemical Co., Ltd.) (viscosity of 2 wt % aqueous solution at 20° C.: about 25 mPa·s), METOLOSE SM100 (trade name, manufactured by Shin-Etsu Chemical Co., Ltd.) (viscosity of 2 wt % aqueous solution at 20° C.: about 100 mPa·s), METOLOSE SM400 (trade name, manufactured by Shin-Etsu Chemical Co., Ltd.) (viscosity of 2 wt % aqueous solution at 20° C.: about 400 mPa·s), METOLOSE SM1500 (trade name, manufactured by Shin-Etsu Chemical Co., Ltd.) (viscosity of 2 wt % aqueous solution at 20° C.: about 1500 mPa·s), METOLOSE SM4000 (trade name, manufactured by Shin-Etsu Chemical Co., Ltd.) (viscosity of 2 wt % aqueous solution at 20° C.: about 4000 mPa·s), METOLOSE SM8000 (trade name, manufactured by Shin-Etsu Chemical Co., Ltd.) (viscosity of 2 wt % aqueous solution at 20° C.: about 8000 mPa·s) and the like; polyethylene oxide such as WSR N-12K (trade name, manufactured by Union Carbide Corporation) (viscosity of 2 wt % aqueous solution at 20° C.: 400-800 mPa·s), WSR N-60K (trade name, manufactured by Union Carbide Corporation) (viscosity of 2 wt % aqueous solution at 20° C.: 2000-4000 mPa·s), WSR 301 (trade name, manufactured by Union Carbide Corporation) (viscosity of 1 wt % aqueous solution at 25° C.: 1500-4500 mPa·s), WSR Coagulant (trade name, manufactured by Union Carbide Corporation) (viscosity of 1 wt % aqueous solution at 25° C.: 4500-7500 mPa·s), WSR 303 (trade name, manufactured by Union Carbide Corporation) (viscosity of 1 wt % aqueous solution at 25° C.: 7500-10000 mPa·s), WSR 308 (trade name, manufactured by Union Carbide Corporation) (viscosity of 1 wt % aqueous solution at 25° C.: 10000-15000 mPa·s) and the like; sodium carboxymethylcellulose such as Sunrose F-150MC (trade name, manufactured by Nippon Paper Chemicals Co., Ltd.) (viscosity of 1 wt % aqueous solution at 25° C.: 1200-1800 mPa·s), Sunrose F-300MC (trade name, manufactured by Nippon Paper Chemicals, Co., Ltd.) (viscosity of 1 wt % aqueous solution at 25° C.: 2500-3000 mPa·s), Sunrose F-1000MC (trade name, manufactured by Nippon Paper Chemicals, Co., Ltd.) (viscosity of 1 wt % aqueous solution at 25° C.: 8000-12000 mPa·s) and the like; and the like. Two or more kinds of these hydrophilic polymers may be mixed at appropriate ratios for use.

The content of the hydrophilic polymer relative to the whole release-controlled part A is, for example, about 5-about 90 wt %, preferably about 10—about 80 wt %.

As the liposoluble base material, for example, carnauba wax, hydrogenated castor oil, hydrogenated rape seed oil, polyglycerol esters of fatty acids and the like can be mentioned.

As other sustained-release base material, for example, cellulose polymers such as ethylcellulose and the like; aminoalkyl methacrylate copolymer RS, ethyl acrylate-methyl methacrylate copolymer suspension (acrylic acid polymers such as Eudragit NE and the like) and the like can be mentioned.

When the release caused by erosion of a base material is to be utilized, the release-controlled part A can further contain, in addition to the active ingredient (preferably further containing a pharmacologically acceptable carrier), for example, an amphiphilic base material such as polyglycolated glyceride (e.g., Gelucire50/13 (trade name, manufactured by GATTEFOSSE) and the like.

When the active ingredient is released in response to the changes in the environmental pH, the release-controlled part A can further contain, in addition to the active ingredient (preferably further containing a pharmacologically acceptable carrier), for example, enteric base materials [e.g., acrylic acid polymers such as methacrylic copolymer L [Eudragit L (trade name, manufactured by Rohm Pharma)], methacrylic copolymer LD [Eudragit L-30D55 (trade name, manufactured by Rohm Pharma)], methacrylic copolymer S [Eudragit S (trade name, manufactured by Rohm Pharma)] and the like, hydroxypropylmethylcellulose polymers [hydroxypropylmethylcellulose phthalate (trade name: HPMCP, Shin-Etsu Chemical), hydroxypropylmethylcellulose acetate succinate (trade name: HPMCAS, Shin-Etsu AQOAT, Shin-Etsu Chemical)], carboxymethylethylcellulose (trade name: CMEC, Freund Corporation), cellulose acetate phthalate (trade name: CAP, Wako Pure Chemical Industries, Ltd.) and the like] and the like.

As one that releases the active ingredient utilizing the inner pressure caused by the swelling of the inside of the composition due to the absorption of the environmental moisture, for example, one utilizing an OROS system (trade name, manufactured by ALZA) and the like can be mentioned.

When the active ingredient is weak acidic—weak alkaline and shows relatively low water solubility, and dissolution and absorption of the active ingredient at the lower small intestine—near the large intestine may become insufficient when used as an oral preparation, a pH adjusting gent and other dissolution aids may be added to the release-controlled part A for the purpose of controlling the dissolution behavior from the release-controlled part A. Variation in the drug dissolution property due to the environmental pH can be reduced by the use of a pH adjusting agent and the like. Suppression of the variation in the drug dissolution property caused by environmental pH is extremely significant in achieving constant efficacy in various patients, because in vivo pH of respective patients may vary.

As the pH adjusting agent, for example, organic acids such as citric acid, tartaric acid, ascorbic acid, malic acid, fumaric acid, malonic acid, succinic acid, maleic acid, aspartic acid, glutamic acid, edetic acid and the like, organic acid salts such as sodium edetate, dibasic sodium citrate, potassium hydrogentartrate and the like, inorganic acids such as phosphoric acid, hydrochloric acid, sulfuric acid and the like, inorganic acid salts such as potassium hydrogen phosphate and the like can be mentioned. Of these, citric acid, tartaric acid, ascorbic acid and the like are preferable. As other dissolution aids, for example, macrogol 4000, macrogol 6000, sodium lauryl sulfate and the like can be mentioned.

The content of the pH adjusting agent and other dissolution aids relative to the whole release-controlled part A varies depending on the kind and the content of the active ingredient, the size of the preparation and the like, it is, for example, 0.5-50 wt %, preferably 2-30 wt %.

The release-controlled part A can take, but not limited to, the form such as tablets, granules, fine granules, pellets, capsules, crystals, pastes, liquids and the like.

When the release-controlled part A is a pharmaceutical composition, it can be prepared by a production method conventionally used in the preparation technical field. For example, when the release-controlled part A is an immediate release part, an active ingredient and a pharmacologically acceptable carrier are mixed and molded, and when the release-controlled part A is a sustained release part, an active ingredient, a pharmacologically acceptable carrier and a hydrophilic polymer are mixed and molded. The dispersion mode of the active ingredient in the molded product may be uniform dispersion or nonuniform dispersion, with preference given to uniform dispersion.

The release-controlled part A can also be prepared by, in addition to the above-mentioned, for example, tumbling granulation methods, in which an active ingredient or a mixture of an active ingredient with hydrophilic polymer, an excipient, lubricant and the like is applied in small portions onto the surface of an inert carrier particle as a core, while spraying a binder dissolved in a suitable solvent such as water, lower alcohol (e.g., methanol, ethanol and the like) and the like, pan coating methods, fluidized bed coating methods or melt granulating methods. As the inert carrier particle, for example, those made of sucrose, lactose, starch, crystalline cellulose or waxes can be used, and the average particle size thereof is preferably from about 100 μm to about 1500 μm.

When the release-controlled part A is a tablet, it can be prepared by, for example, adding the above-mentioned excipient, disintegrant, binder, lubricant and the like to an active ingredient (and a hydrophilic polymer), mixing (where, necessary, further kneading) them and compression molding the mixture.

The release-controlled part B is a functional unit that acts as a (first) sustained release part (corresponding to dissolution of an oral preparation in the upper small intestine—near the lower small intestine) in the controlled release composition of the present invention where the release of the active ingredient is controlled in two or more steps.

The release rate $V_B$ of the active ingredient from the release-controlled part B is not particularly limited as long as it satisfies the definition of the above-mentioned sustained-release, and lower than the release rate $V_A$ of the active ingredient from the release-controlled part A. Preferably, the dissolution rate of an active ingredient at 1 hr after the start of the test is about 5—about 100%, more preferably about 10-50%, when the Japanese Pharmacopoeia Dissolution Test Method 2 (Paddle Method) is performed using a suitable test solution (500 mL or 900 mL) at a paddle rotation of 100 rpm. As the test solution here, those similar to the above-mentioned are used.

Alternatively, the release profile of the active ingredient from the release-controlled part B is also characterized in that the sustained release of the active ingredient from the release-controlled part B preferably occurs for about 1 hr—about 118 hr. more preferably about 2 hr—about 10 hr, when the controlled release composition of the present invention is applied to the intended use (e.g., upon oral administration in the case of an oral preparation).

The release-controlled part B is not particularly limited in the release mechanism of the active ingredient as long as it contains an active ingredient the same as or different from the active ingredient contained in the release-controlled part A, the release rate of the active ingredient satisfies the above-mentioned conditions, and the release of the active ingredient precedes the release of the active ingredient contained in the release-controlled part A, and any, which is similar to those mentioned above for the release-controlled part A, can be used.

For example, as a composition wherein the active ingredient is released from the base material by passive diffusion, matrix compositions using the aforementioned hydrophilic polymers (e.g., hydroxypropylcellulose, hydroxypropylmethylcellulose, polyethylene oxide and the like), matrix compositions using liposoluble base materials (e.g., carnauba wax, hydrogenated castor oil, hydrogenated rape seed oil, polyglycerol esters of fatty acids and the like), matrix compositions using sustained-release base material (e.g., cellulose polymers such as ethylcellulose and the like; aminoalkyl methacrylate copolymer RS, ethyl acrylate-methyl methacrylate copolymer suspensions [acrylic acid polymers such as Eudragit NE and the like] and the like), and the like can be mentioned.

As a composition where the active ingredient is released caused by the erosion of a base material, for example, matrix compositions using an amphiphilic base material such as polyglycolated glyceride (e.g., Gelucire 50/13 (trade name, manufactured by GATTEFOSSE) and the like, and the like can be mentioned.

As a composition where the active ingredient is released in response to the changes in the environmental pH, for example, matrix compositions using enteric base materials [e.g., acrylic acid polymers such as methacrylic copolymer L [Eudragit L (trade name, manufactured by Rohm Pharma)], methacrylic copolymer LD [Eudragit L-30D55 (trade name, manufactured by Rohm Pharma)], methacrylic copolymer S [Eudragit S (trade-name, manufactured by Rohm Pharma)] and the like, hydroxypropylmethylcellulose polymers [hydroxypropylmethylcellulose phthalate (trade name: HPMCP, Shin-Etsu Chemical), hydroxypropylmethylcellulose acetate succinate (trade name: HPMCAS, Shin-Etsu AQOAT, Shin-Etsu Chemical)], carboxymethylethylcellulose (trade name: CMEC, Freund Corporation), cellulose acetate phthalate (trade name: CAP, Wako Pure Chemical Industries, Ltd.) and the like], and the like can be mentioned.

As a composition where the active ingredient is released utilizing the inner pressure caused by the swelling of a base material due to the absorption of the environmental moisture, for example, one utilizing an OROS system (trade name, manufactured by ALZA) and the like can be mentioned.

The active ingredient contained in the release-controlled part B is preferably the same as the one contained in the release-controlled part A. When the active ingredient contained in the release-controlled part B is the same as the one contained in the release-controlled part A, those mentioned above, preferably PPI, steroid $C_{17,20}$ lyase inhibitor and DPP-IV inhibitor, more preferably PPI, can be exemplified. As used herein, by the "same" is meant that the active ingredients contained in the both release-controlled parts are functionally the same. For example, in the case of PPI, the active ingredients contained in each release-controlled part may be the same compound or different compounds as long as they have a PPI activity.

On the other hand, when the active ingredient contained in the release-controlled part B is different from the active ingredient contained in the release-controlled part A, one that can be a combination agent aiming at an addition or synergistic effect of efficacy, reduction of side effects and the like is preferable. For example, in the case of a DPP-IV inhibitor, it can be used in combination with drugs such as a therapeutic agent for diabetes, a therapeutic agent for diabetic complications, an antihyperlipemia agent, an antihypertensive agent, an antiobestic agent, a diuretic, an antithrombotic agent and the like (hereinafter to be abbreviated as a combination drug).

The dose of the combination drug can be determined as appropriate based on the dose clinically employed. The proportion of the DPP-IV inhibitor and a combination drug can be appropriately determined depending on the administration subject, administration route, target disease, condition, combination and the like. When, for example, the administration subject is a human, a combination drug is used in an amount of 0.01-100 parts by weight per 1 part by weight of the DPP-IV inhibitor.

Examples of the above-mentioned therapeutic agent for diabetes include insulin preparations (e.g., animal insulin preparations extracted from pancreas of cattle, swine; human insulin preparations synthesized by genetic engineering techniques using *Escherichia coli* or yeast; zinc insulin; protamine zinc insulin; fragments or derivatives of insulin (e.g., INS-1 and the like)), insulin sensitizers (e.g., pioglitazone hydrochloride, rosiglitazone (maleate), GI-262570, JTT-501, MCC-555, YM-440, KRP-297, CS-011, FK-614, NN-622, AZ-242, BMS-298585, EML-16336, compounds described in WO99/58510 (e.g., (E)-4-[4-(5-methyl-2-phenyl-4-oxazolylmethoxy)benzyloxyimino]-4-phenylbutyric acid)), PPARγ agonists, PPARγ antagonists, PPARγ/α dual agonists, α-glucosidase inhibitors (e.g., voglibose, acarbose, miglitol, emiglitate), biguanides (e.g., phenformin, metformin, buformin), insulin secretagogues [sulfonylureas (e.g., tolbutamide, glibenclamide, gliclazide, chlorpropamide, tolazamide, acetohexamide, glyclopyramide, glimepiride, glipizide, glybuzole and the like), repaglinide, senaglinide, nateglinide, mitiglinide or calcium salt hydrate thereof], GLP-1 receptor agonists [e.g., GLP-1, NN-2211, AC-2993 (exendin-4), BIM-51077, Aib(8,35)hGLP-1 (7,37)NH$_2$], amyrin agonists (e.g., pramlintide), phosphotyrosine phosphatase inhibitors (e.g., vanadic acid), P3 agonists (e.g., CL-316243, SR-58611-A, UL-TG-307, SB-226552, AJ-9677, BMS-196085, AZ40140), gluconeogenesis inhibitors (e.g., glycogen phosphorylase inhibitors, glucose-6-phosphatase inhibitors, glucagon antagonists, somatostatin receptor agonists), SGLT (sodium-glucose cotransporter) inhibitors (e.g., T-1095) and the like.

Examples of the therapeutic agent for diabetic complications include aldose reductase inhibitors (e.g., Tolrestat, Epalrestat, Zenarestat, Zopolrestat, Minalrestat, Fidarestat, SNK-860, CT-112), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole) and the like), neuranagenesis stimulators (e.g., Y-128), PKC inhibitors (e.g., LY-333531), AGE inhibitors (e.g., ALT946, pimagedine, pyratoxanthine, N-phenacylthiazolium bromide (ALT766), EXO-226), active oxygen scavengers (e.g., thioctic acid), cerebral vasodilators (e.g., tiapride, mexiletine), and the like.

Examples of the antihyperlipemia agent include statin compounds which are cholesterol synthesis inhibitors (e.g., cerivastatin, pravastatin, simvastatin, lovastatin, atorvastatin, fluvastatin, itavastatin and salts thereof (e.g., sodium salt)), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid and the like), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, plant sterols (e.g., soysterol, γ-oryzanol) and the like.

Examples of the antihypertensive agent include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan), calcium antagonists (e.g., manidipine, nifedipine, amlodipine, efonidipine, nicardipine), potassium channel openers (e.g., levcromakalim, L-27152, AL 0671, NIP-121), Clonidine and the like.

Examples of the antiobestic agent include antiobestic agents acting on the central nervous system (e.g., Dexfenfluramine, fenfluramine, phentermine, Sibutramine, amfepramone, dexamphetamine, Mazindol, phenylpropanolamine, clobenzorex), pancreatic lipase inhibitors (e.g., orlistat), P3 agonists (e.g., CL-316243, SR-58611-A, UL-TG-307, SB-226552, AJ-9677, BMS-196085, AZ40140), peptide anorexiants (e.g., leptin, CNTF (Ciliary Neurotropic Factor)), cholecystokinin agonists (e.g., lintitript, FPL-15849) and the like.

Examples of the diuretic include xanthine derivatives (e.g., sodium salicylate and theobromine, calcium salicylate and theobromine), thiazide preparations (e.g., ethiazide, cyclopenthiazide, trichloromethyazide, hydrochlorothiazide, hydroflumethiazide, benzylhydrochlorothiazide, penflutizide, polythiazide, methyclothiazide), antialdosterone agents (e.g., spironolactone, triamterene), carbonate dehydratase inhibitors (e.g., acetazolamide), chlorobenzenesulfonamide agents (e.g., chlortalidone, mefruside, indapamide), azosemide, isosorbide, etacrynic acid, piretanide, bumetanide, furosemide and the like.

Examples of the antithrombotic agent include heparin (e.g., heparin sodium, heparin calcium, dalteparin sodium), warfarin (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

The combination drug is preferably an insulin preparation, an insulin sensitizer, an α-glucosidase inhibitor, a biguanide, an insulin secretagogue (preferably sulfonylurea) or the like.

DPP-IV inhibitors and these combination drugs may be processed to give a combination agent aiming at an addition or synergistic effect of the efficacy, reduction of side effects and the like, by adding one or both of them to the release-controlled part A of the controlled release composition of the present invention, and adding the other or both of them to the release-controlled part B. Alternatively, the combination drug may be administered separately as a single preparation.

Of the controlled release compositions of the present invention, a composition containing, as an active ingredient, PPI such as benzimidazole compounds (e.g., lansoprazole and an optically active form thereof) and the above-mentioned imidazole compounds, (particularly, compounds represented by the above-mentioned formulas (I'), (I), (II) and (III), an optically active form thereof), is useful as a pharmaceutical agent, since it has a superior antiulcer activity, a gastric acid secretion-inhibiting action, a mucosa-protecting action, an anti-*Helicobacter pylori* activity and the like, and shows low toxicity. In this case, the controlled release composition of the present invention can be orally administered to mammals (e.g., human, monkey, sheep, horse, dog, cat, rabbit, rat, mouse and the like) for the prophylaxis or treatment of digestive ulcer (e.g., gastric ulcer, duodenal ulcer, anastomotic ulcer etc.), Zollinger-Ellison syndrome, gastritis, reflux esophagitis, Symptomatic Gastroesophageal Reflux Disease (Symptomatic GERD), NUD (Non Ulcer Dyspepsia), stomach cancer (including stomach cancer caused by promoted production of interleukin-1β due to genetic polymorphism of terleukin-1), stomach MALT lymphoma and the like, eradication of *Helicobacter pylori*, suppression of upper gastrointestinal hemorrhage caused by digestive ulcer, acute stress ulcer and hemorrhagic gastritis, suppression of upper gastrointestinal hemorrhage caused by invasive stress (stress caused by major surgery requiring intensive management after operation and cerebrovascular disorder, head trauma, multiple organ failure and extensive burn requiring intensive care), treatment or prophylaxis of ulcer caused by nonsteroidal anti-inflammatory agent; or the treatment, prophylaxis and the like of hyperacidity and ulcer caused by postoperative stress. For eradication of *Helicobacter pylori*, PPI and other active ingredients (e.g., 1 to 3 kinds of active ingredients) may be concurrently used.

As the "other active ingredients", for example, antibacterial agents such as an anti-*Helicobacter pylori* active substance, an imidazole compound, a quinolone compound and the like, and bismuth salt can be mentioned. Particularly, a pharmaceutical agent comprising PPI and an antibacterial agent in combination is preferable. Of these, a combined use with antibacterial agents such as an anti-*Helicobacter pylori* active substance, an imidazole compound and the like is preferable.

As the "anti-*Helicobacter pylori* active substance", for example, antibiotic penicillin (e.g., amoxicillin, benzylpenicillin, piperacillin, mecillinam and the like), antibiotic cefem (e.g., cefixime, cefaclor and the like), antibiotic macrolide (e.g., antibiotic erythromycins such as erythromycin, clarithromycin and the like), antibiotic tetracycline (e.g., tetracycline, minocycline, streptomycin and the like), aminoglycoside antibiotics (e.g., gentamicin, amikacin and the like), imipenem and the like can be mentioned. Of these, antibiotic penicillin, antibiotic macrolide and the like are preferable.

As the "imidazole compound", for example, metronidazole, miconazole and the like can be mentioned.

As the "bismuth salt", for example, bismuth acetate, bismuth citrate and the like can be mentioned.

Antibacterial agents of the "quinolone compounds" are also preferable and, for example, ofloxacin, ciploxacin and the like can be mentioned.

Particularly, for eradication of *Helicobacter pylori*, PPI and antibiotic penicillin (e.g., amoxicillin etc.) and/or antibiotic erythromycin (e.g., clarithromycin etc.) are preferably used in combination.

PPI and these combination drugs may be administered separately, or may be processed to give a combination agent aiming at an addition or synergistic effect of the efficacy, reduction of side effects and the like, by adding one or both of them to the release-controlled part A and adding the other or both of them to the release-controlled part B.

The content of the active ingredient relative to the whole release-controlled part B is, for example, about 1-80 wt %, preferably about 5—about 50 wt %, more preferably about 10—about 30 wt %.

The content of the active ingredient in each release-controlled part relative to the whole active ingredient in the controlled release composition of the present invention is, for example, about 5—about 95 wt % for the release-controlled part A and about 5—about 95 wt % for the release-controlled part B, preferably, about 20—about 80 wt % for the release-controlled part A and about 20—about 80 wt % for the release-controlled part B, more preferably, about 30—about 70 wt % for the release-controlled part A and about 30—about 70 wt % for the release-controlled part B.

In one preferable embodiment, the release-controlled part B contains a hydrophilic polymer as a sustained-release base material in addition to the active ingredient. As specific examples of the hydrophilic base material, those mentioned above for the release-controlled part A can be mentioned.

The viscosity of the hydrophilic polymer contained in the release-controlled part B is, for example, preferably not less than 1 mPa·s, more preferably not less than 4 mPa·s, based on the viscosity of a 2 wt % aqueous solution (measurement temperature: 20° C.).

The content of the hydrophilic polymer relative to the whole release-controlled part B is, for example, about 5—about 90 wt %, preferably about 10—about 80 wt %.

When the release-controlled part A and the release-controlled part B are both sustained-release matrices containing a hydrophilic polymer, the release rate in each release-controlled part can be appropriately set to a desired rate by, for example, controlling the viscosity and the amount of addition of the hydrophilic polymer to be contained. Those of ordinary skill in the art can easily modify such design. For example, using a relatively low viscous hydrophilic polymer for the release-controlled part A, and a relatively highly viscous hydrophilic polymer for the release-controlled part B, the release from the release-controlled part A can be controlled to the release rate $V_A$, which is faster than the release rate $V_B$ from the release-controlled part B (e.g., Examples 1-4 below). Alternatively, using a relatively low content hydrophilic polymer for the release-controlled part A, and a relatively high content hydrophilic polymer for the release-controlled part B, the release from the release-controlled part A can be controlled to the release rate $V_A$, which is faster than the release rate $V_B$ from the release-controlled part B.

The controlled release composition of the present invention containing the release-controlled part A and the release-controlled part B may take any form as long as the release of the active ingredient contained in the release-controlled part B precedes the release of the active ingredient contained in the release-controlled part A and it may take the form such as, but not limited to, for example, tablets, granules, fine granules, pellets, capsules, crystals, pastes and the like. As used herein, by the "precede" is meant that the release of the active ingredient contained in the release-controlled part B starts earlier than the release of the active ingredient contained in the release-controlled part A and the release of the active ingredient contained in the release-controlled part A is started after the completion or during the release (release of the majority of the active ingredient has been completed) of the active ingredient from the release-controlled part B. The relationship in time between the completion of the release of the active ingredients from the both release-controlled parts is not particularly limited, and the release from the release-controlled part B generally ends earlier. As long as the release of the active ingredient from the whole controlled release composition shows a two-step release pattern in which sustained release at a predetermined release rate ($V_B$) changes to immediate release or sustained release at a faster release rate ($V_A$), the release of the active ingredient from the release-controlled part A may finish simultaneously with or before the completion of the release of the active ingredient from the release-controlled part B.

Preferably, the controlled release composition of the present invention has a structure wherein the release-controlled part A is coated with the release-controlled part B. As used herein, by the "coated" is meant a state where the release-controlled part B covers substantially the entire surface of the release-controlled part A. By the "substantially" is meant that the release-controlled part B covers, though not completely, the surface of the release-controlled part A to the extent that the start of the release of the active ingredient from the release-controlled part A can be defined. In contrast, when a part of the release-controlled part A is coated with the release-controlled part B (e.g., spantab type tablet and the like), or is not coated at all (e.g., granule mixture or capsule containing the same and the like), the exposed surface of the release-controlled part A (which is not in contact with the release-controlled part B) needs to undergo a treatment to delay the start of the release of the active ingredient by a different means (e.g., coating of pH-dependent soluble film made of the aforementioned enteric base material etc., known timed release systems such as film soluble type, film withdrawal type, film disintegration type, film permeation type and the like.

When the controlled release composition of the present invention is a pharmaceutical composition, it can be prepared by mixing the active ingredient with a sustained-release base material, preferably the above-mentioned hydrophilic polymer, according to a method conventionally used in the preparation technical field and, for example, coating the release-controlled part A with the obtained mixture. A pharmacologically acceptable carrier may be added in the above-mentioned mixing and/or coating step. As the pharmacologically acceptable carrier, those similar to the above-mentioned for the release-controlled part A can be used. The dispersion mode of the active ingredient in the release-controlled part B of the obtained composition may be uniform dispersion or nonuniform dispersion, with preference given to uniform dispersion.

When the controlled release composition of the present invention is a granule, coating with the release-controlled part B can be performed by, for example, tumbling granulation methods, in which the active ingredient and a base material such as a hydrophilic polymer and the like, or a mixture thereof with a pharmacologically acceptable carrier such as excipient, lubricant and the like is applied in small portions onto the surface of the release-controlled part A as a core, which is prepared by any of the above-mentioned methods, while spraying a binder dissolved in a suitable solvent such as water, lower alcohol (e.g., methanol, ethanol and the like) and the like, pan coating methods, fluidized bed coating methods or molten granulation methods.

Furthermore, when the controlled release composition of the present invention is a tablet, coating with the release-controlled part B can be performed by compression molding a mixture as an outer shell, which is obtained by adding, for example, the above-mentioned excipient, disintegrant, binder, lubricant and the like to the active ingredient and a hydrophilic polymer and mixing them (further kneading where necessary), on the release-controlled part A as a core, which is prepared by any of the above-mentioned methods.

When the active ingredient in the release-controlled part B is markedly inactivated under acidic conditions, the surface of the release-controlled part may be coated with an enteric base material such as acrylic acid polymers including methacrylic acid copolymer L [Eudragit L (trade name, manufactured by Rohm Pharma)], methacrylic acid copolymer LD [Eudragit L-30D55 (trade name, manufactured by Rohm Pharma)], methacrylic acid copolymer S [Eudragit S (trade name, manufactured by Rohm Pharma)] and the like, hydroxypropylmethylcellulose phthalates [HP-50, HP-55, HP-55S (trade names, manufactured by Shin-Etsu Chemical Co., Ltd.) and the like.

In another preferable embodiment, the controlled release composition of the present invention further comprises a release-controlled part C comprising an active ingredient the same as or different from the active ingredient contained in the release-controlled part A and/or the release-controlled part B, which part C is capable of controlling release of the active ingredient to occur at a predetermined rate ($V_c$) faster than the release rate ($V_B$) of the release-controlled part B. In the controlled release composition, the release of the active ingredient from the release-controlled part C precedes the release of the active ingredient from the release-controlled part B. As used herein, by the "precede" is meant the same as mentioned above for the release of the active ingredients contained in the release-controlled part A and the release-controlled part B. Namely, the release of the active ingredient contained in the release-controlled part B is started after the completion or during the release (release of the majority of the active ingredient has been completed) of the active ingredient from the release-controlled part C. The relationship in time between the completion of the release of the active ingredients from the both release-controlled parts is that $V_C$ is generally much faster than $V_B$ and the release from the release-controlled part C generally ends earlier, because the content of the active ingredient is generally higher in the release-controlled part B.

Preferably, the controlled release composition of the present invention has a structure wherein the release-controlled part A is coated with the release-controlled part B, and further, the release-controlled part B is coated with the release-controlled part C. As used herein, by the "coated" is meant the same as mentioned above for the release-controlled part A and the release-controlled part B. In contrast, when a part of the release-controlled part B is coated with the release-controlled part C (e.g., spantab type tablet and the like), or is not coated at all (e.g., granule mixture or capsule containing the same and the like), no particular problem occurs as long as the release of the active ingredient from the release-controlled part C is immediate release. However, when it is sustained release or delayed dissolution, the exposed surface of the release-controlled part B (which is not in contact with the release-controlled part C) needs to undergo a treatment to delay the start of release of the active ingredient by a different means (e.g., coating of pH-dependent soluble film made of the aforementioned enteric base material etc., known timed release systems such as film soluble type, film withdrawal type, film permeation type etc.).

The release-controlled part C is a functional unit responsible for the first release controlling step (corresponding to dissolution of oral preparation in the stomach to near the upper small intestine) of the above-mentioned controlled release composition wherein the release of the active ingredient is controlled in three steps, and acts as an immediate release part or a sustained release part wherein the release rate $V_C$ of the active ingredient is faster than that ($V_B$) of the release-controlled part B (in the latter case, the release-controlled part B is a second sustained release part and the release-controlled part A (when it is a sustained release part) is a third sustained release part).

Preferably, the release rate $V_C$ of the active ingredient from the release-controlled part C is the same as or not less than the release rate $V_A$ of the active ingredient from the release-controlled part A, and specifically, the dissolution rate of an active ingredient at 30 min after the start of the test is not less than 50%, more preferably not less than 85%, when the Japanese Pharmacopoeia Dissolution Test Method 2 (Paddle Method) is performed using a suitable test solution (500 mL or 900 mL) at a paddle rotation of 100 rpm.

Alternatively, the release profile of the active ingredient from the release-controlled part C is also characterized in that the sustained release of the active ingredient from the release-controlled part C is completed within about 2 hr, more preferably within about 30 min after application (e.g., after administration) to the intended use (e.g., upon oral administration in the case of an oral preparation).

The active ingredient contained in the release-controlled part C is preferably the same as that contained in the release-controlled part A. When the active ingredient contained in the release-controlled part C is the same as that contained in the release-controlled part A, which is exactly as mentioned above is preferably exemplified.

On the other hand, when the active ingredient contained in the release-controlled part C is different from that contained in the release-controlled part A, one that can be a combination agent aiming at an addition or synergistic effect of the efficacy, reduction of side effects and the like is preferable and, for example, a combination drug similar to that described for the release-controlled part B can be mentioned.

The content of the active ingredient relative to the whole release-controlled part C is, for example, about 0.1-100 wt %, preferably about 1—about 95 wt %, more preferably about 5—about 90 wt %.

In addition, the content of the active ingredient in each release-controlled part relative to the whole active ingredient in the controlled release composition of the present invention is, for example, about 5-95 wt % for the release-controlled part A, about 5—about 95 wt % for the release-controlled part B and 0—about 40 wt % for the release-controlled part C (when it is 0%, the release-controlled part C does not exist), preferably, about 20—about 75 wt % for the release-controlled part A, about 20—about 75 wt % for the release-controlled part B and about 5—about 30 wt % for the release-controlled part C, more preferably, about 30—about 65 wt % for the release-controlled part A, about 30—about 65 wt % for the release-controlled part B and about 5—about 20 wt % for the release-controlled part C.

The release-controlled part C is preferably an immediate release part. In this case, the release-controlled part may be an active ingredient itself. It is preferable that it contain, in addition to the active ingredient, a carrier acceptable in the field relating to the use of the composition (e.g., pharmacologically acceptable carrier in the case of a pharmaceutical composition). As the pharmacologically acceptable carrier, for example, preparation additives such as the above-mentioned excipient, lubricant, binder, disintegrant, preservative, antioxidant, stabilizer, coloring agent, sweetening agent and the like for the release-controlled part A can be used.

The controlled release composition of the present invention comprising release-controlled part A, release-controlled part B and release-controlled part C can take, but not limited to, forms such as tablets, granules, fine granules, pellets, capsules, crystals, pastes and the like.

When the controlled release composition of the present invention is a pharmaceutical composition, it can be prepared by mixing the active ingredient with a pharmacologically acceptable carrier according to a method conventionally used in the preparation technical field and, for example, coating the above-mentioned composition, wherein the release-controlled part A is coated with the release-controlled part B, with the obtained mixture. The dispersion mode of the active ingredient in the release-controlled part C of the obtained composition may be uniform dispersion or nonuniform dispersion, with preference given to uniform dispersion.

When the controlled release composition of the present invention is a granule, coating with the release-controlled part C can be performed by, for example, tumbling granulation methods, in which the active ingredient or a mixture thereof with a pharmacologically acceptable carrier such as excipient, lubricant and the like is applied in small portions onto the surface of the composition as a core, wherein the release-controlled part A is coated with the release-controlled part B, which is prepared by any of the above-mentioned methods, while spraying a binder dissolved in a suitable solvent such as water, lower alcohol (e.g., methanol, ethanol and the like) and the like, pan coating methods, fluidized bed coating methods or molten granulation methods.

Furthermore, when the controlled release composition of the present invention is a tablet, coating with the release-controlled part C can be performed by compression molding a mixture as an outer shell, which is obtained by adding, for example, the above-mentioned excipient, disintegrant, binder, lubricant and the like to the active ingredient and mixing them (further kneading where necessary), on the composition as a core, wherein the release-controlled part A is coated with the release-controlled part B, which is prepared by any of the above-mentioned methods. In addition, a controlled release composition having the release-controlled part C can be prepared by spraying, using fluidized bed coating methods and the like, an aqueous dispersion prepared by adding, for example, the above-mentioned excipient, disintegrant, binder, lubricant and the like to the active ingredient.

When the active ingredient in the release-controlled part C is markedly inactivated under acidic conditions, the surface of the release-controlled part may be coated with enteric base materials such as acrylic acid polymers including methacrylic acid copolymer L [Eudragit L (trade name, manufactured by Rohm Pharma)], methacrylic acid copolymer LD [Eudragit L-30D55 (trade name, manufactured by Rohm Pharma)], methacrylic acid copolymer S [Eudragit S (trade name, manufactured by Rohm Pharma)] and the like, hydroxypropylmethylcellulose phthalates [HP-50, HP-55, HP-55S (trade names, manufactured by Shin-Etsu Chemical Co., Ltd.) and the like.

The controlled release composition of the present invention is particularly useful as an oral preparation. The composition can realize, after oral administration, sustained drug dissolution (preferably about 1—about 18 hr, more preferably about 2—about 12 hr) in the stomach—near the lower small intestine due to the release of the active ingredient from the release-controlled part B, and a subsequent more rapid drug dissolution (about 30 min—about 6 hr, preferably about 30—about 3 hr) in the lower small intestine—near the large intestine due to the release of the active ingredient from the release-controlled part A. As a result, drug dissolution property and absorbability in the lower small intestine—near the large intestine can be improved, and the drug blood concentration can be maintained within an effective therapeutic range for a longer period of time.

Furthermore, the controlled release composition, wherein the release-controlled part B is coated with a release-controlled part C, can realize rapid drug dissolution and absorption in the first stage (within about 2 hr, preferably about 30 min, after oral administration) due to the dissolution of the active ingredient contained in the release-controlled part C, and rise of the drug blood concentration can be accelerated.

While the present invention is explained in more detail by referring to the following Reference Examples, Synthetic Examples, Comparative Examples, Examples and Experimental Examples, which are not to be construed as limitative. The present invention may be modified within the range that does not go beyond the scope of the present invention.

In the following Reference Examples and Synthetic Examples, room temperature means about 15-30° C.

$^1$H-NMR was measured using Varian Gemini-200 and Mercury-300 and $CDCl_3$, DMSO-$d_6$ and $CD_3OD$ as solvents, wherein chemical shift δ (ppm) from tetramethylsilane as the internal standard was shown.

Other symbols mean the following.
s: singlet
d: doublet
t: triplet
q: quartet
m: multiplet
br: broad
bs: broad singlet
bm: broad multiplet
J: coupling constant Reference Example 1 tert-Butyl 2-hydroxyethyl(methyl)carbamate

To a mixture of 2-(methylamino)ethanol (30.04 g) and ethyl acetate (90 mL) was dropwise added a mixture of di-tert-butyl dicarbonate (87.30 g) and ethyl acetate (10 mL) under ice-cooling. After stirring at room temperature for 2 hrs., the mixture was concentrated under reduced pressure. The residue was dissolved in ethyl acetate (150 mL), washed with water (100 mL) and dried over anhydrous magnesium sulfate. Concentration under reduced pressure gave the title compound (66.19 g) as a colorless oil.

$^1$H-NMR($CDCl_3$): 1.47 (9H, s), 2.92 (3H, s), 3.40 (2H, t, J=5.1 Hz), 3.72-3.80 (2H, m).

Reference Example 2

2-(Methylamino)ethyl Acetate Hydrochloride

To a mixture of 2-(methylamino)ethanol (1.50 g) and ethyl acetate (20 mL) was added di-tert-butyl dicarbonate (4.37 g) under ice-cooling. After stirring under ice-cooling for 1.5 hrs., acetic anhydride (2.08 mL), pyridine (1.78 mL) and 4-dimethylaminopyridine (0.12 g) were added. After stirring at room temperature for 2 hrs., ethyl acetate. (50 mL) was added to the reaction mixture, and the mixture was washed with water (50 mL), a 5% aqueous citric acid solution (50 mL) and saturated brine (50 mL). After drying over anhydrous magnesium sulfate, the mixture was concentrated under reduced pressure. To the residue was added a 4N hydrogen chloride—ethyl acetate solution (20 mL), and the mixture was stirred at room temperature for 2 hrs. Diethyl ether (10 mL) was added, and the precipitated solid was collected by filtration. The solid was dried under reduced pressure to give the title compound (2.93 g) as a white solid.

$^1$H-NMR (DMSO-$d_6$): 2.07 (3H, s), 2.53 (3H, s), 3.12-3.17 (2H, m), 4.24-4.30 (2H, m), 9.29 (2H, br).

Reference Example 3

2-(Methylamino)ethyl Trimethylacetate Hydrochloride

To a mixture of tert-butyl 2-hydroxyethyl(methyl)carbamate (1.75 g) obtained in Reference Example 1 and ethyl acetate (15 mL) was added triethylamine (1.67 mL) and a mixture of trimethylacetyl chloride (1.35 mL), and ethyl acetate (5 mL) was dropwise added. After stirring at room temperature for 2 hrs., pyridine (1.62 mL) was added, and the mixture was stirred overnight at room temperature. Ethyl acetate (50 mL) was added to the reaction mixture, and the mixture was washed with water (50 mL), a 5% aqueous citric acid solution (50 mL) and saturated brine (50 mL), and dried over anhydrous magnesium sulfate. After concentration under reduced pressure, a 4N hydrogen chloride—ethyl acetate solution (10 mL) was added to the residue. After stirring at room temperature for 2 hrs., diethyl ether (10 mL) was added, and the precipitated solid was collected by filtration. The solid was dried under reduced pressure to give the title compound (1.65 g) as a white solid.

$^1$H-NMR (DMSO-$d_6$): 1.18 (9H, s), 2.56 (3H, s), 3.17 (2H, t, J=10.5 Hz), 4.22-4.28 (2H, m), 9.19 (2H, br).

Reference Example 4

2-(Methylamino)ethyl Cyclohexanecarboxylate Hydrochloride

To a mixture of tert-butyl 2-hydroxyethyl(methyl)carbamate (1.75 g) obtained in Reference Example 1 and ethyl acetate (20 mL) were added pyridine (0.97 mL) and 4-dimethylaminopyridine (catalytic amount), and cyclohexanecarbonyl chloride (1.60 mL) was dropwise added. After stirring at room temperature for 2 hrs., pyridine (0.65 mL) and cyclohexanecarbonyl chloride (0.58 mL) were added, and the mixture was stirred overnight at room temperature. Ethyl acetate (50 mL) was added to the reaction mixture, and the mixture was washed with water (50 mL), a 5% aqueous citric acid solution (50 mL) and saturated brine (50 mL), and dried over anhydrous magnesium sulfate. After concentration under reduced pressure, a 4N hydrogen chloride—ethyl acetate solution (10 mL) was added to the residue. After stirring at room temperature for 2 hrs., diethyl ether (10 mL) was added, and the precipitated solid was collected by filtration. The solid was dried under reduced pressure to give the title compound (1.88 g) as a white solid.

$^1$H-NMR (DMSO-$d_6$): 1.10-1.45 (5H, m), 1.54-1.73 (3H, m), 1.83-1.93 (2H, m), 2.29-2.42 (1H, m), 2.54 (3H, s), 3.12-3.18 (2H, m), 4.23-4.29 (2H, m), 9.23 (2H, br).

Reference Example 5

2-(Methylamino)ethyl Benzoate Hydrochloride

To a mixture of 2-(methylamino)ethanol (30.04 g) and ethyl acetate (90 mL) was dropwise added a mixture of di-tert-butyl dicarbonate (87.30 g) and ethyl acetate (10 mL) under ice-cooling. After stirring at room temperature for 1 hr., benzoyl chloride (61.8 g) and pyridine (38.8 mL) were added under ice-cooling. After stirring at room temperature for 1 hr., a solid was filtered off. The solid was washed with ethyl acetate (100 mL) and the filtrate and the washing were combined, which was washed with water (100 mL) and saturated brine (100 mL). After drying over anhydrous magnesium sulfate, the mixture was concentrated under reduced pressure. The residue was dissolved in ethyl acetate (100 mL), a 4N hydrogen chloride—ethyl acetate solution (200 mL) was added, and the mixture was stirred at room temperature for 30 min. Diethyl ether (100 mL) was added and a solid was collected by filtration. The solid was washed twice with ethyl acetate (100 mL) and dried under reduced pressure at 60° C. to give the title compound (57.4 g) as a white solid.

$^1$H-NMR (DMSO-$d_6$): 2.62 (3H, s), 3.32 (2H, m), 4.53 (2H, t, J=9.9 Hz) 7.51-7.57 (2H, m), 7.68 (1H, m), 8.11 (2H, d, J=7.8 Hz), 9.26 (2H, bs).

Reference Example 6

2-(Methylamino)ethyl 4-methoxybenzoate Hydrochloride

To a mixture of tert-butyl 2-hydroxyethyl(methyl)carbamate (1.75 g) obtained in Reference Example 1 and ethyl acetate (10 mL) were added 4-methoxybenzoyl chloride (1.88 g) and pyridine (0.97 mL). After stirring at room temperature for 14 hrs., 4-methoxybenzoyl chloride (0.70 g) and pyridine (0.97 mL) were added and the mixture was stirred at room temperature for 1 hr. Ethyl acetate (80 mL) was added to the reaction mixture, and the mixture was washed with water (20 mL), a saturated aqueous sodium hydrogen carbonate solution (20 mL) and water (20 mL), and dried over anhydrous magnesium sulfate. After concentration under reduced pressure, the residue was dissolved in ethyl acetate (10 mL), and a 4N hydrogen chloride—ethyl acetate solution (10 mL) was added. After stirring at room temperature for 1 hr., diethyl ether (20 mL) was added, and the precipitated solid was collected by filtration. The solid was washed twice with ethyl acetate (15 mL) and dried under reduced pressure at 60° C. to give the title compound (1.99 g) as a white solid.

$^1$H-NMR (DMSO-$d_6$): 2.62 (3H, s), 3.32 (2H, m), 4.48 (2H, t, J=5.0 Hz), 7.07 (2H, d, J=8.7 Hz), 8.06 (2H, d, J=8.7 Hz), 9.04 (2H, bs).

Reference Example 7

2-(Methylamino)ethyl 3-chlorobenzoate Hydrochloride

To a mixture of tert-butyl 2-hydroxyethyl(methyl)carbamate (1.75 g) obtained in Reference Example 1 and ethyl acetate (10 mL) were added 3-chlorobenzoyl chloride (1.92 g) and pyridine (0.97 mL). After stirring at room temperature for 1 hr., the mixture was stirred at 60° C. for 6 hrs. Ethyl acetate (80 mL) was added to the reaction mixture, and the mixture was washed with water (20 mL), a saturated aqueous sodium hydrogen carbonate solution (20 mL) and water (20 mL), and dried over anhydrous magnesium sulfate. After concentration under reduced pressure, a 4N hydrogen chloride—ethyl acetate solution (10 mL) was added to the residue. After stirring at room temperature for 22 hrs., diethyl ether (15 mL) was added, and the precipitated solid was collected by filtration. The solid was washed twice with ethyl acetate (15 mL) and dried under reduced pressure at 60° C. to give the title compound (2.01 g) as a white solid.

$^1$H-NMR (DMSO-$d_6$): 2.63 (3H, s), 3.32 (2H, m), 4.53 (2H, t, J=4.9 Hz), 7.60 (1H, t, J=8.0 Hz), 7.78 (1H, d, J=8.0 Hz), 8.05 (1H, d, J=8.0 Hz), 8.15 (1H, s), 9.07 (2H, bs).

Reference Example 8

2-(Methylamino)ethyl 3,4-difluorobenzoate hydrochloride

To a mixture of tert-butyl 2-hydroxyethyl(methyl)carbamate (1.75 g) obtained in Reference Example 1 and ethyl acetate (10 mL) were added 3,4-difluorobenzoyl chloride (1.77 g) and pyridine (0.97 mL). After stirring at room temperature for 3 days, ethyl acetate (80 mL) was added to the reaction mixture. The mixture was washed with water (20 mL), a saturated aqueous sodium hydrogen carbonate solution (20 mL) and water (20 mL), and dried over anhydrous magnesium sulfate. After concentration under reduced pressure, a 4N hydrogen chloride—ethyl acetate solution (10 mL) was added to the residue. After stirring at room temperature for 4 hrs, the mixture was concentrated under reduced pressure. The residue was washed with ethyl acetate (15 mL), and dried under reduced pressure at 60° C. to give the title compound (2.05 g) as a white solid.

$^1$H-NMR (DMSO-$d_6$): 2.62 (3H, s), 3.32 (2H, m), 4.53 (2H, t, J=5.0 Hz), 7.64 (1H, m), 8.00 (1H, m), 8.25 (1H, m), 9.25 (2H, bs).

Reference Example 9

2-(Methylamino)ethyl 4-trifluoromethoxybenzoate Hydrochloride

To a mixture of tert-butyl 2-hydroxyethyl(methyl)carbamate (1.30 g) obtained in Reference Example 1 and ethyl acetate (10 mL) were added 4-trifluoromethoxybenzoyl chloride (1.83 g) and pyridine (0.72 mL). The mixture was stirred at 60° C. for 25 hrs. Ethyl acetate (60 mL) was added to the reaction mixture, and the mixture was washed with water (30 mL), a saturated aqueous sodium hydrogen carbonate solution (20 mL) and water (20 mL), and dried over anhydrous magnesium sulfate. After concentration under reduced pressure, a 4N hydrogen chloride—ethyl acetate solution (10 mL) was added to the residue. After stirring at room temperature for 14.5 hrs., the mixture was concentrated under reduced pressure. The residue was washed twice with ethyl acetate (15 mL), and dried under reduced pressure at 60° C. to give the title compound (1.83 g) as a white solid.

$^1$H-NMR (DMSO-$d_6$): 2.63 (3H, s), 3.31 (2H, m), 4.54 (2H, t, J=4.9 Hz), 7.55 (2H, d, J=8.5 Hz), 8.24 (2H, d, J=8.5 Hz), 9.02 (2H, bs).

Reference Example 10

2-(Methylamino)ethyl 4-fluorobenzoate Hydrochloride

To a mixture of tert-butyl 2-hydroxyethyl(methyl)carbamate (1.75 g) obtained in Reference Example 1 and ethyl acetate (10 mL) were added 4-fluorobenzoyl chloride (1.74 g) and pyridine (0.97 mL). The mixture was stirred at room temperature for 6.5 hrs. Ethyl acetate (80 mL) was added to the reaction mixture, and the mixture was washed with water (30 mL), a saturated aqueous sodium hydrogen carbonate solution (30 mL), water (30 mL) and saturated brine (30 mL), and dried over anhydrous magnesium sulfate. After concentration under reduced pressure, a 4N hydrogen chloride—ethyl acetate solution (10 mL) was added to the residue. After stirring at room temperature for 1 hr., the precipitated solid was collected by filtration. The solid was washed twice with ethyl acetate (15 mL) and dried under reduced pressure at 60° C. to give the title compound (1.89 g) as a white solid.

$^1$H-NMR (DMSO-$d_6$): 2.62 (3H, s), 3.32 (2H, m), 4.52 (2H, t, J=4.9 Hz), 7.34-7.44 (2H, m), 8.16-8.24 (2H, m), 9.18 (2H, bs).

Reference Example 11

2-(Methylamino)ethyl 3,4,5-trimethoxybenzoate Hydrochloride

To a mixture of tert-butyl 2-hydroxyethyl(methyl)carbamate (1.75 g) obtained in Reference Example 1 and ethyl acetate (10 mL) were added 3,4,5-trimethoxybenzoyl chloride (2.54 g) and pyridine (0.97 mL). After stirring at 60° C. for 14 hrs., 3,4,5-trimethoxybenzoyl chloride (1.30 g), pyridine (0.97 mL) and ethyl acetate (10 mL) were added, and the mixture was stirred at 60° C. for 24 hrs. The reaction mixture was filtered and ethyl acetate (50 mL) and water (30 mL) were added to the filtrate. After partitioning, ethyl acetate layer was washed with 1N hydrochloric acid (30 mL), water (30 mL), an aqueous copper (II) sulfate solution (30 mL), water (30 mL) and saturated brine (30 mL), and dried over anhydrous magnesium sulfate. After concentration under reduced pressure, the residue was purified by silica gel column chromatography (eluted with ethyl acetate:hexane=1:1). A 4N hydrogen chloride—ethyl acetate solution (10 mL) was added to the purified product. After stirring at room temperature for 4 hrs, the mixture was concentrated under reduced pressure. Toluene (10 mL) was added, and the mixture was concentrated under reduced pressure. The residue was suspended in ethyl acetate, and the solid was collected by filtration. After washing with ethyl acetate (15 mL), the solid was dried under reduced pressure to give the title compound (1.79 g) as a white solid.

$^1$H-NMR (DMSO-$d_6$): 2.61 (3H, s), 3.28-3.35 (2H, m), 3.74 (3H, s), 3.87 (6H, s), 4.48-4.54 (2H, m), 7.40 (2H, s), 9.43 (2H, br).

Reference Example 12

2-(Methylamino)ethyl 2-pyridinecarboxylate Dihydrochloride

To a solution (100 mL) of tert-butyl 2-hydroxyethyl(methyl)carbamate (1.75 g) obtained in Reference Example 1, 2-pyridinecarbonyl chloride hydrochloride (2.67 g), pyridine (1.21 mL) and 4-dimethylaminopyridine (0.122 g) in tetrahydrofuran was dropwise added triethylamine (2.09 mL) under ice-cooling, and the mixture was stirred at room temperature for 6 hrs. Water (200 mL) was added to the reaction mixture and the mixture was extracted with ethyl acetate (150 mL). The organic layer was washed successively with a 5% aqueous copper (II) sulfate solution (100 mL), water (100 mL) and saturated brine (100 mL), dried over anhydrous sodium sulfate and evaporated under reduced pressure. The residue was dissolved in ethyl acetate (50 mL) and ethanol (100 mL), and a 4N hydrogen chloride—ethyl acetate solution (15 mL) was added. The mixture was stirred at room temperature for 1 hr. The precipitated solid was collected by filtration, washed twice with ethyl acetate (100 mL), and dried under reduced pressure at 60° C. to give the title compound (1.08 g) as a white solid.

$^1$H-NMR (DMSO-$d_6$): 2.62 (3H, t, J=5.4 Hz), 3.35 (2H, m), 4.63 (2H, t, J=5.0 Hz), 5.26 (1H, bs), 7.77-7.84 (1H, m), 8.14-8.18 (1H, m), 8.36-8.40 (1H, m), 8.70-8.90 (1H, m), 9.48 (2H, br).

Reference Example 13

2-(Methylamino)ethyl Methoxyacetate

To a mixture of tert-butyl 2-hydroxyethyl(methyl)carbamate (1.75 g) obtained in Reference Example 1 and ethyl acetate (10 mL) were added methoxyacetyl chloride (1.20 g) and pyridine (0.97 mL). After stirring at room temperature for 3 hrs., ethyl acetate (70 mL) was added to the reaction mixture. The mixture was washed with water (20 mL), a saturated aqueous sodium hydrogen carbonate solution (20 mL) and water (20 mL), and dried over anhydrous magnesium sulfate. After concentration under reduced pressure, the residue was dissolved in ethyl acetate (5 mL), and a 4N hydrogen chloride—ethyl acetate solution (10 mL) was added. After stirring at room temperature for 1 hr., the mixture was concentrated under reduced pressure. Water (60 mL) and diethyl ether (30 mL) were added to the residue. After stirring, the aqueous layer was separated and taken. The aqueous layer was basified with sodium hydrogen carbonate and extracted twice with ethyl acetate (40 mL). The ethyl acetate layer was dried over anhydrous magnesium sulfate and concentrated under reduced pressure to give the title compound (1.00 g) as a colorless oil.

$^1$H-NMR(CDCl$_3$): 2.40 (1H, bs), 3.06 (3H, s), 3.44 (3H, s), 3.57 (2H, t, J=5.1 Hz), 3.75-3.82 (2H, m), 4.13 (2H, s).

Reference Example 14

Ethyl 2-(methylamino)ethyl Carbonate Hydrochloride

To a mixture of tert-butyl 2-hydroxyethyl(methyl)carbamate (1.75 g) obtained in Reference Example 1 and ethyl acetate (20 mL) were added pyridine (0.97 mL) and 4-dimethylaminopyridine (catalytic amount), and ethyl chlorocarbonate (1.25 mL) was dropwise added. The mixture was stirred overnight at room temperature and ethyl acetate (50 mL) was added. The mixture was washed with water (50 mL), a 5% aqueous citric acid solution (50 mL) and saturated brine (50 mL), and dried over anhydrous magnesium sulfate. After concentration under reduced pressure, a 4N hydrogen chloride—ethyl acetate solution (10 mL) was added to the residue. After stirring at room temperature for 2 hrs., diethyl ether (10 mL) was added, and the precipitated solid was collected by filtration. The solid was dried under reduced pressure to give the title compound (1.66 g) as a white solid.
$^1$H-NMR (DMSO-d$_6$): 1.23 (3H, t, J=7.1 Hz), 2.54 (3H, s), 3.16-3.22 (2H, m), 4.15 (2H, q, J=7.1 Hz), 4.32-4.37 (2H, m), 9.25 (2H, br).

Reference Example 15

Isopropyl 2-(methylamino)ethyl Carbonate Hydrochloride

To a mixture of tert-butyl 2-hydroxyethyl(methyl)carbamate (3.50 g) obtained in Reference Example 1 and ethyl acetate (20 mL) were added isopropyl chlorocarbonate (1.35 g) and pyridine (1.94 mL) under ice-cooling. After stirring under ice-cooling for 3.5 hrs., isopropyl chlorocarbonate (1.84 g) was added, and the mixture was stirred at room temperature for 2.5 hrs. Ethyl acetate (120 mL) was added to the reaction mixture, and the mixture was washed with water (50 mL) and saturated brine (50 mL), and dried over anhydrous magnesium sulfate. After concentration under reduced pressure, a 4N hydrogen chloride—ethyl acetate solution (10 mL) was added to the residue. After stirring at room temperature for 2 hrs., the precipitated solid was collected by filtration. The solid was washed with ethyl acetate (15 mL) and dried under reduced pressure at 60° C. to give the title compound (1.38 g) as a white solid.
$^1$H-NMR (DMSO-d$_6$): 1.25 (6H, d, J=6.2 Hz), 2.56 (3H, s), 3.20 (2H, t, J=5.1 Hz), 4.32 (2H, t, J=5.1 Hz), 4.80 (1H, m), 8.95 (2H, bs).

Reference Example 16

Benzyl 2-(methylamino)ethyl Carbonate Hydrochloride

To a mixture of tert-butyl 2-hydroxyethyl(methyl)carbamate (1.75 g) obtained in Reference Example 1 and ethyl acetate (20 mL) were added pyridine (0.97 mL) and 4-dimethylaminopyridine (catalytic amount), and benzyl chlorocarbonate (1.57 mL) was dropwise added. After stirring at room temperature for 2 hrs., pyridine (0.65 mL) and benzyl chlorocarbonate (1.28 mL) were added. After stirring at room temperature for 5 days, pyridine (0.81 mL) was added under ice-cooling and a solution (5 mL) of benzyl chlorocarbonate (1.43 mL) in ethyl acetate was dropwise added slowly. After stirring at room temperature for 2 hrs., ethyl acetate (50 mL) was added to the mixture. The mixture was washed with water (50 mL), a 5% aqueous citric acid solution (50 mL) and saturated brine (50 mL), and dried over anhydrous magnesium sulfate. After concentration under reduced pressure, a 4N hydrogen chloride—ethyl acetate solution (10 mL) was added to the residue. After stirring at room temperature for 2 hrs., diethyl ether (10 mL) was added, and the precipitated solid was collected by filtration. The solid was dried under reduced pressure to give the title compound (1.99 g) as a white solid.
$^1$H-NMR (DMSO-d$_6$): 2.55 (3H, s), 3.21 (2H, t, J=5.1 Hz), 4.37 (2H, t, J=5.1 Hz), 5.18 (2H, s), 7.30-7.50 (5H, m), 9.07 (2H, br).

Reference Example 17

2-(Methylamino)ethyl tetrahydropyran-4-yl Carbonate Hydrochloride

To a solution (40 mL) of bis(trichloromethyl)carbonate (2.97 g) in tetrahydrofuran was dropwise added a solution (10 mL) of pyridine (2.43 mL) in tetrahydrofuran under ice-cooling. After stirring under ice-cooling for 10 min., a solution (20 mL) of tetrahydropyran-4-ol (1.91 g) in tetrahydrofuran was dropwise added slowly. After stirring at room temperature for 2 hrs., the mixture was concentrated under reduced pressure, and ethyl acetate (50 mL) and water (50 mL) were added to the residue. The ethyl acetate layer was separated and taken, washed with 0.2N hydrochloric acid (20 mL) and saturated brine (50 mL), and dried over anhydrous magnesium sulfate. Concentration under reduced pressure gave tetrahydropyran-4-yl chlorocarbonate (1.53 g). To a mixture of tert-butyl 2-hydroxyethyl(methyl)carbamate (1.40 g) obtained in Reference Example 1 and tetrahydrofuran (20 mL) was added pyridine (0.78 mL), and a solution (10 mL) of tetrahydropyran-4-yl chlorocarbonate (1.53 g) obtained above in tetrahydrofuran was dropwise added, and the mixture was stirred overnight at room temperature. After concentration of the reaction mixture under reduced pressure, water (50 mL) was added, and the mixture was extracted with ethyl acetate (50 mL). The extract was washed with a 5% aqueous citric acid solution (50 mL) and saturated brine (50 mL), and dried over anhydrous magnesium sulfate. After concentration under reduced pressure, the residue was purified by silica gel column chromatography (eluted with ethyl acetate:hexane=4:1, then 3:2). The obtained colorless oil (2.03 g) was dissolved in diethyl ether (2 mL), and a 4N hydrogen chloride—ethyl acetate solution (5 mL) was added. After stirring at room temperature for 30 min., diethyl ether (10 mL) was added and the mixture was stirred overnight. The precipitated solid was collected by filtration and dried under reduced pressure to give the title compound (1.20 g) as a white solid.
$^1$H-NMR (DMSO-d$_6$): 1.50-1.65 (2H, m), 1.87-1.98 (2H, m), 2.54 (3H, s), 3.20 (2H, m), 3.40-3.50 (2H, m), 3.74-3.83 (2H, m), 4.36 (2H, t, J=5.1 Hz), 4.72-4.83 (1H, m), 9.32 (2H, br).

Reference Example 18

2-Methoxyethyl 2-(methylamino)ethyl Carbonate Hydrochloride

To a mixture of tert-butyl 2-hydroxyethyl(methyl)carbamate (1.75 g) obtained in Reference Example 1 and ethyl acetate (20 mL) was added pyridine (1.62 mL) and a solution (5 mL) of 2-methoxyethyl chlorocarbonate (2.77 g) in ethyl acetate was dropwise added slowly, and the mixture was stirred overnight at room temperature. After concentration of the reaction mixture under reduced pressure, water (50 mL) was added, and the mixture was extracted with ethyl acetate (50 mL). The extract was washed with 5% aqueous citric acid solution (50 mL) and saturated brine (50 mL), and dried over anhydrous magnesium sulfate. After concentration under reduced pressure, the residue was dissolved in diethyl ether (2 mL), and a 4N hydrogen chloride—ethyl acetate solution (5 mL) was added. After stirring at room temperature for 30 min., diethyl ether (10 mL) was added, and the mixture was stirred overnight. The precipitated solid was collected by filtration, and dried under reduced pressure to give the title compound (1.56 g) as a white solid.

$^1$H-NMR (DMSO-$d_6$): 2.54 (3H, s), 3.19 (2H, m), 3.26 (3H, s), 3.52-3.57 (2H, m), 4.20-4.25 (2H, m), 4.33-4.39 (2H, m), 9.26 (2H, br).

Reference Example 19 tert-Butyl ethyl(2-hydroxyethyl)carbamate

To a mixture of 2-(ethylamino)ethanol (8.91 g) and ethyl acetate (100 mL) was added di-tert-butyl dicarbonate (21.8 g) under ice-cooling. After stirring at room temperature for 3 days, the mixture was washed with saturated brine (100 mL), and dried over anhydrous magnesium sulfate. Concentration under reduced pressure gave the title compound (19.0 g) as a colorless oil.

$^1$H-NMR(CDCl$_3$): 1.11 (3H, t, J=7.0 Hz), 1.47 (9H, s), 3.27 (2H, q, J=7.0 Hz), 3.37 (2H, t, J=5.2 Hz), 3.73 (2H, q, J=5.2 Hz).

Reference Example 20

2-(Ethylamino)ethyl Acetate Hydrochloride

To a mixture of tert-butyl ethyl(2-hydroxyethyl)carbamate (1.89 g) obtained in Reference Example 19 and ethyl acetate (20 mL) were added acetic anhydride (1.04 mL), pyridine (0.89 mL) and 4-dimethylaminopyridine (0.061 g). After stirring at room temperature for 3 hrs., ethyl acetate (50 mL) was added, and the mixture was washed with water (50 mL), a 5% aqueous citric acid solution (50 mL) and saturated brine (50 mL). After drying over anhydrous magnesium sulfate, the mixture was concentrated under reduced pressure. A 4N hydrogen chloride—ethyl acetate solution (10 mL) was added to the residue, and the mixture was stirred at room temperature for 1 hr. Ethyl acetate (10 mL) and diethyl ether (20 mL) were added, and the precipitated solid was collected by filtration. The solid was dried under reduced pressure to give the title compound (1.54 g) as a white solid.

$^1$H-NMR (DMSO-$d_6$): 1.22 (3H, t, J=7.3 Hz), 2.07 (3H, s), 2.95 (2H, q, J=7.3 Hz), 3.15 (2H, t, J=5.3 Hz), 4.24-74.30 (2H, m), 9.17 (2H, br).

Reference Example 21 tert-Butyl 2-hydroxyethyl(isopropyl)carbamate

To a solution (30 mL) of 2-(isopropylamino)ethanol (10.0 g) in tetrahydrofuran was added di-tert-butyl dicarbonate (22.2 g), and the mixture was stirred at room temperature for 1 hr. The reaction mixture was concentrated under reduced pressure and water (100 mL) was added to the residue. The mixture was extracted with ethyl acetate (200 mL). The ethyl acetate layer was washed with saturated brine (100 mL), dried over anhydrous sodium sulfate and concentrated under reduced pressure to give the title compound (21.21 g) as a colorless oil.

$^1$H-NMR(CDCl$_3$): 1.12 (6H, d, J=6.6 Hz), 3.30 (2H, t, J=5.0 Hz), 3.71 (2H, t, J=5.0 Hz), 3.80-4.30 (1H, m).

Reference Example 22

2-(Isopropylamino)ethyl Acetate Hydrochloride

To a solution (15 mL) of tert-butyl 2-hydroxyethyl(isopropyl)carbamate (5.0 g) obtained in Reference Example 21 in tetrahydrofuran were added pyridine (6.0 mL) and acetic anhydride (2.79 mL) and the mixture was stirred at room temperature for 18 hrs. The reaction mixture was concentrated under reduced pressure, water (50 mL) was added to the residue, and the mixture was extracted with ethyl acetate (100 mL). The ethyl acetate layer was washed with a 5% aqueous citric acid solution (50 mL) and saturated brine (50 mL), dried over anhydrous sodium sulfate and concentrated under reduced pressure. The obtained colorless oil was dissolved in a 4N hydrogen chloride—ethyl acetate solution (10 mL), and the mixture was stirred at room temperature for 1 hr. The precipitated solid was collected by filtration, and dried under reduced pressure to give the title compound (3.14 g) as a colorless solid.

$^1$H-NMR (DMSO-$d_6$): 1.25 (6H, d, J=6.6 Hz), 2.08 (3H, s), 3.10-3.40 (3H, m), 4.29 (2H, t, J=6.0 Hz), 9.11 (2H, br).

Reference Example 23

Ethyl 2-(isopropylamino)ethyl Carbonate Hydrochloride

To a solution (15 mL) of tert-butyl 2-hydroxyethyl(isopropyl)carbamate (5.0 g) obtained in Reference Example 21 in tetrahydrofuran were added pyridine (6.0 mL) and ethyl chlorocarbonate (2.81 mL) and the mixture was stirred at room temperature for 18 hrs. The reaction mixture was concentrated under reduced pressure, and water (50 mL) was added to the residue, and the mixture was extracted with ethyl acetate (100 mL). The ethyl acetate layer was washed with a 5% aqueous citric acid solution (50 mL) and saturated brine (50 mL), dried over anhydrous sodium sulfate and the mixture was concentrated under reduced pressure. The obtained colorless oil was dissolved in a 4N hydrogen chloride—ethyl acetate solution (10 mL), and the mixture was stirred at room temperature for 1 hr. The precipitated solid was collected by filtration and dried under reduced pressure to give the title compound (3.34 g) as a colorless solid.

$^1$H-NMR (DMSO-$d_6$): 1.20-1.30 (9H, m), 3.10-3.40 (3H, m) 4.17 (2H, q, J=7.4 Hz), 4.37 (2H, t, J=5.6 Hz), 9.13 (2H, br).

Reference Example 24 tert-Butyl cyclohexyl(2-hydroxyethyl)carbamate

To a solution (200 mL) of 2-(cyclohexylamino)ethanol (14.3 g) in ethanol was dropwise added di-tert-butyl dicarbonate (21.8 g). After stirring at room temperature for 2 days, the mixture was concentrated under reduced pressure. The residue was dissolved in ethyl acetate (200 mL). The mixture was washed with water (100 mL) and saturated brine (100 mL), and dried over anhydrous sodium sulfate. Concentration under reduced pressure gave the title compound (24.2 g) as a colorless oil.

$^1$H-NMR(CDCl$_3$): 1.26-1.39 (4H, m), 1.47 (9H, s), 1.61-1.81 (6H, m), 3.30-3.40 (2H, m), 3.69 (2H, t, J=5.4 Hz), 3.66-3.90 (2H, br).

Reference Example 25

2-(Cyclohexylamino)ethyl Acetate Hydrochloride

To a solution (50 mL) of tert-butyl cyclohexyl(2-hydroxyethyl)carbamate (2.43 g) obtained in Reference Example 24 in tetrahydrofuran were added pyridine (1.05 mL), acetic anhydride (1.23 mL) and 4-dimethylaminopyridine (0.122 g) under ice-cooling, and the mixture was stirred at room temperature for 12 hrs. Ethyl acetate (100 mL) was added to the reaction mixture and the mixture was washed successively with a saturated aqueous sodium hydrogen carbonate solution (100 mL), a 5% aqueous copper (II) sulfate solution (100 mL) and saturated brine (100 mL), and dried over anhydrous sodium sulfate. The mixture was concentrated under reduced pressure. The residue was dissolved in ethyl acetate (15 mL), and a 4N hydrogen chloride—ethyl acetate solution (15 mL) was added. After stirring at room temperature for 3 hrs., diisopropyl ether (20 mL) was added, and the precipitated solid was collected by filtration to give the title compound (1.78 g) as a white solid.

$^1$H-NMR (DMSO-d$_6$): 1.05-2.03 (10H, m), 2.07 (3H, s), 2.90-3.10 (1H, m), 3.17 (2H, t, J=5.2 Hz), 4.29 (2H, t, J=5.2 Hz), 9.19 (2H, br).

Reference Example 26

2-(Cyclohexylamino)ethyl Ethyl Carbonate Hydrochloride

To a solution (50 mL) of tert-butyl cyclohexyl(2-hydroxyethyl)carbamate (2.43 g) obtained in Reference Example 24 in tetrahydrofuran were added pyridine (1.45 mL), ethyl chlorocarbonate (1.71 mL) and 4-dimethylaminopyridine (0.122 g) under ice-cooling, and the mixture was stirred at room temperature for 15 hrs. Ethyl acetate (100 mL) was added to the reaction mixture, and the mixture was washed successively with a saturated aqueous sodium hydrogen carbonate solution (100 mL), a 5% aqueous copper (II) sulfate solution (100 mL), water (100 mL) and saturated brine (100 mL), and dried over anhydrous sodium sulfate. The mixture was concentrated under reduced pressure and the residue was dissolved in ethyl acetate (15 mL). A 4N hydrogen chloride—ethyl acetate solution (15 mL) was added. After stirring at room temperature for 3 hrs., diisopropyl ether (20 mL) was added, and the precipitated solid was collected by filtration to give the title compound (2.12 g) as a white solid.

$^1$H-NMR (DMSO-d$_6$): 1.01-2.08 (10H, m), 1.23 (3H, t, J=7.0 Hz), 2.90-3.10 (1H, m), 3.21 (2H, t, J=5.2 Hz), 4.16 (2H, q, J=7.0 Hz), 4.39 (2H, t, J=5.2 Hz), 9.27 (2H, br).

Reference Example 27

2-Anilinoethyl Acetate Hydrochloride

To a solution (700 mL) of 2-anilinoethanol (137 g) in tetrahydrofuran were added pyridine (97.1 mL), acetic anhydride (113.2 mL) and 4-dimethylaminopyridine (12.22 g) under ice-cooling, and the mixture was stirred at room temperature for 20 hrs. Ethyl acetate (1 L) was added to the reaction mixture and the mixture was washed successively with water (1 L), a saturated aqueous sodium hydrogen carbonate solution (1 L), a 5% aqueous copper (II) sulfate solution (1 L) and saturated brine (1 L), dried over anhydrous sodium sulfate, and evaporated under reduced pressure. To a solution of the obtained residue in ethyl acetate (700 mL) was added a 4N hydrogen chloride—ethyl acetate solution (250 mL) under ice-cooling, and the precipitated solid was collected by filtration to give the title compound (156 g) as a white solid.

$^1$H-NMR(CD$_3$OD): 2.11 (3H, s), 3.71-3.76 (2H, m), 4.32-4.37 (2H, m), 7.49-7.64 (5H, m).

Reference Example 28 tert-Butyl [2-(methylamino)-3-pyridyl]methyl Carbonate

To a solution (50 mL) of [2-(methylamino)-3-pyridyl]methanol (2 g: synthesized according to the method described in WO 01/32652) in tetrahydrofuran were added di-tert-butyl dicarbonate (3.48 g) and 4-dimethylaminopyridine (0.18 g) and the mixture was refluxed for 1 hr. Water (30 mL) was added to the reaction mixture and the mixture was extracted with ethyl acetate (50 mL). The obtained organic layer was washed with saturated brine (50 mL), and dried over anhydrous sodium sulfate. The residue obtained by concentration under reduced pressure was purified by flash silica gel column chromatography (eluted with ethyl acetate:hexane=1:5) to give the title compound (1.51 g) as a white solid.

$^1$H-NMR(CDCl$_3$): 1.49 (9H, s), 3.02 (3H, d, J=4.8 Hz), 4.99 (2H, s), 5.00 (1H, bs), 6.55 (1H, dd, J=7.0, 5.0 Hz), 7.37 (1H, dd, J=7.0, 1.8 Hz), 8.16 (1H, dd, J=5.0, 1.8 Hz).

Reference Example 29

2-(Methylamino)benzyl Acetate

To a solution (50 mL) of [2-(methylamino)phenyl]methanol (1.37 g: synthesized according to the method described in WO 01/32652) in tetrahydrofuran were added pyridine (1.05 mL), acetic anhydride (1.23 mL) and 4-dimethylaminopyridine (0.18 g), and the mixture was stirred at room temperature for 8 hrs. Water (100 mL) was added to the reaction mixture, and the mixture was extracted with ethyl acetate (100 mL). The organic layer was washed successively with a 5% aqueous copper (II) sulfate solution (50 mL), a saturated aqueous sodium hydrogen carbonate solution (50 mL) and saturated brine (50 mL), and dried over anhydrous sodium sulfate. The solvent was evaporated under reduced pressure and the obtained residue was purified by flash silica gel column chromatography (eluted with ethyl acetate:hexane=1:5, then 1:3) to give the title compound (0.38 g) as a white solid.

1H-NMR(CDCl$_3$): 2.08 (3H, s), 2.87 (3H, s), 4.40 (1H, br), 5.08 (2H, s), 6.64-6.74 (2H, m), 7.17-7.32 (2H, m).

Reference Example 30

2-[(2-Acetyloxyethyl)amino]ethyl Acetate Hydrochloride

To a mixture of 2,2'-iminodiethanol (2.10 g) and ethyl acetate (20 mL) was added di-tert-butyl dicarbonate (4.37 g) under ice-cooling. After stirring for 1.5 hrs. under ice-cooling, acetic anhydride (2.08 mL), pyridine (1.78 mL) and 4-dimethylaminopyridine (0.12 g) were added. After stirring at room temperature for 2 hrs., ethyl acetate (50 mL) was added to the reaction mixture and the mixture was washed with water (50 mL), a 5% aqueous citric acid solution (50 mL) and saturated brine (50 mL). After drying over anhydrous magnesium sulfate, the mixture was concentrated under reduced pressure. A 4N hydrogen chloride—ethyl acetate solution (20 mL) was added to the residue, and the mixture was stirred at room temperature for 2 hrs. Diethyl ether (10 mL) was added, and the precipitated solid was collected by filtration. The solid was dried under reduced pressure to give the title compound (6.18 g) as a white solid.

$^1$H-NMR (DMSO-$d_6$): 2.07 (6H, s), 3.23 (4H, t, J=5.3 Hz), 4.27-4.33 (4H, m), 9.40 (2H, br).

Reference Example 31

(S)-2-Pyrrolidinylmethyl Acetate Hydrochloride

To a mixture of (S)-2-pyrrolidinylmethanol (1.01 g) and ethyl acetate (10 mL) was added di-tert-butyl dicarbonate (2.18 g) under ice-cooling. After stirring for 1 hr. under ice-cooling, acetic anhydride (1.04 mL), pyridine (0.89 mL) and 4-dimethylaminopyridine (0.061 g) were added. After stirring at room temperature for 1 hr., ethyl acetate (50 mL) was added to the reaction mixture, and the mixture was washed with water (50 mL), a 5% aqueous citric acid solution (50 mL) and saturated brine (50 mL). After drying over anhydrous magnesium sulfate, the mixture was concentrated under reduced pressure. A 4N hydrogen chloride—ethyl acetate solution (10 mL) was added to the residue, and the mixture was stirred at room temperature for 1 hr. Diethyl ether (10 mL) was added and the precipitated solid was collected by filtration. The solid was dried under reduced pressure to give the title compound (1.68 g) as a pale-brown solid.

$^1$H-NMR (DMSO-$d_6$): 1.56-2.10 (4H, m), 2.06 (3H, s), 3.05-3.24 (2H, m), 3.63-3.68 (1H, m), 4.15 (1H, dd, J=11.8, 8.1 Hz), 4.26 (1H, dd, J=11.8, 4.1 Hz), 9.21 (1H, br), 9.87 (1H, br).

Reference Example 32

3-(Methylamino)propyl Benzoate Hydrochloride

To a mixture of 3-amino-1-propanol (0.75 g) and ethyl acetate (2.25 mL) was added a solution (0.25 mL) of di-tert-butyl dicarbonate (2.18 g) in ethyl acetate under ice-cooling. After stirring at room temperature for 21.5 hrs., benzoyl chloride (1.30 mL), pyridine (0.98 mL) and 4-dimethylaminopyridine (0.012 g) were added. After stirring at room temperature for 5 hrs., ethyl acetate (32.5 mL) was added to the reaction mixture, and the mixture was washed with water (12.5 mL) and saturated brine (12.5 mL). After drying over anhydrous magnesium sulfate, the mixture was concentrated under reduced pressure. The residue was dissolved in N,N-dimethylformamide (20 mL), and methyl iodide (5 mL) was added. 60% Sodium hydride (0.4 g) was added under ice-cooling. After stirring at room temperature for 3 hrs., the reaction mixture was poured into an ice-cooled aqueous ammonium chloride solution (60 mL). The mixture was extracted with diethyl ether (80 mL). The extract was washed with saturated brine (30 mL), dried-over anhydrous magnesium sulfate, and concentrated under reduced pressure. The residue was purified by silica gel column chromatography (ethyl acetate:hexane=2:1, then ethyl acetate, then acetone: ethyl acetate=1:9) to give 3-[(tert-butoxycarbonyl)(methyl) amino]propyl benzoate (2.52 g) as a colorless oil. A 4N hydrogen chloride—ethyl acetate solution (10 mL) was added, and the mixture was stirred at room temperature for 1 hr. After concentration under reduced pressure, ethyl acetate (10 mL) was added to the residue and the precipitated solid was collected by filtration. After washing with diethyl ether (10 mL), the solid was dried under reduced pressure to give the title compound (1.73 g) as a colorless solid.

$^1$H-NMR (DMSO-$d_6$): 2.02-2.16 (2H, m), 2.56 (3H, s), 3.05 (2H, t, J=7.3 Hz), 4.35 (2H, t, J=6.1 Hz), 7.51 (2H, m), 7.65-7.73 (1H, m), 8.01 (2H, d, J=7.2 Hz), 8.95 (2H, br).

Reference Example 33

2-[(Ethoxycarbonyl)(methyl)amino]ethyl ethyl carbonate

To a solution (1000 mL) of 2-(methylamino)ethanol (100 g) in ethyl acetate was added pyridine (222 mL), ethyl chlorocarbonate (240 mL) was dropwise added over 2 hr. under ice-cooling. After the completion of the dropwise addition, the reaction mixture was stirred at room temperature for 18 hrs. Water (300 mL) was added, and the ethyl acetate layer was separated and washed with 1N hydrochloric acid (200 mL) and saturated brine (200 mL). After drying over anhydrous sodium sulfate, the layer was concentrated under reduced pressure, and the residue was distilled under reduced pressure to give the title compound (180 g) as a colorless fraction having a boiling point of 95-100° C. (pressure: 0.1-0.2 mmHg).

$^1$H-NMR(CDCl$_3$): 1.20-1.40 (6H, m), 2.97 (3H, s), 3.50-3.60 (2H, m), 4.05-4.35 (6H, m).

Reference Example 34

2-[(Chlorocarbonyl)(methyl)amino]ethyl Ethyl Carbonate

To a solution (1500 mL) of 2-[(ethoxycarbonyl)(methyl) amino]ethyl ethyl carbonate (150 g) obtained in Reference Example 33 in acetonitrile was added phosphorus oxychloride (200 mL), and the mixture was refluxed for 4 days. The reaction mixture was concentrated under reduced pressure and the residue was added to a mixture of water (500 mL)—ice (700 g)—ethyl acetate (300 mL) by portions with stirring. After stirring for 1 min., saturated brine (500 mL) was added, and the mixture was extracted with ethyl acetate (500 mL). The ethyl acetate layer was washed successively with saturated brine (300 mL), a saturated aqueous sodium hydrogen carbonate solution (300 mL) and saturated brine (300 mL), dried over anhydrous sodium sulfate and concentrated under reduced pressure. The residue was distilled under reduced pressure to give the title compound (77 g) as a colorless fraction having a boiling point of 100-105° C. (pressure: 0.1-0.2 mmHg).

$^1$H-NMR(CDCl$_3$): 1.33 (3H, t, J=7.2 Hz), 3.12 (3H×0.4, s) 3.22 (3H×0.6, s), 3.68 (2H×0.6, t, J=4.8 Hz), 3.78 (2H×0.4, t, J=4.8 Hz), 4.23 (2H, q, J=7.2 Hz), 4.30-4.40 (2H, m).

Reference Example 35 tert-Butyl 4-hydroxybutylcarbamate

To a mixture of 4-aminobutanol (3.57 g) and ethyl acetate (9 mL) was dropwise added a mixture of di-tert-butyl dicarbonate (8.73 g) and ethyl acetate (1 mL) under ice-cooling. After stirring at room temperature for 24 hrs., the mixture was concentrated under reduced pressure. The residue was dissolved in ethyl acetate (200 mL), and the mixture was washed with water (50 mL), 1N hydrochloric acid (40 mL), water (30 mL) and saturated brine (30 mL) and dried over anhydrous magnesium sulfate. Concentration under reduced pressure gave the title compound (7.54 g) as a colorless oil.

$^1$H-NMR(CDCl$_3$): 1.44 (9H, s), 1.47-1.61 (4H, m), 3.07-3.22 (2H, m), 3.61-3.76 (2H, m), 4.62 (1H, bs).

Reference Example 36

4-[(tert-Butoxycarbonyl)amino]butyl Acetate

To a mixture of tert-butyl 4-hydroxybutylcarbamate (3.83 g) obtained in Reference Example 35 and ethyl acetate (20 mL) were added pyridine (1.80 mL) and acetic anhydride (2.27 g), and the mixture was stirred at room temperature for 9 hrs. Ethyl acetate (100 mL) was added to the reaction mixture, and the mixture was washed with water (50 mL), an aqueous copper sulfate solution (30 mL), water (30 mL) and saturated brine (30 mL) and dried over anhydrous magnesium sulfate. Concentration under reduced pressure gave the title compound (4.55 g) as a colorless oil.

$^1$H-NMR(CDCl$_3$): 1.44 (9H, s), 1.51-1.69 (4H, m), 2.05 (3H, s), 3.15 (2H, m), 4.07 (2H, t, J=6.5 Hz), 4.55 (1H, bs).

Reference Example 37

4-(Methylamino)butyl Acetate Hydrochloride

To a solution (20 mL) of 4-[(tert-butoxycarbonyl)amino] butyl acetate (4.50 g) obtained in Reference Example 36 and methyl iodide (4.85 mL) in N,N-dimethylformamide was added sodium hydride (60% in oil, 0.94 g) under ice-cooling. After stirring at room temperature for 4 hrs., the reaction mixture was poured into an ice—aqueous ammonium chloride solution. The mixture was extracted with diethyl ether (120 mL), and the diethyl ether layer was washed with saturated brine (30 mL) and dried over anhydrous magnesium sulfate. After concentration under reduced pressure, the residue was purified by silica gel column chromatography (eluted with ethyl acetate:hexane=1:9). To the purified product was added a 4N hydrogen chloride—ethyl acetate solution (20 mL), and the mixture was stirred at room temperature for 2 hrs. Diethyl ether (40 mL) was added, and the precipitated solid was collected by filtration. The solid was dried under reduced pressure to give the title compound (2.28 g) as a white solid.

$^1$H-NMR (DMSO-d$_6$): 1.58-1.70 (4H, m), 2.01 (3H, s), 2.50 (3H, s), 2.82-2.90 (2H, m), 4.00 (2H, t, J=6.0 Hz), 8.90 (2H, br).

Reference Example 38

4-[(tert-Butoxycarbonyl)amino]butyl Ethyl Carbonate

To a mixture of tert-butyl 4-hydroxybutylcarbamate (3.71 g) obtained in Reference Example 35 and ethyl acetate (20 mL) were added pyridine (1.71 mL) and ethyl chlorocarbonate (2.55 g) under ice-cooling, and the mixture was stirred at room temperature for 24 hrs. Ethyl acetate (100 mL) was added to the reaction mixture, and the mixture was washed with water (50 mL), an aqueous copper sulfate solution (30 mL), water (30 mL) and saturated brine (30 mL) and dried over anhydrous magnesium sulfate. Concentration under reduced pressure gave the title compound (4.92 g) as a colorless oil.

$^1$H-NMR(CDCl$_3$): 1.31 (3H, t, J=7.1 Hz), 1.44 (9H, s), 1.46-1.80 (4H, m), 3.15 (2H, m), 4.11-4.25 (4H, m), 4.54 (1H, bs).

Reference Example 39

Ethyl 4-(methylamino)butyl Carbonate Hydrochloride

To a solution (20 mL) of 4-[(tert-butoxycarbonyl)amino] butyl ethyl carbonate (4.90 g) obtained in Reference Example 38 and methyl iodide (4.67 mL) in N,N-dimethylformamide was added sodium hydride (60% in oil, 0.90 g) under ice-cooling. After stirring at room temperature for 6 hrs., the reaction mixture was poured into an ice—aqueous ammonium chloride solution, and extracted with diethyl ether (120 mL). The diethyl ether layer was washed with saturated brine (30 mL) and dried over anhydrous magnesium sulfate. After concentration under reduced pressure, the residue was purified by silica gel column chromatography (eluted with ethyl acetate:hexane=1:9). To the purified product was added a 4N hydrogen chloride—ethyl acetate solution (20 mL), and the mixture was stirred at room temperature for 2 hrs. Diethyl ether (40 mL) was added, and the precipitated solid was collected by filtration. The solid was dried under reduced pressure to give the title compound (2.86 g) as a white solid.

$^1$H-NMR (DMSO-d$_6$): 1.21 (3H, t, J=7.1 Hz), 1.51-1.73 (4H, m), 2.50 (3H, s), 2.82-2.94 (2H, m), 4.05-4.15 (4H, m), 8.88 (2H, br).

Reference Example 40 tert-Butyl 3-hydroxypropylcarbamate

To a mixture of 3-aminopropanol (7.51 g) and ethyl acetate (30 mL) was dropwise added a mixture of di-tert-butyl dicarbonate (21.8 g) and ethyl acetate (3 mL) under ice-cooling. After stirring at room-temperature for 22 hrs., the mixture was concentrated under reduced pressure. The residue was dissolved in ethyl acetate (200 mL), washed with water (80 mL), 1N hydrochloric acid (60 mL), water (50 mL) and saturated brine (50 mL), and dried over anhydrous sodium sulfate. Concentration under reduced pressure gave the title compound (16.01 g) as a colorless oil.

$^1$H-NMR(CDCl$_3$): 1.45 (9H, s), 1.62-1.70 (2H, m), 3.24 (2H, q, J=6.6 Hz), 3.66 (2H, q, J=5.1 Hz), 4.73 (1H, bs).

Reference Example 41

3-[(tert-Butoxycarbonyl)amino]propyl Acetate

To a mixture of tert-butyl 3-hydroxypropylcarbamate (8.00 g) obtained in Reference Example 40 and ethyl acetate (50 mL) were added pyridine (4.06 mL) and acetic anhydride (5.13 g), and the mixture was stirred at room temperature for 21 hrs. Ethyl acetate (200 mL) was added to the reaction mixture, and the mixture was washed with water (100 mL), an aqueous copper sulfate solution (40 mL), water (60 mL) and saturated brine (60 mL), and dried over anhydrous sodium sulfate. Concentration under reduced pressure gave the title compound (8.34 g) as a colorless oil.

$^1$H-NMR(CDCl$_3$): 1.44 (9H, s), 1.77-1.86 (2H, m), 2.06 (3H, s) 3.20 (2H, q, J=6.3 Hz), 4.12 (2H, t, J=6.3 Hz), 4.67 (1H, bs).

Reference Example 42

3-(Methylamino)propyl Acetate Hydrochloride

To a solution (80 mL) of 3-[(tert-butoxycarbonyl)amino]propyl acetate (17.28 g) obtained in Reference Example 41 and methyl iodide (19.8 mL) in N,N-dimethylformamide was added sodium hydride (60% in oil, 3.82 g) under ice-cooling. After stirring at room temperature for 15 hrs., the reaction mixture was poured into an ice—aqueous ammonium chloride solution and extracted with diethyl ether (300 mL). The diethyl ether layer was washed with saturated brine (100 mL), and dried over anhydrous sodium sulfate. After concentration under reduced pressure, the residue was purified by silica gel column chromatography (eluted with ethyl acetate:hexane=1:8). To the purified product was added a 4N hydrogen chloride—ethyl acetate solution (40 mL), and the mixture was stirred at room temperature for 2 hrs. Diethyl ether (100 mL) was added, and the precipitated solid was collected by filtration. The solid was dried under reduced pressure to give the title compound (2.93 g) as a white solid.

$^1$H-NMR (DMSO-$d_6$): 1.85-1.97 (2H, m), 2.02 (3H, s), 2.50 (3H, s), 2.87-2.96 (2H, m), 4.06 (2H, t, J=6.3 Hz), 8.87 (2H, br).

Reference Example 43

3-[(tert-Butoxycarbonyl)amino]propyl Ethyl Carbonate

To a mixture of tert-butyl 3-hydroxypropylcarbamate (8.00 g) obtained in Reference Example 40 and ethyl acetate (50 mL) were added pyridine (4.06 mL) and ethyl chlorocarbonate (5.95 g) under ice-cooling, and the mixture was stirred at room temperature for 24 hrs. Ethyl acetate (100 mL) was added to the reaction mixture, and the mixture was washed with water (50 mL), an aqueous copper sulfate solution (30 mL), water (30 mL) and saturated brine (30 mL), and dried over anhydrous sodium sulfate. Concentration under reduced pressure gave the title compound (9.31 g) as a colorless oil.

$^1$H-NMR(CDCl$_3$): 1.31 (3H, t, J=7.1 Hz), 1.44 (9H, s), 1.82-1.90 (2H, m), 3.22 (2H, t, J=6.3 Hz), 4.15-4.23 (4H, m), 4.68 (1H, bs).

Reference Example 44

Ethyl 3-(methylamino)propyl Carbonate Hydrochloride

To a solution (40 mL) of 3-[(tert-butoxycarbonyl)amino]propyl ethyl carbonate (9.31 g) obtained in Reference Example 43 and methyl iodide (9.00 mL) in N,N-dimethylformamide was added sodium hydride (60% in oil, 1.82 g) under ice-cooling. After stirring at room temperature for 12 hrs., the reaction mixture was poured into an ice—aqueous ammonium chloride solution and the mixture was extracted with diethyl ether (200 mL). The diethyl ether layer was washed with saturated brine (100 mL), and dried over anhydrous sodium sulfate. After concentration under reduced pressure, the residue was purified by silica gel column chromatography (eluted with ethyl acetate:hexane=1:8). To the purified product was added a 4N hydrogen chloride—ethyl acetate solution (40 mL), and the mixture was stirred at room temperature for 2 hrs. Diethyl ether (200 mL) was added, and the precipitated solid was collected by filtration. The solid was dried under reduced pressure to give the title compound (4.98 g) as a white solid.

$^1$H-NMR (DMSO-$d_6$): 1.21 (3H, t, J=7.1 Hz), 1.91-2.00 (2H, m), 2.50 (3H, s), 2.88-2.98 (2H, m), 4.08-4.16 (4H, m), 8.90 (2H, br).

Reference Example 45 tert-Butyl(2,3-dihydroxypropyl)methylcarbamate

To a mixture of 3-(methylamino)-1,2-propanediol (24.5 g) and ethyl acetate (50 mL) was dropwise added a mixture of di-tert-butyl dicarbonate (51.4 g) and ethyl acetate (10 mL) under ice-cooling. After stirring at room temperature for 15 hrs., the mixture was concentrated under reduced pressure. The residue was dissolved in ethyl acetate (150 mL), and the solution was washed with water (80 mL), 1N hydrochloric acid (60 mL), water (50 mL) and saturated brine (50 mL), and dried over anhydrous sodium sulfate. Concentration under reduced pressure gave the title compound (26.9 g) as a colorless oil.

$^1$H-NMR(CDCl$_3$): 1.47 (9H, s), 2.92 (3H, s), 3.20-3.36 (2H, m), 3.41 (2H, bs), 3.50-3.62 (2H, m), 3.73-3.88 (1H, m).

Reference Example 46

3-(Methylamino)propane-1,2-diyl Diacetate Hydrochloride

To a mixture of tert-butyl(2,3-hydroxypropyl)methylcarbamate (10.26 g) obtained in Reference Example 45 and ethyl acetate (50 mL) were added pyridine (10.11 mL) and acetic anhydride (12.76 g), and the mixture was stirred at room temperature for 24 hrs. Ethyl acetate (300 mL) was added to the reaction mixture, and the mixture was washed with water (150 mL), an aqueous copper sulfate solution (100 mL), water (100 mL) and saturated brine (100 mL), and dried over anhydrous sodium sulfate. After concentration under reduced pressure, the residue was purified by silica gel column chromatography (eluted with ethyl acetate:hexane=1:8). To the purified product was added a 4N hydrogen chloride—ethyl acetate solution (40 mL), and the mixture was stirred at room temperature for 3 hrs. Diethyl ether (100 mL) was added, and the precipitated solid was collected by filtration. The solid was dried under reduced pressure to give the title compound (2.76 g) as a white solid.

$^1$H-NMR (DMSO-$d_6$): 2.03 (3H, s), 2.07 (3H, s), 2.55 (3H, s), 3.18-3.22 (2H, m), 4.09-4.28 (2H, m), 5.20-5.27 (1H, m), 9.01 (2H, br).

Reference Example 47

Diethyl 3-(methylamino)propane-1,2-diyl Biscarbonate Hydrochloride

To a mixture of tert-butyl(2,3-dihydroxypropyl)methylcarbamate (15.53 g) obtained in Reference Example 45 and ethyl acetate (100 mL) were added pyridine (18.35 mL) and ethyl chlorocarbonate (24.62 g) under ice-cooling, and the mixture was stirred at room temperature for 96 hrs. Ethyl acetate (300 mL) was added to the reaction mixture, and the mixture was washed with water (150 mL), an aqueous copper sulfate solution (100 mL), water (100 mL) and saturated brine (100 mL), and dried over anhydrous sodium sulfate. After concentration under reduced pressure, the residue was purified by silica gel column chromatography (eluted with ethyl acetate:hexane=1:6). To the purified product was added a 4N hydrogen chloride—ethyl acetate solution (80 mL), and the mixture was stirred at room temperature for 3 hrs. Diethyl ether (200 mL) was added, and the precipitated solid was collected by filtration. The solid was dried under reduced pressure to give the title compound (5.93 g) as a white solid.

$^1$H-NMR (DMSO-$d_6$): 1.20-1.28 (6H, m), 2.57 (3H, s), 3.12-3.28 (2H, m), 4.10-4.43 (6H, m), 5.13-5.22 (1H, m), 9.14 (2H, br).

Reference Example 48

2-Ethoxyethyl 2-(methylamino)ethyl Carbonate Hydrochloride

To a solution (20 mL) of bis(trichloromethyl)carbonate (2.97 g) in tetrahydrofuran was dropwise added a solution (10 mL) of 2-ethoxyethanol (1.80 g) in tetrahydrofuran under ice-cooling. Then a solution (10 mL) of pyridine (2.43 mL) in tetrahydrofuran was added dropwise, and the mixture was stirred at room temperature for 2 hrs. The reaction mixture was concentrated under reduced pressure and water (50 mL) was added to the residue. The mixture was extracted with ethyl acetate (50 mL). The ethyl acetate layer was washed with 0.2N hydrochloric acid (20 mL) and saturated brine (50 mL), dried over anhydrous magnesium sulfate, and concentrated under reduced pressure to give 2-ethoxyethyl chlorocarbonate (1.29 g). A solution (15 mL) of tert-butyl 2-hydroxyethyl(methyl)carbamate (1.23 g) obtained in Reference Example 1 in tetrahydrofuran was added pyridine (0.68 mL), and a solution (5 mL) of 2-ethoxyethyl chlorocarbonate obtained above in tetrahydrofuran was dropwise added to the mixture, and the mixture was stirred at room temperature for 3 days. After concentration of the reaction mixture under reduced pressure, water (50 mL) was added thereto and the mixture was extracted with ethyl acetate (50 mL). The ethyl acetate layer was washed with a 5% aqueous citric acid solution (50 mL) and saturated brine (50 mL), dried over anhydrous magnesium sulfate. The mixture was concentrated under reduced pressure and the residue was purified by silica gel column chromatography (eluted with ethyl acetate:hexane=1:5, then 2:3). The purified product (1.60 g) was dissolved in diethyl ether (3 mL) and a 4N hydrogen chloride—ethyl acetate solution (3 mL) was added. The mixture was stirred overnight at room temperature, and the precipitated solid was collected by filtration and dried under reduced pressure to give the title compound (0.94 g) as a white solid.

$^1$H-NMR (DMSO-$d_6$): 1.10 (3H, t, J=7.0 Hz), 2.57 (3H, s), 3.18-3.25 (2H, m), 3.44 (2H, q, J=7.0 Hz), 3.56-3.60 (2H, m), 4.19-4.24 (2H, m), 4.30-4.37 (2H, m), 8.79 (2H, br).

Reference Example 49

3-Methoxypropyl 2-(methylamino)ethyl Carbonate Hydrochloride

To a mixture of lithium aluminum hydride (2.85 g) and diethyl ether (100 mL) was dropwise added slowly a solution (50 mL) of methyl 3-methoxypropanoate (11.8 g) in tetrahydrofuran under ice-cooling. After stirring at room temperature for 1 hr., the mixture was again ice-cooled and water (3 mL) and a 10% aqueous sodium hydroxide solution (3 mL) were dropwise added. The mixture was allowed to reach room temperature, and water (9 mL) was dropwise added. The mixture was stirred for a while. The precipitate was filtered off and the filtrate was concentrated under reduced pressure to give 3-methoxypropanol (7.64 g) as a colorless oil.

$^1$H-NMR(CDCl$_3$): 1.83 (2H, quintet, J=5.8 Hz), 2.43 (1H, t, J=5.3 Hz), 3.36 (3H, s), 3.57 (2H, t, J=6.0 Hz), 3.77 (2H, q, J=5.5 Hz).

To a solution (50 mL) of bis(trichloromethyl)carbonate (4.45 g) in tetrahydrofuran was dropwise added N-ethyldiisopropylamine (5.75 mL) under ice-cooling. After stirring for a while, a solution (15 mL) of 3-methoxypropanol (2.70 g) obtained above in tetrahydrofuran was dropwise added. The mixture was stirred for 30 min. under ice-cooling and at room temperature for 1 day. After concentration of the reaction mixture under reduced pressure, diluted hydrochloric acid (50 mL) was added to the residue, and the mixture was extracted with ethyl acetate (80 mL). The ethyl acetate layer was washed with 0.2N hydrochloric acid (30 mL) and saturated brine (30 mL), dried over anhydrous magnesium sulfate and concentrated under reduced pressure to give 3-methoxypropyl chlorocarbonate (4.39 g). To a solution (20 mL) of tert-butyl 2-hydroxyethyl(methyl)carbamate (1.75 g) obtained in Reference Example 1 in tetrahydrofuran was added pyridine (0.97 mL) and a solution (5 mL) of a 3-methoxypropyl chlorocarbonate (1.83 g) obtained above in tetrahydrofuran was dropwise added, and the mixture was stirred at room temperature for 2 hrs. A solution (5 mL) of pyridine (0.65 mL) and 3-methoxypropyl chlorocarbonate (1.22 g) in tetrahydrofuran was added and the mixture was further stirred for 1 hr. The reaction mixture was concentrated under reduced pressure and water (50 mL) was added to the residue. The mixture was extracted with ethyl acetate (80 mL), and the ethyl acetate layer was washed with a 5% aqueous citric acid solution (50 mL) and saturated brine (50 mL), dried over anhydrous magnesium sulfate and concentrated under reduced pressure. The residue was purified by silica gel column chromatography (eluted with ethyl acetate:hexane=1:9, then 3:7). The purified product (3.40 g) was dissolved in diethyl ether (5 mL) and a 4N hydrogen chloride—ethyl acetate solution (5 mL) was added. The mixture was stirred overnight at room temperature and the reaction mixture was concentrated under reduced pressure. Diethyl ether was added for crystallization to give the title compound (2.06 g) as a colorless solid.

$^1$H-NMR (DMSO-$d_6$): 1.78-1.90 (2H, m), 2.54 (3H, s), 3.15-3.25 (2H, m), 3.23 (3H, s), 3.33-3.42 (2H, m), 4.16 (2H, t, J=6.0 Hz), 4.36 (2H, t, J=6.0 Hz), 9.27 (2H, br).

Reference Example 50

2-(Methylamino)ethyl N,N-dimethylglycinate Dihydrochloride

A mixture of tert-butyl 2-hydroxyethyl(methyl)carbamate (3.50 g) obtained in Reference Example 1, N,N-dimethylglycine hydrochloride (5.29 g), 1-ethyl-3-[3-(dimethylamino)propyl]carbodiimide hydrochloride (7.67 g), triethylamine (5.58 mL), 4-dimethylaminopyridine (1.22 g) and N,N-dimethylformamide (50 mL) was stirred overnight at room temperature. The reaction mixture was concentrated under reduced pressure and a saturated aqueous sodium hydrogen carbonate solution (50 mL) was added to the residue. The mixture was extracted with ethyl acetate (100 mL). The ethyl acetate layer was washed with saturated brine (50 mL), dried over anhydrous magnesium sulfate and concentrated under reduced pressure. The residue was purified by silica gel column chromatography (eluted with methanol:ethyl acetate=5:95, then 20:80). 1N Hydrochloric acid (24 mL) was added to the purified product (2.46 g), and the mixture was stirred overnight at room temperature. The reaction mixture was concentrated under reduced pressure to give the title compound (2.14 g) as a colorless solid.

¹H-NMR (DMSO-d$_6$): 2.52 (3H, s), 2.85 (6H, s), 3.20 (2H, m) 4.30 (2H, s), 4.43-4.49 (2H, m), 9.60 (2H, br), 10.81 (1H, br).

Reference Example 51

S-[2-(Methylamino)ethyl]thioacetate Hydrochloride

To a solution (50 mL) of tert-butyl 2-hydroxyethyl(methyl) carbamate (3.50 g) obtained in Reference Example 1, thioacetic acid (1.72 mL) and triphenylphosphine (7.87 g) in tetrahydrofuran was dropwise added slowly a solution (10 mL) of diisopropyl azodicarboxylate (5.91 mL) in tetrahydrofuran under ice-cooling. The mixture was stirred under ice-cooling for 1 hr. and at room temperature for 2 hrs. The reaction mixture was again ice-cooled and a solution (10 mL) of triphenylphosphine (7.87 g) and diisopropyl azodicarboxylate (5.91 mL) in tetrahydrofuran was added. The mixture was stirred under ice-cooling for 30 min. Thioacetic acid (1.14 mL) was added and the mixture was stirred under ice-cooling for 30 min. and at room temperature overnight. The reaction mixture was concentrated under reduced pressure and hexane and diisopropyl ether were added to the residue. The precipitate was filtered off and the filtrate was concentrated under reduced pressure. This step was repeated and a saturated aqueous sodium hydrogen carbonate solution (50 mL) was added. The mixture was extracted with ethyl acetate (100 mL). The ethyl acetate layer was washed with saturated brine (50 mL), dried over anhydrous magnesium sulfate and concentrated under reduced pressure. The residue was purified by silica gel column chromatography (eluted with ethyl acetate:hexane=5:95, and then 15:85). A 4N hydrogen chloride—ethyl acetate solution (10 mL) was added to the purified product (4.47 g) and the mixture was stirred overnight at room temperature. The reaction mixture was concentrated under reduced pressure and ethyl acetate and diethyl ether were added to the residue for crystallization to give the title compound (1.79 g) as a pale-yellow solid.

¹H-NMR (DMSO-d$_6$): 2.38 (3H, s), 2.52 (3H, s), 2.96-3.08 (2H, m), 3.12-3.20 (2H, m), 9.35 (2H, br).

Reference Example 52

Ethyl 2-[2-(methylamino)ethoxy]ethyl Carbonate Hydrochloride

To a mixture of 2-(2-aminoethoxy)ethanol (99.52 g) and ethyl acetate (200 mL) was dropwise added a mixture of di-tert-butyl dicarbonate (208.57 g) and ethyl acetate (50 mL) under ice-cooling. After stirring at room temperature for 60 hrs., the mixture was concentrated under reduced pressure. The residue was dissolved in ethyl acetate (500 mL), washed with water (200 mL), 1N hydrochloric acid (200 mL), water (300 mL) and saturated brine (300 mL), and dried over anhydrous sodium sulfate. Concentration under reduced pressure gave tert-butyl [2-(2-hydroxyethoxy)ethyl]carbamate (169.2 g) as a colorless oil.

¹H-NMR(CDCl$_3$): 1.45 (9H, s), 3.33 (2H, q, J=5.1 Hz), 3.54-3.59 (4H, m), 3.74 (2H, q, J=5.1 Hz), 4.88 (2H, bs).

To a mixture of tert-butyl [2-(2-hydroxyethoxy)ethyl]carbamate (53.93 g) obtained above and ethyl acetate (350 mL) were added pyridine (53.78 mL) and ethyl chlorocarbonate (70.57 g) under ice-cooling, and the mixture was stirred at room temperature for 96 hrs. Ethyl acetate (500 mL) was added to the reaction mixture, and the mixture was washed with water (500 mL), an aqueous copper sulfate solution (200 mL), water (300 mL) and saturated brine (300 mL) and dried over anhydrous sodium sulfate. Concentration under reduced pressure gave 2-[2-[(tert-butoxycarbonyl)amino]ethoxy] ethyl ethyl carbonate (93.19 g) as a colorless oil.

¹H-NMR(CDCl$_3$): 1.32 (3H, t, J=7.2 Hz), 1.44 (9H, s), 3.32 (2H, t, J=5.1 Hz), 3.54 (2H, t, J=5.1 Hz), 3.67-3.74 (2H, m), 4.21 (2H, q, J=7.2 Hz), 4.26-4.31 (2H, m), 4.91 (1H, bs).

To a solution (350 mL) of 2-[2-[(tert-butoxycarbonyl) amino]ethoxy]ethyl ethyl carbonate (93.15 g) obtained above and methyl iodide (83.6 mL) in N,N-dimethylformamide was added sodium hydride (60% in oil, 16.12 g) under ice-cooling. After stirring at room temperature for 24 hrs., the reaction mixture was poured into an ice—aqueous ammonium chloride solution, and extracted with diethyl ether (800 mL). The diethyl ether layer was washed with saturated brine (300 mL), and dried over anhydrous magnesium sulfate. After concentration under reduced pressure, the residue was purified by silica gel column chromatography (eluted with ethyl acetate:hexane=1:8). To the purified product was added a 4N hydrogen chloride—ethyl acetate solution (300 mL) was added, and the mixture was stirred at room temperature for 2 hrs. Diethyl ether (300 mL) was added, and the precipitated solid was collected by filtration. The solid was dried under reduced pressure to give the title compound (33.21 g) as a white solid.

¹H-NMR (DMSO-d$_6$): 1.21 (3H, t, J=7.2 Hz), 2.51 (3H, s), 3.02-3.09 (2H, m), 3.65-3.72 (4H, m), 4.12 (2H, q, J=7.2 Hz), 4.22 (2H, t, J=4.5 Hz), 9.06 (2H, br).

Reference Example 53

Ethyl 2-[methyl[[2-(methylamino)ethoxy]carbonyl] amino]ethyl Carbonate Hydrochloride To a solution (100 mL) of bis(trichloromethyl)carbonate (11.87 g) in tetrahydrofuran was dropwise added a solution (20 mL) of pyridine (9.71 mL) in tetrahydrofuran under ice-cooling. After stirring under ice-cooling for 30 min., a solution (20 mL) of tert-butyl 2-hydroxyethyl(methyl)carbamate (17.52 g) obtained in Reference Example 1 in tetrahydrofuran was dropwise added and the mixture was stirred at room temperature for 15 hrs. After concentration under reduced pressure, water (500 mL) and anhydrous sodium sulfate were added to the residue. After filtration, the filtrate was concentrated under reduced pressure. To the obtained residue was added a solution (50 mL) of 2-(methylamino)ethanol (5.00 g) in ethyl acetate and triethylamine (10.0 mL) under ice-cooling and the mixture was stirred at room temperature for 15 hrs. Ethyl acetate (300 mL) was added to the reaction mixture, the mixture was washed with water (150 mL) and saturated brine (200 mL) and dried over anhydrous sodium sulfate. After concentration under reduced pressure, to a mixture of the residue and ethyl acetate (100 mL) were added pyridine (2.91 mL) and ethyl chlorocarbonate (3.44 g) under ice-cooling, and the mixture was stirred at room temperature for 48 hrs. Ethyl acetate (200 mL) was added to the reaction mixture, the mixture was washed with water (100 mL), an aqueous copper sulfate solution (50 mL), water (50 mL) and saturated brine (50 mL), and dried over anhydrous sodium sulfate. The mixture was concentrated under reduced pressure and the residue was purified by silica gel column chromatography (eluted with ethyl acetate:hexane=1:3). To the purified product was added a 4N hydrogen chloride—ethyl acetate solution (30 mL), and the mixture was stirred at room temperature for 3 hrs. Diethyl ether (100 mL) was added, and the precipitated solid was collected by filtration. The solid was dried under reduced pressure to give the title compound (2.90 g) as a white solid.

¹H-NMR (DMSO-d₆): 1.21 (3H, t, J=7.2 Hz), 2.57 (3H, bs), 2.86 (1.5H, s), 2.93 (1.5H, s), 3.16 (2H, bs), 3.34 (1H, bs), 3.48 (1H, t, J=5.1 Hz), 3.58 (1H, t, J=5.1 Hz), 4.12 (2H, q, J=7.2 Hz), 4.16-4.24 (4H, m), 8.94 (1H, br).

Reference Example 54

2-(Methylamino)ethyl 1-methylpiperidine-4-carboxylate Dihydrochloride

A mixture of ethyl piperidine-4-carboxylate (4.72 g), methyl iodide (2.24 mL), potassium carbonate (8.29 g) and acetonitrile (50 mL) was stirred at room temperature for 2 hrs. The reaction mixture was concentrated under reduced pressure and water (150 mL) was added. The mixture was extracted with ethyl acetate (150 mL). The ethyl acetate layer was washed with saturated brine (100 mL), dried over anhydrous magnesium sulfate, and concentrated under reduced pressure. A 1N aqueous sodium hydroxide solution (20 mL) was added to the residue (2.64 g), and the mixture was stirred overnight at room temperature. The reaction mixture was neutralized by adding 1N hydrochloric acid (20 mL) and the mixture was concentrated under reduced pressure. Ethanol was added to the residue, and the precipitate was filtered off. The filtrate was concentrated under reduced pressure. This step was repeated and ethanol and ethyl acetate were added to the residue for crystallization to give 1-methylpiperidine-4-carboxylic acid (1.79 g) as a colorless solid.

¹H-NMR(CD₃OD): 1.80-1.98 (2H, m), 2.00-2.14 (2H, m), 2.28-2.42 (1H, m), 2.78 (3H, s), 2.88-3.04 (2H, m), 3.32-3.44 (2H, m).

A mixture of 1-methylpiperidine-4-carboxylic acid (1.72 g) obtained above, tert-butyl 2-hydroxyethyl(methyl)carbamate (1.75 g) obtained in Reference Example 1, 1-ethyl-3-[3-(dimethylamino)propyl]carbodiimide hydrochloride (2.30 g), 4-dimethylaminopyridine (0.24 g) and acetonitrile (50 mL) was stirred at room temperature for 16 hrs. The reaction mixture was concentrated under reduced pressure and a saturated aqueous sodium hydrogen carbonate solution (50 mL) was added to the residue. The mixture was extracted with ethyl acetate (100 mL). The ethyl acetate layer was washed with saturated brine (50 mL), dried over anhydrous magnesium sulfate and concentrated under reduced pressure. The residue was purified by basic silica gel column chromatography (eluted with ethyl acetate:hexane=50:50, then 80:20). 1N Hydrochloric acid (25 mL) was added to the purified product (2.73 g), and the mixture was stirred overnight at room temperature. The reaction mixture was concentrated under reduced pressure and isopropanol was added. The mixture was again concentrated under reduced pressure and the precipitated solid was collected by filtration to give the title compound (1.72 g) as a colorless solid.

¹H-NMR (DMSO-d₆): 1.70-2.20 (4H, m), 2.40-3.50 (13H, m) 4.31 (2H, m), 9.25 (2H, br), 10.77 (1H, br).

Reference Example 55

2-[[4-(Aminocarbonyl)phenyl]amino]ethyl acetate

A mixture of 4-fluorobenzonitrile (6.06 g), 2-aminoethanol (3.71 g), potassium carbonate (8.29 g) and dimethyl sulfoxide (50 mL) was stirred at 100° C. overnight. Water (200 mL) was added to the reaction mixture and the mixture was extracted with ethyl acetate (200 mL×4). The ethyl acetate layer was washed with saturated brine (100 mL), dried over anhydrous magnesium sulfate and concentrated under reduced pressure. The residue was purified by silica gel column chromatography (eluted with ethyl acetate:hexane=30:70, then 50:50, then 80:20, then ethyl acetate) to give 4-[(2-hydroxyethyl)amino]benzonitrile (5.89 g) as a yellow solid.

¹H-NMR(CDCl₃): 2.04 (1H, t, J=4.8 Hz), 3.33 (2H, m), 3.86 (2H, q, J=4.8 Hz), 4.66 (1H, br), 6.58 (2H, d, J=8.7 Hz), 7.39 (2H, d, J=8.7 Hz)

A mixture of 4-[(2-hydroxyethyl)amino]benzonitrile (0.81 g) obtained above, potassium hydroxide. (1.12 g) and tert-butanol (20 mL) was stirred at 100° C. for 1 hr. Water (100 mL) was added to the reaction mixture, and the mixture was extracted with ethyl acetate (100 mL). The ethyl acetate layer was washed with saturated brine (80 mL), dried over anhydrous magnesium sulfate and concentrated under reduced pressure. To a solution (10 mL) of the residue (0.83 g), pyridine (0.49 mL) and 4-dimethylaminopyridine (0.061 g) in tetrahydrofuran was dropwise added a solution (1 mL) of acetic anhydride (0.57 mL) in tetrahydrofuran. The mixture was stirred at room temperature for 1 hr., water (80 mL) was added, and the mixture was extracted with ethyl acetate (100 mL). The ethyl acetate layer was washed with saturated brine (80 mL), dried over anhydrous magnesium sulfate and concentrated under reduced pressure. The residue was purified by silica gel column chromatography (eluted with ethyl acetate:hexane=30:70, then 60:40) to give the title compound (0.68 g) as a colorless solid.

¹H-NMR(CDCl₃): 2.08 (3H, s), 3.44 (2H, q, J=5.6 Hz), 4.29 (2H, t, J=5.4 Hz), 4.48 (1H, br), 6.59 (2H, d, J=8.9 Hz), 7.43 (2H, d, J=8.9 Hz).

Reference Example 56

2-(Methylamino)ethyl 1-methyl-4-piperidinyl Carbonate Dihydrochloride

To a solution (40 mL) of N,N'-carbonyldiimidazole (3.36 g) in tetrahydrofuran was dropwise added slowly a solution (10 mL) of tert-butyl 2-hydroxyethyl(methyl)carbamate (3.30 g) obtained in Reference Example 1 in tetrahydrofuran under ice-cooling. The mixture was stirred under ice-cooling for 40 min. and at room temperature for 2 hrs. N,N'-Carbonyldiimidazole (0.31 g) was added and the mixture was further stirred for 3 days. The reaction mixture was concentrated under reduced pressure and ethyl acetate (150 mL) was added to the residue. The mixture was washed with saturated brine (100 mL×2), water (50 mL×3) and saturated brine (50 mL), dried over anhydrous magnesium sulfate and concentrated under reduced pressure to give 2-[(tert-butoxycarbonyl)(methyl)amino]ethyl 1H-imidazole-1-carboxylate (5.24 g) as a colorless oil.

¹H-NMR(CDCl₃): 1.39 (9H×0.5, s), 1.42 (9H×0.5, s), 2.94 (3H, m) 3.63 (2H, m), 4.51 (2H, t, J=5.3 Hz), 7.06 (1H, m), 7.42 (1H, m), 8.13 (1H, s).

A mixture of 2-[(tert-butoxycarbonyl)(methyl)amino] ethyl 1H-imidazole-1-carboxylate (1.35 g) obtained above, 1-methyl-4-piperidinol (1.38 g) and acetonitrile (20 mL) was stirred overnight at room temperature. 1-Methyl-4-piperidinol (0.92 g) was added and the mixture was stirred overnight. The reaction mixture was concentrated under reduced pressure and a saturated aqueous sodium hydrogen carbonate solution (50 mL) was added to the residue. The mixture was extracted with ethyl acetate (100 mL). The ethyl acetate layer was washed with saturated brine (50 mL), dried over anhydrous magnesium sulfate and concentrated under reduced pressure. 1N Hydrochloric acid (12 mL) was added to the residue (1.60 g), and the mixture was stirred overnight at room temperature. The reaction mixture was concentrated under reduced pressure, water, isopropanol and ethyl acetate were added, and the precipitated solid was collected by filtration to give the title compound (1.09 g) as a colorless solid.
$^1$H-NMR (DMSO-$d_6$): 1.85-2.20 (4H, m), 2.55 (3H, s), 2.70 (3H×0.5, s), 2.73 (3H×0.5, s), 2.90-3.50 (6H, m), 4.38 (2H, m), 4.65-5.00 (1H, m), 9.21 (2H, br), 11.10 (1H, br).

Synthetic Example 1

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 30 min., 2-(methylamino)ethyl acetate hydrochloride (0.77 g) obtained in Reference Example 2 was added. A solution (1 mL) of triethylamine (0.70 mL) in tetrahydrofuran was dropwise added and the mixture was stirred at room temperature for 1 hr. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The mixture was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (catalytic amount) were added, and the mixture was stirred at 60° C. overnight. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate), and further by silica gel column chromatography (eluted with ethyl acetate:hexane=2:1, then ethyl acetate, then acetone:ethyl acetate=1:4, then 1:1) to give the title compound (1.13 g) as a yellow amorphous solid.
$^1$H-NMR(CDCl$_3$): 2.10 (3H, s), 2.24 (3H, s), 3.09 (3H, bs), 3.60-4.00 (2H, br), 4.25-4.50 (4H, m), 4.89 (1H, d, J=13.3 Hz), 5.05 (1H, d, J=13.3 Hz), 6.65 (1H, d, J=5.5 Hz), 7.35-7.51 (3H, m), 7.80-7.90 (1H, m), 8.35 (1H, d, J=5.5 Hz).

Synthetic Example 2

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl trimethylacetate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., 2-(methylamino)ethyl trimethylacetate hydrochloride (0.98 g) obtained in Reference Example 3 was added. A solution (1 mL) of triethylamine (0.70 mL) in tetrahydrofuran was dropwise added, and the mixture was stirred overnight at room temperature. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2). Crystallization from acetone-diisopropyl ether and recrystallization from acetone-diisopropyl ether gave the title compound (1.01 g) as a colorless solid.
$^1$H-NMR(CDCl$_3$): 1.23 (9H, s), 2.23 (3H, s), 3.08 (3H, bs), 3.40-4.30 (2H, br), 4.30-4.50 (4H, m), 4.80-5.20 (2H, br), 6.64 (1H, d, J=5.7 Hz), 7.35-7.50 (3H, m), 7.78-7.88 (1H, m), 8.35 (1H, d, J=5.7 Hz).

Synthetic Example 3

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl cyclohexanecarboxylate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 30 min., 2-(methylamino)ethyl cyclohexanecarboxylate hydrochloride (1.11 g) obtained in Reference Example 4 was added. A solution (1 mL) of triethylamine (0.70 mL) in tetrahydrofuran was dropwise added, and the mixture was stirred at room temperature for 1 hr. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-methylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2). Crystallization from acetone-diisopropyl ether and recrystallization from acetone-diisopropyl ether gave the title compound (1.11 g) as a colorless solid.
$^1$H-NMR(CDCl$_3$): 1.10-1.55 (5H, m), 1.55-1.82 (3H, m), 1.84-1.98 (2H, m), 2.23 (3H, s), 2.27-2.40 (1H, m), 3.08 (3H, bs), 3.40-4.30 (2H, br), 4.30-4.50 (4H, m), 4.80-5.15 (2H, br), 6.64 (1H, d, J=5.4 Hz), 7.35-7.48 (3H, m), 7.84 (1H, d, J=6.9 Hz), 8.34 (1H, d, J=5.4 Hz).

Synthetic Example 4

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl benzoate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., 2-(methylamino)ethyl benzoate hydrochloride (1.08 g) obtained in Reference Example 5 was added. A solution (1 mL) of triethylamine (0.70 mL) in tetrahydrofuran was dropwise added, and the mixture was stirred overnight at room temperature. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2). Crystallization from acetone-diethyl ether and recrystallization from acetone-diethyl ether gave the title compound (1.09 g) as a colorless solid.

$^1$H-NMR(CDCl$_3$): 2.22 (3H, s), 3.12 (3H, bs), 3.50-4.30 (2H, br), 4.37 (2H, q, J=7.8 Hz), 4.68 (2H, m), 4.80-5.20 (2H, br), 6.63 (1H, d, J=5.7 Hz), 7.26-7.48 (5H, m), 7.53-7.61 (1H, m), 7.82 (1H, d, J=8.1 Hz), 8.04 (2H, d, J=7.2 Hz), 8.33 (1H, d, J=5.7 Hz).

Synthetic Example 5

2-[Methyl[[2-[[[3-methyl-4-(2,2,2-trifluoroethoxy)-2-pyridyl]methyl]sulfinyl]-1H-benzimidazol-1-yl]carbonyl]amino]ethyl benzoate To a solution (30 mL) of bis(trichloromethyl)carbonate (0.99 g) in tetrahydrofuran was dropwise added a solution (2 mL) of pyridine (0.81 mL) in tetrahydrofuran under ice-cooling. After stirring under ice-cooling for 30 min., 2-(methylamino)ethyl benzoate hydrochloride (2.16 g) obtained in Reference Example 5 was added. After addition of a solution (2 mL) of triethylamine (1.39 mL) in tetrahydrofuran, the mixture was stirred at room temperature for 1 hr. After concentration under reduced pressure, ethyl acetate (100 mL) and water (100 mL) were added to the residue, and the mixture was stirred. The ethyl acetate layer was separated and taken, washed with saturated brine (50 mL) and dried over anhydrous magnesium sulfate. After concentration under reduced pressure, the residue was dissolved in tetrahydrofuran (40 mL). 2-[[[3-Methyl-4-(2,2,2-trifluoroethoxy)-2-pyridyl]methyl]sulfinyl]-1H-benzimidazole (2.90 g), triethylamine (2.20 mL) and 4-dimethylaminopyridine (0.096 g) were added, and the mixture was stirred at 60° C. for 2 hr. After concentration under reduced pressure, ethyl acetate (150 mL) and water (80 mL) were added to the residue, and the mixture was stirred. The ethyl acetate layer was separated and taken, washed with saturated brine (50 mL) and dried over anhydrous magnesium sulfate. After concentration under reduced pressure, the residue was purified by silica gel column chromatography (eluted with ethyl acetate:hexane=1:1, then ethyl acetate). Recrystallization from acetone gave the title compound (2.62 g) as a colorless solid.

$^1$H-NMR(CDCl$_3$): 2.22 (3H, s), 3.13 (3H, bs), 3.68-3.98 (2H, bm), 4.38 (2H, q, J=7.8 Hz), 4.69 (2H, m), 4.80-5.10 (2H, bm), 6.64 (1H, d, J=5.7 Hz), 7.27-7.48 (5H, m), 7.59 (1H, m), 7.83 (1H, m), 8.06 (2H, d, J=6.0 Hz), 8.35 (1H, d, J=5.7 Hz).

Synthetic Example 6

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-methoxybenzoate To a solution (18 mL) of bis(trichloromethyl)carbonate (0.584 g) in tetrahydrofuran was dropwise added a solution (1 mL) of pyridine (0.49 mL) in tetrahydrofuran under ice-cooling. After stirring under ice-cooling for 40 min., 2-(methylamino)ethyl 4-methoxybenzoate hydrochloride (1.48 g) obtained in Reference Example 6 was added. A solution (1 mL) of triethylamine (0.84 mL) in tetrahydrofuran was added and the mixture was stirred at room temperature for 80 min. After concentration under reduced pressure, ethyl acetate (80 mL) and water (50 mL) were added to the residue and the mixture was stirred. The ethyl acetate layer was separated and taken, washed with saturated brine (30 mL) and dried over anhydrous magnesium sulfate. After concentration under reduced pressure, the residue was dissolved in tetrahydrofuran (25 mL). (R)-2-[[[3-Methyl-4-(2,2,2-trifluoroethoxy)-2-pyridyl]methyl]sulfinyl]-1H-benzimidazole (1.55 g), triethylamine (1.17 mL) and 4-dimethylaminopyridine (0.051 g) were added, and the mixture was stirred at 60° C. for 3 hrs. After concentration under reduced pressure, ethyl acetate (150 mL) and water (50 mL) were added to the residue, and the mixture was stirred. The ethyl acetate layer was separated and taken, washed with saturated brine (50 mL) and dried over anhydrous magnesium sulfate. After concentration under reduced pressure, the residue was purified by silica gel column chromatography (eluted with ethyl acetate:hexane=1:1, then ethyl acetate). Recrystallization from ethyl acetate-hexane gave the title compound (1.08 g) as a colorless solid.

$^1$H-NMR(CDCl$_3$): 2.22 (3H, s), 3.11 (3H, bs), 3.68-3.90 (2H, bm), 3.85 (3H, s), 4.37 (2H, q, J=7.9 Hz), 4.58-4.72 (2H, m), 4.82-5.14 (2H, bm), 6.63 (1H, d, J=5.7 Hz), 6.91 (2H, d, J=9.0 Hz), 7.27-7.40 (3H, m), 7.82 (1H, m), 7.99 (2H, d, J=9.0 Hz), 8.33 (1H, d, J=5.7 Hz).

Synthetic Example 7

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3-chlorobenzoate To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., 2-(methylamino)ethyl 3-chlorobenzoate hydrochloride (1.50 g) obtained in Reference Example 7 was added. A solution (1 mL) of triethylamine (0.84 mL) in tetrahydrofuran was added and the mixture was stirred at room temperature for 2 hrs. After concentration under reduced pressure, ethyl acetate (80 mL) and water (40 mL) were added to the residue and the mixture was stirred. The ethyl acetate layer was separated and taken, washed with saturated brine (25 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.44 g), triethylamine (1.09 mL) and 4-dimethylaminopyridine (0.048 g) were added, and the mixture was stirred at 60° C. for 3 hrs. After concentration under reduced pressure, ethyl acetate (80 mL) and water (40 mL) were added to the residue and the mixture was stirred. The ethyl acetate layer was separated and taken, washed with saturated brine (30 mL) and dried over anhydrous magnesium sulfate. After concentration under reduced pressure, the residue was purified by basic silica gel column chromatography (eluted with ethyl acetate: hexane=1:2, then 1:1) to give the title compound (0.84 g) as colorless syrup.

$^1$H-NMR(CDCl$_3$): 2.21 (3H, s), 3.12 (3H, bs), 3.78-4.08 (2H, bm), 4.38 (2H, q, J=7.8 Hz), 4.64-5.08 (4H, bm), 6.64 (1H, d, J=5.2 Hz), 7.34-7.42 (4H, m), 7.56 (1H, m), 7.82 (1H, m), 7.94 (1H, d, J=7.6 Hz), 8.02 (1H, s), 8.34 (1H, d, J=5.2 Hz).

Synthetic Example 8

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4-difluorobenzoate To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., 2-(methylamino)ethyl 3,4-difluorobenzoate hydrochloride (1.51 g) obtained in Reference Example 8 was added. A solution (1 mL) of triethylamine (0.84 mL) in tetrahydrofuran was added and the mixture was stirred at room temperature for 3 hrs. After concentration under reduced pressure, ethyl acetate (80 mL) and water (50 mL) were added to the residue and the mixture was stirred. The ethyl acetate layer was separated and taken, washed with saturated brine (30 mL) and dried over anhydrous magnesium sulfate. The layer was concentrated under reduced pressure, and the residue was dissolved in tetrahydrofuran (25 mL). (R)-2-[[[3-Methyl-4-(2,2,2-trifluoroethoxy)-2-pyridyl]methyl]sulfinyl]-1H-benzimidazole (1.71 g), triethylamine (1.29 mL) and 4-dimethylaminopyridine (0.056 g) were added, and the mixture was stirred at 60° C. for 17 hrs. After concentration under reduced pressure, ethyl acetate (100 mL) and water (50 mL) were added to the residue, and the mixture was stirred. The ethyl acetate layer was separated and taken, and the aqueous layer was extracted with ethyl acetate (20 mL). Ethyl acetate layers were combined, washed with saturated brine (30 mL) and dried over anhydrous magnesium sulfate. After concentration under reduced pressure, the residue was purified by silica gel column chromatography (eluted with ethyl acetate:hexane=1:1, then 2:1), and further by basic silica gel column chromatography (eluted with ethyl acetate:hexane=1:1). Crystallization from acetone-diisopropyl ether and recrystallization from ethyl acetate-hexane gave the title compound (1.37 g) as a colorless solid.

$^1$H-NMR(CDCl$_3$): 2.21 (3H, s), 3.11 (3H, bs), 3.82-4.08 (2H, bm), 4.38 (2H, q, J=7.8 Hz), 4.60-5.14 (4H, bm), 6.63 (1H, d, J=5.7 Hz), 7.20 (1H, m), 7.33-7.41 (3H, m), 7.78-7.92 (3H, m), 8.33 (1H, d, J=5.7 Hz).

Synthetic Example 9

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-trifluoromethoxybenzoate To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., 2-(methylamino)ethyl 4-trifluoromethoxybenzoate hydrochloride (1.79 g) obtained in Reference Example 9 was added. A solution (1 mL) of triethylamine (0.84 mL) in tetrahydrofuran was added and the mixture was stirred at room temperature for 1.5 hrs. After concentration under reduced pressure, ethyl acetate (80 mL) and water (50 mL) were added to the residue and the mixture was stirred. The ethyl acetate layer was separated and taken, washed with saturated brine (30 mL) and dried over anhydrous magnesium sulfate. After concentration under reduced pressure, the residue was dissolved in tetrahydrofuran (25 mL). (R)-2-[[[3-Methyl-4-(2,2,2-trifluoroethoxy)-2-pyridyl]methyl]sulfinyl]-1H-benzimidazole (1.57 g), triethylamine (1.18 mL) and 4-dimethylaminopyridine (0.052 g) were added, and the mixture was stirred at 60° C. for 4.5 hrs. After concentration under reduced pressure, ethyl acetate (100 mL) and water (50 mL) were added to the residue, and the mixture was stirred. The ethyl acetate layer was separated and taken, and the aqueous layer was extracted with ethyl acetate (30 mL). The ethyl acetate layers were combined, washed with saturated brine (30 mL) and dried over anhydrous magnesium sulfate. After concentration under reduced pressure, the residue was purified by silica gel column chromatography (eluted with ethyl acetate:hexane=1:1), and further by basic silica gel column chromatography (eluted with ethyl acetate:hexane=1:1) to give the title compound (1.44 g) as colorless syrup.

$^1$H-NMR(CDCl$_3$): 2.22 (3H, s), 3.11 (3H, bs), 3.85-4.05 (2H, bm), 4.38 (2H, q, J=7.8 Hz), 4.60-5.12 (4H, bm), 6.64 (1H, d, J=5.7 Hz), 7.24 (2H, d, J=8.7 Hz), 7.25-7.40 (3H, m), 7.82 (1H, d, J=7.2 Hz), 8.09 (2H, d, J=8.7 Hz), 8.33 (1H, d, J=5.7 Hz).

Synthetic Example 10

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-fluorobenzoate To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., 2-(methylamino)ethyl 4-fluorobenzoate hydrochloride (1.40 g) obtained in Reference Example 10 was added. A solution (1 mL) of triethylamine (0.84 mL) in tetrahydrofuran was added and the mixture was stirred at room temperature for 2 hrs. After concentration under reduced pressure, ethyl acetate (80 mL) and water (40 mL) were added to the residue and the mixture was stirred. The ethyl acetate layer was separated and taken, washed with saturated brine (30 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.32 g), triethylamine (1.00 mL) and 4-dimethylaminopyridine (0.049 g) were added, and the mixture was stirred at 60° C. for 14.5 hrs. After concentration under reduced pressure, ethyl acetate (150 mL) and water (50 mL) were added to the residue, and the mixture was stirred. The ethyl acetate layer was separated and taken, washed with saturated brine (30 mL) and dried over anhydrous magnesium sulfate. After concentration under reduced pressure, the residue was crystallized from ethyl acetate:hexane=1:1 and the solid was collected by filtration. Recrystallization from acetone gave the title compound (1.39 g) as a colorless solid.

¹H-NMR(CDCl₃): 2.22 (3H, s), 3.12 (3H, bs), 3.78-4.20 (2H, bm), 4.38 (2H, q, J=7.8 Hz), 4.58-5.08 (4H, bm), 6.65 (1H, d, J=5.6 Hz), 7.11 (2H, t, J=8.4 Hz), 7.28-7.44 (3H, m), 7.81-7.86 (1H, m), 8.03-8.11 (2H, m), 8.35 (1H, d, J=5.6 Hz).

Synthetic Example 11

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4,5-trimethoxybenzoate To a solution (30 mL) of bis(trichloromethyl)carbonate (0.60 g) in tetrahydrofuran was dropwise added a solution (1 mL) of pyridine (0.49 mL) in tetrahydrofuran under ice-cooling. After stirring under ice-cooling for 10 min., 2-(methylamino)ethyl 3,4,5-teimethoxybenzoate hydrochloride (1.22 g) obtained in Reference Example 11 was added. A solution (1 mL) of triethylamine (0.84 mL) in tetrahydrofuran was dropwise added and the mixture was stirred at room temperature for 1 hr. After concentration under reduced pressure, water (50 mL) was added to the residue. The mixture was extracted with ethyl acetate (50 mL). The ethyl acetate layer was washed with dilute hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred at 60° C. for 3 hrs. and at room temperature for 2 days. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2) to give the title compound (1.56 g) as a yellow amorphous solid.

¹H-NMR(CDCl₃): 2.21 (3H, s), 3.12 (3H, bs), 3.50-4.30 (2H, br), 3.83 (6H, s), 3.90 (3H, s), 4.38 (2H, q, J=7.8 Hz), 4.67 (2H, m), 4.80-5.15 (2H, br), 6.64 (1H, d, J=5.7 Hz), 7.25-7.40 (5H, m), 7.78-7.86 (1H, m), 8.33 (1H, d, J=5.7 Hz).

Synthetic Example 12

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 2-pyridinecarboxylate To a solution (30 mL) of bis(trichloromethyl)carbonate (0.422 g) in tetrahydrofuran was dropwise added pyridine (0.345 mL) under ice-cooling. After stirring under ice-cooling for 30 min., 2-(methylamino)ethyl 2-pyridinecarboxylate dihydrochloride (1.08 g) obtained in Reference Example 12 was added. After dropwise addition of triethylamine (1.19 mL), the mixture was stirred at room temperature for 2 hrs. The precipitated solid was filtered off and the filtrate was concentrated under reduced pressure. The residue was dissolved in tetrahydrofuran (10 mL), and (R)-2-[[[3-methyl-4-(2,2,2-trifluoroethoxy)-2-pyridyl]methyl]sulfinyl]-1H-benzimidazole (1.31 g), triethylamine (0.99 mL) and 4-dimethylaminopyridine (0.043 g) were added. The mixture was stirred at 60° C. for 24 hrs. Ethyl acetate (100 mL) was added to the reaction mixture, and the mixture was washed with water (100 mL) and saturated brine (100 mL), dried over anhydrous sodium sulfate, and concentrated under reduced pressure. The residue was purified by basic silica gel column chromatography (eluted with ethyl acetate:hexane=4:1). Crystallization from acetone-diethyl ether gave the title compound (0.9 g) as a white solid.

¹H-NMR(CDCl₃): 2.22 (3H, s), 3.16 (3H, s), 3.80-4.20 (2H, m), 4.38 (2H, q, J=7.8 Hz), 4.60-5.10 (4H, m), 6.64 (1H, d, J=5.8 Hz), 7.29-7.40 (2H, m), 7.47-7.52 (2H, m), 7.81-7.89 (2H, m), 8.14 (1H, d, J=7.8 Hz), 8.34 (1H, d, J=5.8 Hz), 8.75-8.79 (1H, m).

Synthetic Example 13

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl methoxyacetate To a solution (15 mL) of bis(trichloromethyl)carbonate (0.652 g) in tetrahydrofuran was dropwise added a solution (1 mL) of pyridine (0.55 mL) in tetrahydrofuran under ice-cooling. After stirring under ice-cooling for 30 min., 2-(methylamino)ethyl methoxyacetate (0.99 g) obtained in Reference Example 13 was added. The mixture was stirred at room temperature for 3 hrs. After concentration under reduced pressure, ethyl acetate (80 mL) and water (50 mL) were added to the residue and the mixture was stirred. The ethyl acetate layer was separated and taken, washed with saturated brine (30 mL) and dried over anhydrous magnesium sulfate. After concentration under reduced pressure, the residue was dissolved in tetrahydrofuran (15 mL). (R)-2-[[[3-Methyl-4-(2,2,2-trifluoroethoxy)-2-pyridyl]methyl]sulfinyl]-1H-benzimidazole (1.13 g), triethylamine (0.86 mL) and 4-dimethylaminopyridine (0.037 g) were added, and the mixture was stirred at 60° C. for 4 days. After concentration under reduced pressure, ethyl acetate (80 mL) and water (30 mL) were added to the residue, and the mixture was stirred. The ethyl acetate layer was separated and taken, and the ethyl acetate layer was washed with a saturated aqueous sodium hydrogen carbonate solution (30 mL) and water (30 mL), and dried over anhydrous magnesium sulfate. After concentration under reduced pressure, the residue was purified by silica gel column chromatography (eluted with ethyl acetate, then acetone:ethyl acetate=1:3), and further by basic silica gel column chromatography (eluted with ethyl acetate:hexane=1:1, then 3:1) to give the title compound (0.588 g) as colorless syrup.

¹H-NMR(CDCl₃): 2.32 (3H, s), 2.68 (3H, s), 3.48 (3H, s), 3.69-4.02 (4H, m), 4.38 (2H, q, J=7.8 Hz), 4.67 (2H, t, J=6.6 Hz), 4.99 (1H, d, J=13.9 Hz), 5.12 (1H, d, J=13.9 Hz), 6.63 (1H, d, J=5.7 Hz), 7.29-7.46 (2H, m), 7.62 (1H, m), 7.81 (1H, m), 8.25 (1H, d, J=5.7 Hz).

Synthetic Example 14

Ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (40 mL) of bis(trichloromethyl)carbonate (1.31 g) in tetrahydrofuran was dropwise added a solution (2 mL) of pyridine (1.07 mL) in tetrahydrofuran under ice-cooling. After stirring under ice-cooling for 10 min., ethyl 2-(methylamino)ethyl carbonate hydrochloride (2.02 g) obtained in Reference Example 14 was added. A solution (2 mL) of triethylamine (1.84 mL) in tetrahydrofuran was dropwise added and the mixture was stirred at room temperature for 1 hr. After concentration under reduced pressure, water (100 mL) was added to the residue, and the mixture was extracted with ethyl acetate (100 mL). The ethyl acetate layer was washed with 0.2N hydrochloric acid (50 mL) and saturated brine (100 mL) and dried over anhydrous magnesium sulfate. After concentration under reduced pressure, the residue was dissolved in tetrahydrofuran (50 mL). (R)-2-[[[3-Methyl-4-(2,2,2-trifluoroethoxy)-2-pyridyl]methyl]sulfinyl]-1H-benzimidazole (3.69 g), triethylamine (2.09 mL) and 4-dimethylaminopyridine (0.12 g) were added, and the mixture was stirred at 60° C. for 6 hrs. and at room temperature for 8 hrs. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was purified by basic silica gel column chromatography (eluted with ethyl acetate:hexane=3:7, then ethyl acetate). Crystallization from diethyl ether and recrystallization from diethyl ether gave the title compound (3.84 g) as a colorless solid.

$^1$H-NMR(CDCl$_3$): 1.32 (3H, t, J=7.2 Hz), 2.23 (3H, s), 3.10 (3H, bs), 3.50-4.20 (2H, br), 4.22 (2H, q, J=7.2 Hz), 4.39 (2H, q, J=7.9 Hz), 4.45 (2H, m), 4.80-5.15 (2H, br), 6.65 (1H, d, J=5.6 Hz), 7.36-7.50 (3H, m), 7.84 (1H, d, J=7.8 Hz), 8.35 (1H, d, J=5.6 Hz).

Synthetic Example 15

Isopropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., isopropyl 2-(methylamino)ethyl carbonate hydrochloride (0.99 g) obtained in Reference Example 15 was added. A solution (1 mL) of triethylamine (0.70 mL) in tetrahydrofuran was dropwise added and the mixture was stirred at room temperature for 1 hr. Bis(trichloromethyl)carbonate (0.50 g), a solution (1 mL) of pyridine (0.40 mL) in tetrahydrofuran and a solution (1 mL) of triethylamine (0.70 mL) in tetrahydrofuran were successively added and the mixture was stirred at room temperature for 1 hr. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred at 60° C. for 12 hrs. and at room temperature for 3 days. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2), and further by basic silica gel column chromatography (eluted with ethyl acetate:hexane=3:7, then ethyl acetate). Crystallization from diethyl ether and recrystallization from acetone-diisopropyl ether gave the title compound (0.58 g) as a colorless solid.

$^1$H-NMR(CDCl$_3$): 1.31 (6H, d, J=6.3 Hz), 2.23 (3H, s), 3.08 (3H, bs), 3.40-4.30 (2H, br), 4.37 (2H, q, J=7.9 Hz), 4.32-4.53 (2H, m), 4.80-5.20 (3H, m), 6.63 (1H, d, J=5.7 Hz), 7.35-7.50 (3H, m), 7.83 (1H, d, J=7.2 Hz), 8.34 (1H, d, J=5.7 Hz).

Synthetic Example 16

Isopropyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate To a solution (20 mL) of bis(trichloromethyl)carbonate (0.582 g) in tetrahydrofuran was dropwise added a solution (1 mL) of pyridine (0.49 mL) in tetrahydrofuran under ice-cooling. After stirring under ice-cooling for 30 min., isopropyl 2-(methylamino)ethyl carbonate hydrochloride (1.18 g) obtained in Reference Example 15 was added. A solution (1 mL) of triethylamine (0.84 mL) in tetrahydrofuran was added and the mixture was stirred at room temperature for 2 hrs. After concentration under reduced pressure, ethyl acetate (80 mL) and water (30 mL) were added to the residue, and the mixture was stirred. The ethyl acetate layer was separated and taken, washed with saturated brine (30 mL) and dried over anhydrous magnesium sulfate. After concentration under reduced pressure, the residue was dissolved in tetrahydrofuran (25 mL). 2-[[[3-Methyl-4-(2,2,2-trifluoroethoxy)-2-pyridyl]methyl]sulfinyl]-1H-benzimidazole (1.73 g), triethylamine (1.31 mL) and 4-dimethylaminopyridine (0.057 g) were added, and the mixture was stirred at 60° C. for 5 hrs. After concentration under reduced pressure, ethyl acetate (100 mL) and water (50 mL) were added to the residue, and the mixture was stirred. The ethyl acetate layer was separated and taken, washed with saturated brine (50 mL) and dried over anhydrous magnesium sulfate. After concentration under reduced pressure, the residue was purified by basic silica gel column chromatography (eluted with ethyl acetate:hexane=1:1), and further by silica gel column chromatography (eluted with ethyl acetate:hexane=1:1, then 2:1). Crystallization from diisopropyl ether-hexane and recrystallization from diisopropyl ether gave the title compound (1.20 g) as a colorless solid.

$^1$H-NMR(CDCl$_3$): 1.31 (6H, d, J=6.6 Hz), 2.23 (3H, s), 3.08 (3H, bs), 3.50-3.90 (2H, bm), 4.38 (2H, q, J=7.8 Hz), 4.36-4.58 (2H, bm), 4.79-5.15 (3H, m), 6.64 (1H, d, J=5.7 Hz), 7.35-7.48 (3H, m), 7.83 (1H, d, J=7.5 Hz), 8.34 (1H, d, J=5.7 Hz).

Synthetic Example 17

Benzyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., benzyl 2-(methylamino)ethyl carbonate hydrochloride (1.08 g) obtained in Reference Example 16 was added. A solution (1 mL) of triethylamine (0.70 mL) in tetrahydrofuran was dropwise added, and the mixture was stirred overnight at room temperature. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by flash silica gel column chromatography (eluted with acetone:hexane=1:3, then 3:2). Crystallization from acetone-diethyl ether and recrystallization from acetone-diethyl ether gave the title compound (1.17 g) as a colorless solid.

$^1$H-NMR(CDCl$_3$): 2.22 (3H, s), 3.05 (3H, bs), 3.50-4.20 (2H, br) 4.37 (2H, q, J=7.8 Hz), 4.46 (2H, m), 4.80-5.10 (2H, br), 5.17 (2H, s), 6.62 (1H, d, J=5.6 Hz), 7.26-7.48 (8H, m), 7.77-7.88 (1H, m), 8.33 (1H, d, J=5.6 Hz).

Synthetic Example 18

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate To a solution (20 mL) of bis(trichloromethyl)carbonate (0.48 g) in tetrahydrofuran was dropwise added a solution (1 mL) of pyridine (0.39 mL) in tetrahydrofuran under ice-cooling. After stirring under ice-cooling for 20 min., 2-(methylamino)ethyl tetrahydropyran-4-yl carbonate hydrochloride (0.96 g) obtained in Reference Example 17 was added. A solution (1 mL) of triethylamine (0.67 mL) in tetrahydrofuran was dropwise added, and the mixture was stirred at room temperature for 2 hrs. After concentration under reduced pressure, water (50 mL) was added to the residue. The mixture was extracted with ethyl acetate (50 mL). The ethyl acetate layer was washed with 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.26 g), triethylamine (0.71 mL) and 4-dimethylaminopyridine (0.042 g) were added, and the mixture was stirred at 60° C. for 6 hrs. and at room temperature for 8 hrs. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate). Crystallization from diethyl ether and recrystallization from acetone-diisopropyl ether gave the title compound (1.45 g) as a colorless solid.

$^1$H-NMR(CDCl$_3$): 1.64-1.81 (2H, m), 1.92-2.03 (2H, m), 2.23 (3H, s), 3.09 (3H, bs), 3.40-4.30 (2H, br), 3.45-3.57 (2H, m), 3.87-3.97 (2H, m), 4.38 (2H, q, J=7.8 Hz), 4.45 (2H, m), 4.77-5.15 (3H, m), 6.64 (1H, d, J=5.7 Hz), 7.35-7.50 (3H, m), 7.83 (1H, d, J=6.9 Hz), 8.35 (1H, d, J=5.7 Hz).

Synthetic Example 19

2-Methoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 10 min., 2-methoxyethyl 2-(methylamino)ethyl carbonate hydrochloride (1.07 g) obtained in Reference Example 18 was added. A solution (1 mL) of triethylamine (0.84 mL) in tetrahydrofuran was dropwise added and the mixture was stirred at room temperature for 1 hr. After concentration under reduced pressure, water (50 mL) was added to the residue. The mixture was extracted with ethyl acetate (50 mL). The ethyl acetate layer was washed with 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.85 g), triethylamine (1.05 mL) and 4-dimethylaminopyridine (0.061 g) were added, and the mixture was stirred at 60° C. for 6 hrs. and at room temperature for 8 hrs. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate). Crystallization from ethyl acetate-diethyl ether and recrystallization from ethyl acetate-diisopropyl ether gave the title compound (1.39 g) as a colorless solid.

$^1$H-NMR(CDCl$_3$): 2.23 (3H, s), 3.09 (3H, bs), 3.37 (3H, s), 3.50-4.20 (2H, br), 3.59-3.65 (2H, m), 4.28-4.33 (2H, m), 4.38 (2H, q, J=7.8 Hz), 4.46 (2H, m), 4.80-5.15 (2H, br), 6.64 (1H, d, J=5.7 Hz), 7.35-7.47 (3H, m), 7.83 (1H, d, J=7.8 Hz), 8.34 (1H, d, J=5.7 Hz).

Synthetic Example 20

2-[Ethyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate To a solution (30 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 10 min., 2-(ethylamino)ethyl acetate hydrochloride (0.67 g) obtained in Reference Example 20 was added. A solution (1 mL) of triethylamine (0.84 mL) in tetrahydrofuran was dropwise added and the mixture was stirred at room temperature for 1 hr. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred overnight at 60° C. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate) to give the title compound (1.58 g) as a yellow amorphous solid.

¹H-NMR(CDCl₃): 1.25 (3H, m), 2.08 (3H, s), 2.23 (3H, s), 3.30-4.10 (4H, br), 4.23-4.45 (2H, m), 4.38 (2H, q, J=7.8 Hz), 4.75-5.20 (2H, br), 6.64 (1H, d, J=5.7 Hz), 7.35-7.46 (3H, m), 7.84 (1H, d, J=6.9 Hz), 8.36 (1H, d, J=5.7 Hz).

Synthetic Example 21

2-[Isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate To a solution (10 mL) of bis(trichloromethyl)carbonate (0.543 g) in tetrahydrofuran was dropwise added a solution (5 mL) of pyridine (0.445 mL) in tetrahydrofuran under ice-cooling, and the mixture was stirred at 0° C. for 30 min. 2-(Isopropylamino)ethyl acetate hydrochloride (1.0 g) obtained in Reference Example 22 was added to the reaction mixture. A solution (5 mL) of triethylamine (0.805 mL) in tetrahydrofuran was added, and the mixture was stirred at room temperature for 30 min. The reaction mixture was concentrated under reduced pressure, water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The obtained oil was dissolved in tetrahydrofuran (5 mL), and added to a solution (20 mL) of (R)-2-[[[3-methyl-4-(2,2,2-trifluoroethoxy)-2-pyridyl]methyl]sulfinyl]-1H-benzimidazole (1.73 g), triethylamine (1.53 mL) and 4-dimethylaminopyridine (0.134 g) in tetrahydrofuran. The mixture was stirred at 40° C. for 12 hrs. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The residue was purified by silica gel column chromatography (eluted with ethyl acetate:hexane=2:1, then ethyl acetate) to give the title compound (1.50 g) as a pale-yellow amorphous solid.

¹H-NMR(CDCl₃): 1.20-1.40 (6H, m), 2.05 (3H×0.4, s), 2.11 (3H×0.6, s), 2.18 (3H×0.6, s), 2.27 (3H×0.4, s), 3.40-3.60 (1H, m), 3.70-4.60 (6H, m), 4.70-5.25 (2H, m), 6.65 (1H, d, J=5.8 Hz), 7.30-7.50 (3H, m), 7.75-7.90 (1H, m), 8.37 (1H, d, J=5.8 Hz).

Synthetic Example 22

Ethyl 2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (10 mL) of bis(trichloromethyl)carbonate (0.467 g) in tetrahydrofuran was dropwise added a solution (5 mL) of pyridine (0.381 mL) in tetrahydrofuran under ice-cooling, and the mixture was stirred at 0° C. for 30 min. Ethyl 2-(isopropylamino)ethyl carbonate hydrochloride (1.0 g) obtained in Reference Example 23 was added to the reaction mixture. A solution (5 mL) of triethylamine (0.69 mL) in tetrahydrofuran was dropwise added, and the mixture was stirred at 0° C. for 15 min. and at room temperature for 30 min. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The obtained oil was dissolved in tetrahydrofuran (5 mL), and added to a solution (20 mL) of (R)-2-[[[3-methyl-4-(2,2,2-trifluoroethoxy)-2-pyridyl]methyl]sulfinyl]-1H-benzimidazole (1.48 g), triethylamine (1.32 mL) and 4-dimethylaminopyridine (0.115 g) in tetrahydrofuran, and the mixture was stirred at 40° C. for 12 hrs. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The residue was purified by silica gel column chromatography (eluted with ethyl acetate:hexane=2:1, then ethyl acetate) to give the title compound (1.20 g) as a pale-yellow amorphous solid.

¹H-NMR(CDCl₃): 1.20-1.40 (9H, m), 2.17 (3H×0.6, s) 2.27 (3H×0.4, s), 3.40-3.70 (1H, m), 3.75-4.65 (8H, m), 4.70-5.30 (2H, m), 6.64 (1H, d, J=5.8 Hz), 7.35-7.55 (3H, m), 7.75-7.90 (1H, m), 8.38 (1H, d, J=5.8 Hz).

Synthetic Example 23

2-[Cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate To a solution (10 mL) of bis(trichloromethyl)carbonate (0.593 g) in tetrahydrofuran was dropwise added pyridine (0.485 mL) under ice-cooling. After stirring under ice-cooling for 30 min., 2-(cyclohexylamino)ethyl acetate hydrochloride (1.33 g) obtained in Reference Example 25 was added. Triethylamine (0.84 mL) was dropwise added, and the mixture was stirred at room temperature for 2 hrs. Ethyl acetate (50 mL) was added to the reaction mixture and the mixture was washed with water (50 mL) and saturated brine (50 mL), dried over anhydrous magnesium sulfate and concentrated under reduced pressure. The residue was dissolved in tetrahydrofuran (20 mL), and (R)-2-[[[3-methyl-4-(2,2,2-trifluoroethoxy)-2-pyridyl]methyl]sulfinyl]-1H-benzimidazole (1.61 g), triethylamine (1.21 mL) and 4-dimethylaminopyridine (0.053 g) were added. The mixture was stirred at 60° C. for 24 hrs. Ethyl acetate (50 mL) was added to the reaction mixture, and the mixture was washed with water (20 mL) and saturated brine (50 mL), dried over anhydrous sodium sulfate, and concentrated under reduced pressure. The residue was purified by flash silica gel column chromatography (eluted with ethyl acetate:hexane=1:4, then ethyl acetate) to give the title compound (2.12 g) as a pale-yellow amorphous solid.

¹H-NMR(CDCl₃): 1.00-2.42 (16H, m), 3.30-3.70 (2H, m), 3.80-4.00 (1H, m), 4.27-4.42 (2H, m), 4.40 (2H, q, J=8.2 Hz), 4.78 (1H×0.5, d, J=13.2 Hz), 4.97 (2H×0.5, s), 5.20 (1H×0.5, d, J=13.2 Hz), 6.67 (1H, d, J=5.8 Hz), 7.36-7.46 (3H, m), 7.81-7.91 (1H, m), 8.39 (1H, d, J=5.8 Hz).

Synthetic Example 24

2-[Cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl ethyl carbonate To a solution (10 mL) of bis(trichloromethyl)carbonate (0.238 g) in tetrahydrofuran was dropwise added pyridine (0.20 mL) under ice-cooling. After stirring under ice-cooling for 30 min., 2-(cyclohexylamino)ethyl ethyl carbonate hydrochloride (0.605 g) obtained in Reference Example 26 was added. Triethylamine (0.335 mL) was dropwise added, and the mixture was stirred at room temperature for 2 hrs. Ethyl acetate (50 mL) was added to the reaction mixture, and the mixture was washed with water (50 mL) and saturated brine (50 mL), dried over anhydrous magnesium sulfate and concentrated under reduced pressure. The residue was dissolved in tetrahydrofuran (10 mL), and (R)-2-[[[3-methyl-4-(2,2,2-trifluoroethoxy)-2-pyridyl]methyl]sulfinyl]-1H-benzimidazole (0.60 g), triethylamine (0.45 mL) and 4-dimethylaminopyridine (0.02 g) were added. The mixture was stirred at 60° C. for 24 hrs. Ethyl acetate (50 mL) was added to the reaction mixture, and the mixture was washed with water (20 mL) and saturated brine (50 mL), dried over anhydrous sodium sulfate, and concentrated under reduced pressure. The residue was purified by flash silica gel column chromatography (eluted with ethyl acetate:hexane=1:4, then ethyl acetate) to give the title compound (0.92 g) as a pale-yellow amorphous solid.

$^1$H-NMR(CDCl$_3$): 1.02-2.27 (16H, m), 3.40-4.60 (9H, m), 4.78 (1H×0.5, d, J=13.2 Hz), 4.97 (2H×0.5, s), 5.44 (1H×0.5, d, J=13.2 Hz), 6.69 (1H, d, J=5.6 Hz), 7.32-7.54 (3H, m), 7.80-7.91 (1H, m), 8.38 (1H, d, J=5.6 Hz).

Synthetic Example 25

2-[[[ (R)-2-[[[3-Methyl-4-(2,2,2-trifluoroethoxy)-2-pyridyl]methyl]sulfinyl]-1H-benzimidazol-1-yl]carbonyl](phenyl)amino]ethyl acetate To a solution (350 mL) of bis(trichloromethyl)carbonate (13.4 g) in tetrahydrofuran was dropwise added pyridine (10.38 mL) under ice-cooling. After stirring under ice-cooling for 30 min., 2-anilinoethyl acetate hydrochloride (25.9 g) obtained in Reference Example 27 was added. Triethylamine (18.4 mL) was dropwise added, and the mixture was stirred at room temperature for 2 hrs. After concentration under reduced pressure, ethyl acetate (500 mL), and water (500 mL) were added to the residue, and the mixture was stirred. The ethyl acetate layer was separated and taken, washed with saturated brine (500 mL), dried over anhydrous magnesium sulfate and concentrated under reduced pressure to give 2-[(chlorocarbonyl)(phenyl)amino]ethyl acetate. This was dissolved in tetrahydrofuran (300 mL), (R)-2-[[[3-methyl-4-(2,2,2-trifluoroethoxy)-2-pyridyl]methyl]sulfinyl]-1H-benzimidazole (41.2 g), triethylamine (15.6 mL) and 4-dimethylaminopyridine (1.363 g) were added, and the mixture was stirred at 60° C. for 3 hrs. Ethyl acetate (800 mL) was added to the reaction mixture, and the mixture was washed twice with water (800 mL) and with saturated brine (800 mL), dried over anhydrous sodium sulfate, and concentrated under reduced pressure. The residue was purified by basic silica gel column chromatography (eluted with ethyl acetate:hexane=3:7, then 1:1). Crystallization from diethyl ether gave the title compound (54.1 g) as a white solid.

$^1$H-NMR(CDCl$_3$): 2.00 (3H, s), 2.25 (3H, s), 4.15-4.48 (6H, m), 4.83 (1H, d, J=13.6 Hz), 5.05 (1H, d, J=13.6 Hz), 6.67 (1H, d, J=5.4 Hz), 7.03-7.45 (8H, m), 7.64-7.69 (1H, m), 8.40 (1H, d, J=5.4 Hz).

Synthetic Example 26

2-[[[2-[[[3-Methyl-4-(2,2,2-trifluoroethoxy)-2-pyridyl]methyl]sulfinyl]-1H-benzimidazol-1-yl]carbonyl](phenyl)amino]ethyl acetate To a solution (10 mL) of 2-[(chlorocarbonyl)(phenyl)amino]ethyl acetate (0.58 g) prepared in the same manner as in Synthetic Example 25 in tetrahydrofuran were added 2-[[[3-methyl-4-(2,2,2-trifluoroethoxy)-2-pyridyl]methyl]sulfinyl]-1H-benzimidazole (0.739 g), triethylamine (0.558 mL) and 4-dimethylaminopyridine (0.024 g), and the mixture was stirred at 60° C. for 15 hrs. Ethyl acetate (30 mL) was added to the reaction mixture, and the mixture was washed with water (50 mL) and saturated brine (50 mL), dried over anhydrous sodium sulfate, and concentrated under reduced pressure. The residue was purified by flash silica gel column chromatography (eluted with acetone:hexane=1:4, then 3:2). Crystallization from diethyl ether gave the title compound (0.779 g) as a white solid.

$^1$H-NMR(CDCl$_3$): 1.99 (3H, s), 2.25 (3H, s), 4.20-4.48 (6H, m), 4.83 (1H, d, J=13.6 Hz), 5.05 (1H, d, J=13.6 Hz), 6.67 (1H, d, J=5.8 Hz), 7.03-7.45 (8H, m), 7.64-7.69 (1H, m), 8.40 (1H, d, J=5.8 Hz).

Synthetic Example 27 tert-Butyl [2-[methyl[[(R)-2-[[[3-methyl-4-(2,2,2-trifluoroethoxy)-2-pyridyl]methyl]sulfinyl]-1H-benzimidazol-1-yl]carbonyl]amino]-3-pyridyl]methyl carbonate To a solution (20 mL) of bis(trichloromethyl)carbonate (0.30 g) in tetrahydrofuran was dropwise added pyridine (0.24 mL) under ice-cooling. After stirring under ice-cooling for 30 min., tert-butyl [2-(methylamino)-3-pyridyl]methyl carbonate (0.71 g) obtained in Reference Example 28 was added, and the mixture was stirred at room temperature for 2 hrs. The precipitated solid was filtered off and the filtrate was concentrated under reduced pressure. The residue was dissolved in tetrahydrofuran (20 mL), (R)-2-[[[3-methyl-4-(2,2,2-trifluoroethoxy)-2-pyridyl]methyl]sulfinyl]-1H-benzimidazole (0.92 g), triethylamine (0.70 mL) and 4-dimethylaminopyridine (0.031 g) were added, and the mixture was stirred at 60° C. for 1 hr. Water (50 mL) was added to the reaction mixture and the mixture was extracted twice with ethyl acetate (50 mL). The ethyl acetate layer was washed with saturated brine (50 mL), dried over anhydrous sodium sulfate, and concentrated under reduced pressure. The residue was purified by flash silica gel column chromatography (eluted with acetone:hexane=1:2), and further by basic silica gel column chromatography (eluted with ethyl acetate) to give the title compound (0.38 g) as a pale-yellow amorphous solid.

$^1$H-NMR(CDCl$_3$): 1.46 (9H, s), 2.25 (3H, s), 3.54 (3H, s), 4.37 (2H, q, J=8.0 Hz), 4.95 (2H, s), 5.15 (1H, d, J=14.0 Hz), 5.27 (1H, d, J=14.0 Hz), 6.63 (1H, d, J=5.4 Hz), 7.26-7.45 (3H, m), 7.69-7.87 (3H, m), 8.33 (1H, d, J=5.4 Hz), 8.44-8.46 (1H, m).

Synthetic Example 28

2-[Methyl[[(R)-2-[[[3-methyl-4-(2,2,2-trifluoroethoxy)-2-pyridyl]methyl]sulfinyl]-1H-benzimidazol-1-yl]carbonyl]amino]benzyl acetate To a solution (30 mL) of bis(trichloromethyl)carbonate (1.46 g) in tetrahydrofuran was dropwise added pyridine (1.16 mL) under ice-cooling. After stirring under ice-cooling for 30 min., 2-(methylamino)benzyl acetate (2.57 g) obtained in Reference Example 29 was added. The mixture was stirred at room temperature for 3 hrs. The precipitated solid was filtered off and the filtrate was concentrated under reduced pressure. The residue was dissolved in tetrahydrofuran (40 mL), (R)-2-[[[3-methyl-4-(2,2,2-trifluoroethoxy)-2-pyridyl]methyl]sulfinyl]-1H-benzimidazole (4.41 g), triethylamine (3.33 mL) and 4-dimethylaminopyridine (0.15 g) were added, and the mixture was stirred at 60° C. for 18 hrs. Water (100 mL) was added to the reaction mixture, and the mixture was extracted with ethyl acetate (100 mL). The ethyl acetate layer was washed with saturated brine (100 mL), dried over anhydrous sodium sulfate, and concentrated under reduced pressure. The residue was purified by flash silica gel column chromatography (eluted with acetone:hexane=1:4, then 1:2). Crystallization from ethyl acetate-diethyl ether-hexane gave the title compound (2.76 g) as a white solid.

$^1$H-NMR(CDCl$_3$): 2.10 (3H, s), 2.00-2.30 (3H, br), 3.20-3.50 (3H, br), 4.38 (2H, q, J=7.6 Hz), 4.70-5.20 (2H, m), 5.20-5.50 (2H, m), 6.65 (1H, d, J=5.4 Hz), 7.10-7.82 (8H, m), 8.38 (1H, d, J=5.4 Hz).

Synthetic Example 29

2-[[2-(Acetyloxy)ethyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 10 min., 2-[(2-acetyloxyethyl)amino]ethyl acetate hydrochloride (1.13 g) obtained in Reference Example 30 was added. A solution (1 mL) of triethylamine (0.70 mL) in tetrahydrofuran was dropwise added, and the mixture was stirred at room temperature for 2 hrs. The precipitated solid was filtered off and the filtrate was concentrated under reduced pressure. Ethyl acetate (20 mL) was added to the residue, the precipitated solid was filtered off and the filtrate was concentrated under reduced pressure. The residue was dissolved in tetrahydrofuran (30 mL). (R)-2-[[[3-Methyl-4-(2,2,2-trifluoroethoxy)-2-pyridyl]methyl]sulfinyl]-1H-benzimidazole (1.48 g), triethylamine (1.12 mL) and 4-dimethylaminopyridine (catalytic amount) were added, and the mixture was stirred at 60° C. overnight. After concentration under reduced pressure, water (50 mL) was added to the residue. The mixture was extracted with ethyl acetate (50 mL). The ethyl acetate layer was washed with saturated brine (50 mL) and dried over anhydrous magnesium sulfate. After concentration under reduced pressure, the residue was purified by silica gel column chromatography (eluted with ethyl acetate:hexane=1:1, then ethyl acetate), and further by basic silica gel column chromatography (eluted with ethyl acetate:hexane=1:1, then ethyl acetate). The resulting product was dissolved in ethyl acetate (20 mL), activated carbon was added and the mixture was stirred overnight. The activated carbon was filtered off and the filtrate was concentrated under reduced pressure to give the title compound (1.60 g) as a yellow amorphous solid.

$^1$H-NMR(CDCl$_3$): 2.06 (3H, s), 2.08 (3H, s), 2.24 (3H, s), 3.40-4.45 (8H, m), 4.39 (2H, q, J=7.9 Hz), 4.88 (1H, d, J=13.2 Hz), 5.05 (1H, d, J=13.2 Hz), 6.66 (1H, d, J=5.6 Hz), 7.38-7.50 (3H, m), 7.87 (1H, d, J=6.9 Hz), 8.36 (1H, d, J=5.6 Hz).

Synthetic Example 30

[(2S)-1-[[(R)-2-[[[3-Methyl-4-(2,2,2-trifluoroethoxy)-2-pyridyl]methyl]sulfinyl]-1H-benzimidazol-1-yl]carbonyl]-2-pyrrolidinyl]methyl acetate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 1 hr., (S)-2-pyrrolidinylmethyl acetate hydrochloride (0.90 g) obtained in Reference Example 31 was added. A solution (1 mL) of triethylamine (0.70 mL) in tetrahydrofuran was dropwise added, and the mixture was stirred at room temperature for 2 hrs. After concentration under reduced pressure, water (50 mL) was added to the residue, and the mixture was extracted with ethyl acetate (50 mL). The extract was dried over anhydrous magnesium sulfate and concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g) were added, and the mixture was stirred at 60° C. for 1 day and at room temperature for 2 days. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate) and further by silica gel column chromatography (eluted with ethyl acetate:hexane=3:1, then ethyl acetate, then acetone:ethyl acetate=1:4, then 2:3) to give the title compound (0.80 g) as a pale-yellow amorphous solid.

$^1$H-NMR(CDCl$_3$): 1.80-2.30 (4H, m), 2.09 (3H, s), 2.30 (3H, s), 3.39 (1H, m), 3.50-3.62 (1H, m), 4.20-4.45 (4H, m), 4.58 (1H, m), 4.89 (1H, d, J=13.5 Hz), 4.96 (1H, d, J=13.5 Hz), 6.65 (1H, d, J=5.9 Hz), 7.36-7.48 (3H, m), 7.89 (1H, d, J=8.7 Hz), 8.38 (1H, d, J=5.9 Hz).

Synthetic Example 31

Ethyl [methyl[[(R)-2-[[[3-methyl-4-(2,2,2-trifluoroethoxy)-2-pyridyl]methyl]sulfinyl]-1H-benzimidazol-1-yl]carbonyl]amino]acetate To a solution (30 mL) of bis(trichloromethyl)carbonate (0.50 g) in tetrahydrofuran was dropwise added a solution (1 mL) of pyridine (0.40 mL) in tetrahydrofuran under ice-cooling. After stirring under ice-cooling for 30 min., sarcosine ethyl ester hydrochloride (0.77 g) was added. A solution (1 mL) of triethylamine (0.70 mL) in tetrahydrofuran was dropwise added and the mixture was stirred at room temperature for 1 hr. The precipitated solid was filtered off and the filtrate was concentrated under reduced pressure. Water (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was dissolved in tetrahydrofuran (33 mL). (R)-2-[[[3-Methyl-4-(2,2,2-trifluoroethoxy)-2-pyridyl]methyl]sulfinyl]-1H-benzimidazole sodium salt (1.37 g) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate) to give the title compound (0.40 g) as a yellow amorphous solid.

$^1$H-NMR(CDCl$_3$): 1.33 (3H, t, J=7.1 Hz), 2.24 (3H, s), 3.10 (3H, bs), 3.70-4.30 (2H, br), 4.28 (2H, q, J=7.1 Hz), 4.38 (2H, q, J=7.8 Hz), 4.82-5.10 (2H, br), 6.63 (1H, d, J=5.5 Hz), 7.34-7.52 (2H, m), 7.70-7.90 (2H, m), 8.32 (1H, d, J=5.5 Hz).

Synthetic Example 32

2-[[[5-Methoxy-2-[[(4-methoxy-3,5-dimethyl-2-pyridyl)methyl]sulfinyl]-1H-benzimidazol-1-yl]carbonyl](methyl)amino]ethyl benzoate To a solution (10 mL) of bis(trichloromethyl)carbonate (0.344 g) in tetrahydrofuran was dropwise added a solution (5 mL) of pyridine (0.281 mL) in tetrahydrofuran under ice-cooling, and the mixture was stirred at 0° C. for 30 min. 2-(Methylamino)ethyl benzoate hydrochloride (0.750 g) obtained in Reference Example 5 was added to the reaction mixture. A solution (5 mL) of triethylamine (0.485 mL) in tetrahydrofuran was added, and the mixture was stirred at 0° C. for 1 hr. and at room temperature for 30 min. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The obtained oil was dissolved in tetrahydrofuran (5 mL), the mixture was added to a solution (10 mL) of 5-methoxy-2-[[(4-methoxy-3,5-dimethyl-2-pyridyl)methyl]sulfinyl]-1H-benzimidazole (1.0 g), triethylamine (0.808 mL) and 4-dimethylaminopyridine (0.071 g) in tetrahydrofuran, and the mixture was stirred at 40° C. for 18 hrs. The reaction mixture was concentrated under reduced pressure and water (30 mL) was added to the residue. The mixture was extracted with ethyl acetate (50 mL). The ethyl acetate layer was washed with saturated brine (30 mL), dried over anhydrous sodium sulfate, and concentrated under reduced pressure. The residue was purified by silica gel column chromatography (eluted with ethyl acetate:hexane=1:1, then ethyl acetate) to give a 1:1 mixture (1.50 g) of the title compound and 2-[[[6-methoxy-2-[[(4-methoxy-3,5-dimethyl-2-pyridyl)methyl]sulfinyl]-1H-benzimidazol-1-yl]carbonyl](methyl)amino]ethyl benzoate as a pale-yellow amorphous solid.

$^1$H-NMR(CDCl$_3$): 2.05-2.35 (6H, m), 3.00-3.30 (3H, br), 3.60-4.40 (8H, m), 4.60-5.10 (4H, m), 6.80-7.00 (2H, m), 7.20-7.70 (4H, m), 7.95-8.25 (3H, m).

Synthetic Example 33

3-[Methyl[[(R)-2-[[[3-methyl-4-(2,2,2-trifluoroethoxy)-2-pyridyl]methyl]sulfinyl]-1H-benzimidazol-1-yl]carbonyl]amino]propyl benzoate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 1 hr., 3-(methylamino)propyl benzoate hydrochloride (1.38 g) obtained in Reference Example 32 was added. A solution (1 mL) of triethylamine (0.84 mL) in tetrahydrofuran was dropwise added, and the mixture was stirred at room temperature for 2 hrs. After concentration under reduced pressure, water (40 mL) was added to the residue, and the mixture was extracted with ethyl acetate (80 mL). The ethyl acetate layer was washed with saturated brine (25 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.63 g), triethylamine (1.23 mL) and 4-dimethylaminopyridine (0.054 g) were added, and the mixture was stirred at 60° C. for 4 hrs. After concentration under reduced pressure, water (40 mL) was added to the residue, and the mixture was extracted with ethyl acetate (80 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 1:1) to give the title compound (1.26 g) as a yellow amorphous solid.

$^1$H-NMR(CDCl$_3$): 2.21 (3H, s), 2.20-2.30 (2H, bm), 3.06 (3H, bs), 3.60-3.75 (2H, bm), 4.36 (2H, q, J=7.8 Hz), 4.30-4.50 (2H, bm), 4.80-5.15 (2H, bm), 6.62 (1H, d, J=5.7 Hz), 7.26-7.44 (5H, m), 7.54 (1H, m), 7.81 (1H, m), 7.93-8.03 (2H, bm), 8.35 (1H, d, J=5.7 Hz).

Synthetic Example 34

2-[Methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 20 min., 2-(methylamino)ethyl tetrahydropyran-4-yl carbonate hydrochloride (1.43 g) obtained in Reference Example 17 was added. A solution (1 mL) of triethylamine (0.84 mL) in tetrahydrofuran was dropwise added, and the mixture was stirred at room temperature for 3 hrs. After concentration under reduced pressure, water (30 mL) was added to the residue, and the mixture was extracted with ethyl acetate (80 mL). The ethyl acetate layer was washed with saturated brine (20 mL), dried over anhydrous magnesium sulfate and concentrated under reduced pressure. The residue was dissolved in tetrahydrofuran (20 mL). 2-[[[3-Methyl-4-(2,2,2-trifluoroethoxy)-2-pyridyl]methyl]sulfinyl]-1H-benzimidazole (1.63 g), triethylamine (1.23 mL) and 4-dimethylaminopyridine (0.027 g) were added, and the mixture was stirred at 60° C. for 17.5 hrs. After concentration under reduced pressure, water (50 mL) was added to the residue, and the mixture was extracted with ethyl acetate (120 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 1:1), then by silica gel column chromatography (eluted with ethyl acetate:hexane=1:1, then 2:1). Crystallization from diethyl ether gave the title compound (1.23 g) as a colorless solid.

$^1$H-NMR(CDCl$_3$): 1.64-1.81 (2H, m), 1.92-2.03 (2H, m), 2.23 (3H, s), 3.10 (3H, bs), 3.40-4.30 (2H, br), 3.46-3.59 (2H, m), 3.87-3.99 (2H, m), 4.39 (2H, q, J=7.9 Hz), 4.45 (2H, m), 4.77-5.15 (3H, m), 6.65 (1H, d, J=5.4 Hz), 7.35-7.50 (3H, m), 7.85 (1H, m), 8.36 (1H, d, J=5.4 Hz).

Synthetic Example 35

Ethyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 30 min., ethyl 2-(methylamino)ethyl carbonate hydrochloride (1.10 g) obtained in Reference Example 14 was added. A solution (1 mL) of triethylamine (0.84 mL) in tetrahydrofuran was dropwise added, and the mixture was stirred at room temperature for 3 hrs. After concentration under reduced pressure, water (30 mL) was added to the residue, and the mixture was extracted with ethyl acetate (80 mL). The ethyl acetate layer was washed with saturated brine (30 mL) and dried over anhydrous magnesium sulfate. The layer was concentrated under reduced pressure, and the residue was dissolved in tetrahydrofuran (20 mL). 2-[[[3-Methyl-4-(2,2,2-trifluoroethoxy)-2-pyridyl]methyl]sulfinyl]-1H-benzimidazole (1.63 g), triethylamine (1.23 mL), 4-dimethylaminopyridine (0.054 g) was added, and the mixture was stirred at 60° C. for 14 hrs. After concentration under reduced pressure, water (40 mL) was added to the residue, and the mixture was extracted with ethyl acetate (100 mL). The ethyl acetate layer was washed with saturated brine (30 mL), and dried over anhydrous magnesium sulfate. After concentration under reduced pressure, the residue was purified by basic silica gel column chromatography (eluted with ethyl acetate:hexane=1:2, then 1:1), and then by silica gel column chromatography (eluted with ethyl acetate:hexane=1:1, then 2:1) to give the title compound (1.27 g) as a yellow amorphous solid.

$^1$H-NMR(CDCl$_3$): 1.32 (3H, t, J=7.1 Hz), 2.23 (3H, s), 3.09 (3H, bs), 3.50-4.76 (4H, br), 4.21 (2H, q, J=7.1 Hz), 4.38 (2H, q, J=7.9 Hz), 4.84-5.14 (2H, m), 6.64 (1H, d, J=5.6 Hz), 7.36-7.46 (3H, m), 7.83 (1H, d, J=7.2 Hz), 8.34 (1H, d, J=5.6 Hz).

Synthetic Example 36

Ethyl 2-[methyl[[(S)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 1 hr., ethyl 2-(methylamino)ethyl carbonate hydrochloride (1.10 g) obtained in Reference Example 14 was added. A solution (1 mL) of triethylamine (0.84 mL) in tetrahydrofuran was dropwise added, and the mixture was stirred at room temperature for 2 hrs. After concentration under reduced pressure, water (30 mL) was added to the residue, and the mixture was extracted with ethyl acetate (80 mL). The ethyl acetate layer was washed with saturated brine (30 mL), and dried over anhydrous magnesium sulfate. The layer was concentrated under reduced pressure, and the residue was dissolved in tetrahydrofuran (20 mL). (S)-2-[[[3-Methyl-4-(2,2,2-trifluoroethoxy)-2-pyridyl]methyl]sulfinyl]-1H-benzimidazole (1.15 g), triethylamine (0.87 mL) and 4-dimethylaminopyridine (0.035 g) were added, and the mixture was stirred at 60° C. for 12 hrs. After concentration under reduced pressure, water (30 mL) was added to the residue, and the mixture was extracted with ethyl acetate (100 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 1:1). Crystallization from diethyl ether gave the title compound (0.40 g) as a colorless solid.

$^1$H-NMR(CDCl$_3$): 1.32 (3H, t, J=7.2 Hz), 2.23 (3H, s), 3.10 (3H, bs), 3.50-4.56 (4H, br), 4.22 (2H, q, J=7.2 Hz), 4.38 (2H, q, J=7.9 Hz), 4.84-5.14 (2H, m), 6.65 (1H, d, J=5.6 Hz), 7.34-7.50 (3H, m), 7.85 (1H, m), 8.36 (1H, d, J=5.6 Hz).

Synthetic Example 37

Ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 30 min., ethyl 2-(methylamino)ethyl carbonate hydrochloride (1.10 g) obtained in Reference Example 14 was added. A solution (1 mL) of triethylamine (0.84 mL) in tetrahydrofuran was dropwise added, and the mixture was stirred at room temperature for 2.5 hrs. After concentration under reduced pressure, water (30 mL) was added to the residue, and the mixture was extracted with ethyl acetate (80 mL). The ethyl acetate layer was washed with saturated brine (30 mL) and dried over anhydrous magnesium sulfate. The layer was concentrated under reduced pressure, and the residue was dissolved in tetrahydrofuran (20 mL). 5-Methoxy-2-[[(4-methoxy-3,5-dimethyl-2-pyridyl)methyl]sulfinyl]-1H-imidazo[4,5-b]pyridine (1.44 g) synthesized by the method described in JP-A-63-146882, triethylamine (1.16 mL) and 4-dimethylaminopyridine (0.049 g) were added, and the mixture was stirred at 60° C. for 6 hrs. After concentration under reduced pressure, water (30 mL) was added to the residue, and the mixture was extracted with ethyl acetate (100 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 1:1). Crystallization from diethyl ether gave the title compound (0.721 g) as a colorless solid.

$^1$H-NMR(CDCl$_3$): 1.25-1.34 (3H, m), 2.23 (6H, s), 3.15, 3.32 (total 3H, s), 3.72 (3H, s), 3.90-4.53 (9H, m), 4.86 (1H, d, J=13.4 Hz), 4.95 (1H, d, J=13.4 Hz), 6.79 (1H, d, J=8.7 Hz), 7.95 (1H, d, J=8.7 Hz), 8.22 (1H, s).

Synthetic Example 38

2-[[[5-Methoxy-2-[[(4-methoxy-3,5-dimethyl-2-pyridyl)methyl]sulfinyl]-3H-imidazo[4,5-b]pyridin-3-yl]carbonyl](methyl)amino]ethyl acetate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 30 min., 2-(methylamino)ethyl acetate hydrochloride (0.922 g) obtained in Reference Example 2 was added. A solution (1 mL) of triethylamine (0.84 mL) in tetrahydrofuran was dropwise added, and the mixture was stirred at room temperature for 2 hrs. After concentration under reduced pressure, water (30 mL) was added to the residue, and the mixture was extracted with ethyl acetate (80 mL). The ethyl acetate layer was washed with saturated brine (30 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-imidazo[4,5-b]pyridine (0.85 g) synthesized by the method described in JP-A-63-146882, triethylamine (0.70 mL) and 4-dimethylaminopyridine (0.025 g) were added, and the mixture was stirred at 60° C. for 5 hrs. After concentration under reduced pressure, water (30 mL) was added to the residue, and the mixture was extracted with ethyl acetate (90 mL). The ethyl acetate layer was washed with saturated brine (30 mL) and dried over anhydrous magnesium sulfate. After concentration under reduced pressure, the residue was purified by basic silica gel column chromatography (eluted with ethyl acetate:hexane=1:2, then 1:1). Crystallization from diethyl ether gave the title compound (0.173 g) as a colorless solid.

$^1$H-NMR(CDCl$_3$): 2.04, 2.09 (total 3H, s), 2.24 (6H, s), 3.13, 3.30 (total 3H, s), 3.45-3.97 (2H, m), 3.72 (3H, s), 3.97 (3H, s), 4.15-4.50 (2H, m), 4.85 (1H, d, J=13.1 Hz), 4.96 (1H, d, J=13.1 Hz), 6.80 (1H, d, J=8.9 Hz), 7.96 (1H, d, J=8.9 Hz), 8.22 (1H, s).

Synthetic Example 39

2-[[[5-Methoxy-2-[[(4-methoxy-3,5-dimethyl-2-pyridyl)methyl]sulfinyl]-3H-imidazo[4,5-b]pyridin-3-yl]carbonyl](phenyl)amino]ethyl acetate To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 30 min., 2-anilinoethyl acetate hydrochloride (0.647 g) obtained in Reference Example 27 was added. A solution (1 mL) of triethylamine (0.419 mL) in tetrahydrofuran was dropwise added, and the mixture was stirred at room temperature for 3 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-imidazo[4,5-b]pyridine (0.867 g) synthesized by the method described in JP-A-63-146882, triethylamine (0.697 mL) and 4-dimethylaminopyridine (0.020 g) were added, and the mixture was stirred at 60° C. for 10 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:1). Crystallization from diethyl ether gave the title compound (0.311 g) as a colorless solid.

$^1$H-NMR(CDCl$_3$): 1.96 (3H, s), 2.23 (3H, s), 2.25 (3H, s), 3.72 (3H, s), 4.01 (3H, s), 4.12-4.52 (4H, m), 4.78-5.22 (2H, m), 6.62 (1H, d, J=8.7 Hz), 7.02-7.18 (3H, m), 7.32-7.48 (2H, m), 7.73 (1H, d, J=8.7 Hz), 8.26 (1H, s).

Synthetic Example 40

4-[Methyl[[(R)-2-[[[3-methyl-4-(2,2,2-trifluoroethoxy)-2-pyridyl]methyl]sulfinyl]-1H-benzimidazol-1-yl]carbonyl]amino]butyl acetate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., 4-(methylamino)butyl acetate hydrochloride (1.08 g) obtained in Reference Example 37 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.02 g), triethylamine (0.77 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (0.93 g) as a yellow amorphous solid.

$^1$H-NMR(CDCl$_3$): 1.65-1.85 (4H, m), 2.03 (3H, s), 2.23 (3H, s) 3.02 (3H, bs), 3.45-3.63 (2H, m), 4.03-4.13 (2H, m), 4.37 (2H, q, J=7.8 Hz), 4.85-5.13 (2H, m), 6.64 (1H, d, J=5.6 Hz), 7.36-7.46 (3H, m), 7.84 (1H, d, J=8.4 Hz), 8.35 (1H, d, J=5.6 Hz).

Synthetic Example 41

Ethyl 4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl carbonate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., ethyl 4-(methylamino)butyl carbonate hydrochloride (1.27 g) obtained in Reference Example 39 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.26 g), triethylamine (0.95 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (1.08 g) as a yellow amorphous solid.

$^1$H-NMR(CDCl$_3$): 1.31 (3H, t, J=7.2 Hz), 1.73-1.91 (4H, m) 2.23 (3H, s), 3.01 (3H, bs), 3.50-3.62 (2H, m), 4.15-4.22 (4H, m), 4.38 (2H, q, J=7.8 Hz), 4.87-5.13 (2H, m), 6.64 (1H, d, J=5.4 Hz), 7.35-7.46 (3H, m), 7.83 (1H, d, J=7.8 Hz), 8.35 (1H, d, J=5.4 Hz).

Synthetic Example 42

Ethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl carbonate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., ethyl 3-(methylamino)propyl carbonate hydrochloride (1.18 g) obtained in Reference Example 44 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.10 g), triethylamine (0.83 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (0.88 g) as a yellow amorphous solid.

$^1$H-NMR(CDCl$_3$): 1.29 (3H, t, J=7.2 Hz), 2.10-2.20 (2H, m), 2.22 (3H, s), 3.02 (3H, bs), 3.55-3.77 (2H, m), 4.14-4.30 (4H, m), 4.37 (2H, q, J=7.8 Hz), 4.83-5.13 (2H, m), 6.64 (1H, d, J=5.6 Hz), 7.35-7.46 (3H, m), 7.82 (1H, d, J=8.1 Hz), 8.35 (1H, d, J=5.6 Hz).

Synthetic Example 43

3-[Methyl[[(R)-2-[[[3-methyl-4-(2,2,2-trifluoroethoxy)-2-pyridyl]methyl]sulfinyl]-1H-benzimidazol-1-yl]carbonyl]amino]propyl acetate To a solution (40 mL) of bis(trichloromethyl)carbonate (1.19 g) in tetrahydrofuran was dropwise added a solution (2 mL) of pyridine (0.95 mL) in tetrahydrofuran under ice-cooling. After stirring under ice-cooling for 30 min., 3-(methylamino)propyl acetate hydrochloride (1.90 g) obtained in Reference Example 42 was added. A solution (2 mL) of triethylamine (1.68 mL) in tetrahydrofuran was dropwise added, and the mixture was stirred at room temperature for 3 hrs. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was dissolved in tetrahydrofuran (40 mL). (R)-2-[[[3-Methyl-4-(2,2,2-trifluoroethoxy)-2-pyridyl]methyl]sulfinyl]-1H-benzimidazole (1.99 g), triethylamine (1.50 mL) and 4-dimethylaminopyridine (catalytic amount) were added, and the mixture was stirred at 60° C. overnight. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was purified by basic silica gel column chromatography (eluted with ethyl acetate:hexane=1:2, then 1:1) to give the title compound (1.22 g) as a yellow amorphous solid.

$^1$H-NMR(CDCl$_3$): 1.97 (3H, s), 2.05-2.15 (2H, m), 2.22 (3H, s), 3.03 (3H, bs), 3.42-3.72 (2H, m), 4.10-4.22 (2H, m), 4.37 (2H, q, J=7.8 Hz), 4.85-5.13 (2H, m), 6.64 (1H, d, J=5.6 Hz), 7.24-7.44 (3H, m), 7.83 (1H, d, J=7.5 Hz), 8.35 (1H, d, J=5.6 Hz).

Synthetic Example 44

3-[Methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl diacetate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., 3-(methylamino)propane-1,2-diyl diacetate hydrochloride (1.35 g) obtained in Reference Example 46 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.27 g), triethylamine (0.96 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (0.64 g) as a yellow amorphous solid.

$^1$H-NMR(CDCl$_3$): 2.05 (3H, s), 2.13 (3H, s), 2.23 (3H, s), 3.07 (3H, bs), 3.42-3.95 (2H, m), 4.06-4.43 (2H, m), 4.38 (2H, q, J=7.8 Hz), 4.85-5.05 (2H, m), 5.42-5.50 (1H, m), 6.63-6.66 (1H, m), 7.38-7.51 (3H, m), 7.78-7.85 (1H, m), 8.33-8.36 (1H, m).

Synthetic Example 45

Diethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl biscarbonate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., diethyl 3-(methylamino)propane-1,2-diyl biscarbonate hydrochloride (1.71 g) obtained in Reference Example 47 was added. A solution (1 mL) of triethylamine (0.84 mL) in tetrahydrofuran was dropwise added, and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.53 g), triethylamine (1.16 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (1.42 g) as a yellow amorphous solid.

$^1$H-NMR(CDCl$_3$): 1.28-1.34 (6H, m), 2.22 (3H, s), 3.07 (3H, bs), 3.42-4.60 (10H, m), 4.85-5.08 (2H, m), 5.30-5.42 (1H, m), 6.62-6.64 (1H, m), 7.37-7.42 (3H, m), 7.80-7.83 (1H, m), 8.32-8.35 (1H, m).

Synthetic Example 46

2-[[[5-Methoxy-2-[[(4-methoxy-3,5-dimethyl-2-pyridyl)methyl]sulfinyl]-3H-imidazo[4,5-b]pyridin-3-yl]carbonyl](methyl)amino]ethyl 3-chlorobenzoate To a solution (7 mL) of bis(trichloromethyl)carbonate (0.194 g) in tetrahydrofuran was dropwise added a solution (1 mL) of pyridine (0.162 mL) in tetrahydrofuran under ice-cooling. After stirring under ice-cooling for 30 min., 2-(methylamino)ethyl 3-chlorobenzoate hydrochloride (0.50 g) obtained in Reference Example 7 was added. A solution (1 mL) of triethylamine (0.279 mL) in tetrahydrofuran was dropwise added, and the mixture was stirred at room temperature for 2.5 hrs. After concentration under reduced pressure, water (15 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-imidazo[4,5-b]pyridine (0.445 g) synthesized by the method described in JP-A-63-146882, triethylamine (0.357 mL) and 4-dimethylaminopyridine (0.012 g) were added, and the mixture was stirred at 60° C. for 14 hrs. After concentration under reduced pressure, water (30 mL) was added to the residue, and the mixture was extracted with ethyl acetate (70 mL). The ethyl acetate layer was washed with saturated brine (20 mL) and dried over anhydrous magnesium sulfate. After concentration under reduced pressure, the residue was purified by basic silica gel column chromatography (eluted with ethyl acetate:hexane=1:2, then 1:1) to give the title compound (0.360 g) as a colorless amorphous solid.

$^1$H-NMR(CDCl$_3$): 2.21 (3H, s), 2.23 (3H, s), 3.32, 3.38 (total 3H, s), 3.72 (3H, s), 3.81 (3H, s), 3.92-4.09 (2H, m), 4.50-4.73 (2H, m), 4.87 (1H, d, J=13.4 Hz), 4.94 (1H, d, J=13.4 Hz), 6.77 (1H, d, J=8.8 Hz), 7.36 (1H, m), 7.52 (1H, m), 7.80-8.03 (3H, m), 8.20 (1H, s).

Synthetic Example 47

2-[Methyl[[2-[[[3-methyl-4-(2,2,2-trifluoroethoxy)-2-pyridyl]methyl]sulfinyl]-1H-benzimidazol-1-yl]carbonyl]amino]ethyl acetate To a solution (20 mL) of bis(trichloromethyl)carbonate (0.582 g) in tetrahydrofuran was dropwise added a solution (1 mL) of pyridine (0.485 mL) in tetrahydrofuran under ice-cooling. After stirring under ice-cooling for 1 hr., 2-(methylamino)ethyl acetate hydrochloride (0.922 g) obtained in Reference Example 2 was added. A solution (1 mL) of triethylamine (0.84 mL) in tetrahydrofuran was dropwise added, and the mixture was stirred at room temperature for 2.5 hrs. After concentration under reduced pressure, water (40 mL) was added to the residue, and the mixture was extracted with ethyl acetate (80 mL). The ethyl acetate layer was washed with saturated brine (25 mL) and dried over anhydrous magnesium sulfate. After concentration under reduced pressure, the residue was dissolved in tetrahydrofuran (15 mL). 2-[[[3-Methyl-4-(2,2,2-trifluoroethoxy)-2-pyridyl]methyl]sulfinyl]-1H-benzimidazole (1.10 g), triethylamine (0.84 mL) and 4-dimethylaminopyridine (0.036 g) were added, and the mixture was stirred at 60° C. for 4.5 hrs. After concentration under reduced pressure, water (40 mL) was added to the residue, and the mixture was extracted with ethyl acetate (80 mL). The ethyl acetate layer was washed with saturated brine (30 mL) and dried over anhydrous magnesium sulfate. After concentration under reduced pressure, the residue was purified by silica gel column chromatography (eluted with ethyl acetate:hexane=1:1, then 2:1) to give the title compound (1.18 g) as a colorless solid.

$^1$H-NMR(CDCl$_3$): 2.10 (3H, s), 2.24 (3H, s), 3.09 (3H, bs), 3.60-4.00 (2H, br), 4.25-4.50 (2H, m), 4.38 (2H, q, J=7.8 Hz), 4.84-5.18 (2H, m), 6.64 (1H, d, J=5.6 Hz), 7.36-7.48 (3H, m), 7.85 (1H, d, J=7.8 Hz), 8.35 (1H, d, J=5.6 Hz).

Synthetic Example 48

Ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate A solution of (R)-2-[[[3-methyl-4-(2,2,2-trifluoroethoxy)-2-pyridyl]methyl]sulfinyl]-1H-benzimidazole (130 g), triethylamine (63.8 mL), 4-dimethylaminopyridine (0.86 g) and 2-[(chlorocarbonyl)(methyl)amino]ethyl ethyl carbonate (84.8 g) obtained in Reference Example 34 in tetrahydrofuran (813 mL) was stirred at 45-50° C. for 18 hrs. The reaction mixture was concentrated under reduced pressure and water (300 mL) was added to the residue, and the mixture was extracted with ethyl acetate (700 mL). The ethyl acetate layer was washed 3 times with saturated brine (300 mL), and anhydrous magnesium sulfate (130 g) and activated carbon (13 g) were added. The mixture was stirred at room temperature for 30 min. and filtrated. The filtrate was concentrated under reduced pressure and the residue was dissolved in diethyl ether (600 mL) containing triethylamine (0.49 mL), and the mixture was concentrated under reduced pressure. This step was further repeated twice. The obtained oily substance was dissolved in ethanol (200 mL) containing triethylamine (2.45 mL) and water (120 mL) was dropwise added under ice-cooling. The precipitated crystals were collected by filtration, washed 3 times with ice-cooled ethanol-water (volume ratio 1:1, 150 mL) and dried to give the title compound (172.2 g) as a colorless solid. $^1$H-NMR(CDCl$_3$) showed the same chart as with the compound obtained in Synthetic Example 14.

Synthetic Example 49

2-Ethoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (20 mL) of bis(trichloromethyl)carbonate (0.43 g) in tetrahydrofuran was dropwise added a solution (1 mL) of pyridine (0.35 mL) in tetrahydrofuran under ice-cooling. After stirring under ice-cooling for 10 min., 2-ethoxyethyl 2-(methylamino)ethyl carbonate hydrochloride (0.82 g) obtained in Reference Example 48 was added. A solution (1 mL) of triethylamine (0.60 mL) in tetrahydrofuran was dropwise added, and the mixture was stirred at room temperature for 3 days. After concentration under reduced pressure, water (50 mL) was added to the residue and the mixture was extracted with ethyl acetate (50 mL). The ethyl acetate layer was washed with 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. for 6 hrs. and at room temperature for 11 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate:hexane=7:3) to give the title compound (1.39 g) as a yellow amorphous 1 solid.

$^1$H-NMR(CDCl$_3$): 1.19 (3H, t, J=6.9 Hz), 2.23 (3H, s), 3.09 (3H, bs), 3.40-4.20 (2H, br), 3.53 (2H, q, J=6.9 Hz), 3.63-3.69 (2H, m), 4.27-4.34 (2H, m), 4.39 (2H, q, J=7.8 Hz), 4.47 (2H, m), 4.80-5.20 (2H, m), 6.65 (1H, d, J=5.6 Hz), 7.30-7.52 (3H, m), 7.84 (1H, d, J=7.5 Hz), 8.35 (1H, d, J=5.6 Hz).

Synthetic Example 50

3-Methoxypropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate To a solution (20 mL) of bis(trichloromethyl)carbonate (0.53 g) in tetrahydrofuran was dropwise added a solution (1 mL) of pyridine (0.44 mL) in tetrahydrofuran under ice-cooling. After stirring under ice-cooling for 5 min., 3-methoxypropyl 2-(methylamino)ethyl carbonate hydrochloride (0.82 g) obtained in Reference Example 49 was added. A solution (1 mL) of triethylamine (0.75 mL) in tetrahydrofuran was dropwise added and the mixture was stirred at room temperature for 1 hr. After concentration under reduced pressure, water (50 mL) was added to the residue and the mixture was extracted with ethyl acetate (50 mL). The ethyl acetate layer was washed with 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. for 6 hrs. and at room temperature for 6 hours. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=3:7, then ethyl acetate:hexane=7:3). Crystallization from diethyl ether gave the title compound (0.70 g) as a colorless solid.

$^1$H-NMR(CDCl$_3$): 1.94 (2H, quintet, J=6.2 Hz), 2.23 (3H, s), 3.09 (3H, bs), 3.31 (3H, s), 3.40-4.20 (2H, br), 3.44 (2H, t, J=6.2 Hz), 4.25 (2H, t, J=6.5 Hz), 4.38 (2H, q, J=7.8 Hz), 4.44 (2H, m), 4.80-5.20 (2H, m), 6.64 (1H, d, J=5.6 Hz), 7.35-7.48 (3H, m), 7.83 (1H, d, J=7.8 Hz), 8.34 (1H, d, J=5.6 Hz).

Synthetic Example 51

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl N,N-dimethylglycinate 2-(Methylamino)ethyl N,N-dimethylglycinate dihydrochloride (1.06 g) obtained in Reference Example 50 was added to tetrahydrofuran (40 mL) and the mixture was stirred for a while, to which bis(trichloromethyl)carbonate (0.77 g) was added. After ice-cooling, a solution (5 mL) of triethylamine (2.17 mL) in tetrahydrofuran was dropwise added and the mixture was stirred at room temperature for 3 hrs. The precipitated solid was filtered off and ethyl acetate (80 mL) was added. The mixture was washed with an ice-cooled aqueous sodium hydrogen carbonate solution (50 mL) and saturated brine (50 mL×2) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. for 6 hrs. and at room temperature for 3 days. 4-Dimethylaminopyridine (0.037 g) was added, and the mixture was further stirred at 60° C. for 6 hrs. After concentration under reduced pressure, an aqueous sodium hydrogen carbonate solution (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate, then methanol:ethyl acetate=1:19). Crystallization from diethyl ether gave the title compound (0.41 g) as a colorless solid.

$^1$H-NMR(CDCl$_3$): 2.23 (3H, s), 2.35 (6H, s), 3.08 (3H, bs), 3.21 (2H, s), 3.50-4.20 (2H, br), 4.38 (2H, q, J=7.8 Hz), 4.44 (2H, m), 4.80-5.18 (2H, m), 6.64 (1H, d, J=5.6 Hz), 7.36-7.48 (3H, m), 7.84 (1H, d, J=6.9 Hz), 8.35 (1H, d, J=5.6 Hz).

Synthetic Example 52

S-[2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl]thioacetate S-[2-(Methylamino)ethyl]thioacetate hydrochloride (0.75 g) obtained in Reference Example 51 was added to tetrahydrofuran (30 mL) and the mixture was stirred for a while, to which bis(trichloromethyl)carbonate (0.66 g) was added. After ice-cooling, a solution (10 mL) of triethylamine (1.85 mL) in tetrahydrofuran was dropwise added and the mixture was stirred under ice-cooling for 30 min. and at room temperature for 30 min. The precipitated solid was filtered off and ethyl acetate (50 mL) was added to the filtrate. The mixture was washed with ice-cooled 0.2N hydrochloric acid (20 mL) and saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]

methyl]sulfinyl]-1H-benzimidazole (0.96 g), triethylamine (0.54 mL) and 4-dimethylaminopyridine (0.032 g) were added, and the mixture was stirred at 60° C. for 6 hrs. and at room temperature for 8 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by silica gel column chromatography (eluted with acetone:hexane=3:7, then acetone:hexane=7:3) to give the title compound (1.19 g) as a yellow amorphous solid.

$^1$H-NMR(CDCl$_3$): 2.23 (3H, s), 2.34 (3H, s), 3.10 (3H, bs), 3.22 (2H, t, J=6.6 Hz), 3.67 (2H, m), 4.38 (2H, q, J=7.8 Hz), 4.80-5.20 (2H, m), 6.64 (1H, d, J=5.7 Hz), 7.35-7.50 (3H, m), 7.83 (1H, d, J=6.9 Hz), 8.35 (1H, d, J=5.7 Hz).

Synthetic Example 53

Ethyl 2-[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]ethyl carbonate To a solution (40 mL) of bis(trichloromethyl)carbonate (1.19 g) in tetrahydrofuran was dropwise added a solution (2 mL) of pyridine (0.95 mL) in tetrahydrofuran under ice-cooling. After stirring under ice-cooling for 30 min., ethyl 2-[2-(methylamino)ethoxy]ethyl carbonate hydrochloride (2.73 g) obtained in Reference Example 52 was added. A solution (2 mL) of triethylamine (1.68 mL) in tetrahydrofuran was dropwise added, and the mixture was stirred at room temperature for 3 hrs. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was dissolved in tetrahydrofuran (40 mL). (R)-2-[[[3-Methyl-4-(2,2,2-trifluoroethoxy)-2-pyridyl]methyl]sulfinyl]-1H-benzimidazole (2.80 g), triethylamine (2.11 mL) and 4-dimethylaminopyridine (catalytic amount) were added, and the mixture was stirred at 60° C. overnight. After concentration under reduced pressure, water (100 mL) was added to the residue, and the mixture was extracted with ethyl acetate (100 mL). The ethyl acetate layer was washed with saturated brine (100 mL) and dried over anhydrous magnesium sulfate. After concentration under reduced pressure, the residue was purified by basic silica gel column chromatography (eluted with ethyl acetate:hexane=1:2, then 1:1) to give the title compound (2.19 g) as a yellow amorphous solid.

$^1$H-NMR(CDCl$_3$): 1.28 (3H, t, J=7.2 Hz), 2.24 (3H, s), 3.10 (3H, bs), 3.38-3.80 (6H, m), 4.18 (2H, q, J=7.2 Hz), 4.27-4.34 (2H, m), 4.38 (2H, q, J=8.4 Hz), 4.83-5.30 (2H, m), 6.65 (1H, d, J=5.7 Hz), 7.35-7.50 (3H, m), 7.84 (1H, d, J=7.8 Hz), 8.36 (1H, d, J=5.7 Hz).

Synthetic Example 54

Ethyl 2-[methyl[[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]carbonyl]amino]ethyl carbonate To a solution (20 mL) of bis(trichloromethyl)carbonate (0.59 g) in tetrahydrofuran was dropwise added a solution (1 mL) of pyridine (0.49 mL) in tetrahydrofuran under ice-cooling. After stirring under ice-cooling for 30 min., ethyl 2-[methyl[[2-(methylamino)ethoxy)carbonyl]amino]ethyl carbonate hydrochloride (1.71 g) obtained in Reference Example 53 was added. A solution (1 mL) of triethylamine (0.84 mL) in tetrahydrofuran was dropwise added and the mixture was stirred at room temperature for 3 hrs. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (1.59 g), triethylamine (1.20 mL) and 4-dimethylaminopyridine (catalytic amount) were added, and the mixture was stirred at 60° C. overnight. After concentration under reduced pressure, water (50 mL) was added to the residue and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:2, then 1:1) to give the title compound (1.62 g) as a yellow amorphous solid.

$^1$H-NMR(CDCl$_3$): 1.24-1.31 (3H, m), 2.24 (3H, bs), 2.97-2.99 (3H, m), 3.10 (3H, bs), 3.55-3.58 (2H, m), 4.09-4.50 (10H, m), 4.88-5.08 (2H, m), 6.65 (1H, t, J=5.7 Hz), 7.36-7.48 (3H, m), 7.85 (1H, d, J=6.9 Hz), 8.36 (1H, d, J=5.7 Hz).

Synthetic Example 55

Ethyl 2-[[[5-methoxy-2-[[(4-methoxy-3,5-dimethyl-2-pyridyl)methyl]sulfinyl]-1H-benzimidazol-1-yl]carbonyl](methyl)amino]ethyl carbonate To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 1 hr., ethyl 2-(methylamino)ethyl carbonate hydrochloride (0.551 g) obtained in Reference Example 14 was added. A solution (1 mL) of triethylamine (0.418 mL) in tetrahydrofuran was dropwise added, and the mixture was stirred at room temperature for 2 hrs. After concentration under reduced pressure, water (15 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-benzimidazole (0.817 g), triethylamine (0.661 mL) and 4-dimethylaminopyridine (0.012 g) were added, and the mixture was stirred at 60° C. for 12 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2, then 1:1) to give a 3:2 mixture (0.92 g) of the title compound and ethyl 2-[[[6-methoxy-2-[[(4-methoxy-3,5-dimethyl-2-pyridyl)methyl]sulfinyl]-1H-benzimidazol-1-yl]carbonyl](methyl)amino]ethyl carbonate as a pale-yellow amorphous solid.

$^1$H-NMR(CDCl$_3$): 1.27-1.34 (3H, m), 2.10-2.30 (3H, m), 2.23 (3H, s) 2.99-3.23 (3H, m), 3.40-3.85 (2H, m), 3.69 (6/5H, s), 3.71 (9/5H, s), 3.86 (6/5H, s), 3.88 (9/5H, s), 4.14-

4.25 (2H, m), 4.38-4.60 (2H, m) 4.82-5.06 (2H, m), 6.92-7.08 (7/5H, m), 7.33 (3/5H, d, J=9.0 Hz), 7.66 (1H, m), 8.21 (1H, s).

Synthetic Example 56

2-[[[5-Methoxy-2-[[(4-methoxy-3,5-dimethyl-2-pyridyl)methyl]sulfinyl]-1H-benzimidazol-1-yl]carbonyl](phenyl)amino]ethyl acetate To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 30 min., 2-anilinoethyl acetate hydrochloride (0.647 g) obtained in Reference Example 27 was added. A solution (1 mL) of triethylamine (0.419 mL) in tetrahydrofuran was dropwise added, and the mixture was stirred at room temperature for 3 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 5-Methoxy-2-[[(4-methoxy-3,5-dimethyl-2-pyridyl)methyl]sulfinyl]-1H-benzimidazole (0.829 g), triethylamine (0.669 mL) and 4-dimethylaminopyridine (0.012 g) were added, and the mixture was stirred at 60° C. for 14 hrs. After concentration under reduced pressure, water (40 mL) was added to the residue, and the mixture was extracted with ethyl acetate (80 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2) to give a 1:1 mixture (1.10 g) of the title compound and 2-[[[6-methoxy-2-[[(4-methoxy-3,5-dimethyl-2-pyridyl)methyl]sulfinyl]-1H-benzimidazol-1-yl]carbonyl](phenyl)amino]ethyl acetate as a colorless amorphous solid.

$^1$H-NMR(CDCl$_3$): 1.99 (3H, s), 2.19 (1.5H, s), 2.21 (1.5H, s), 2.25 (3H, s), 3.70 (1.5H, s), 3.71 (3H, s), 3.78 (1.5H, s), 3.84 (1.5H, s), 4.15-4.56 (4H, m), 4.74-4.80 (1H, m), 4.91-4.98 (1H, m), 6.83-6.91 (1.5H, m), 7.04-7.19 (3.5H, m), 7.25-7.53 (2.5H, m), 7.51 (0.5H, d, J=8.7 Hz), 8.25 (1H, s).

Synthetic Example 57

Ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate To a solution (10 mL) of (S)-5-methoxy-2-[[(4-methoxy-3,5-dimethyl-2-pyridyl)methyl]sulfinyl]-1H-benzimidazole (1.34 g) synthesized by the method described in Synthetic Example 1 of JP-A-10-504290 in tetrahydrofuran were added 2-[(chlorocarbonyl)(methyl)amino]ethyl ethyl carbonate (0.9 mL) obtained in Reference Example 34, triethylamine (1.08 mL) and 4-dimethylaminopyridine (0.010 g), and the mixture was stirred at 60° C. for 6 hrs. After concentration under reduced pressure, water (30 mL) was added to the residue and the mixture was extracted with ethyl acetate (50 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2, then 1:1) to give a 3:2 mixture (0.92 g) of the title compound and ethyl 2-[[[(S)-6-methoxy-2-[[(4-methoxy-3,5-dimethyl-2-pyridyl)methyl]sulfinyl]-1H-benzimidazol-1-yl]carbonyl](methyl)amino]ethyl carbonate as a pale-yellow amorphous solid.

$^1$H-NMR(CDCl$_3$): 1.25-1.34 (3H, m), 2.10-2.30 (3H, m), 2.23 (3H, s), 2.99-3.23 (3H, m), 3.40-3.85 (2H, m), 3.69 (6/5H, s), 3.71 (9/5H, s), 3.86 (6/5H, s), 3.88 (9/5H, s), 4.14-4.25 (2H, m), 4.38-4.60 (2H, m), 4.79-5.05 (2H, m), 6.92-7.08 (7/5H, m), 7.33 (3/5H, d, J=9.3 Hz), 7.65 (1H, m), 8.21 (1H, s).

Synthetic Example 58

Ethyl 2-[[[2-[[[4-(3-methoxypropoxy)-3-methyl-2-pyridyl]methyl]sulfinyl]-1H-benzimidazol-1-yl]carbonyl](methyl)amino]ethyl carbonate To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 30 min., ethyl 2-(methylamino)ethyl carbonate hydrochloride (0.551 g) obtained in Reference Example 14 was added. A solution (1 mL) of triethylamine (0.418 mL) in tetrahydrofuran was dropwise added, and the mixture was stirred at room temperature for 2.5 hrs. After concentration under reduced pressure, water (15 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 2-[[[4-(3-Methoxypropoxy)-3-methyl-2-pyridyl]methyl]sulfinyl]-1H-benzimidazole (0.723 g), triethylamine (0.528 mL) and 4-dimethylaminopyridine (0.012 g) were added, and the mixture was stirred at 60° C. for 17 hrs. After concentration under reduced pressure, water (40 mL) was added to the residue, and the mixture was extracted with ethyl acetate (80 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2), then by silica gel column chromatography (eluted with ethyl acetate:hexane=1:1, then ethyl acetate) to give the title compound (0.44 g) as a colorless amorphous solid.

$^1$H-NMR(CDCl$_3$): 1.31 (3H, t, J=7.1 Hz), 2.05 (2H, m), 2.18 (3H, s), 3.08 (3H, bs), 3.34 (3H, s), 3.54 (2H, t, J=6.1 Hz), 3.61-4.01 (2H, m), 4.08 (2H, t, J=6.3 Hz), 4.21 (2H, t, J=7.1 Hz), 4.38-4.54 (2H, m), 4.81-5.12 (2H, m), 6.68 (1H, d, J=5.6 Hz), 7.34-7.48 (3H, m), 7.83 (1H, d, J=7.8 Hz), 8.27 (1H, d, J=5.6 Hz).

Synthetic Example 59

2-[[[2-[[[4-(3-Methoxypropoxy)-3-methyl-2-pyridyl]methyl]sulfinyl]-1H-benzimidazol-1-yl]carbonyl](phenyl)amino]ethyl acetate To a solution (10 mL) of bis(trichloromethyl)carbonate (0.291 g) in tetrahydrofuran was dropwise added a solution (1 mL) of pyridine (0.243 mL) in tetrahydrofuran under ice-cooling. After stirring under ice-cooling for 30 min., 2-anilinoethyl acetate hydrochloride (0.647 g) obtained in Reference Example 27 was added. A solution (1 mL) of triethylamine (0.419 mL) in tetrahydrofuran was dropwise added, and the mixture was stirred at room temperature for 3 hrs. After concentration under reduced pressure, water (20 mL) was added to the residue, and the mixture was extracted with ethyl acetate (50 mL). The ethyl acetate layer was washed with saturated brine (15 mL) and dried over anhydrous magnesium sulfate. After concentration under reduced pressure, the residue was dissolved in tetrahydrofuran (10 mL). 2-[[[4-(3-Methoxypropoxy)-3-methyl-2-pyridyl]methyl]sulfinyl]-1H-benzimidazole (0.877 g), triethylamine (0.641 mL) and 4-dimethylaminopyridine (0.012 g) were added, and the mixture was stirred at 60° C. for 16 hrs. After concentration under reduced pressure, water (40 mL) was added to the residue, and the mixture was extracted with ethyl acetate (80 mL). The ethyl acetate layer was washed with saturated brine (15 mL) and dried over anhydrous magnesium sulfate. After concentration under reduced pressure, the residue was purified by basic silica gel column chromatography (eluted with ethyl acetate:hexane=1:2), then by silica gel column chromatography (eluted with ethyl acetate) to give the title compound (0.93 g) as a colorless amorphous solid.

$^1$H-NMR(CDCl$_3$): 1.99 (3H, s), 2.07 (3H, s), 2.19 (3H, s), 3.35 (3H, s), 3.54 (2H, t, J=6.2 Hz), 4.09 (2H, t, J=6.2 Hz), 4.14-4.40 (4H, m), 4.80 (1H, d, J=13.7 Hz), 5.00 (1H, d, J=13.7 Hz), 6.71 (1H, d, J=5.7 Hz), 7.03-7.34 (7H, m), 7.38 (1H, m), 7.65 (1H, m), 8.32 (1H, d, J=5.7 Hz).

Synthetic Example 60

2-[[[5-(Difluoromethoxy)-2-[[(3,4-dimethoxy-2-pyridyl)methyl]sulfinyl]-1H-benzimidazol-1-yl]carbonyl](methyl)amino]ethyl ethyl carbonate To a solution (8 mL) of bis(trichloromethyl)carbonate (0.174 g) in tetrahydrofuran was dropwise added a solution (1 mL) of pyridine (0.146 mL) in tetrahydrofuran under ice-cooling. After stirring under ice-cooling for 1 hr., ethyl 2-(methylamino)ethyl carbonate hydrochloride (0.330 g) obtained in Reference Example 14 was added. A solution (1 mL) of triethylamine (0.250 mL) in tetrahydrofuran was dropwise added, and the mixture was stirred at room temperature for 3 hrs. After concentration under reduced pressure, water (10 mL) was added to the residue, and the mixture was extracted with ethyl acetate (30 mL). The ethyl acetate layer was washed with saturated brine (10 mL) and dried over anhydrous magnesium sulfate. After concentration under reduced pressure, the residue was dissolved in tetrahydrofuran (8 mL). 5-(Difluoromethoxy)-2-[[(3,4-dimethoxy-2-pyridyl)methyl]sulfinyl]-1H-benzimidazole (0.432 g), triethylamine (0.279 mL) and 4-dimethylaminopyridine (0.008 g) were added, and the mixture was stirred at 60° C. for 17.5 hrs. After concentration under reduced pressure, water (20 mL) was added to the residue, and the mixture was extracted with ethyl acetate (50 mL). The ethyl acetate layer was washed with saturated brine (10 mL) and dried over anhydrous magnesium sulfate. After concentration under reduced pressure, the residue was purified by basic silica gel column chromatography (eluted with ethyl acetate:hexane=1:2, then 1:1), then by silica gel column chromatography (eluted with ethyl acetate:hexane=2:1, then ethyl acetate) to give a 1:1 mixture (0.09 g) of the title compound and 2-[[[6-(difluoromethoxy)-2-[[(3,4-dimethoxy-2-pyridyl)methyl]sulfinyl]-1H-benzimidazol-1-yl]carbonyl]methylamino]ethyl ethyl carbonate as a pale-yellow amorphous solid.

$^1$H-NMR(CDCl$_3$): 1.31 (3H, t, J=7.2 Hz), 3.06 (3H, s), 3.42-3.98 (2H, m), 3.87 (3H, s), 3.90 (3H, s), 4.21 (2H, q, J=7.2 Hz), 4.36-4.54 (2H, m), 4.90 (1H, d, J=13.2 Hz), 4.98 (1H, d, J=13.2 Hz), 6.54 (0.5H, t, J=73.5 Hz), 6.61 (0.5H, t, J=73.5 Hz), 6.78 (1H, d, J=5.3 Hz), 7.15-7.25 (1.5H, m), 7.44 (0.5H, d, J=9.0 Hz), 7.59 (0.5H, s), 7.80 (0.5H, d, J=9.0 Hz), 8.17 (1H, d, J=5.3 Hz).

Synthetic Example 61

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methylpiperidine-4-carboxylate 2-(Methylamino)ethyl 1-methylpiperidine-4-carboxylate dihydrochloride (0.98 g) obtained in Reference Example 54 was added to tetrahydrofuran (50 mL) and the mixture was stirred for a while, to which bis(trichloromethyl)carbonate (0.53 g) was added. After ice-cooling, a solution (50 mL) of triethylamine (2.01 mL) in tetrahydrofuran was dropwise added and the mixture was stirred at room temperature for 3 hrs. Ethyl acetate (100 mL) was added and the mixture was washed with an aqueous sodium hydrogen carbonate solution (100 mL) and saturated brine (80 mL) and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl]methyl]sulfinyl]-1H-benzimidazole (0.74 g), triethylamine (0.56 mL) and 4-dimethylaminopyridine (0.049 g) were added, and the mixture was stirred at 60° C. overnight. After concentration under reduced pressure, an aqueous sodium hydrogen carbonate solution (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=7:3, then ethyl acetate, then methanol:ethyl acetate=1:19) to give the title compound (0.78 g) as a yellow-green amorphous solid.

$^1$H-NMR(CDCl$_3$): 1.65-2.05 (6H, m), 2.23 (3H, s), 2.25 (3H, s), 2.24-2.38 (1H, m), 2.75-2.85 (2H, m), 3.07 (3H, bs), 3.40-4.10 (2H, br), 4.38 (2H, q, J=7.8 Hz), 4.40 (2H, m), 4.80-5.10 (2H, br), 6.64 (1H, d, J=5.6 Hz), 7.36-7.47 (3H, m), 7.84 (1H, d, J=7.8 Hz), 8.35 (1H, d, J=5.6 Hz).

Synthetic Example 62

2-[[4-(Aminocarbonyl)phenyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate To a solution (20 mL) of bis(trichloromethyl)carbonate (0.45 g) in tetrahydrofuran was dropwise added a solution (10 mL) of 2-[[4-(aminocarbonyl)phenyl]amino]ethyl acetate (0.67 g) obtained in Reference Example 55 and triethylamine (0.63 mL) in tetrahydrofuran under ice-cooling, and the mixture was stirred at room temperature for 1 hr. After concentration under reduced pressure, water (50 mL) was added to the residue and the mixture was extracted with ethyl acetate (50 mL). The ethyl acetate layer was washed with 0.2N hydrochloric acid (20 mL) and saturated brine (50 mL) and dried over anhydrous magnesium sulfate. After concentration under reduced pressure, the residue was dissolved in tetrahydrofuran (30 mL). (R)-2-[[[3-Methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g) were added, and the mixture was stirred at 60° C. for 30 min. and at room temperature overnight. After concentration under reduced pressure, an aqueous sodium hydrogen carbonate solution (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate: hexane=4:6, then 6:4, then 8:2) to give the title compound (1.26 g) as a yellow amorphous solid.

$^1$H-NMR(CDCl$_3$): 1.99 (3H, s), 2.26 (3H, s), 4.15-4.55 (4H, m), 4.41 (2H, q, J=7.9 Hz), 4.80-5.20 (2H, br), 6.69 (1H, d, J=5.7 Hz), 7.26-7.38 (3H, m), 7.48 (2H, d, J=8.9 Hz), 7.54 (2H, d, J=8.9 Hz), 7.66-7.73 (1H, m), 8.39 (1H, d, J=5.7 Hz).

Synthetic Example 63

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methyl-4-piperidinyl carbonate 2-(Methylamino)ethyl 1-methyl-4-piperidinyl carbonate dihydrochloride (1.01 g) obtained in Reference Example 56 was added to tetrahydrofuran (30 mL). After stirring for a while, the mixture was ice-cooled. Bis(trichloromethyl)carbonate (0.69 g) was added and a solution (10 mL) of triethylamine (1.95 mL) in tetrahydrofuran was dropwise added. After stirring under ice-cooling for 1 hr. and at room temperature for 1 hr., the precipitated solid was filtered off. After concentration under reduced pressure, ethyl acetate (50 mL) was added, and the mixture was washed with an ice-cooled aqueous sodium hydrogen carbonate solution (50 mL) and saturated brine (50 mL), and dried over anhydrous magnesium sulfate. The layer was concentrated under reduced pressure, and the residue was dissolved in tetrahydrofuran (20 mL). (R)-2-[[[3-Methyl-4-(2,2,2-trifluoroethoxy)-2-pyridyl] methyl]sulfinyl]-1H-benzimidazole (1.11 g), triethylamine (0.63 mL) and 4-dimethylaminopyridine (0.037 g) were added, and the mixture was stirred at 60° C. overnight. After concentration under reduced pressure, an aqueous sodium hydrogen carbonate solution (50 mL) was added to the residue, and the mixture was extracted with ethyl acetate (50 mL). The ethyl acetate layer was washed with saturated brine (50 mL) and dried over anhydrous magnesium sulfate. After concentration under reduced pressure, the residue was purified by basic silica gel column chromatography (eluted with ethyl acetate:hexane=1:1, then ethyl acetate, then methanol: ethyl acetate=1:19) to give the title compound (0.70 g) as a yellow amorphous solid.

$^1$H-NMR(CDCl$_3$): 1.70-1.86 (2H, m), 1.90-2.04 (2H, m), 2.23 (3H, s), 2.28 (3H, s), 2.10-2.35 (2H, m), 2.60-2.72 (2H, m), 3.08 (3H, bs), 3.40-4.20 (2H, br), 4.39 (2H, q, J=7.9 Hz), 4.44 (2H, m), 4.60-4.74 (1H, m), 4.80-5.15 (2H, br), 6.65 (1H, d, J=5.9 Hz), 7.35-7.52 (3H, m), 7.84 (1H, d, J=7.5 Hz), 8.35 (1H, d, J=5.9 Hz).

Synthetic Example 64

2-[[4-(Aminocarbonyl)phenyl][[2-[[[3-methyl-4-(2,2,2-trifluoroethoxy)-2-pyridyl]methyl]sulfinyl]-1H-benzimidazol-1-yl]carbonyl]amino]ethyl acetate To a solution (5 mL) of bis(trichloromethyl)carbonate (0.12 g) in tetrahydrofuran was dropwise added a solution (5 mL) of 2-[[4-(aminocarbonyl)phenyl]amino]ethyl acetate (0.22 g) obtained in Reference Example 55 and triethylamine (0.17 mL) in tetrahydrofuran under ice-cooling, and the mixture was stirred at room temperature for 30 min. Water (20 mL) was added, and the mixture was extracted with ethyl acetate (30 mL). The ethyl acetate layer was washed with saturated brine (20 mL) and dried over anhydrous magnesium sulfate. After concentration under reduced pressure, the residue was dissolved in tetrahydrofuran (10 mL). 2-[[[3-Methyl-4-(2,2,2-trifluoroethoxy)-2-pyridyl]methyl]sulfinyl]-1H-benzimidazole (0.37 g), triethylamine (0.28 mL) and 4-dimethylaminopyridine (0.012 g) were added, and the mixture was stirred at 60° C. for 1 hr. After concentration under reduced pressure, an aqueous sodium hydrogen carbonate solution (20 mL) was added to the residue, and the mixture was extracted with ethyl acetate (30 mL). The ethyl acetate layer was washed with saturated brine (20 mL) and dried over anhydrous magnesium sulfate. After concentration under reduced pressure, the residue was purified by basic silica gel column chromatography (eluted with ethyl acetate:hexane=3:7, then 5:5, then 8:2) to give the title compound (0.34 g) as a pale-yellow amorphous solid.

$^1$H-NMR(CDCl$_3$): 1.99 (3H, s), 2.26 (3H, s), 4.15-4.55 (4H, m), 4.41 (2H, q, J=7.9 Hz), 4.80-5.20 (2H, br), 6.69 (1H, d, J=5.9 Hz), 7.26-7.40 (3H, m), 7.47 (2H, d, J=8.8 Hz), 7.54 (2H, d, J=8.8 Hz), 7.65-7.74 (1H, m), 8.38 (1H, d, J=5.9 Hz).

Synthetic Example 65

(−)-Ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate 5-Methoxy-2-[[(4-methoxy-3,5-dimethyl-2-pyridyl)methyl]sulfinyl]-1H-imidazo[4,5-b]pyridine synthesized according to the method described in JP-A-63-146882 was subjected to preparative HPLC for optical resolution to give a (−) enantiomeric form (0.10 g) thereof. To a solution (5 mL) of this form in tetrahydrofuran were added 2-[(chlorocarbonyl)(methyl)amino]ethyl ethyl carbonate (0.081 g) obtained in Reference Example 34, triethylamine (0.080 mL) and 4-dimethylaminopyridine (0.007 g) and the mixture was stirred at 50° C. for 18 hrs. After concentration under reduced pressure, water (30 mL) was added to the residue and the mixture was extracted with ethyl acetate (50 mL). The ethyl acetate layer was washed with saturated brine (30 mL) and dried over anhydrous sodium sulfate. After concentration under reduced pressure, the residue was purified by basic silica gel column chromatography (eluted with ethyl acetate: hexane=2:1) to give the title compound (0.053 g) as a colorless oil.

$^1$H-NMR(CDCl$_3$): 1.30 (3H, t, J=7.1 Hz), 2.24 (6H, s), 3.15, 3.32 (total 3H, s), 3.73 (3H, s), 3.90-4.55 (9H, m), 4.85 (1H, d, J=13.2 Hz), 4.97 (1H, d, J=13.2 Hz), 6.80 (1H, d, J=8.8 Hz), 7.96 (1H, d, J=8.8 Hz), 8.23 (1H, s).

Synthetic Example 66

(+)-Ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate 5-Methoxy-2-[[(4-methoxy-3,5-dimethyl-2-pyridyl)methyl]sulfinyl]-1H-imidazo[4,5-b]pyridine synthesized according to the method described in JP-A-63-146882 was subjected to preparative HPLC for optical resolution to give a (+) enantiomeric form (0.10 g) thereof. To a solution (5 mL) of this form in tetrahydrofuran were added 2-[(chlorocarbonyl)(methyl)amino]ethyl ethyl carbonate (0.081 g) obtained in Reference Example 34, triethylamine (0.080 mL) and 4-dimethylaminopyridine (0.007 g) and the mixture was stirred at 50° C. for 18 hrs. After concentration under reduced pressure, water (30 mL) was added to the residue and the mixture was extracted with ethyl acetate (50 mL). The ethyl acetate layer was washed with saturated brine (30 mL) and dried over anhydrous sodium sulfate. After concentration under reduced pressure, the residue was purified by basic silica gel column chromatography (eluted with ethyl acetate: hexane=2:1) to give a 2:1 mixture (0.115 g) of the title compound and (+)-ethyl 2-[[[5-methoxy-2-[[(4-methoxy-3,5-dimethyl-2-pyridyl)methyl]sulfinyl]-1H-imidazo[4,5-b]pyridin-1-yl]carbonyl](methyl)amino]ethyl carbonate as a colorless oil.

$^1$H-NMR(CDCl$_3$): 1.20-1.38 (3H, m), 2.24 (6H, s), 3.08, 3.15, 3.33 (total 3H, s), 3.73 (3H, s), 3.88-4.55 (9H, m), 4.78-5.05 (2H, m), 6.80, 6.86 (1H, d, J=8.8 Hz), 7.76, 7.96 (1H, d, J=8.8 Hz), 8.21, 8.22 (total 1H, s).

In the following Comparative Examples 1 and 2, Examples 1-3 and Experimental Examples 1 and 2, optically active R form of lansoprazole (hereinafter to be referred to as Compound A) was used as an active ingredient. In Comparative Examples and Examples, cornstarch, lactose and hydroxypropylmethylcellulose used were the Japanese Pharmacopoeia 14th Edition compatible products.

Comparative Example 1

Compound A (450 mg) and HPMC (trade name: Metolose 65SH-4000, manufactured by Shin-Etsu Chemical Co., Ltd.) (1550 mg) were mixed in a mortar and 200 mg of the obtained mixture was tableted using a hydraulic pump press (manufactured by RIKEN SEIKI) to give a tablet (comparative preparation 1) having a diameter of 8 mm.

Comparative Example 2

Compound A (450 mg), HPMC (trade name, Metolose 65SH-4000, manufactured by Shin-Etsu Chemical Co., Ltd.) (1085 mg) and methacrylic acid copolymer L (trade name: Eudragit L100, manufactured by Rohm Pharma) (465 mg) were mixed in a mortar and 200 mg of the obtained mixture was tableted using a hydraulic pump press (manufactured by RIKEN SEIKI) to give a tablet (comparative preparation 2) having a diameter of 8 mm.

Comparative Example 3

Ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate obtained in Synthetic Example 14 (compound 14) (900 mg) and HPMC (trade name: Metolose 65SH-4000, manufactured by Shin-Etsu Chemical Co., Ltd.) (2600 mg) were mixed in a mortar and 350 mg of the obtained mixture was tableted using a hydraulic pump press (manufactured by RIKEN SEIKI) to give a tablet (comparative preparation 3) having a diameter of 9 mm.

Example 1

Compound A (113 mg), lactose (303 mg), cornstarch (50 mg) and low-substituted hydroxypropylcellulose (trade name: L-HPC, manufactured by Shin-Etsu Chemical Co., Ltd.) (35 mg) were mixed in a mortar and 50 mg of the obtained mixture was tableted using a hydraulic pump press (manufactured by RIKEN SEIKI) to give a tablet having a diameter of 5 mm. Compound A (450 mg) and HPMC. (trade name: Metolose 65SH-4000, manufactured by Shin-Etsu Chemical Co., Ltd.) (1550 mg) were mixed in a mortar and 150 mg of the obtained mixture was used as an outer shell, which was tableted with the obtained tablet as an inner core using a hydraulic pump press (manufactured by RIKEN SEIKI) to give a dry coated tablet (preparation 1) having a diameter of 8 mm.

Example 2

Compound A (113 mg), lactose (303 mg), cornstarch (50 mg) and low-substituted hydroxypropylcellulose (trade name: L-HPC, manufactured by Shin-Etsu Chemical Co., Ltd.) (35 mg) were mixed in a mortar and 50 mg of the obtained mixture was tableted using a hydraulic pump press (manufactured by RIKEN SEIKI) to give a tablet having a diameter of 5 mm. Compound A (450 mg), HPMC (trade name: Metolose 65SH-4000, manufactured by Shin-Etsu Chemical Co., Ltd.) (1085 mg) and methacrylic acid copolymer L (trade name: Eudragit L100, manufactured by Rohm Pharma) (465 mg) were mixed in a mortar and 150 mg of the obtained mixture was used as an outer shell, which was tableted with the obtained tablet as an inner core using a hydraulic pump press (manufactured by RIKEN SEIKI) to give a dry coated tablet (preparation 2) having a diameter of 8 mm.

Example 3

Compound A (225 mg), lactose (125 mg), cornstarch (50 mg) and low-substituted hydroxypropylcellulose (trade name: L-HPC, manufactured by Shin-Etsu Chemical Co., Ltd.) (10 mg) were mixed in a mortar and 50 mg of the obtained mixture was tableted using a hydraulic pump press (manufactured by RIKEN SEIKI) to give a tablet having a diameter of 5 mm. Compound A (225 mg), HPMC (trade name: TC-5R, manufactured by Shin-Etsu Chemical Co., Ltd.) (350 mg) and HPMC (trade name: TC-5S, manufactured by Shin-Etsu Chemical Co., Ltd.) (225 mg) were mixed in a mortar and 150 mg of the obtained mixture was used as a outer shell, which was tableted with the obtained tablet as an inner core using a hydraulic pump press (manufactured by RIKEN SEIKI) to give a dry coated tablet having a diameter of 8 mm. Furthermore, Compound A (100 mg), lactose (300 mg), cornstarch (50 mg) and low-substituted hydroxypropylcellulose (trade name: L-HPC, manufactured by Shin-Etsu Chemical Co., Ltd.) (50 mg) were mixed in a mortar and 100 mg of the obtained mixture was used as an outer shell, which was tableted with the obtained tablet as an inner core using a hydraulic pump press (manufactured by RIKEN SEIKI) to give a dry coated tablet (preparation 3) having a diameter of 10 mm.

Example 4

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate obtained in Synthetic Example 1 (compound 1) (113 mg), lactose (303 mg), cornstarch (50 mg) and low-substituted hydroxypropylcellulose (trade name: L-HPC, manufactured by Shin-Etsu Chemical Co., Ltd.) (35 mg) were mixed in a mortar and 50 mg of the obtained mixture was tableted using a hydraulic pump press (manufactured by RIKEN SEIKI) to give a tablet having a diameter of 5 mm. Compound 1 (450 mg) and HPMC (trade name: Metolose 65SH-4000, manufactured by Shin-Etsu Chemical Co., Ltd.) (1550 mg) were mixed in a mortar and 150 mg of the obtained mixture was used as an outer shell, which was tableted with the obtained tablet as an inner core using a hydraulic pump press (manufactured by RIKEN SEIKI) to give a dry coated tablet (preparation 4) having a diameter of 8 mm.

Example 5

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 2-pyridinecarboxylate obtained in Synthetic Example 12 (compound 12) (113 mg), lactose (303 mg), cornstarch (50 mg) and low-substituted hydroxypropylcellulose (trade name: L-HPC, manufactured by Shin-Etsu Chemical Co., Ltd.) (35 mg) were mixed in a mortar and 50 mg of the obtained mixture was tableted using a hydraulic pump press (manufactured by RIKEN SEIKI) to give a tablet having a diameter of 5 mm. Compound 12 (450 mg) and HPMC (trade name: Metolose 65SH-4000, manufactured by Shin-Etsu Chemical Co., Ltd.) (1550 mg) were mixed in a mortar and 150 mg of the obtained mixture was used as an outer shell, which was tableted with the obtained tablet as an inner core using a hydraulic pump press (manufactured by RIKEN SEIKI) to give a dry coated tablet (preparation 5) having a diameter of 8 mm.

Example 6

Compound 14 (113 mg), lactose (303 mg), cornstarch (50 mg) and low-substituted hydroxypropylcellulose (trade name: L-HPC, manufactured by Shin-Etsu Chemical Co., Ltd.) (35 mg) were mixed in a mortar and 50 mg of the obtained mixture was tableted using a hydraulic pump press (manufactured by RIKEN SEIKI) to give a tablet having a diameter of 5 mm. Compound 14 (450 mg) and HPMC (trade name: Metolose 65SH-4000, manufactured by Shin-Etsu Chemical Co., Ltd.) (1550 mg) were mixed in a mortar and 150 mg of the obtained mixture was used as an outer shell, which was tableted with the obtained tablet as an inner core using a hydraulic pump press (manufactured by RIKEN SEIKI) to give a dry coated tablet (preparation 6) having a diameter of 8 mm.

Example 7

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate obtained in Synthetic Example 18 (compound 18) (113 mg), lactose (303 mg), cornstarch (50 mg) and low-substituted hydroxypropylcellulose (trade name: L-HPC, manufactured by Shin-Etsu Chemical Co., Ltd.) (35 mg) were mixed in a mortar and 50 mg of the obtained mixture was tableted using a hydraulic pump press (manufactured by RIKEN SEIKI) to give a tablet having a diameter of 5 mm. Compound 18 (450 mg) and HPMC (trade name: Metolose 65SH-4000, manufactured by Shin-Etsu Chemical Co., Ltd.) (1550 mg) were mixed in a mortar and 150 mg of the obtained mixture was used as an outer shell, which was tableted with the obtained tablet as an inner core using a hydraulic pump press (manufactured by RIKEN SEIKI) to give a dry coated tablet (preparation 7) having a diameter of 8 mm.

Example 8

2-[Cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate obtained in Synthetic Example 23 (compound 23) (113 mg), lactose (303 mg), cornstarch (50 mg) and low-substituted hydroxypropylcellulose (trade name: L-HPC, manufactured by Shin-Etsu Chemical Co., Ltd.) (35 mg) were mixed in a mortar and 50 mg of the obtained mixture was tableted using a hydraulic pump press (manufactured by RIKEN SEIKI) to give a tablet having a diameter of 5 mm. Compound 23 (450 mg) and HPMC (trade name: Metolose 65SH-4000, manufactured by Shin-Etsu Chemical Co., Ltd.) (1550 mg) were mixed in a mortar and 150 mg of the obtained mixture was used as an outer shell, which was tableted with the obtained tablet as an inner core using a hydraulic pump press (manufactured by RIKEN SEIKI) to give a dry coated tablet (preparation 8) having a diameter of 8 mm.

Example 9

2-[[[(R)-2-[[[3-Methyl-4-(2,2,2-trifluoroethoxy)-2-pyridyl]methyl]sulfinyl]-1H-benzimidazol-1-yl]carbonyl](phenyl)amino]ethyl acetate obtained in Synthetic Example 25 (compound 25) (113 mg), lactose (303 mg), cornstarch (50 mg) and low-substituted hydroxypropylcellulose (trade name: L-HPC, manufactured by Shin-Etsu Chemical Co., Ltd.) (35 mg) were mixed in a mortar and 50 mg of the obtained mixture was tableted using a hydraulic pump press (manufactured by RIKEN SEIKI) to give a tablet having a diameter of 5 mm. Compound 25 (450 mg) and HPMC (trade name: Metolose 65SH-4000, manufactured by Shin-Etsu Chemical Co., Ltd.) (1550 mg) were mixed in a mortar and 150 mg of the obtained mixture was used as an outer shell, which was tableted with the obtained tablet as an inner core using a hydraulic pump press (manufactured by RIKEN SEIKI) to give a dry coated tablet (preparation 9) having a diameter of 8 mm.

Example 10

2-[[2-(Acetyloxy)ethyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate obtained in Synthetic Example 29 (compound 29) (113 mg), lactose (303 mg), cornstarch (50 mg) and low-substituted hydroxypropylcellulose (trade name: L-HPC, manufactured by Shin-Etsu Chemical Co., Ltd.) (35 mg) were mixed in a mortar and 50 mg of the obtained mixture was tableted using a hydraulic pump press (manufactured by RIKEN SEIKI) to give a tablet having a diameter of 5 mm. Compound 29 (450 mg) and HPMC (trade name: Metolose 65SH-4000, manufactured by Shin-Etsu Chemical Co., Ltd.) (1550 mg) were mixed in a mortar and 150 mg of the obtained mixture was used as an outer shell, which was tableted with the obtained tablet as an inner core using a hydraulic pump press (manufactured by RIKEN SEIKI) to give a dry coated tablet (preparation 10) having a diameter of 8 mm.

Example 11

Ethyl 4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl carbonate obtained in Synthetic Example 41 (compound 41) (113 mg), lactose (303 mg), cornstarch (50 mg) and low-substituted hydroxypropylcellulose (trade name: L-HPC, manufactured by Shin-Etsu Chemical Co., Ltd.) (35 mg) were mixed in a mortar and 50 mg of the obtained mixture was tableted using a hydraulic pump press (manufactured by RIKEN SEIKI) to give a tablet having a diameter of 5 mm. Compound 41 (450 mg) and HPMC (trade name: Metolose 65SH-4000, manufactured by Shin-Etsu Chemical Co., Ltd.) (1550 mg) were mixed in a mortar and 150 mg of the obtained mixture was used as an outer shell, which was tableted with the obtained tablet as an

Example 12

2-Ethoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate obtained in Synthetic Example 49 (compound 49) (113 mg), lactose (303 mg), cornstarch (50 mg) and low-substituted hydroxypropylcellulose (trade name: L-HPC, manufactured by Shin-Etsu Chemical Co., Ltd.) (35 mg) were mixed in a mortar and 50 mg of the obtained mixture was tableted using a hydraulic pump press (manufactured by RIKEN SEIKI) to give a tablet having a diameter of 5 mm. Compound 49 (450 mg), HPMC (trade name: Metolose 65SH-4000, manufactured by Shin-Etsu Chemical Co., Ltd.) (1550 mg) were mixed in a mortar and 150 mg of the obtained mixture was used as an outer shell, which was tableted with the obtained tablet as an inner core using a hydraulic pump press (manufactured by RIKEN SEIKI) to give a dry coated tablet (preparation 12) having a diameter of 8 mm.

Example 13

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl N,N-dimethylglycinate obtained in Synthetic Example 51 (compound 51) (113 mg), lactose (303 mg), cornstarch (50 mg) and low-substituted hydroxypropylcellulose (trade name: L-HPC, manufactured by Shin-Etsu Chemical Co., Ltd.) (35 mg) were mixed in a mortar and 50 mg of the obtained mixture was tableted using a hydraulic pump press (manufactured by RIKEN SEIKI) to give a tablet having a diameter of 5 mm. Compound 51 (450 mg) and HPMC (trade name: Metolose 65SH-4000, manufactured by Shin-Etsu Chemical Co., Ltd.) (1550 mg) were mixed in a mortar and 150 mg of the obtained mixture was used as an outer shell, which was tableted with the obtained tablet as an inner core using a hydraulic pump press (manufactured by RIKEN SEIKI) to give a dry-coated tablet (preparation 13) having a diameter of 8 mm.

Example 14

Compound 14 (400 mg), lactose (160 mg), cornstarch (80 mg) and low-substituted hydroxypropylcellulose (trade name: L-HPC, manufactured by Shin-Etsu Chemical Co., Ltd.) (160 mg) were mixed in a mortar and 80 mg of the obtained mixture was tableted using a hydraulic pump press (manufactured by RIKEN SEIKI) to give a tablet having a diameter of 6 mm. Compound 14 (400 mg), HPMC (trade name: TC-5R, manufactured by Shin-Etsu Chemical Co., Ltd.) (700 mg), HPMC (trade name: Metolose 65SH-4000, manufactured by Shin-Etsu Chemical Co., Ltd.) (700 mg) and granulated sugar (400 mg) were mixed in a mortar and 220 mg of the obtained mixture was used as an outer shell, which was tableted with the obtained tablet as an inner core using a hydraulic pump press (manufactured by RIKEN SEIKI) to give a dry coated tablet having a diameter of 9 mm. Furthermore, compound 14 (100 mg), lactose (250 mg), cornstarch (50 mg) and low-substituted hydroxypropylcellulose (trade name: L-HPC, manufactured by Shin-Etsu Chemical Co., Ltd.) (100 mg) were mixed in a mortar and 50 mg of the obtained mixture was used as an outer shell, which was tableted with the obtained tablet as am inner core using a hydraulic pump press (manufactured by RIKEN SEIKI) to give a dry coated tablet (preparation 14) having a diameter of 10 mm.

Example 15

In the same manner as in Example 14, a diameter of 9 mm dry coated tablet comprising 40 mg of compound 14 in an inner core having a diameter of 6 mm, and 40 mg of compound 14 in an outer shell was obtained. The obtained dry coated tablet was coated with a compound 14-containing suspension having the following composition using a HI-COATER HC-LABO (manufactured by Freund Corporation) to give a preparation 15 coated with an outermost layer containing 10 mg of compound 14 per one dry coated tablet. Composition of Coating Solution:

| | |
|---|---|
| hydroxypropylcellulose (trade name: HPC-SL, manufactured by Nippon Soda Co., Ltd.): | 2.5 g |
| low-substituted hydroxypropylcellulose (trade name: L-HPC, manufactured by Shin-Etsu Chemical Co., Ltd.): | 2.5 g |
| compound 14: | 10 g |
| purified water: | 105 g |

Experimental Example 1

The drug dissolution property of the controlled release composition of the present invention, which contains release-controlled parts A and B, was evaluated by a dissolution test.

To be specific, preparations 1 and 2 obtained in Examples 1 and 2 were subjected to a dissolution test (Paddle Method, 0.1% sodium dodecylsulfate-containing phosphate buffer (pH 6.8, 500 mL, 100 rpm, using a sinker). As a control group, comparative preparations 1 and 2 obtained in Comparative Examples 1 and 2 were subjected to a similar dissolution test. The results are shown in FIG. 1.

From the comparison with comparative preparations, the controlled release composition of the present invention has been shown to have multistep releaseability. It has been also clarified that the releaseability of the active ingredient from the release-controlled part B can be controlled by changing the kind (composition) of the polymer contained in the release-controlled part B in the composition of the present invention.

Experimental Example 2

The drug dissolution property of the controlled release composition of the present invention, which contains release-controlled parts A, B and C, was evaluated by a dissolution test.

Figure 2:
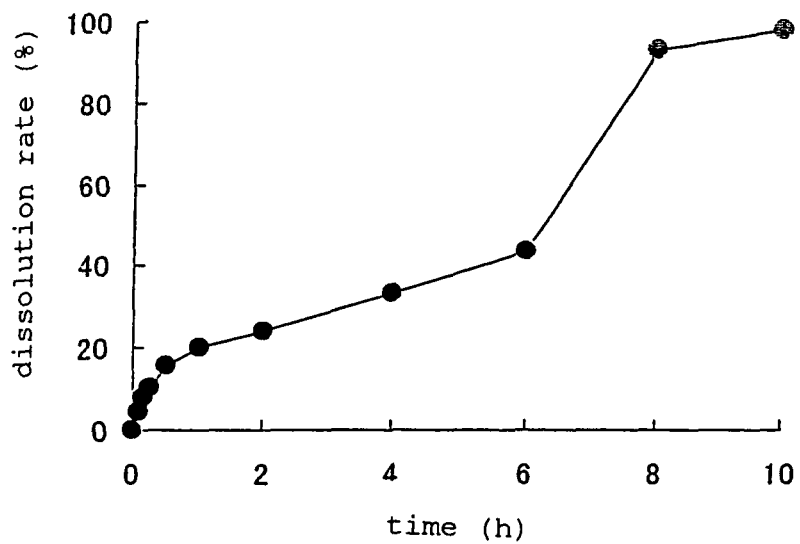
FIG. 2 shows a drug dissolution profile of the controlled release composition of the present invention containing the release-controlled parts A, B and C [preparation 3], wherein the vertical axis shows dissolution rate (%) and the transverse axis shows time (h) after the start of the test.

To be specific, preparation 3 obtained in Example 3 was subjected to a dissolution test (Paddle Method, 0.1% sodium dodecylsulfate-containing phosphate buffer (pH 6.8, 500 mL, 100 rpm, using a sinker). The results are shown in FIG. 2.

From the comparison with comparative preparations (see FIG. 1), the controlled release composition of the present invention has been shown to have multistep releaseability. It has been also clarified that the releaseability of the active ingredient from each release-controlled part can be controlled by changing the kind of the carrier contained in each release-controlled part and the ratio of the active ingredient in each release-controlled part, in the composition of the present invention.

Experimental Example 3

The preparation of the present invention was evaluated by dissolution property.

Figure 3:
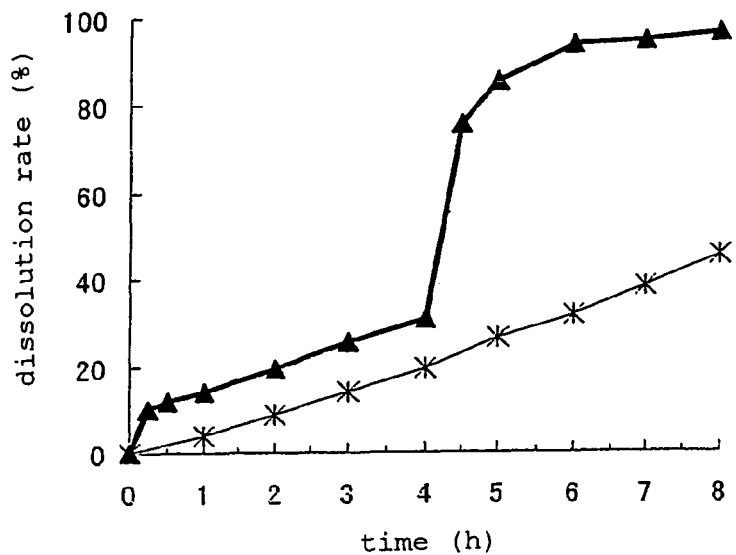
FIG. 3 shows drug dissolution profiles of the controlled release composition of the present invention containing the release-controlled parts A, B and C [preparation 14 (▲)] and a sustained-release preparation consisting of a single release-controlled part [comparative preparation 3 (*)], wherein the vertical axis shows dissolution rate (%) and the transverse axis shows time (h) after the start of the test.

To be specific, preparation 14 obtained in Example 14 was subjected to a dissolution test (Paddle Method, 0.1% sodium dodecylsulfate-containing phosphate buffer (pH 6.8, 500 mL, 100 rpm, using a sinker). As a control example, comparative preparation 3 obtained in Comparative Example 3 was subjected to a similar dissolution test. From the results shown in FIG. 3, the controlled release composition of the present invention has been shown to have multistep releaseability of rapid release in the first stage, sustained release in the middle stage and more rapid release than in the middle stage in the last stage.

Experimental Example 4

The preparation of the present invention was evaluated by the absorbability.

Figure 4:
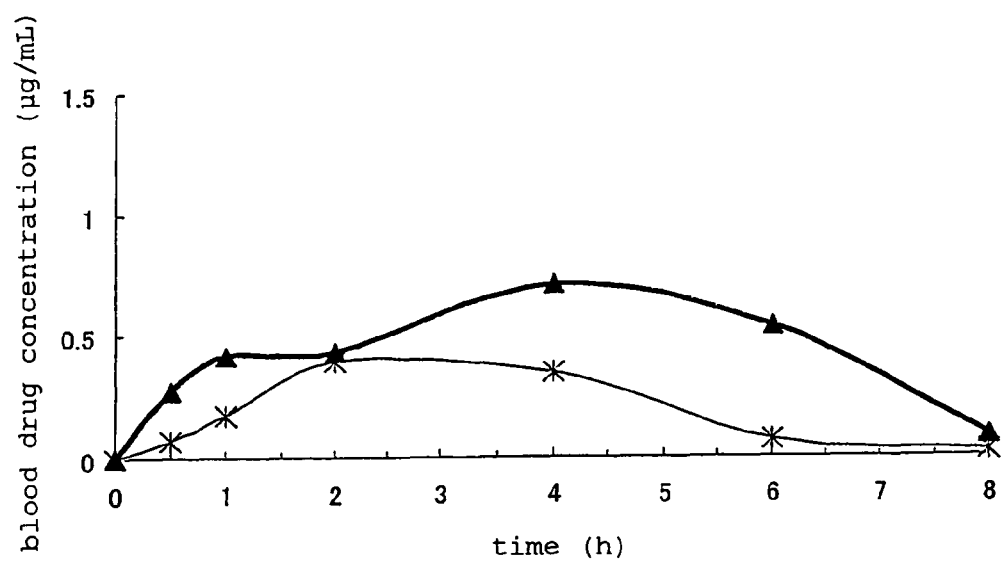
FIG. 4 shows the time-course changes in the drug blood concentration in beagle dogs after oral administration of [preparation 14 (▲)] or [comparative preparation 3 (*)], wherein the vertical axis shows drug blood concentration (μg/mL) and the transverse axis shows time (h) after oral administration.

To be specific, one tablet of preparation 14 obtained in Example 14 was orally administered to beagle dogs under fasting and changes in the drug blood concentration were evaluated. As a control example, similar evaluation was performed using comparative preparation 3 obtained in Comparative Example 3. From the results shown in FIG. 4, in comparative preparation 3 showing constant sustained release, the blood concentration decreased after 4 hr from administration, which has indicated lower absorption in the lower small intestine—large intestine. In contrast, the preparation 14 of the present invention maintained high blood concentration even after 4 hr from administration, which has clarified that a constant effective blood concentration is maintained for a long time.

INDUSTRIAL APPLICABILITY

The controlled release composition of the present invention shows a drug release profile characterized by a sustained drug release in the first and middle stages or middle stage, and a more rapid drug release in the last stage, and therefore, when used as a preparation for oral administration, it can maintain an effective blood concentration for an extended period of time even for a drug that shows lower absorbability due to the lower drug dissolution property in the lower small intestine—near the large intestine when used as a conventional sustained-release preparation.

The invention claimed is:

1. An oral controlled release composition showing release of an active ingredient controlled in two or more steps at different release rates, which consists essentially of
   1) a release-controlled part A comprising lansoprazole or a salt thereof or an optically active form thereof as an active ingredient, low-substituted hydroxypropylcellulose and a hydrophilic polymer, wherein the release-controlled part A is a sustained-release matrix, and wherein the release of the active ingredient from the release-controlled part A is maintained for 30 min-6 hr; and
   2) a release-controlled part B comprising lansoprazole or a salt thereof or an optically active form thereof as an active ingredient and a hydrophilic polymer, wherein the release-controlled part B is a sustained-release matrix, and wherein the release of the active ingredient from the release-controlled part B is maintained for 1-18 hr;
   wherein the release-controlled part A is directly coated with the release-controlled part B; and
   the active ingredient is contained in each release-controlled part in a weight ratio of A:5-95% and B:5-95%.

2. The oral controlled release composition of claim 1, wherein the dosage form is selected from the group consisting of a tablet, a granule, a pellet and a capsule.

3. An oral controlled release composition showing release of an active ingredient controlled in two or more steps at different release rates, which consists essentially of
   1) a release-controlled part A comprising lansoprazole or a salt thereof or an optically active form thereof as an active ingredient, low-substituted hydroxypropylcellulose and a hydrophilic polymer, wherein the release-controlled part A is a sustained-release matrix, and wherein the release of the active ingredient from the release-controlled part A is maintained for 30 min-6 hr;
   2) a release-controlled part B comprising lansoprazole or a salt thereof or an optically active form thereof as an active ingredient and a hydrophilic polymer, wherein the release-controlled part B is a sustained-release matrix, and wherein the release of the active ingredient from the release-controlled part B is maintained for 1-18 hr; and
   3) a release-controlled part C comprising lansoprazole or a salt thereof or an optically active form thereof as an active ingredient and low-substituted hydroxypropylcellulose, wherein the release of the active ingredient from the release-controlled part C is immediate release; and
   wherein the release-controlled part A is directly coated with the release-controlled part B; the release-controlled part B is coated with the release-controlled part C; and the active ingredient is contained in each release-controlled part in a weight ratio of A:5-95%, B:5-95% and C:40% or less.

4. The oral controlled release composition of claim 3, wherein the active ingredient is contained in each release-controlled part in a weight ratio of A:20-75%, B:20-75% and C:5-30%.

5. The oral controlled release composition of claim 3, which is a solid composition for oral administration, wherein the release of the active ingredient contained in the release-controlled part C completes within 2 hr after administration.

6. The oral controlled release composition of claim 3, wherein the dosage form is selected from the group consisting of a tablet, a granule, a pellet and a capsule.

* * * * *